(12) United States Patent
Jary et al.

(10) Patent No.: US 7,875,609 B2
(45) Date of Patent: Jan. 25, 2011

(54) UREA DERIVATIVES, PROCESSES FOR THEIR PREPARATION, THEIR USE AS MEDICAMENTS, AND PHARMACEUTICAL COMPOSITIONS CONTAINING THEM

(75) Inventors: Hélène Jary, Paris (FR); Taoues Temal, Saint-Gratien (FR); Pierre DePrez, Thiais (FR)

(73) Assignee: Galapagos Sasu, Romainville (FR)

( * ) Notice: Subject to any disclaimer, the term of this patent is extended or adjusted under 35 U.S.C. 154(b) by 929 days.

(21) Appl. No.: 11/591,097

(22) Filed: Oct. 31, 2006

(65) Prior Publication Data

US 2007/0179134 A1 Aug. 2, 2007

(30) Foreign Application Priority Data

Nov. 25, 2005 (FR) .................................. 05 11940

(51) Int. Cl.
- A61K 31/535 (2006.01)
- C07D 417/12 (2006.01)
- C07D 417/14 (2006.01)
- C07D 295/125 (2006.01)

(52) U.S. Cl. .............. 514/234.5; 514/236.2; 514/236.5; 544/122; 544/124; 544/133; 544/134; 544/137; 544/140

(58) Field of Classification Search ................. 544/134, 544/122, 124, 133, 137, 140; 514/236.2, 514/234.5

See application file for complete search history.

(56) References Cited

U.S. PATENT DOCUMENTS

| | | | |
|---|---|---|---|
| 3,897,242 A | 7/1975 | Martin | |
| 4,521,583 A | 6/1985 | Kohli | |
| 4,579,947 A | 4/1986 | Devlin et al. | |
| 4,594,373 A | 6/1986 | Kohli | |
| 5,227,397 A | 7/1993 | Saccomano et al. | |
| 5,242,947 A | 9/1993 | Cherksey et al. | |
| 5,312,928 A | 5/1994 | Goldin et al. | |
| 5,849,732 A | 12/1998 | Suzuki et al. | |
| 5,891,912 A | 4/1999 | Kawashima et al. | |
| 5,968,980 A | 10/1999 | Kawashima et al. | |
| 6,011,068 A | 1/2000 | Nemeth et al. | |
| 6,022,894 A | 2/2000 | Del Mar et al. | |
| 6,031,003 A | 2/2000 | Nemeth et al. | |
| 6,211,244 B1 | 4/2001 | Van Wagenen et al. | |
| 6,221,913 B1 | 4/2001 | Petrie et al. | |
| 6,313,146 B1 | 11/2001 | Van Wagenen et al. | |
| 6,596,746 B1 | 7/2003 | Das et al. | |
| 7,084,167 B2 | 8/2006 | Ruat et al. | |
| 7,157,498 B2 | 1/2007 | Dauban et al. | |
| 7,585,886 B2 | 9/2009 | Hachiya et al. | |
| 7,605,261 B2 | 10/2009 | DePrez et al. | |
| 2004/0053925 A1 | 3/2004 | Deprez et al. | |
| 2004/0082588 A1 | 4/2004 | Evans et al. | |
| 2007/0173502 A1 | 7/2007 | DePrez et al. | |
| 2008/0125424 A1* | 5/2008 | DePrez et al. ............ 514/233.8 |
| 2009/0054463 A1 | 2/2009 | DePrez et al. | |
| 2009/0062366 A1 | 3/2009 | Hachiya et al. | |

FOREIGN PATENT DOCUMENTS

| | | |
|---|---|---|
| EP | 0415413 A | 3/1991 |
| JP | 58-109464 | 6/1983 |
| JP | 08-041006 | 2/1996 |
| JP | 09-012455 | 1/1997 |
| JP | 10-195037 | 7/1998 |
| JP | 11-139969 | 5/1999 |
| WO | WO 92/08700 | 5/1992 |
| WO | WO 93/23368 | 11/1993 |
| WO | WO 94/14436 | 7/1994 |
| WO | WO 95/11221 | 4/1995 |
| WO | WO 96/12697 | 5/1996 |
| WO | WO 97/37967 | 10/1997 |
| WO | WO 99/07672 | 2/1999 |
| WO | WO 00/62778 | 10/2000 |
| WO | WO 01/00576 | 1/2001 |
| WO | WO 02/059102 | 8/2002 |
| WO | WO 2004/030669 | 4/2004 |
| WO | WO 2005/115975 | 12/2005 |
| WO | WO 2006/117211 | 11/2006 |
| WO | WO 2006/123725 | 11/2006 |
| WO | WO 2007/060026 | 5/2007 |
| WO | WO 2008/006625 | 1/2008 |
| WO | WO 2009/009122 | 1/2009 |

OTHER PUBLICATIONS

Nemeth et al., "Pharmacological Regulation of Parathyroid Hormone Secretion", Current Pharmaceutical Design, pp. 2077-2087, 8, 2002.

(Continued)

Primary Examiner—Rebecca L Anderson
(74) Attorney, Agent, or Firm—Greenlee Sullivan P.C.

(57) ABSTRACT

The present invention provides compounds of Formula (I):

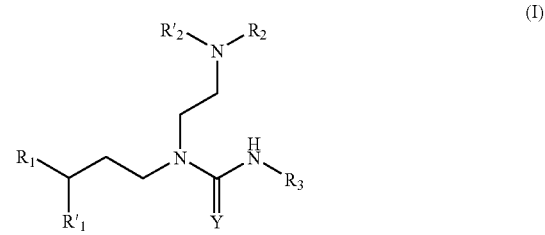

in which $R_1$, $R'_1$, $R_2$, $R'_2$, $R_3$, and Y have the meanings given in the description are useful in the treatment of conditions susceptible to modulating ion channels, to a process for their preparation, their application by way of medicaments, and to pharmaceutical compositions containing them.

60 Claims, No Drawings

OTHER PUBLICATIONS

Cho et al. (1999) "Bioisosterism: Interchange of 4-OH to 4-NH2 in Vanillin or Homovanillin Ring of Capsaicinoids," *Arch. Pharm. Res.* 22(2):184-188.

Golub, T.R. et al. (1999) "Molecular Classification of Cancer: Class Discovery and Class Prediction by Gene Expression Monitoring" Science vol. 286 pp. 531-537.

Huff, J.R. (Aug. 1991) "HIV Protease: A Novel Chemotherapeutic Target for AIDS" *J. Med. Chem.* 34(8):2305-2314.

Kuklin (1996) "Preparation and Pharmacological Properties of Sulfur-Containing Amides of Dicarboxylic Acids," CAPLUS Accession No. 1996:369326.

Kuro et al. (2000) "Effects of SA7060, a Novel Dual Inhibitor of Neutral Endopeptidase and Angiotensin-Converting Enzyme, on Deoxycorticosterone Acetate-Salt-Induced Hypertension in Rats," *Biol. Pharm. Bull.* 23(7):820-825.

Lala et al. (1998) "Role of Nitric Oxide in Tumor Progression: Lessons from Experimental Tumors," *Cancer Metastasis Rev.* 17:91-106.

Muller et al. (1977) "Boron Compounds. 7. Synthesis and Molecular Structure of 1,5-Diethyl-2,3-Diphenyl-1,3,5-Triaza-2-Bora-Cyclooctane-4-One: The Product of Aminoboronation," *Z. Anorg. Allg. Chem.*433:268-274.

Munroe et al. et al. (1995) "Potent, Orally Bioavailable HIV-1 Protease Inhibitors Containing Noncoded D-Amino Acids," *Bioorg. Med. Chem. Lett.* 5(23):2897-2902.

Nomura et al (1998) "Synthesis of Physiologically Active Substances. 19. Synthesis and Pesticidal Activity of Ureas and Amides with Bicyclic Monoterpenyl Derivatives (mites)," CAPLUS Accession No. 1998:757076.

Nowick et al. (1992) "Molecular Scaffolds I: Intramolecular Hydrogen Bonding in a Family of Di- and Triureas," *J. Org. Chem.* 57:3763-3765.

Nowick et al. (1997) "The Propensities of Amino Acids to Form Parallel β-Sheets," *J. Am. Chem. Soc.* 119:10903-10908.

Nowick et al. (1995) "Molecular Scaffolds. 2. Intramolecular Hydrogen Bonding in 1,2-Diaminoethane Diureas," *J. Am. Chem. Soc.* 117:89-99.

Uribe et al. (1979) "Rotational Isomerism of 1-Dicyclohexyl-3-tert-butyl Urea in the Solid State," CAPLUS Accession No. 1979:203395.

Vaino et al. (Jul. 5, 2000) "Euclidean Shape-Encoded Combinatorial Chemical Libraries," *Proc. Nat. Acad. Sci.* USA 97(14):7692-7696.

CNN web page, URL: http://www.cnn.com/2003/HEALTH/conditions/09/24/alzheimers.drug.ap/index.html Retrieved Aug. 19, 2010 (Way back Machine).

International Search Report of WO 02/059102, 2002.

* cited by examiner

UREA DERIVATIVES, PROCESSES FOR THEIR PREPARATION, THEIR USE AS MEDICAMENTS, AND PHARMACEUTICAL COMPOSITIONS CONTAINING THEM

CROSS-REFERENCE TO RELATED APPLICATIONS

This application claims the benefit of French Application No. 0511940 filed Nov. 25, 2005, which is incorporated herein by reference in its entirety.

FIELD OF THE INVENTION

The present invention relates to urea derivatives useful in the physiological modulation of the activity of inorganic ions, particularly through their effect on inorganic ion receptors and especially on membrane calcium receptors capable of binding extracellular calcium; to processes for the preparation thereof; to their use as medicaments; to pharmaceutical compositions containing them; and to the methods of use.

BACKGROUND OF THE INVENTION

Extracellular calcium concentration is precisely regulated in the organism and one of the key elements of this regulation is the calcium receptor known as the Ca sensing receptor or CaSR. A receptor of this type at the surface of specific cells can detect the presence of calcium. Specific cells of the organism respond not only to chemical signals, but also to ions such as extracellular calcium ions ($Ca^{2+}$): changes in the concentration of these extracellular $Ca^{2+}$ ions can modify the functional responses of these cells. These cells include parathyroid cells which secrete the parathyroid hormone known as PTH. Parathyroid cells thus have at their surface the calcium receptor (CaSR), which detects changes in extracellular calcium concentration, and initiates the functional response of this cell, which is a modulation of the secretion of the parathyroid hormone (PTH). PTH, by acting in particular on the bone cells or on the renal cells, increases the calcium level in the blood. This increase then acts as a negative control on PTH secretion. The reciprocal relationship between calcium concentration and PTH level is an essential mechanism for calcium homeostasis maintenance.

The cloning of the calcium receptor by Brown in 1993 consequently demonstrated two possible signalling pathways for this G protein coupled receptor: one pathway by activation of the Gi protein (sensitive to the pertussis toxin) which stimulates phospholipase C and inhibits adenylate cyclase; the other pathway by activating the Gq protein responsible for mobilising intracellular calcium. These two signalling pathways, either independently of one another or together, can be activated so as to trigger the associated biological effect.

On its extracellular portion, the calcium receptor is a low affinity receptor which is stimulated by millimolar concentrations of agonists, in particular the calcium ion $Ca^{2+}$. In addition, this receptor can also be activated by some divalent metals (magnesium) or trivalent metals (gadolinium, lanthanum, etc.) or else by polycationic compounds such as neomycin or spermin.

Novel compounds acting on the transmembrane portion of the receptor have been identified by Edward F. Nemeth et al (company NPS, U.S. Pat. No. 6,211,244) and allow the calcium receptor to be modulated allosterically. The action of first generation and second generation compounds on the pharmacological regulation of parathyroid hormone (PTH) secretion is described, for example, by E. F. Nemeth in Current Pharmaceutical Design, 2002, 8, 2077-2087. In particular, the compound AMG073 (cinacalcet, Sensipar®, Mimpara®) acts as an agonist of the calcium receptor and was first sold in the United States in 2004 for the treatment of secondary hyperparathyroidism (Idrugs, 2003, 6, 587-592 J. Iqbal, M. Zaidi, A. E. Schneider).

SUMMARY OF THE INVENTION

Thus, in a first aspect, the present invention provides a compound of formula (I):

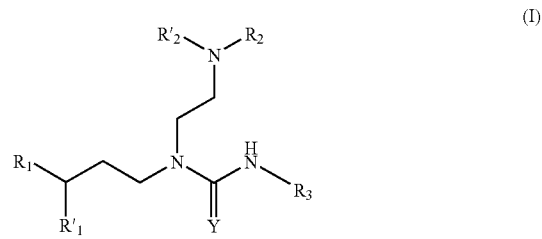

wherein:

Y is oxygen or sulphur;

$R_1$ and $R'_1$ are the same or different, and each represents an aryl group, a heteroaryl group, or $R_1$ and $R'_1$, together with the carbon atom to which they are linked, form a fused ring structure of formula:

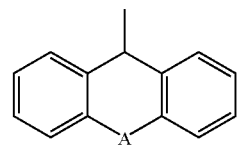

in which A represents a single bond, a methylene group, a dimethylene group, oxygen, nitrogen or sulphur, said sulphur optionally being in the sulphoxide or sulphone forms, wherein each of $R_1$ and $R'_1$, or said fused ring structure formed thereby, is optionally substituted by at least one substituent selected from the group c wherein the group c consists of: halogen atoms, hydroxyl, carboxyl, linear and branched alkyl, hydroxyalkyl, haloalkyl, thioalkyl, alkenyl, and alkynyl groups; linear and branched alkoxyl groups; linear and branched alkylthio groups; hydroxycarbonylalkyl; alkylcarbonyl; alkoxycarbonylalkyl; alkoxycarbonyl; trifluoromethyl; trifluoromethoxyl; —CN; —NO$_2$; alkylsulphonyl groups optionally in the sulphoxide or sulphone forms; wherein any alkyl component has from 1 to 6 carbon atoms, and any alkenyl or alkynyl components have from 2 to 6 carbon atoms, and wherein, when there is more than one substituent, then each said substituent is the same or different, $R_2$ and $R'_2$, which may be the same or different, each represents: a hydrogen atom; a linear or branched alkyl group containing from 1 to 6 carbon atoms and optionally substituted by at least one halogen atom, hydroxy or alkoxy group containing from 1 to 6 carbon atoms; an alkylaminoalkyl or dialkylaminoalkyl group wherein each alkyl group contains from 1 to 6 carbon atoms, or $R_2$ and $R'_2$, together with the nitrogen atom to which they are linked, form a saturated or unsaturated heterocycle containing 0, 1 or 2 additional heteroatoms and having 5, 6, or 7 ring atoms, said heterocycle being optionally substituted by at least one substituent selected from the group c defined above, and wherein, when there is more than one substituent, said substituent is the same or different, $R_3$ represents a group of formula —$(CH_2)_p$—Ar—$R_n$, in which p is 0 or 1 and, when p is 1, $(CH_2)_p$ may be substituted by methyl, chlorine, fluorine, hydroxy, or trimethyl, Ar represents an aryl or heteroaryl group, n is equal to the number of positions that can be substituted on Ar, and wherein each R, which may be the same or different, represents a hydrogen atom or a substituent selected from the group consisting of:

group a, in which group a consists of: halogen atoms; hydroxyl; trifluoromethyl; linear and branched alkyl, alkenyl, alkynyl, and alkoxyl groups, all optionally further substituted by one or more of hydroxy groups, halogen atoms, alkoxy groups, amino groups, and alkylthio groups; linear and branched alkoxyl groups; linear and branched thioalkyl groups; aryl groups; aralkyl groups; aralkoxy groups; aryloxy groups; perfluoroalkyl; perfluoroalkoxy; —CN;

the groups —$NR_4R_5$, —$C(=X)NR_4R_5$, —O—$C(=X)NR_4R_5$, —$SO_2NR_4R_5$, or -Alk-$NR_4R_5$, in which X is oxygen or sulphur, Alk is an alkyl group, and $R_4$ and $R_5$ are the same or different and are H, alkyl, aralkyl, aryl, heteroaryl or heteroaralkyl and are optionally further substituted by one or more substituents selected from trifluoromethyl, halogen atoms and hydroxyl groups;

the groups —$NZC(=X)(NH)_qR_6$, -Alk-$NZC(=X)(NH)_qR_6$, —$C(=X)R_6$, or -Alk-$C(=X)(NH)_qR_6$, in which Z is H or $C(=X)R_6$ wherein each X and each $R_6$ is the same or different, q is 0 or 1 and, when q is 1, $(NH)_q$ is optionally substituted with a methyl, ethyl, or trifluoromethyl group, X is oxygen or sulphur, Alk is an alkyl group, and $R_6$ is H, OH, alkyl, aralkyl, aryl, heteroaryl or heteroaralkyl and is optionally further substituted by one or more substituents selected from trifluoromethyl, halogen atoms and hydroxyl groups or, when $C(=X)$ is CO, then $C(=X)R_6$ may form an ester or thioester grouping;

the groups —$NHSO_2R_7$, —$SO_2R_7$, —$SOR_7$, or —$SR_7$, in which $R_7$ is OH or amino, or $R_7$ is alkyl, aralkyl, alkylamino, aralkylamino, aryl, heteroaryl or heteroaralkyl, optionally further substituted by one or more substituents selected from trifluoromethyl, halogen atoms and hydroxyl groups;

and saturated or unsaturated heterocyclyl groups, said heterocyclyl groups being mono- or bi-cyclic and being optionally substituted by one or more substituents, which may be the same or different, selected from the group b, wherein the group b consists of: halogen atoms; hydroxyl; carboxyl; aldehyde groups; linear and branched alkyl, alkenyl, alkynyl, hydroxyalkyl, hydroxyalkenyl, hydroxyalkynyl, haloalkyl, haloalkenyl, and haloalkynyl groups; linear and branched alkoxyl groups; linear and branched thioalkyl groups; alkoxycarbonyl; hydroxycarbonylalkyl; alkoxycarbonylalkyl; perfluoroalkyl; perfluoroalkoxy; —CN; acyl; amino, alkylamino, dialkylamino, acylamino, and diacylamino groups; alkyl groups substituted with an amino, alkylamino, dialkylamino, acylamino, or diacylamino group; $CONH_2$; alkylamido groups; alkylthio and the oxidised sulphoxide and sulphone forms thereof; sulphonyl, alkylsulphonyl groups; and sulphonamide, alkylsulphonamide, and di(alkylsulphonyl)amino groups, wherein, in groups a and b, any alkyl components contain from 1 to 6 carbon atoms, and any alkenyl or alkynyl components contain from 2 to 6 carbon atoms, and are optionally substituted by at least one halogen atom or hydroxy group, and wherein any aryl component is optionally a heteroaryl group, and when n is at least two, then two adjacent groups R may form a 5, 6, or 7 membered fused carbocyclic or heterocyclic ring with Ar, said fused ring being optionally further substituted with an oxo group or a substituent selected from group b as defined above, provided that, when p is 0, Ar is not thiazolyl or oxazolyl, either unfused or fused with a monocyclic aryl or a monocyclic heteroaryl in which the or any heteroatom is nitrogen, and salts and esters thereof.

It will be appreciated that compounds of formula (I) may be in any racemic, enantiomeric or diastereoisomeric isomeric form. Salts include addition salts with inorganic and organic acids or bases. Esters are as described below. Salts and esters can be pharmaceutically acceptable.

In one aspect, the invention provides compounds wherein $R_1$ and $R'_1$, are the same or different, and each represents a monocyclic aryl group, a monocyclic heteroaryl group, or $R_1$ and $R'_1$, together with the carbon atom to which they are linked, form a fused ring structure of formula:

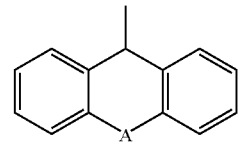

in which A is as defined, wherein each of $R_1$ and $R'_1$, or said fused ring structure formed thereby, is optionally substituted by at least one substituent selected from the group c as defined above.

In one aspect, $R_1$ and $R'_1$, each represent a phenyl, pyridinyl, or thienyl radical, or $R_1$ and $R'_1$ represents a fused ring structure as defined, wherein each of $R_1$ and $R'_1$, or said fused ring structure formed thereby, is optionally substituted as defined. In another aspect, each of $R_1$ and $R'_1$, or said fused ring structure formed thereby, is optionally substituted by at least one substituent selected from the group c': fluorine and chlorine atoms, hydroxyl, linear and branched alkyl, alkylthio, hydroxyalkyl, and fluoroalkyl groups; linear and branched alkoxyl groups; trifluoromethyl; trifluoromethoxyl; —CN; alkylcarbonyl groups; alkylsulphonyl groups, and any alkyl component has from 1 to 4 carbon atoms, and wherein, when there is more than one substituent, then each said substituent is the same or different.

In one aspect, each of $R_1$ and $R'_1$, or said fused ring structure formed thereby, is optionally substituted by at least one substituent selected from the group consisting of: fluorine and chlorine atoms, hydroxy groups, linear or branched alkoxy groups containing from 1 to 5 carbon atoms, linear or branched alkyl groups containing from 1 to 5 carbon atoms, trifluoromethyl and trifluoromethoxy groups, and —CN groups, and wherein, when there is more than one substituent, then each said substituent is the same or different.

$R_2$ and $R'_2$, which may be the same or different, each may represent a methyl or ethyl group, or, together with the nitrogen atom to which they are linked, form a morpholinyl, thiomorpholinyl, piperidinyl, piperazinyl, or homopiperazinyl group optionally substituted at least one substituent selected from the group consisting of: chlorine atoms, hydroxyl groups, trifluoromethyl groups, hydroxyl groups, alkoxy groups, hydroxyalkyl groups, and alkyl groups.

In one aspect, $R_2$ and $R'_2$, together with the nitrogen atom to which they are linked, form a morpholinyl group optionally substituted by at least one substituent selected from the group consisting of: trifluoromethyl groups and alkyl groups. Any such optional substituent can be at least one methyl group.

In another aspect, $R_2$ and $R'_2$, together with the nitrogen atom to which they are linked, form a morpholinyl group or thiomorpholinyl group.

In one aspect, Ar is an aryl or heteroaryl group selected from the group consisting of: phenyl, naphthyl, monocyclic heteroaryls, and bicyclic heteroaryls. Ar can be selected from the group consisting of: phenyl, naphthyl, thienyl, thiazolyl, isothiazolyl, furanyl, oxazolyl, isoxazolyl, imidazolyl, triazolyl, indolyl, pyrrolyl, pyridinyl, pyrazinyl, pyrimidinyl, and pyridazinyl groups. In one aspect, Ar is a phenyl group.

The invention provides compounds wherein each R is selected from hydrogen and substituents a': fluorine atoms; chlorine atoms; hydroxyl groups; carboxyl groups; aldehyde groups; linear and branched alkyl, hydroxyalkyl, and fluoroalkyl groups; linear and branched alkoxyl groups; linear and branched thioalkyl groups; alkoxycarbonyl groups; benzylcarbonyl groups; hydroxycarbonylalkyl groups; alkoxycarbonylalkyl groups; trifluoromethyl groups; trifluoromethoxy groups; —CN groups; amino, alkylamino, dialkylamino, acylamino, and diacylamino groups; alkoxycarbonylamino, alkylcarbonylamino groups; alkylaminocarbonyloxy groups; alkyl groups substituted with an amino, alkylamino, dialkylamino, acylamino, or diacylamino group; $CONH_2$; alkylamido groups; alkylthio; alkylsulphoxide; sulphonyl, and alkylsulphonyl groups; sulphonamide, alkylsulphonamide, and di(alkylsulphonyl)amino groups; trifluoromethylsulphoxide; trifluoromethylsulphonyl groups; trifluoromethylsulphonamide, and di(trifluoromethylsulphonyl)amino groups; alkylcarbonylalkyl; and saturated monocyclic heterocyclyl groups, said heterocyclyl groups being optionally substituted by one or more substituents, which may be the same or different, selected from the group b as defined above.

In one aspect, each R is selected from hydrogen and substituents a": chlorine atoms; hydroxyl groups; carboxyl groups; linear and branched alkyl, hydroxyalkyl; linear and branched alkoxyl groups; alkoxycarbonyl groups; hydroxycarbonylalkyl groups; alkoxycarbonylalkyl groups; trifluoromethyl groups; trifluoromethoxy groups; —CN groups; amino, alkylamino, and dialkylamino groups; alkoxycarbonylamino, alkylcarbonylamino groups; alkylaminocarbonyloxy groups; alkyl groups substituted with an amino, alkylamino, or dialkylamino group; $CONH_2$; alkylcarbonylalkyl; alkylthio; sulphonyl and alkylsulphonyl groups; sulphonamide, alkylsulphonamide, and di(alkylsulphonyl)amino groups; trifluoromethylsulphoxide; trifluoromethylsulphonyl groups; trifluoromethylsulphonamide, and di(trifluoromethylsulphonyl)amino groups; pyrrolidinyl, piperidinyl piperazinyl, morpholinyl, and thiomorpholinyl groups optionally substituted by one or more substituents, which may be the same or different, selected from the group b as defined above.

In one aspect, any pyrrolidinyl, piperidinyl piperazinyl, morpholinyl, and thiomorpholinyl groups of substituents b are selected from substituents b' consisting of: chlorine atoms; hydroxyl groups; linear and branched alkyl, hydroxyalkyl, and alkoxyl groups; trifluoromethyl groups; trifluoromethoxy groups; —CN groups; amino, alkylamino, and dialkylamino groups; sulphonyl, alkylsulphonyl groups; and sulphonamide, alkylsulphonamide, and di(alkylsulphonyl) amino groups. In another aspect, any such pyrrolidinyl, piperidinyl piperazinyl, morpholinyl, and thiomorpholinyl groups are unsubstituted.

In one aspect, any alkyl, alkenyl or alkynyl component can have no more than 4 carbon atoms.

Any alkylsulphonyl substituent can be a trifluoromethyl or methylsulphonyl substituent, and, in one aspect, a methylsulphonyl substituent, such as a methylsulphonylamino, or methylsulphonamide substituent.

In the compounds of the present invention, Y may be oxygen or sulphur. In one aspect, Y is oxygen, such the compounds of the invention are urea derivatives.

The substituents $R_1$ and $R'_1$, can be the same or different. In one aspect, they can be monocyclic and 5- or 6-membered.

In the compounds of the present invention, where a sulphur atom is present, other than when present as part of a >C=S group, then it may be present in the sulphoxide (SO) or sulphone ($SO_2$) forms, where desired.

In general, carboxyl groups are in the form —COOH, and branched alkyl may take the form of singly or multiply branched alkyl, such as t-butyl or 4-methylpentyl, for example. Alkyl groups can contain from 1 to 6 carbons, and, in one aspect, from 1 to 4 carbon atoms. Methyl and ethyl can be used as substituents. Similar considerations apply to hydroxyalkyl, haloalkyl, alkylthio, alkenyl, and alkynyl groups. Hydroxyalkyl may be substituted by one or more hydroxyl groups. Thioalkyl groups typically take the form HS-Alk-, where Alk indicates an alkyl group. Hydroxycarbonylalkyl typically take the form HOOC-Alk-. Alkylcarbonyl groups take the form Alk-CO—, while alkoxycarbonylalkyl groups take the form AlkOCOAlk-. Alkoxycarbonyl groups take the form AlkOCO—. Alkylthio groups take the form Alk-S— and are optionally in the sulphoxide (Alk-SO—) or sulphone (Alk-$SO_2$—) forms. Any alkyl component can have from 1 to 6 carbon atoms, so that alkoxycarbonylalkyl may be hexyl-5-pentanoate or methylmethanoate for example. Alkenyl and alkynyl components have from 2 to 6 carbon atoms, and take the form of an alkyl group possessing at least one double or triple bond between adjacent carbons. In one aspect, there is only one such unsaturated bond per alkenyl or alkynyl substituent.

Where multiple substituents are selected from a common group, such as substituents a, b or c, then each substituent is the same or different.

$R_2$ and $R'_2$, when representing alkyl, can be methyl or ethyl, and, in one aspect can be unsubstituted or substituted with one or more fluorine atoms. Similar considerations apply when $R_2$ and $R'_2$ represent alkylamino or dialkylamino groups.

When $R_2$ and $R'_2$ form a heterocycle, in one aspect, it can be saturated and contain 5 or 6 ring atoms, said heterocycle being optionally substituted by at least one substituent selected from the group c as defined.

When $R_2$ and $R'_2$ represent an unsaturated heterocycle, the additional heteroatoms, if any, may typically be selected from oxygen, sulphur and nitrogen. Exemplary unsaturated heterocycles include, imidazole, pyrazole, indazole, benzimidazole, purine, azabenzimidazole, triazole, pyrrole, indole, isoindazole, and azaindole.

More generally, when $R_2$ and $R'_2$, together with the nitrogen atom to which they are linked, form a heterocycle, then the heterocycle can be saturated. Some saturated heterocycles are morpholinyl, thiomorpholinyl, piperazinyl, homopiperazinyl, and piperidinyl groups, for example, morpholinyl and thiomorpholinyl, and particularly morpholinyl.

There is no particular restriction on the nature of the aryl or heteroaryl group represented by Ar. In one aspect, this group can be monocyclic or bicyclic containing 5, 6, 9 or 10 ring atoms.

In $R_n$, n is equal to the number of ring atoms on the aryl or heteroaryl group that are available for substitution, which will exclude the linking atom. Thus, n is equal to 5 for phenyl. In one aspect, at least two groups R represent H or Cl.

In $R_3$, $(CH_2)_p$ can be a straight bond or is methyl or methyl substituted with another methyl.

The moiety $C(=X)$ may be present in R as part of acyl, ester, or amide group, for example. X may be sulphur or oxygen. In one aspect, where there is more than one moiety $C(=X)$, then each occurrence can be carbonyl.

When a group R comprises Alk, in one aspect, Alk can be methylene or ethylene.

When a group R comprises the moiety $NR_4R_5$, in one aspect, each of $R_4$ and $R_5$ can be separately selected from hydrogen, methyl, ethyl, hydroxymethyl and hydroxyethyl.

When a group R comprises the moiety —NZC(=X), then in one aspect Z can be H. Where there is more than one occurrence, in one aspect, every occurrence is H.

When a group R comprises the group $R_6$, then $R_6$ can be hydrogen, hydroxy, alkyl, or trifluoromethyl.

When a group R represents a group —NZC(=X)(NH)$_q$ $R_6$, -Alk-NZC(=X)(NH)$_q R_6$, —C(=X)(NH)$_q R_6$, or -Alk-C (=X)(NH)$_q R_6$, then q can be 0 or 1. When q is 1, then in one aspect, meanings for (NH)$_q R_6$ can be amino, methylamino and dimethylamino, for example, amino.

When a group R represents a group —NZC(=X)(NH)$_q$ $R_6$, -Alk-NZC(=X)(NH)$_q R_6$, —C(=X)(NH)$_q R_6$, or -Alk-C (=X)(NH)$_q R_6$, then in one aspect —C(=X)(NH)$_q R_6$ can be a carboxylic ester moiety, where q is 0 and $R_6$ can represent an alkoxy, akenyloxy, alkynyloxy, aryloxy or aralkyloxy group, and can be optionally further substituted by one or more substituents selected from trifluoromethyl, halogen atoms and hydroxyl groups, for example, chlorine, fluorine, hydroxy, and/or phenyl.

When at least one R represents a group —NHSO$_2R_7$, —SO$_2R_7$, —SOR$_7$, or —SR$_7$, then $R_7$ can be OH, amino, alkyl, hydroxyalkyl, or trifluoromethyl.

In one aspect, no more than two substituents R are selected from said substituents a.

In the group a, and elsewhere, hydroxyalkenyl and hydroxyalkynyl groups are as defined above for alkenyl and alkynyl, and have one or more hydroxyl groups present. Similarly, haloalkyl, haloalkenyl, and haloalkynyl groups have one or more halogen atoms present thereon, for example, selected from iodine, bromine, chlorine and fluorine. Perhalo substituents can be perfluoro substituents, such as trifluoromethyl. Where an alkyl group is specified herein, then this may include haloalkyl, particularly fluoroalkyl, and trifluoromethyl groups. In one aspect, it can be unsubstituted alkyl. In one aspect, haloalkyl group can be trifluoromethyl. Linear and branched alkoxyl groups and linear and branched thioalkyl groups are as defined above for linear and branched alkyl groups. Aralkoxy groups take the form Ar-AlkO—, while aryloxy groups take the form ArO—, where Ar is an aryl or heteroaryl group. It will be understood that similar considerations apply to aralkoxycarbonyl and aryloxycarbonyl, and other groups specifying aralkoxy and aryloxy.

Acyl groups are those consisting of a carboxylic acid residue linked via the —CO— moiety. Alkyl-, aralkyl-, and arylamido groups have the appropriate groups linked via the nitrogen, such as Alk-CONH—. Amido takes the form of —CONH—, so that alkylamido takes the form alkyl-CONH—, for example, while aralkylamido takes the form aryl-alkyl-CONH—.

Sulphonamide, alkylsulphonamide, di(alkylsulphonyl) amino, aralkylsulphonamide, di(aralkylsulphonyl)amino, arylsulphonamide, and di(arylsulphonyl)amino are of the form sulphonyl or disulphonyl substituted on nitrogen, such as Alk-SO$_2$—NH—.

Alkoxycarbonylamino groups take the form Alk-O—CONH—, and aralkoxycarbonylamino, aryloxycarbonylamino, alkylcarbonylamino, aralkylcarbonylamino, and arylcarbonylamino groups should be construed accordingly. Alkylaminocarbonyloxy groups take the form Alk-NH-COO—, and aralkylaminocarbonyloxy and arylaminocarbonyloxy groups should be construed accordingly.

The invention further provides pharmaceutical compositions comprising compounds of formula (I), their salts and esters, and a pharmaceutically acceptable diluent or carrier. A method for the treatment of cancers, in particular of the parathyroid and the digestive tract, comprising the administration of an effective amount of a compound of claim 1 to a patient in need thereof.

In one aspect, the invention provides methods for the treatment of neurodegenerative diseases, comprising the administration of an effective amount of a compound of formula (I) to a patient in need thereof. In another aspect, the invention provides methods for the treatment of bone and articular metabolism diseases, in particular osteoporosis, osteopaenia and Paget's disease, rheumatoid arthritis and osteoarthritis, comprising the administration of an effective amount of a compound of formula (I) to a patient in need thereof. In one aspect, methods of the invention include methods for the treatment of abnormal calcium homeostasis or methods for the treatment of hyperplasia and parathyroid adenoma. In another aspect, the methods of the invention includes methods for the treatment of intestinal malabsorption, or biliary lithiasis and renal lithiasis. The invention further provides methods for the treatment of hyperparathyroidism, comprising the administration of an effective amount of a compound of claim 1 to a patient in need thereof. In one aspect, hyperparathyroidism is observed in the event of renal insufficiency. In another aspect, the invention provides methods for the reduction of ionised serum calcium level during the treatment of hypercalcaemia, comprising the administration of an effective amount of a compound of formula (I) to a patient in need thereof. The invention further provides methods for the treatment of cardiovascular diseases, for example, hypertension. In one aspect, methods of the invention include methods for the treatment of vascular calcification. In another aspect, the invention provides methods for the treatment of diarrhea, comprising the administration of an effective amount of a compound of formula (I) to a patient in need thereof.

DETAILED DESCRIPTION OF THE INVENTION

One group of compounds of formula (I) is defined as follows:

$R_1$ and $R'_1$, which may be the same or different, represent an aryl radical, a heteroaryl radical, an aryl or heteroaryl radical substituted by one or more halogen atoms, by one or more hydroxy groups, by one or more linear or branched alkyl, fluoroalkyl or alkoxy radicals containing from 1 to 6 carbon atoms, by one or more trifluoromethyl, trifluoromethoxy, —CN, —NO$_2$, acetyl, carboxyl, carboalkoxy, thioalkyl groups and the oxidised sulfoxide and sulfone forms thereof, or $R_1$ and $R'_1$, form, with the carbon atom to which they are linked, a cycle of formula:

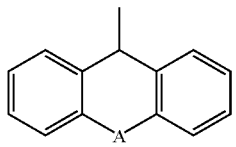

in which A represents a single bond, a —$CH_2$-group, an oxygen, sulfur or nitrogen atom optionally substituted by an alkyl or an acetyl, $R_2$ and $R'_2$ form, with the nitrogen atom to which they are linked, a saturated heterocycle containing 4 or 5 carbon atoms which may optionally be substituted by one or more linear or branched alkyl radicals containing from 1 to 6 carbon atoms, said heterocycle optionally containing a further heteroatom, which may itself optionally be substituted by an $R_5$ radical, in which $R_5$ represents a hydrogen atom, a linear or branched alkyl radical containing from 1 to 6 carbon atoms, a carboalkoxy radical, or $R_2$ and $R'_2$, which may be the same or different, represent a hydrogen atom, a linear or branched alkyl radical containing from 1 to 6 carbon atoms optionally substituted by a hydroxy or alkoxy radical containing from 1 to 6 carbon atoms, $R_3$ represents an aryl radical, a heteroaryl, a substituted aryl radical or a heteroaryl substituted by one or more groups selected from a halogen atom, a hydroxy radical, an alkyl, fluoroalkyl, hydroxyalkyl or alkoxyalkyl radical, which may be linear or branched, containing from 1 to 6 carbon atoms, a linear or branched alkoxy group containing from 1 to 6 carbon atoms, a —CO—OR or —CO—NHR radical in which R represents a hydrogen atom or an alkyl, benzyl or aralkyl radical, optionally substituted by one or more fluorine atoms or hydroxy groups, or $R_3$ represents an aryl radical or a heteroaryl substituted by:
  an aldehyde radical, a linear or branched —CHOH-alkyl or —CO-alkyl radical, containing from 1 to 6 carbon atoms, a trifluoromethyl or trifluoromethoxy radical, a —CN group, a thioalkyl radical and the oxidised, sulfoxide or sulfone forms thereof, linear or branched, containing from 1 to 6 carbon atoms, an —$SO_2$—$(CH_2)_n$—OH group in which n represents an integer of 1, 2 or 3, an —$SO_p$—$CF_3$ group, in which p represents an integer of 0, 1 or 2, or
  an amino, alkylamino, dialkylamino, —NH—CO-alkyl, —NHCOObenzyl, —$NHSO_2$alkyl, —$NHSO_2CF_3$ group, an amido, alkylamido, dialkylamido or hydroxyalkylamido group, a thioamido group or
  a phenyl group, optionally substituted by one or more halogen, alkyl, hydroxy, alkoxy, carboxy, carboalkoxy or amino groups and the NHCOalkyl, $NHSO_2$alkyl and NHCOOalkyl, NHCOObenzyl forms thereof,
  a heteroaryl group optionally substituted by one or more halogen, alkyl, hydroxy or alkoxy groups containing from 1 to 6 carbon atoms, amino groups and the NHCOalkyl, $NHSO_2$alkyl and NHCOOalkyl, carboxy or carboalkoxy forms thereof, said linear or branched alkyls or alkoxy containing from 1 to 6 carbon atoms, or $R_3$ represents a heteroaryl, excluding the thiazolyl, oxazolyl, benzothiazolyl or benzoxazolyl groups, which may optionally be substituted, or $R_3$ represents a —$CH_2$-aryl, —$CH_2$-heteroaryl, —CH($CH_3$)-aryl or —CH($CH_3$)-heteroaryl radical, aryls or heteroaryls being optionally substituted, said products of formula (I) being in all possible racemic, enantiomeric and diastereoisomeric isomeric forms, as well as the addition salts with inorganic and organic acids or with inorganic and organic bases of said products of formula (I).

Exemplary meanings of the terms used in this group and elsewhere herein are as follows:

the term aryl group designates unsaturated, monocyclic radicals or radicals consisting of condensed carbocyclic rings. Examples of an aryl radical include the phenyl, naphth-1-yl and naphth-2-yl, indane, indene or tetrahydronaphthyl or oxotetrahydronaphthyl radicals, the term substituted aryl denotes that the aryl group is substituted by one or more groups of the halogen, alkyl, fluoroalkyl, hydroxy, alkoxy, fluoroalkoxy, carboxy, carboalkoxy, nitrile, nitro or thioalkyl type and the oxidised sulfoxide and sulfone forms thereof, $SCF_3$ and other thiofluoroalkyl groups and the oxidised forms thereof, amino groups and the NHCO-alkyl, $NHSO_2$-alkyl, NHCOO-alkyl, NHCOObenzyl derivatives thereof, by a substituted or unsubstituted aryl, by a substituted or unsubstituted heteroaryl, or by a heterocycle, the term heterocycle designates, for example, morpholinyl, thiomorpholinyl, piperazinyl, N-alkylpiperazinyl, piperidinyl, pyrrolidinyl, imidazolidinyl, 2,6-dimethyl morpholinyl, quinuclidinyl, homopiperazinyl radicals, the term halogen atom designates the chlorine, fluorine, bromine or iodine atom, or for example, the fluorine or chlorine atom, the term linear or branched alkyl radical containing from 1 to 6 carbon atoms designates, for example, the methyl, ethyl, propyl, isopropyl, butyl, isobutyl, secbutyl, tertbutyl, pentyl and isopentyl radicals as well as the linear or branched positional isomers thereof, the term fluoroalkyl designates a linear or branched alkyl in which one or more or all the hydrogen atoms are replaced by one or more fluorine atoms, the term linear or branched alkoxy radical containing from 1 to 6 carbon atoms designates, for example, the methoxy, ethoxy, propoxy, isopropoxy and butoxy radicals, linear, secondary or tertiary or pentoxy, as well as the linear or branched positional isomers thereof, the term linear or branched thioalkyl radical containing from 1 to 6 carbon atoms designates radicals such as, in particular, thiomethyl, thioethyl, thiopropyl, thioisopropyl, thiobutyl, thioisobutyl, thiosec-butyl and thiotertbutyl radicals, as well as the linear or branched positional isomers thereof, the term heteroaryl designates for example a 2-pyridinyl, 3-pyridinyl, 4-pyridinyl, pyrrolyl, furanyl, 1,2,3-triazolyl, 1,2,4-triazolyl, tetrazolyl, imidazolyl, oxazolyl, thiazolyl, benzothiazolyl, pyrazolyl, isoxazolyl, pyridinazyl, pyridazinyl, pyrimidinyl, pyrazinyl, 1,2,4-triazinyl, 1,3,5-triazinyl, benzofuranyl, benzimidazolyl, indazolyl, tetraquinolinyl, quinolinyl, tetrahydroisoquinolinyl, isoquinolinyl, indolyl, carbazolyl, indolinyl, alpha- or beta-carbolinyl, thienyl, benzothienyl, benzoxazolyl, oxadiazole, 2,3 dihydroindolyl, isoindolyl, purinyl, naphthyridinyl, quinoxalinyl, carbazolyl, benzodioxinyl, 2,3 dihydrobenzodioxinyl, oxodihydro isobenzofuran or isobenzofuran radical, the term substituted heteroaryl means that the heteroaryl group is substituted by one or more groups of the halogen, alkyl, fluoroalkyl, alkoxy, fluoroalkoxy, carboxy, carboalkoxy, nitrile, nitro or thioalkyl type and the oxidised sulfoxide and sulfone forms thereof, amino groups and the NHCO-alkyl, NHCO-fluoroalkyl, NHSO$_2$-alkyl, NHSO$_2$-fluoroalkyl, NHCOO-alkyl, NHCOO-benzyl, heterocycle, substituted or unsubstituted aryl or substituted or unsubstituted heteroaryl derivatives thereof.

Within this group, the invention provides compounds of formula (I) in which $R_1$, $R'_1$, $R_2$ and $R'_2$ have the meaning given above and $R_3$ represents a phenyl radical, a heteroaryl radical, a substituted phenyl radical, a heteroaryl radical substituted by one or more groups selected from a halogen atom, a hydroxy radical, a linear or branched alkyl, fluoroalkyl, hydroxyalkyl or alkoxyalkyl radical containing from 1 to 6 carbon atoms, a linear or branched alkoxy or alkoxycarbonyl group containing from 1 to 6 carbon atoms, a —CO—OR or —CO—NHR radical in which R represents a hydrogen atom or an alkylbenzyl or aralkyl radical optionally substituted by one or more fluorine atoms or hydroxy groups, or $R_3$ represents an aryl or heteroaryl radical substituted by:
- an aldehyde radical, a linear or branched —CHOH-alkyl or —CO-alkyl radical, containing from 1 to 6 carbon atoms, a trifluoromethyl or trifluoromethoxy radical, a —CN group, a thioalkyl radical and the oxidised, sulfoxide or sulfone forms thereof, linear or branched, containing from 1 to 6 carbon atoms, an —SO$_2$—(CH$_2$)n-OH group in which n represents an integer of 1, 2 or 3, an —SO$_p$—CF$_3$ group, in which p represents an integer of 0, 1 or 2,
- an amino, alkylamino, dialkylamino, —NH—CO-alkyl, —NHCOObenzyl, —NHSO$_2$alkyl or —NHSO$_2$CF$_3$ group, an amido, alkylamido, dialkylamido or hydroxyalkylamido group, a thioamido group,
- a phenyl group optionally substituted by a halogen, alkyl, hydroxy, alkoxy, carboxy, carboalkoxy or amino group and the NHCOalkyl, NHSO$_2$alkyl, NHCOOalkyl and NHCOObenzyl forms thereof,
- a heteroaryl group optionally substituted by a halogen, alkyl, hydroxy or alkoxy group containing from 1 to 6 carbon atoms, an amino group and the NH—COalkyl, NHSO$_2$alkyl and NHCOOalkyl forms thereof, carboxy or carboalkoxy groups, said linear or branched alkyls or alkoxy containing from 1 to 6 carbon atoms, or $R_3$ represents a heteroaryl, excluding the thiazolyl, oxazolyl, benzothiazolyl or benzoxazolyl groups, which may optionally be substituted, or $R_3$ represents a benzyl, chlorobenzyl, methylthienyl or ethyl-1-naphthyl radical, and more particularly the products of formula (I), in which $R_1$, $R'_1$, $R_2$ and $R'_2$ have the meaning given above and $R_3$ represents a phenyl radical, a phenyl radical substituted by one or more groups selected from a halogen atom, a hydroxy radical, an alkyl, fluoroalkyl, hydroxyalkyl or alkoxyalkyl radical, linear or branched, containing from 1 to 6 carbon atoms, a linear or branched alkoxy or alkoxycarbonyl group containing from 1 to 6 carbon atoms, a —CO—OR or —CO—NHR radical in which R represents a hydrogen atom or an alkyl, benzyl or aralkyl radical optionally substituted by one or more fluorine atoms or hydroxy groups, or $R_3$ represents a phenyl radical substituted by:
- an aldehyde radical, a linear or branched —CHOH-alkyl or —CO-alkyl radical, containing from 1 to 6 carbon atoms, a trifluoromethyl, trifluoromethoxy radical, a —CN group, a thioalkyl radical and the oxidised, sulfoxide or sulfone forms thereof, linear or branched, containing from 1 to 6 carbon atoms, an —SO$_2$—(CH$_2$)n-OH group in which n represents an integer of 1, 2 or 3, an —SO$_p$—CF$_3$ group, in which p represents an integer of 0, 1 or 2,
- an amino, alkylamino, dialkylamino, —NH—CO-alkyl, —NHCOObenzyl, —NHSO$_2$alkyl, —NHSO$_2$CF$_3$ group, an amido, alkylamido, dialkylamido or hydroxyalkylamido group, a thioamido group,
- a phenyl group optionally substituted by a halogen, alkyl, hydroxy, alkoxy, carboxy, carboalkoxy or amino group and the NHCOalkyl, NHSO$_2$alkyl and NHCOOalkyl, NHCOObenzyl forms thereof,
- a heteroaryl group optionally substituted by a halogen, alkyl, hydroxy or alkoxy group containing from 1 to 6 carbon atoms, an amino group and the NHCOalkyl, NHSO$_2$alkyl and NHCOOalkyl, carboxy or carboalkoxy forms thereof, said linear or branched alkyls or alkoxy containing from 1 to 6 carbon atoms, or $R_3$ represents a benzyl, chlorobenzyl, methylthienyl or ethyl-1-naphthyl radical, or $R_3$ represents a benzodioxolyl, dihydrobenzodioxinyl, 3-oxo-1,3-dihydroisobenzofuraryl, 8-oxotetrahydronaphthalenyl, 2,3-dihydroindolyl, indazolyl, carbazolyl, isoquinolyl, quinolinyl, thiophenyl, pyridinyl, benzimidazolyl, pyrazolyl, pyrimidinyl, isoxazolyl or isothiazolyl radical, optionally substituted by one or more chlorine or fluorine atoms, a linear or branched alkyl, fluoroalkyl, alkoxy or carboalkoxy group containing from 1 to 3 carbon atoms or substituted by an optionally substituted phenyl or thiazolyl group. As with all other definitions, unless otherwise indicated or apparent from the context, said compounds of formula (I) may be in all possible racemic, enantiomeric and diastereoisomeric isomeric forms, as well as the addition salts with inorganic and organic acids or with inorganic and organic bases of said products of formula (I).

The invention further provides:
the compounds of formula (I), as defined above, in which $R_1$ and $R'_1$, represent a phenyl radical, a pyridinyl radical, a thienyl radical, a substituted phenyl, substituted pyridinyl or substituted thienyl radical, substituted by one or more fluorine or chlorine atoms, by one or more hydroxy groups, by one or more alkoxy groups, linear or branched, containing from 1 to 6 carbon atoms, by one or more linear or branched alkyl groups containing from 1 to 6 carbon atoms, by one or more trifluoromethyl or trifluoromethoxy groups, by a —CN group.

In one aspect, the invention provides compounds of formula (I) as defined in above, in which $R_1$ and $R'_1$ represent a phenyl radical and the compounds of formula (I) as defined above, in which $R_2$ and $R'_2$ form, with the nitrogen atom to which they are linked, a morpholinyl, dimethylmorpholinyl, piperidinyl, thiomorpholinyl or N-alkyl piperazinyl radical or $R_2$ and $R'_2$ represent a methyl or ethyl radical.

In one aspect, the invention provides compounds formula (I), as defined above, in which:
$R_3$ represents a phenyl radical, a phenyl radical substituted by one or more groups selected from a fluorine, chlorine, bromine or iodine atom, a hydroxy radical, a methyl, ethyl, propyl, isopropyl, butyl, isobutyl, hydroxymethyl, hydroxyethyl, methoxymethyl, methoxyethyl, methoxy, ethoxy, propoxy, methoxycarbonyl, ethoxycarbonyl, propoxycarbonyl, isopropoxycarbonyl, butoxycarbonyl, isobutoxycarbonyl, tertbutoxycarbonyl or pentafluoropentoxycarbonyl radical, a piperidinylmethyl group, an aldehyde radical, —CH$_2$OH, —CHOH—CH$_3$, —CO-alkyl radical, linear or branched, containing from 1 to 6 carbon atoms, a trifluoromethyl or trifluoromethoxy radical, a —CN group, a thiomethyl, thioethyl or thioisopropyl radical and the oxidised, sulfoxide and sulfone forms thereof, an —S(O)$_2$—(CH$_2$)n-OH group, in which n represents an integer of 1, 2 or 3, an —S(O)$_2$—CF$_3$ group, an —S—CF$_3$ group, an amino, methylamino, ethylamino, dimethylamino, diethylamino, —NH—CO-methyl, —NH—CO-ethyl, —NHSO$_2$-methyl, —NHSO$_2$-ethyl, —NHCOOmethyl, —NHCOOethyl, —NHCOObenzyl group, an amido, methylamido, dimethylamido or hydroxymethylamido or hydroxyethylamido group, a thioamide —CS—NH$_2$ group, or R$_3$ represents a phenyl radical substituted by a phenyl group, a pyridinyl, morpholinyl, furanyl, thiophenyl, oxazolyl, isoxazolyl, benzoxazolyl, benzimidazolyl, benzothiazolyl, tetrazolyl or pyrazolyl group, said groups optionally being substituted by one or more chlorine or fluorine atoms, an alkyl, fluoroalkyl, alkoxy or carboalkoxy group, linear or branched, containing from 1 to 3 carbon atoms, or R$_3$ represents a benzyl, chlorobenzyl, methylthienyl, ethyl-1-naphthyl radical, or R$_3$ represents a benzodioxolyl, dihydrobenzodioxinyl, 3-oxo-1,3-dihydroisobenzofuraryl, 8-oxotetrahydronaphthalenyl, 2,3-dihydroindolyl, indazolyl, carbazolyl, isoquinolyl, quinolinyl, thiophenyl, pyridinyl, benzimidazolyl, pyrazolyl, pyrimidinyl, isoxazolyl or isothiazolyl radical, optionally substituted by one or more chlorine or fluorine atoms, an alkyl, fluoroalkyl, alkoxy, acetyl or carboalkoxy group linear or branched containing from 1 to 3 carbon atoms or by a phenyl group.

In one aspect, the invention provides compounds of formula (I), in which R$_1$ and R'$_1$ represent a phenyl group, R$_2$ and R'$_2$ form, with the nitrogen atom to which they are linked, a morpholinyl radical and R$_3$ represents a phenyl group optionally substituted by one or more chlorine or fluorine atoms, by one or more radicals from a —CO—OR radical, in which R represents a hydrogen atom, an alkyl radical, a —CO-alkyl radical, said alkyl radicals, linear or branched, containing from 1 to 6 carbon atoms, a trifluoromethyl or trifluoromethoxy radical, a thioalkyl or alkylsulfone radical, an oxazolyl or methyltetrazolyl, furanyl or thienyl group.

Addition salts with inorganic or organic acids of the products of formula (I) can optionally be salts formed between a molecule of formula (I) and one, two or three acid molecules. These salts may be, for example, salts formed with hydrochloric, hydrobromic, hydroiodic, nitric, sulphuric, phosphoric, propionic, acetic, trifluoroacetic, formic, benzoic, maleic, fumaric, succinic, tartaric, citric, oxalic, glyoxylic, aspartic or ascorbic acids, alkylmonosulphonic acids such as, for example, methanesulphonic acid, ethanesulphonic acid, propanesulphonic acid, alkyldisulphonic acids such as, for example, methanedisulphonic acid, alpha-, beta-ethane disulphonic acid, arylmonosulphonic acids such as benzenesulphonic acid and aryl disulphonic acids.

Stereoisomerism can be defined broadly as isomerism of compounds having the same general formulae, but of which the different groups are disposed differently in space such as, in particular, in monosubstituted cyclohexanes of which the substituent can be in the axial or equatorial position, and the various possible rotational configurations of ethane derivatives. However, there is another type of stereoisomerism due to the different spatial arrangements of substituents fixed either on double bonds or on rings, which is often called geometric isomerism or cis-trans isomerism. The term stereoisomers is used in its broadest sense in the present application and therefore relates to all of the above-mentioned compounds.

In one aspect, the invention provides compounds of the invention, as are medicaments containing them:

3-[3-(3,3-diphenylpropyl)-3-(2-morpholin-4-ylethyl)ureido]benzoic acid methyl ester;
3-(4-chlorophenyl)-1-(3,3-diphenylpropyl)-1-(2-morpholin-4-ylethyl)urea;
3-(3-chlorophenyl)-1-(3,3-diphenylpropyl)-1-(2-morpholin-4-ylethyl)urea;
3-(2-chlorophenyl)-1-(3,3-diphenylpropyl)-1-(2-morpholin-4-ylethyl)urea;
1-(3,3-diphenylpropyl)-3-(3-fluoro-5-trifluoromethylphenyl)-1-(2-morpholin-4-yl)urea;
3-(3,4-dichlorophenyl)-1-(3,3-diphenylpropyl)-1-(2-morpholin-4-ylethyl)urea;
3-(3,4-dimethoxyphenyl)-1-(3,3-diphenylpropyl)-1-(2-morpholin-4-ylethyl)urea;
1-(3,3-diphenylpropyl)-3-(3-methoxyphenyl)-1-(2-morpholin-4-ylethyl)urea;
4-[3-(3,3-diphenylpropyl)-3-(2-morpholin-4-ylethyl)ureido]benzoic acid ethyl ester;
1-(3,3-diphenylpropyl)-1-(2-morpholin-4-ylethyl)-3-(4-trifluoromethoxyphenyl)urea;
3-(3-bromophenyl)-1-(3,3-diphenylpropyl)-1-(2-morpholin-4-ylethyl)urea;
1-(3,3-diphenylpropyl)-1-(2-morpholin-4-ylethyl)-3-(3-trifluoromethylphenyl)urea;
3-(3,5-bis-trifluoromethylphenyl)-1-(3,3-diphenylpropyl)-1-(2-morpholin-4-ylethyl)urea;
3-(4-bromo-6-trifluoromethyl-phenyl)-1-(3,3-diphenylpropyl)-1-(2-morpholin-4-ylethyl)urea;
3-(4-bromophenyl)-1-(3,3-diphenylpropyl)-1-(2-morpholin-4-ylethyl)urea;
4-methoxy-5-[3-(3,3-diphenylpropyl)-3-(2-morpholin-4-ylethyl)ureido]benzoic acid methyl ester;
4-chloro-5-[3-(3,3-diphenylpropyl)-3-(2-morpholin-4-ylethyl)ureido]benzoic acid methyl ester;
2-chloro-5-[3-(3,3-diphenylpropyl)-3-(2-morpholin-4-ylethyl)ureido]benzoic acid methyl ester;
3-(3-cyanophenyl)-1-(3,3-diphenylpropyl)-1-(2-morpholin-4-ylethyl)urea;
3-(4-cyanophenyl)-1-(3,3-diphenylpropyl)-1-(2-morpholin-4-ylethyl)urea;
3-[3-(3,3-diphenylpropyl)-3-(2-morpholin-4-ylethyl)ureido]benzoic acid tertbutyl ester;
3-(2-cyanophenyl)-1-(3,3-diphenylpropyl)-1-(2-morpholin-4-ylethyl)urea;
3-(3-acetylphenyl)-1-(3,3-diphenylpropyl)-1-(2-morpholin-4-ylethyl)urea;
1-(3,3-diphenylpropyl)-3-(3-methylsulphanylphenyl)-1-(2-morpholin-4-ylethyl)urea;
1-(3,3-diphenylpropyl)-1-(2-morpholin-4-ylethyl)-3-(3-trifluoromethoxyphenyl)urea;
1-(3,3-diphenylpropyl)-1-(2-morpholin-4-ylethyl)-3-(3-ethylsulphonyl-6-methoxyphenyl)urea;
1-(3,3-diphenylpropyl)-3-[3-(2-hydroxyethanesulfonyl)phenyl]-1-(2-morpholin-4-yl-ethyl)urea;
3-[3-(3,3-diphenylpropyl)-3-(2-morpholin-4-ylethyl)ureido]-2-methylbenzoic acid methyl ester;
1-(3,3-diphenylpropyl)-1-(2-morpholin-4-ylethyl)-3-(3-trifluoromethanesulfonyl-phenyl)urea;
1-(3,3-diphenylpropyl)-1-(2-morpholin-4-ylethyl)-3-(3-propionylphenyl)urea;
1-(3,3-diphenylpropyl)-1-(2-morpholin-4-ylethyl)-3-(3-trifluoromethylsulfanyl-phenyl)urea;
1-(3,3-diphenylpropyl)-3-(3-methanesulfonylphenyl)-1-(2-morpholin-4-ylethyl)urea;
1-(3,3-diphenylpropyl)-3-(3-ethylsulfanylphenyl)-1-(2-morpholin-4-ylethyl)urea;

1-(3,3-diphenylpropyl)-3-(3-isopropylsulfanylphenyl)-1-(2-morpholin-4-ylethyl)urea;
3-(4-chloro-3-methylsulfanylphenyl)-1-(3,3-diphenylpropyl)-1-(2-morpholin-4-yl-ethyl)urea;
3-(3,5-dichlorophenyl)-1-(3,3-diphenylpropyl)-1-(2-morpholin-4-ylethyl)urea;
1-(3,3-diphenylpropyl)-3-(3-iodophenyl)-1-(2-morpholin-4-ylethyl)urea;
3-(4-chloro-3-trifluoromethylphenyl)-1-(3,3-diphenylpropyl)-1-(2-morpholin-4-ylethyl)urea;
3-(3-dimethylaminophenyl)-1-(3,3-diphenylpropyl)-1-(2-morpholin-4-ylethyl)urea;
3-[3-(3,3-diphenylpropyl)-3-(2-morpholin-4-ylethyl)ureido]benzoic acid tertbutyl ester hydrochloride;
3-(4-chloro-3-trifluoromethylphenyl)-1-(3,3-diphenylpropyl)-1-(2-morpholin-4-ylethyl)urea hydrochloride;
1-(3,3-diphenylpropyl)-3-(3-methanesulphinylphenyl)-1-(2-morpholin-4-ylethyl)urea;
3-[3-(3,3-diphenylpropyl)-3-(2-morpholin-4-ylethyl)ureido]benzoic acid;
2-chloro-5-[3-(3,3-diphenylpropyl)-3-(2-morpholin-4-ylethyl)ureido]benzoic acid;
3-[3-(3,3-diphenylpropyl)-3-(2-morpholin-4-ylethyl)ureido]benzoic acid isopropyl ester;
3-[3-(3,3-diphenylpropyl)-3-(2-morpholin-4-ylethyl)ureido]benzoic acid isopropyl ester hydrochloride;
3-[3-(3,3-diphenylpropyl)-3-(2-morpholin-4-ylethyl)ureido]benzoic acid 2-hydroxy ester;
2-chloro-5-[3-(3,3-diphenylpropyl)-3-(2-morpholin-4-ylethyl)ureido]benzoic acid isopropyl ester;
2-chloro-5-[3-(3,3-diphenylpropyl)-3-(2-morpholin-4-ylethyl)ureido]benzoic acid isopropyl ester hydrochloride;
3-[3-(3,3-diphenylpropyl)-3-(2-morpholin-4-ylethyl)ureido]benzoic acid benzyl ester;
2-chloro-5-[3-(3,3-diphenylpropyl)-3-(2-morpholin-4-ylethyl)ureido]benzamide;
3-[3-(3,3-diphenylpropyl)-3-(2-morpholin-4-ylethyl)ureido]-n-(2-hydroxy-ethyl)-benzamide;
3-[3-(3,3-diphenylpropyl)-3-(2-morpholin-4-ylethyl)ureido]thiobenzamide;
1-(3,3-diphenylpropyl)-3-[3-(4-methylthiazol-2-yl)-phenyl]-1-(2-morpholin-4-ylethyl)urea;
1-(3,3-diphenylpropyl)-3-(3-hydroxymethylphenyl)-1-(2-morpholin-4-ylethyl)urea;
3-(4-chloro-3-hydroxymethylphenyl)-1-(3,3-diphenylpropyl)-1-(2-morpholin-4-ylethyl)urea;
1-(3,3-diphenylpropyl)-3-(3-formylphenyl)-1-(2-morpholin-4-ylethyl)urea;
3-(4-chloro-3-formylphenyl)-1-(3,3-diphenylpropyl)-1-(2-morpholin-4-ylethyl)urea;
3-[4-chloro-3-(1-hydroxyethyl)phenyl]-1-(3,3-diphenylpropyl)-1-(2-morpholin-4-ylethyl)urea;
1-(3,3-diphenylpropyl)-3-(3-methoxymethylphenyl)-1-(2-morpholin-4-ylethyl)urea;
1-(3,3-diphenylpropyl)-1-(2-morpholin-4-ylethyl)-3-(3-piperidin-1-ylmethyl-phenyl)urea;
1-(3,3-diphenylpropyl)-1-(2-morpholin-4-ylethyl)-3-(3-oxazol-5-ylphenyl)urea;
1-(3,3-diphenylpropyl)-1-(2-morpholin-4-ylethyl)-3-(3-oxazol-5-ylphenyl)urea hydrochloride;
1-(3,3-diphenylpropyl)-1-(2-morpholin-4-ylethyl)-3-(3-oxazol-5-yl-4-chlorophenyl)urea;
3-[4-chloro-3-(1-methyl-1h-tetrazol-5-yl)phenyl]-1-(3,3-diphenylpropyl)-1-(2-morpholin-4-ylethyl)urea;
3-[4-chloro-3-(2-methyl-2h-tetrazol-5-yl)phenyl]-1-(3,3-diphenylpropyl)-1-(2-morpholin-4-ylethyl)urea;
3-biphenyl-4-yl-1-(3,3-diphenylpropyl)-1-(2-morpholin-4-ylethyl)urea;
biphenyl-3-yl-1-(3,3-diphenylpropyl)-1-(2-morpholin-4-ylethyl)urea;
1-(3,3-diphenylpropyl)-1-(2-morpholin-4-ylethyl)-3-(3-pyridin-3-ylphenyl)urea;
(1-(3,3-diphenylpropyl)-3-(3-furan-3-ylphenyl)-1-(2-morpholin-4-ylethyl)urea;
1-(3,3-diphenylpropyl)-3-(3-furan-2-ylphenyl)-1-(2-morpholin-4-ylethyl)urea;
1-(3,3-diphenylpropyl)-3-(3-furan-2-ylphenyl)-1-(2-morpholin-4-ylethyl)urea hydrochloride;
3-[3-(5-chlorothiophen-2-yl)-phenyl]-1-(3,3-diphenylpropyl)-1-(2-morpholin-4-ylethyl)urea;
1-(3,3-diphenylpropyl)-1-(2-morpholin-4-ylethyl)-3-(3-thiophen-3-ylphenyl)urea;
1-(3,3-diphenylpropyl)-3-(2'-methoxybiphenyl-3-yl)-1-(2-morpholin-4-ylethyl)urea;
3-(2',4'-dichlorobiphenyl-3-yl)-1-(3,3-diphenylpropyl)-1-(2-morpholin-4-ylethyl)urea;
1-(3,3-diphenylpropyl)-3-[3-(3-methylisoxazol-5-yl)-phenyl]-1-(2-morpholin-4-ylethyl)urea;
3-[3-(1h-benzimidazole-2-yl)-phenyl]-1-(3,3-diphenylpropyl)-1-(2-morpholin-4-ylethyl)urea;
3-(3-benzothiazol-2-ylphenyl)-1-(3,3-diphenylpropyl)-1-(2-morpholin-4-ylethyl)urea;
1-(3,3-diphenylpropyl)-1-(2-morpholin-4-ylethyl)-3-[3-(2h-tetrazol-5-yl)phenyl]urea hydrochloride;
1-(3,3-diphenylpropyl)-3-[3-(2-methyl-2h-tetrazol-5-yl)phenyl]-1-(2-morpholin-4-ylethyl)urea;
1-(3,3-diphenylpropyl)-3-[3-(1-methyl-1h-tetrazol-5-yl)phenyl]-1-(2-morpholin-4-ylethyl)urea;
1-(3,3-diphenylpropyl)-3-[3-(2-methyl-2h-tetrazol-5-yl)phenyl]-1-(2-morpholin-4-ylethyl)urea;
1-(3,3-diphenylpropyl)-3-[3-(1-methyl-1h-tetrazol-5-yl)phenyl]-1-(2-morpholin-4-ylethyl)urea;
3-benzo[1,3]dioxol-5-yl-1-(3,3-diphenylpropyl)-1-(2-morpholin-4-ylethyl)urea;
3-(2,3-dihydro-benzo[1,4]dioxin-6-yl)-1-(3,3-diphenylpropyl)-1-(2-morpholin-4-ylethyl)urea;
1-(3,3-diphenylpropyl)-1-(2-morpholin-4-ylethyl)-3-(3-oxo-1,3-dihydroisobenzofuran-5-yl)urea;
1-(3,3-diphenylpropyl)-1-(2-morpholin-4-ylethyl)-3-(8-oxo-5,6,7,8-tetrahydro-naphthalen-2-yl)urea;
3-(1-acetyl-2,3-dihydro-1h-indol-6-yl)-1-(3,3-diphenylpropyl)-1-(2-morpholin-4-ylethyl)urea;
1-(3,3-diphenylpropyl)-3-(1h-indazol-6-yl)-1-(2-morpholin-4-ylethyl)urea;
1-(3,3-diphenylpropyl)-3-(9-ethyl-9h-carbazol-3-yl)-1-(2-morpholin-4-ylethyl)urea;
1-(3,3-diphenylpropyl)-3-isoquinolin-7-yl-1-(2-morpholin-4-ylethyl)urea;
3-(2-chloro-benzyl)-1-(3,3-diphenylpropyl)-1-(2-morpholin-4-ylethyl)urea;
1-(3,3-diphenylpropyl)-1-(2-morpholin-4-ylethyl)-3-thiophen-2-ylmethylurea;
1-(3,3-diphenylpropyl)-1-(2-morpholin-4-ylethyl)-3-(1-naphthalen-1-ylethyl)urea;
3-[3-(3,3-diphenylpropyl)-3-(2-morpholin-4-ylethyl)ureido]thiophene-2-carboxylic acid methyl ester;
1-(3,3-diphenylpropyl)-1-(2-morpholin-4-ylethyl)-3-pyridin-3-ylurea;
1-(3,3-diphenylpropyl)-3-[3-(2-methyl-2h-tetrazol-5-yl)phenyl]-1-(2-morpholin-4-ylethyl)urea;
3-(1-benzyl-1h-benzimidazol-2-yl)-1-(3,3-diphenylpropyl)-1-(2-morpholin-4-ylethyl)urea;

1-(3,3-diphenylpropyl)-3-(2-methyl-5-phenyl-2,5-dihydro-1h-pyrazol-3-yl)-1-(2-morpholin-4-ylethyl)urea;
3-(4,6-dimethylpyridin-2-yl)-1-(3,3-diphenylpropyl)-1-(morpholin-4-ylethyl)urea;
1-(3,3-diphenylpropyl)-3-(4-methoxy-6-methylpyrimidin-2-yl)-1-(2-morpholin-4-ylethyl)urea;
1-(3,3-diphenylpropyl)-1-(2-morpholin-4-ylethyl)-3-pyrazin-2-ylurea;
1-(3,3-diphenylpropyl)-1-(2-morpholin-4-ylethyl)-3-(4-thiazol-2-ylpyrimidin-2-yl)urea;
1-(3,3-diphenylpropyl)-3-(5-methylisoxazol-3-yl)-1-(2-morpholin-4-ylethyl)urea;
1-(3,3-diphenylpropyl)-3-(3-methyl-5-phenylisoxazol-4-yl)-1-(2-morpholin-4-ylethyl)urea;
3-[3-(2-chloro-6-fluorophenyl)-5-methylisoxazol-4-yl]-1-(3,3-diphenylpropyl)-1-(2-morpholin-4-ylethyl)urea;
1-(3,3-diphenylpropyl)-3-(5-methyl-3-phenylisoxazol-4-yl)-1-(2-morpholin-4-ylethyl)urea;
1-(3,3-diphenylpropyl)-1-(2-morpholin-4-ylethyl)-3-(5-phenyl-2h-pyrazol-3-yl)urea;
1-(3,3-diphenylpropyl)-1-(2-morpholin-4-ylethyl)-3-(3-phenyl-[1,2,4]thiadiazol-5-yl)urea;
5-[3,3-diphenylpropyl)-3-(2-morpholin-4-ylethyl)ureido]-3-propyl-isoxazole-4-carboxylic acid ethyl ester;
3-(3,4-dimethyl-isoxazol-5-yl)-1-(3,3-diphenylpropyl)-1-(2-morpholin-4-ylethyl)urea;
3-[3-[2-(9h-fluoren-9-yl)-ethyl]-3-(2-morpholin-4-ylethyl)ureido]benzoic acid methyl ester;
3-[3-[2-(9h-fluoren-9-yl)ethyl]-3-(2-morpholin-4-ylethyl)ureido]benzoic acid methyl ester;
3-[3-(2-methyl-2h-tetrazol-5-yl)phenyl]-1-(2-morpholin-4-ylethyl)-1-(3-phenyl-3-thiophen-2-ylpropyl)urea;
1-(2-morpholin-4-ylethyl)-3-(3-oxazol-5-ylphenyl)-1-(3-phenyl-3-thiophen-2-yl-propyl)urea dihydrochloride;
3-[3-(2-morpholin-4-ylethyl)-3-(3-phenyl-3-thiophen-2-yl-propyl)ureido]benzoic acid methyl ester;
1-(3,3-di-thiophen-2-ylpropyl)-3-[3-(2-methyl-2h-tetrazol-5-yl)phenyl]-1-(2-morpholin-4-ylethyl)urea;
3-[3-(3,3-dithiophen-2-yl-propyl)-3-(2-morpholin-4-yl-ethyl)ureido]benzoic acid methyl ester;
1-(3,3-dithiophen-2-ylpropyl)-1-(2-morpholin-4-ylethyl)-3-(3-oxazol-5-ylphenyl)urea dihydrochloride;
1-(3,3-diphenylpropyl)-3-[3-(2-methyl-2h-tetrazol-5-yl)phenyl]-1-(2-thiomorpholin-4-ylethyl)urea;
1-[2-(2,6-dimethylmorpholin-4-yl)-ethyl]-1-(3,3-diphenylpropyl)-3-[3-(2-methyl-2h-tetrazol-5-yl)phenyl]urea;
3-(5,6-dimethyl-1h-benzoimidazol-2-yl)-1-(3,3-diphenylpropyl)-1-(2-morpholin-4-ylethyl)urea;
1-(3,3-diphenylpropyl)-3-(1-methyl-1h-benzoimidazol-2-yl)-1-(2-morpholin-4-ylethyl)-urea;
3-(1h-benzoimidazol-2-yl)-1-(3,3-diphenylpropyl)-1-(2-morpholin-4-ylethyl)urea;
1-(3,3-diphenylpropyl)-1-(2-morpholin-4-yl-ethyl)-3-(5-phenylsulfanyl-1h-benzoimidazol-2-yl)-urea;
1-(3,3-diphenylpropyl)-1-(2-morpholin-4-ylethyl)-3-(5-oxo-1-phenyl-4,5-dihydro-1h-pyrazol-3-yl)urea;
1-(3,3-diphenylpropyl)-3-(5-methyl-2-phenyl-2h-pyrazol-3-yl)-1-(2-morpholin-4-ylethyl)urea;
1-(3,3-diphenylpropyl)-1-(2-morpholin-4-ylethyl)-3-(5-phenyl[1,3,4]thiadiazol-2-yl)-urea;
3-[3-(3,3-diphenylpropyl)-3-(2-morpholin-4-yl-ethyl)ureido]-5-phenylthiophene-2-carboxylic acid methyl ester;
3-[2-(4-chlorophenylsulfanyl)-6-methoxypyridin-3-yl]-1-(3,3-diphenylpropyl)-1-(2-morpholin-4-yl-ethyl)urea;
2-[3-(3,3-diphenylpropyl)-3-(2-morpholin-4-ylethyl)ureido]-4,5,6,7-tetrahydrobenzo[b]thiophene-3-carboxylic acid ethyl ester;
6-[3-(3,3-diphenylpropyl)-3-(2-morpholin-4-ylethyl)ureido]nicotinic acid methyl ester;
3-(3-chloro-5-trifluoromethylpyridin-2-yl)-1-(3,3-diphenylpropyl)-1-(2-morpholin-4-ylethyl)urea;
3-(6-chloro-2-methylsulfanylpyrimidin-4-yl)-1-(3,3-diphenylpropyl)-1-(2-morpholin-4-ylethyl)urea;
2-(4-chlorobenzyl)-5-[3-(3,3-diphenylpropyl)-3-(2-morpholin-4-ylethyl)-ureido]oxazole-4-carboxylic acid ethyl ester;
1-(3,3-diphenylpropyl)-3-(4-methoxybenzo[d]isoxazol-3-yl)-1-(2-morpholin-4-ylethyl)urea;
1-(3,3-diphenylpropyl)-3-(2-methyl-5-thiophen-2-yl-2h-pyrazol-3-yl)-1-(2-morpholin-4-ylethyl)urea;
6-[3-(3,3-diphenylpropyl)-3-(2-morpholin-4-ylethyl)ureido]nicotinamide; and
1-(3,3-diphenylpropyl)-1-(2-morpholin-4-ylethyl)-3-(1,4,6-trimethyl-1h-pyrazolo[3,4-b]pyridin-3-yl)urea hydrochloride.

The present invention relates, in particular, to the compounds of formula (I) as defined above, corresponding to the product formulae of examples 1 to 144 described hereinafter in the experimental section.

In the following processes, and elsewhere herein wherein referred to, $R_1$, $R_1'$, $R_2$, $R_2'$, and $R_3$ are synonymous with $R_1$, $R_1'$, $R_2$, $R_2'$, and $R^3$, respectively.

The present invention further relates to a process for preparing products of formula (I), as defined above, and the salts and/or isomers thereof, the process being characterised in that a compound of formula (II):

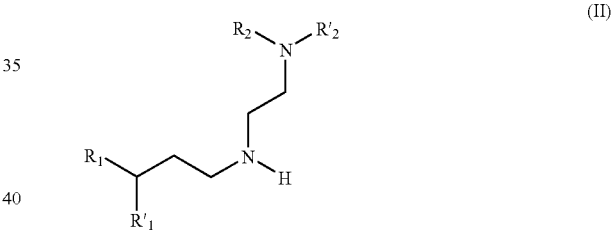

in which $R_1$, $R_1'$, $R_2$ and $R_2'$ are as defined,
is reacted with an isocyanate of formula (A):

in which $R_3$ is as defined, thereby to obtain the desired product of formula (I), which may optionally be converted into another product of formula (I) and, if desired, may further be salified to obtain a salt thereof, and/or the product obtained may optionally be subjected to a resolution reaction to resolve the racemic forms in order to obtain the required isomeric forms.

Under the conditions for carrying out this process of the invention:
  the product of formula (II) is reacted with the product of formula (A) within an anhydrous organic solvent such as dichloromethane, and/or
  the isocyanate of formula (A) may be generated in situ from the carboxylic acid $R_3COOH$ of formula (A') by the action of diphenylphosphoryl azide (DPPA) within an anhydrous solvent such as toluene and a base such as triethylamine.

According to a variation of the process for preparing products of formula (I), as defined above, these products may be prepared by a process which is characterised in that a compound of formula (IV):

 (IV)

in which $R_3$ is as defined, is subjected either to the action of triphosgene to obtain an activated intermediate which is reacted with a compound of formula (II):

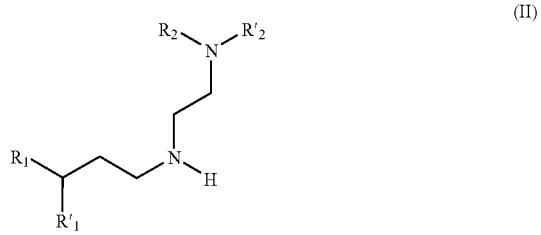 (II)

in which $R_1$, $R'_1$, $R_2$ and $R'_2$ are as defined, or to the action of carbonyl diimidazole, then to a compound of formula (II) above, to obtain the desired product of formula (I), in which $R_1$, $R'_1$, $R_2$, $R'_2$ and $R_3$ are as defined, which can optionally be further salified in order to obtain the salt thereof and/or, if desired, subjected to a resolution reaction to resolve the racemic forms in order to obtain the required isomeric forms thereof.

Under the conditions for carrying out the invention, this process is characterised in that:

the compound of formula (IV) is reacted with triphosgene within an anhydrous organic solvent such as dichloromethane in the presence of an amine such as triethylamine or diisopropylethylamine in order to obtain as an intermediate a carbamoyl chloride which is reacted with a compound of formula (II) within an anhydrous organic solvent such as dichloromethane, the compound of formula (IV) is reacted with carbonyl diimidazole within an anhydrous organic solvent such as dichloromethane.

According to the invention, the compounds of formula (II) may be prepared by a process which is characterised in that a compound of formula (V):

 (V)

in which $R_1$ and $R'_1$ are as defined, is subjected to the action of a compound of formula (VI):

 (VI)

in which $R_2$ and $R'_2$ are as defined, to obtain the desired compound of formula (II) in which $R_1$, $R'_1$, $R_2$ and $R'_2$ are as defined.

Under the conditions for carrying out the invention, this process for preparing compounds of formula (II) is characterised in that:

the compound of formula (V) is reacted with the product of formula (VI) under reflux of the mixture in the presence of acetonitrile, triethylamine and potassium carbonate.

The compounds of formula (II) can also be prepared by a process which is characterised in that a compound of formula (VII):

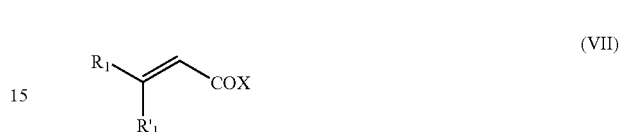 (VII)

in which $R_1$ and $R'_1$ are as defined and X represents a hydroxy radical or a chlorine atom, is subjected to the action of a compound of formula (VIII):

 (VIII)

in which $R_2$ and $R'_2$ are as defined, in the presence of an inert organic solvent to obtain a product of formula (IX):

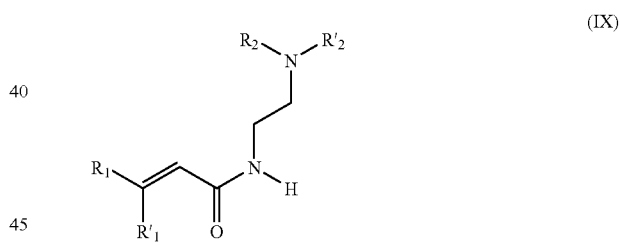 (IX)

in which $R_1$, $R'_1$, $R_2$ and $R'_2$ are as defined, whereafter the product of formula (IX) thus obtained is reduced in order to obtain the desired product of formula (II) in which $R_1$, $R'_1$, $R_2$ and $R'_2$ are as defined.

Under the exemplary conditions for carrying out the invention, this process for preparing products of formula (II) is characterised in that:

the compound of formula (VII) is reacted with the compound of formula (VIII) within an anhydrous organic solvent such as dichloromethane; and/or the compounds of formula (IX) is reduced using $LiAlH_4$ and optionally in the presence of $AlCl_3$ within an anhydrous organic solvent such as tetrahydrofuran or diethyl ether.

According to a variation, the compounds of formula (II), as defined above, may also be prepared by a preparation process, characterised in that a compound of formula (X):

in which $R_1$ and $R'_1$ are as defined, is subjected to oxidation in order to obtain a compound of formula (XI):

in which $R_1$ and $R'_1$ are as defined, then to the action of a compound of formula (VIII), for a stage of reductive amination in the presence of a reducing agent such as $NaBH_3CN$:

in which $R_2$ and $R'_2$ are as defined, in the presence of an inert organic solvent, in order to obtain the desired product of formula (II) in which $R_1$, $R'_1$, $R_2$ and $R'_2$ are as defined.

Finally the compounds of formula (II) may be prepared by a process characterised in that an amine of formula (V) is subjected to acylation with chloroacetyl chloride, followed by reaction with the amine $NHR_2R'_2$ in order to obtain the amide of formula (XII):

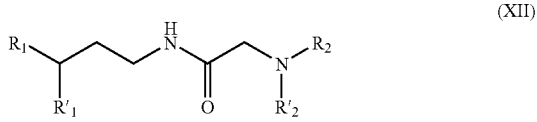

in which $R_1$, $R'_1$, $R_2$ and $R'_2$ are as defined, followed by reduction of the amide of formula (XII) in order to obtain the desired amine of formula (II) in which $R_1$, $R'_1$, $R_2$ and $R'_2$ are as defined.

Under the exemplary conditions for carrying out the invention, this process for preparing products of formula (II) is characterised in that:
the compound of formula (XII) if formed from the amine $R_2R'_2NH$ within an inert organic solvent such as DMF, and/or
the compound of formula (XII) is reduced using $LiAlH_4$ and optionally in the presence of $AlCl_3$ within an anhydrous organic solvent such as tetrahydrofuran or diethyl ether.

To prepare a compound of formula (I) in which $R^3$ represents an aryl substituted by an alkylsulphone, a product of formula (I) in which $R^3$ represents an aryl substituted by a thioalkyl will generally first be prepared, after which this product is then oxidised in order to obtain the desired product of formula (I). This process is hereinafter called method "G".

To prepare a compound of formula (I) in which $R_3$ represents an aryl substituted by a —COOH radical, an ester of said product of formula (I) is first prepared in which this carboxy group is protected (product of formula (I) in which $R^3$ represents an aryl substituted by a —COOR group in which R represents an alkyl or aralkyl radical), then this ester is saponified in order to obtain the corresponding acid of formula (I) which may optionally be salified. This process is hereinafter called method "H".

The compounds of formula (I) in which $R^3$ represents an aryl substituted by an alkoxycarbonyl radical may be prepared:
either by employing the above-described general process,
or by esterification of the corresponding benzoic acid (product of general formula (I) in which $R^3$ represents a benzoic acid radical), by means of an iodised derivative of formula $R_4$—I in which $R_4$ represents an alkyl or hydroxyalkyl radical and I represents an iodine atom.
This process is hereinafter called method "I".

The compounds of formula (I) in which $R^3$ represents an aryl substituted by a group —CO—$R_4$ in which $R_4$ represents an amino, alkylamino, dialkylamino group, may be prepared by reaction of a corresponding benzoic acid derivative (product of general formula (I) in which $R^3$ represents a benzoic acid residue) with an amine of formula: H—$R_4$, by methods known to those skilled in the art. This process is hereinafter called method "J".

The compounds of formula (I) in which $R^3$ represents an aryl substituted by a thioamide group may be prepared by starting from the product of general formula (I) in which $R^3$ represents an aryl substituted by a nitrile group by reaction of diethyl dithiophosphate. This process is hereinafter called method "K".

The compounds of formula (I) in which $R^3$ represents an aryl substituted by a thiazolyl group may be prepared by action of a halogenated alpha-ketone on a product of general formula (I) in which $R^3$ represents an aryl substituted by a thioamide group.

The compounds of formula (I) in which $R^3$ represents an aryl substituted by an oxazolyl group may be prepared by reaction of tosylmethyl isocyanide with a product of general formula (I) in which $R^3$ represents an aryl substituted by an aldehyde group.

The compounds of formula (I) in which $R^3$ represents an aryl substituted by a substituted or unsubstituted benzimidazole group may be prepared by reaction of substituted or unsubstituted 1,2-phenylenediamine with a product of general formula (I) in which $R^3$ represents an aryl substituted by an ester group.

Similarly, starting from the same product of general formula (I), the compounds with $R^3$ representing an aryl substituted by a substituted or unsubstituted benzothiazole group may be prepared by reaction with substituted or unsubstituted 2-aminothiophenol.

The compounds of formula (I) in which $R^3$ represents an aryl substituted by a primary alcohol, aldehyde group may be prepared by reducing the corresponding ester (product of general formula (I) in which $R^3$ represents an aryl substituted by an ester).

The compounds of formula (I) in which $R^3$ represents an aryl substituted by a secondary or tertiary $CH_2$-alkoxy or $CH_2$-amine group may be prepared by starting from the product of general formula (I) in which $R^3$ represents an aryl substituted by a primary alcohol group $CH_2OH$. These products are prepared by direct action of an alkyl halide on the hydroxy function or by indirect action of an alcohol or a primary or secondary amine after prior activation of this hydroxy group via a mesylate or halide. This process is hereinafter called method "L".

The compounds of formula (I) in which $R^3$ represents an aryl substituted by a phenyl group, an aryl group substituted by an aryl or heteroaryl, optionally substituted, may be prepared by a Suzuki coupling reaction by means of a boric acid derivative of formula Ar—B—(OH)$_2$ in which argon represents the residue of a substituted or unsubstituted aryl group, a substituted or unsubstituted heteroaryl, starting from a product of general formula (I) in which $R^3$ represents an aryl group substituted by a bromine atom. This process is hereinafter called methods "M" and "N", depending on the technology employed.

Finally, according to a variation of the preparation process, the compounds of formula (I) in which $R^3$ represents a phenyl group substituted by a tetrazole or alkyltetrazole radical, may be obtained by starting from the corresponding nitrile (product of general formula (I) in which $R^3$ represents an aryl substituted by a nitrile group) by reaction with a tributyl tin azide in order to obtain products of formula (I) in which $R^3$ represents a phenyl group substituted by a tetrazole radical, followed by a reaction with an alkyl halide in order to obtain the product of formula (I) in which $R^3$ represents a phenyl group substituted by an alkyltetrazole radical.

The above-described compounds may, if desired, be subjected to salification reactions, for example using an inorganic or organic acid or an inorganic or organic base, by conventional methods known to the person skilled in the art.

The possible optically active forms of the above-described products may be prepared by resolving the racemic forms by conventional methods known to the person skilled in the art.

The above reactions are further illustrated in the accompanying, non-limiting Examples.

The compounds of formula (I) as defined above and their addition salts with acids or bases have beneficial pharmacological properties.

The compounds of the present invention can thus act on an inorganic ion, especially calcium receptor and thus modulate one or more activities of the receptor.

Compounds of the present application which act on calcium receptors may thus be used, in particular, for the treatment or prevention of diseases or disorders linked with abnormal physiological behaviour of inorganic ion receptors and, in particular, of calcium receptors such as membrane calcium receptors capable of binding extracellular calcium (Ca sensing receptor CaSR).

The compounds of the present invention as defined above are capable of modulating the activity of the calcium receptor. The products of the present invention can thus act as agonists or antagonists of the calcium receptor. While the compounds of the invention are believed to exert their effects by interacting with the calcium sensing receptor (CaSR), the mechanism of action by which the compounds act is not a limiting embodiment of the invention.

In one aspect, the compounds of the present invention can be used in regulating the serum levels of PTH and extracellular $Ca^{2+}$. In one aspect, the compounds of the present invention possess agonistic properties toward the calcium receptor and can therefore be used, to participate in a reduction of the serum levels in the parathyroid hormone known as PTH: for example, for the treatment of diseases such as hyperparathyroidism. Similarly, abnormalities in calcium homeostasis can be treated with these compounds, in particular hypercalcaemia. Still in the region of the parathyroid, the compounds of formula (I) as defined can treat hyperplasia and parathyroid adenoma.

In another aspect, the compounds of the present invention can be used to reduce bone resorption which depends directly on the fluctuation of circulating PTH levels: these compounds could be useful, in particular, for the treatment of diseases such as osteoporosis, osteopaenia Paget's disease and the reconstruction of fractures. They can also be used in the treatment and prophylaxis of polyarthritis and osteoarthritis.

It will be appreciated that reference to treatment herein includes reference to all applicable forms of treatment and prophylaxis.

With regard to digestion, the compounds and compositions of the present invention may also be used for the treatment of motor disorders (such as diarrhoea or constipation), functional digestive disorders, ulcerous diseases, sarcoidosis, familial adenomatous polyposis, polyps of the intestine and colon, cancer of the colon and intestinal malabsorption.

In a further aspect, the compounds of the present invention can be used for the treatment or prevention of diseases or disorders such as, in particular: inappropriate antidiuretic hormone secretion (ADH syndrome), convulsions, stroke, cranial traumatism, diseases of the spinal marrow, neurodegenerative diseases (such as Alzheimer's disease, Parkinson's disease and Huntington's chorea), dementia, migraine, cerebral hypoxia, abnormalities in growth hormone secretion, psychiatric diseases (such as depression, anxiety, obsessive behaviour disorder, schizophrenia, post-traumatic stress, and neuroleptic malignant syndrome).

The compounds of formula (I) of the present invention may also possess therapeutic properties in regard of the following: thrombopaenia, platelet hypo- or hyper-coagulability, arterial hypertension, cardiac insufficiency, prevention or attenuation of renal toxicity of aminosides, renal lithiasis, pancreas insufficiency, diabetes, psoriasis, breast adenoma and cancer, cirrhosis, biliary lithiasis, and obesity.

In one aspect, the invention provides methods of inhibiting, decreasing or preventing vascular calcification in an individual. The method comprises administering to the individual a therapeutically effective amount of the compound of the invention. In one aspect, administration of the compound of the invention retards or reverses the formation, growth or deposition of extracellular matrix hydroxyapatite crystal deposits. In another aspect of the invention, administration of the compound of the invention prevents the formation, growth or deposition of extracellular matrix hydroxyapatite crystal deposits.

In one aspect, the compounds of the invention may be used to prevent or treat atherosclerotic calcification and medial calcification and other conditions characterized by vascular calcification. In one aspect, vascular calcification may be associated with chronic renal insufficiency or end-stage renal disease. In another aspect, vascular calcification may be associated with pre- or post-dialysis or uremia. In a further aspect, vascular calcification may be associated with diabetes mellitus I or II. In yet another aspect, vascular calcification may be associated with a cardiovascular disorder.

In one aspect, administration of an effective amount of the compounds of the invention can reduce serum PTH without causing aortic calcification. In another aspect, administration of the compounds of the invention can reduce serum creatinine level or can prevent increase of serum creatinine level. In another aspect, administration of the compounds of the invention can attenuates parathyroid (PT) hyperplasia.

The compounds of the invention may be administered alone or in combination with other drugs for treating vascular calcification, such as vitamin D sterols and/or RENAGEL®. Vitamin D sterols can include calcitriol, alfacalcidol, doxercalciferol, maxacalcitol or paricalcitol. In one aspect, the compounds of the invention can be administered before or after administration of vitamin D sterols. In another aspect, the compounds of the invention can be co-administered with vitamin D sterols. The methods of the invention can be practiced to attenuate the mineralizing effect of calcitriol on vascular tissue. In one aspect, the methods of the invention can be used to reverse the effect of calcitriol of increasing the serum levels of calcium, phosphorus and Ca×P product thereby preventing or inhibiting vascular calcification. In another aspect, the compounds of the invention of the invention can be used to stabilize or decrease serum creatinine levels. In one aspect, in addition to creatinine level increase due to a disease, a further increase in creatinine level can be due to treatment with vitamin D sterols such as calcitriol. In addition, the compounds of the invention may be administered in conjunction with surgical and non-surgical treatments. In one aspect, the methods of the invention can be practiced in injunction with dialysis.

In one aspect, the compounds of the invention can be used for treating abnormal intestinal motilities disorders such as diarrhea. The methods of the invention comprise administering to the individual a therapeutically effective amount of the compounds of Formula I. In a further aspect, diarrhea can be exudative diarrhea, i.e., resulting from direct damage to the small or large intestinal mucosa. This type of diarrhea can be caused by infectious or inflammatory disorders of the gut. In one aspect, exudative diarrhea can be associated with chemotherapy, radiation treatment, inflammation or toxic traumatic injury. In another aspect, exudative diarrhea can be associated with a gastrointestinal or abdominal surgery. In another aspect, diarrhea can be due to acceleration of intestinal transit (rapid transit diarrhea). Such condition may occur because the rapid flow-through impairs the ability of the gut to absorb water.

In one aspect, the invention provides the compounds and pharmaceutical compositions for treating abnormal gastric fluid secretion/absorption disorders in conjunction with treating underlying causes of, for example, diarrhea or with other treatment methods. In one aspect, calcimimetics can be administered to a subject before, after or concurrently with oral rehydration therapy. For example, oral rehydration therapy may contain the following ingredients: sodium, potassium, chloride, bicarbonate, citrate and glucose. In another aspect, the compounds of the invention can be administered to a subject before, after or concurrently with an antimotility agent, such as loperamide(Imodium), diphenoxylate, or bismuth subsalicylate (Pepto-Bismol). In another aspect, compounds of the invention can be administered with antibiotics (e.g., trimethoprim-sulfamethoxazole (Bactrim DS), ciprofloxacin (Cipro), norfloxacin (Noroxin), ofloxacin (Floxin), doxycycline (Vibramycin), erythromycin). In one aspect, the compounds of the invention can be administered together with calcium or polyamines such as spermine, spermidine, putrescine, and ornithine metabolites or amino acids such of L-tryptophan, L-phenylalanine. In another aspect, the compounds of the invention can be administered together with sodium and glucose. In addition, the compounds of the invention may be administered in conjunction with surgical and non-surgical treatments.

The invention further provides methods for modulating intestinal fluid secretion and absorption. In one aspect, the purpose can be to increase fluid absorption and/or decrease fluid secretion in a subject and thus the methods of the invention can comprise administering an effective amount of a pharmaceutical composition comprising a compound of the invention.

The invention provides methods of modulation the absorption or secretion of a drug, poison or nutrient in the intestinal tract of a subject, comprising administering an effective amount of a pharmaceutical composition comprising a compound of the invention together with a pharmaceutically acceptable carrier to the subject. In one aspect, the invention provides methods of treatment of a malassimilation or a malabsorption of a subject, comprising administering an effective amount of a pharmaceutical composition comprising a compound of Formula I together with a pharmaceutically acceptable carrier to the subject.

Methods of the invention comprising administering a pharmaceutical composition of the invention can also be practiced to treat malnutrition in a subject. For example, a subject can be malnourished if the subject is grossly underweight (weight for height is below 80% of the standard), grossly overweight (weight for height above 120% of the standard), if the subject unintentionally lost 10% or more of body weight, has a gastrointestinal tract surgery, experienced nutrient losses (e.g., from diarrhea, dialysis, vomiting), has increased metabolic needs (e.g., due to pregnancy, lactation, increased physical activity, fever, injury), is an alcoholic or chronic drug user (antibiotics, antidepressants, diuretics), has medical conditions which interfere with nutrient intake, absorption, metabolism, or utilization, has poor dentition (particularly in the elderly subjects), or has mouth sores due to herpes, HIV or chemotherapy. In another aspect, the subject can be malnourished due to dietary risk factors (e.g., loss of appetite, inadequate food or nutrient intake, lack of variety of foods, fad, weight-loss diets, inadequate fiber, excessive fat, sodium, sugar, excess alcohol, eats too few fruits, vegetables) or due to social risk factors (e.g., chronic ill health, poverty, inadequate money to buy food, low socioeconomic status, immobility or inability to purchase, store, or cook food, social isolation, eats alone most of the time, substance abuser, conditions which limit subject's ability to eat). Further, the methods of the invention can be practiced when a subject has limited access to nutrients such as during survival following environmental disasters, survival at sea, marooning and deep-sea living or space travel.

The present invention further provides pharmaceutical compositions comprising compounds of formula (I), in any and all possible racemic, enantiomeric and diastereoisomeric isomeric forms, as well as the pharmaceutically acceptable addition salts thereof with inorganic and organic acids or inorganic or organic bases. In one aspect the present invention provides pharmaceutical composition comprising a compound of formula (I), and/or an addition salt thereof.

The invention further relates to the use of the compounds of formula (I) as defined above and/or their pharmaceutically acceptable salts:

for the manufacture of medicaments for the treatment or prevention of diseases or disorders linked to abnormal physiological behaviour of inorganic ion receptors and in particular of the calcium receptor, characterised in that the calcium receptor is expressed in at least one of the parathyroid, the thyroid, the bone cells, the renal cells, the lung, the brain, the pituitary gland, the hypothalamus, the gastrointestinal cells, the pancreas cells, the skin cells, the cells of the central or peripheral nervous system and the smooth muscle cells, for the manufacture of medicaments for the prevention or treatment of cancers, in particular of the parathyroid and/or the digestive tract, for the manufacture of medicaments for the prevention or treatment of neurodegenerative diseases, for the manufacture of medicaments for the prevention or treatment of bone and articular metabolism diseases, in particular osteoporosis, osteopaenia and Paget's disease, rheumatoid arthritis and/or osteoarthritis, for the manufacture of medicaments for the prevention or treatment of abnormal calcium homeostasis, for the manufacture of medicaments for the prevention or treatment of hyperplasia and/or parathyroid adenoma, for the manufacture of medicaments for the prevention or treatment of intestinal malabsorption, for the manufacture of medicaments for the prevention or treatment of biliary lithiasis and/or renal lithiasis, for the manufacture of medicaments for the prevention or treatment of hyperparathyroidism, characterised in that secondary hyperparathyroidism is observed in the event of renal insufficiency, for the manufacture of medicaments for the prevention or treatment of ionised serum calcium level reduction during the treatment of hypercalcaemia, for the manufacture of medicaments for the prevention or treatment of cardiovascular diseases.

The compounds of formula (I) and their pharmaceutically acceptable salts may be administered to animals, for example, to mammals and, in particular, to humans, as therapeutic or prophylactic medicaments.

They may be administered as they are or in a mixture with one or more compounds of formula (I) or else in the form of a pharmaceutical composition containing as the active compound an effective dose of at least one product of formula (I) and/or their pharmaceutically acceptable salts and common pharmaceutically inert excipients and/or additives.

These pharmaceutical compositions can be administered buccally, enterally or parenterally or topically to the skin and mucous membranes or by intravenous or intramuscular injection.

The medicaments may therefore be administered orally, for example in the form of pills, tablets, coated tablets, gel-coated tablets, granules, hard and soft capsules, solutions, syrups, emulsions, suspensions or aerosol mixtures.

The medicaments may however be effectively administered rectally, for example in the form of suppositories, or as pessaries, or parenterally, for example in the form of injectable solutions or infusions, microcapsules or implants, percutaneously, for example in the form of an ointment, solutions, pigments or colorants, transdermally (patches) or by other methods, for example in the form of an aerosol or nasal spray.

The medicaments according to the present invention may therefore be formulated as pharmaceutical compositions containing one or more products of formula (I) as defined above.

Pharmaceutical compositions of this type can therefore constitute the form in which the products of formula (I) as defined above are used in the therapeutic application thereof.

The pharmaceutical compositions according to the invention are prepared by conventional methods, pharmaceutically inert organic or inorganic excipients being added to the compounds of formula (I) and/or their pharmaceutically acceptable salts.

These compositions may therefore be solid or liquid and may have any pharmaceutical forms commonly employed in human medicine, for example, simple tablets or dragees, pills, tablets, hard capsules, droplets, granules, injectable preparations, ointments, creams or gels; they are prepared by conventional methods.

Excipients such as lactose, cornstarch or derivatives thereof, talc, stearic acid or the salts thereof, for example, may be used for producing pills, tablets, coated tablets and hard gelatin capsules.

Suitable vehicles for soft gelatin capsules or suppositories include, for example, fats, semi-solid or liquid polyol waxes and natural or modified oils, etc. Appropriate vehicles for the preparation of solutions, for example injectable solutions, emulsions or syrups include, for example, water, alcohols, glycerol, polyols, sucrose, invert sugars, glucose, vegetable oils, etc. Suitable vehicles for microcapsules or implants include, for example, glyoxylic and lactic acid copolymers. The pharmaceutical preparations normally contain from 0.5% to 90% by weight of products of formula (I) and/or the physiologically acceptable salts thereof.

The active principle may be incorporated in excipients which are normally used in these pharmaceutical compositions, such as talc, gum arabic, lactose, starch, magnesium stearate, cocoa butter, aqueous or non-aqueous vehicles, fats of animal or vegetable origin, paraffin derivatives, glycols, various wetting agents, dispersants or emulsifiers and preservatives.

In addition to the active principles and excipients, the pharmaceutical compositions may contain additives such as, for example, diluents, disintegrating agents, binders, lubricants, wetting agents, stabilisers, emulsifiers, preservatives, sweeteners, colorants, flavourings or aromatising agents, thickeners, buffers and also solvents or solubilisers or retarding agents and also salts to modify osmotic pressure, coating agents or antioxidants.

They can also contain two or more products of formula (I) and/or their pharmaceutically acceptable salts as defined above. Moreover, in addition to at least one or more products of formula (I) and/or their pharmaceutically acceptable salts, they can contain at least one or more other active principle which can be used therapeutically or prophylactically.

Pharmaceutical compositions of this type contain as active compound an effective dose of at least one product of formula (I) and/or its pharmaceutically acceptable salts as well as one or more pharmaceutically acceptable excipients and/or vehicles and optionally one or more conventional additives.

The present invention thus extends to pharmaceutical compositions containing at least one of the medicaments as defined above as the active ingredient.

When using the products of formula (I), the doses can vary within wide limits and will be determined by the skilled physician, taking into account such factors as the age, weight and sex of the patient. Other factors to be taken into consideration include the compound employed, the nature and severity of the disease to be treated, whether the condition is serious or chronic, and whether a prophylactic treatment is being employed.

The pharmaceutical compositions normally contain from 0.2 to 500 mg, for example, from 1 to 200 g of compound of formula (I) and/or their pharmaceutically acceptable salts.

In the case of oral administration, the daily dose varies generally from 0.05 to 10 mg/kg and for example from 0.1 to 8 mg/kg, in particular from 0.1 to 6 mg/kg. For an adult, for example, a daily dose varying from 5 to 500 mg could be considered.

In the case of intravenous administration, the daily dose varies approximately from 0.05 to 6 mg/kg and for example from 0.1 to 5 mg/kg.

The daily dose may be divided into a plurality of portions, for example 2, 3 or 4 portions, in particular if a large amount of active ingredient is to be administered. It may possibly be necessary to administer the various doses in an increasing or decreasing manner, depending on the behaviour in an individual case. These doses may be applied multiple times per day, once a day, once every other day, or any other regimen deemed appropriate by the skilled physician. Apart from the use of the products of formula (I) as defined above as medicaments, their use as a vehicle or support for active compounds for transporting these active compounds specifically toward a site of action can also be envisaged (Drug targeting, see Targeted Drug Delivery, R. C. Juliano, Handbook of Experimental Pharmacology, Vol. 100, Ed. Born, G. V. R. et al, Springer Verlag). The active compounds which may be transported are, in particular, those used for the treatment or prevention of the above-mentioned diseases.

The pharmaceutical compositions according to the present invention can thus be used as medicaments for the above-mentioned therapeutic applications.

The experimental section hereinafter gives examples of preparation of products of formula (I). These examples illustrate the invention without limiting it in any way.

As mentioned hereinafter, the compounds of formula (I) may be obtained by starting from compounds of formula (II). These compounds of formula (II) may be obtained as described above, and as shown in the three methods of synthesis described below:

Method I:

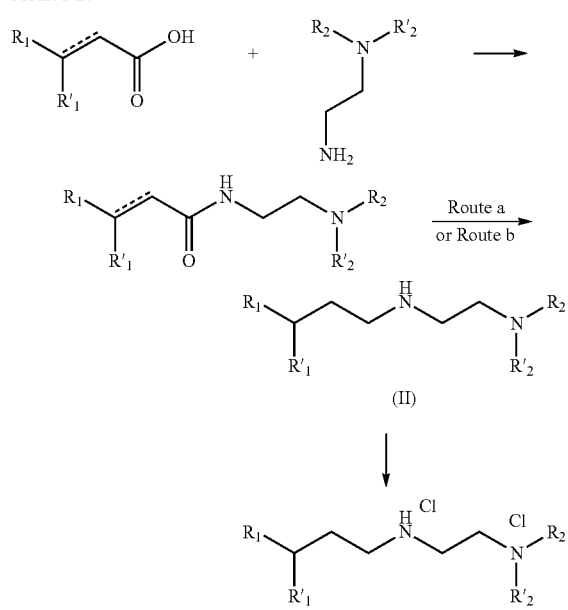

Method II:

Method IIa: Single bond
Method IIb: Double bond

Method III:

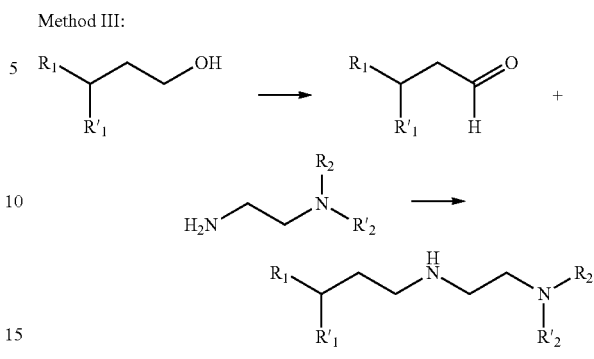

Method IV:

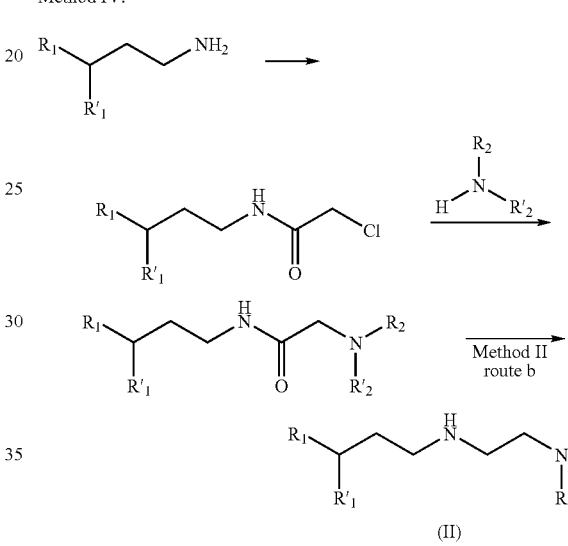

The preparation of 3,3-diphenyl-propyl)(2-morpholin-4-yl-ethyl)-amine of formula (II) by methods I, II and III will be described hereinafter by way of example:

Method I: Alkylation

Preparation of 3,3-(diphenylpropyl)(2-morpholin-4-yl-ethyl)amine 35 g (165.6 mmol) of gem-diphenylpropylamine, 700 mL of acetonitrile, 6.2 g (33.1 mmol) of N-(2-chloroethyl) morpholine in hydrochloride form, 4.62 ml (33.1 mmol) of triethylamine and 9.16 g (66.24 mmol) of potassium carbonate are introduced in succession into a flask placed under argon and topped by a condenser. The reaction medium is heated under reflux for 5 days. The acetonitrile is eliminated on a rotary evaporator and the mixture is taken up with water and dichloromethane. The aqueous phase is extracted with dichloromethane, then the organic phases are combined, washed with a saturated NaCl solution and dried over MgSO$_4$. After evaporation, a mixture of the desired product and gem-diphenylpropylamine introduced in a large excess is obtained.

Purification of the crude reaction product by flash chromatography over silica gel (elution gradient: heptane 100%, $CH_2Cl_2$ 100% then $CH_2Cl_2$/MeOH/$NH_4OH$ 98/2/0.1 to 90/10/0.1) leads to 7.18 g of secondary amine (yield=67%).

Method II: Peptide Coupling and Reduction

Preparation of
N-(2-morpholin-4-ylethyl)-3,3-diphenylpropionamide 25 g (0.11 mmol, 1 eq.) of 3,3-diphenyl propanoic acid are dissolved in 75 mL of $CH_2Cl_2$ under argon. 16.42 g (0.12 mmol, 1.1 eq.) of HOBt and 23.30 g (0.12 mmol, 1.1 eq.) of EDC, HCl are added. The solution is stirred for 45 min. at room temperature then 16 mL (0.12 mmol, 1.1 eq.) of 4-(2-aminoethyl)morpholine are added dropwise. The solution is stirred for 1 hour 30 min. at room temperature and the colour of the mixture changes from yellow to orange.

Some 0.1 M HCl is added to the mixture. The organic phase is washed twice with 0.1 M HCl, three times with a saturated sodium bicarbonate solution and once with brine. It is then dried over $MgSO_4$, filtered and concentrated. The solid obtained is recrystallised in 40 mL of AcOEt. 32.43 g of a white powder are recovered (yield=87%).

Preparation of
3,3-(diphenylpropyl)(2-morpholin-4-ylethyl)amine

Route a: Reduction by $LiAlH_4$ 10 g (29.55 mmol, 1 eq.) of N-(2-morpholin-4-ylethyl)-3,3-diphenylpropionamide are dissolved in a 4/1 mixture of diethyl ether and THF under argon. 65 mL (35.45 mmol, 2.2 eq.) of 1 M $LiAlH_4$ in THF are added dropwise and the mixture is heated under reflux (50° C.) for 21 hours. 4.9 mL of water, 2.5 mL of 15% aqueous NaOH then a further 12.3 mL of water are added to the reaction mixture. After stirring for 15 min, the aqueous phase is extracted with $CH_2Cl_2$. The organic phase is subsequently washed with water then brine, dried over $MgSO_4$, filtered and concentrated. The crude mixture obtained is filtered over silica (eluent: 9/1/0.1 $CH_2Cl_2$/MeOH/$NH_4OH$) and an amorphous paste is recovered (9.6 g, yield=100%).

Route b: Reduction by $LiAlH_4$/$AlCl_3$ 27.6 g (0.21 mol, 0.5 eq.) of $AlCl_3$ are added batchwise to a solution of 140 g (0.42 mol, 1.0 eq.) of N-(2-morpholin-4-ylethyl)-3,3-diphenylpropionamide in 3.5 L of THF (slightly exothermic addition) under an inert atmosphere and at 0° C. in a 5 L flask. Once the medium has become homogeneous, still at 0° C., 23.6 g (0.62 mol, 1.5 eq.) of $LiAlH_4$ are added in small batches so that the temperature does not exceed 5° C. (initially a markedly exothermic addition). The temperature of the reaction medium is then raised progressively under reflux of the THF and heating is continued for 1 hour.

The mixture is then cooled to 0° C. and 1 L of water is added carefully (initially dropwise). It is important to observe the prescribed dilutions because the medium thickens markedly during this hydrolysis. The resultant suspension is filtered, and the salts are rinsed with 2 L of ethyl acetate. All of the filtrates are placed in a 10 L reactor and decanted. The aqueous phase is extracted again with 2 L of ethyl acetate and the organic fractions are collected, washed with 2 L of a saturated aqueous solution of NaCl and concentrated under reduced pressure. The oil thus obtained is taken up in 1 L of ethyl acetate, dried over sodium sulphate, filtered and concentrated until dry under reduced pressure to lead to the obtaining of 130 g of a yellow oil.

Purification is carried out during salification, as follows: 500 mL (1 mol, 2.5 eq.) of a 2.5 M solution of hydrochloric acid are added to the foregoing oil and the mixture is concentrated under reduced pressure. 500 mL of ethanol are added and the mixture is concentrated again. This last procedure is carried out 3 more times and the salt crystallises during this treatment. The last time the ethanol is concentrated to a total mass of 480 g (corresponding to 2 parts of ethanol) and the suspension obtained is cooled to 0° C., then filtered and washed with 150 mL of cold ethanol. After drying under a vacuum created by a vane pump, 122 g (72%) of (3,3-diphenylpropyl)(2-morpholin-4-ylethyl)amine dihydrochloride are obtained in the form of a white crystalline solid.

Method IIa: Peptide Coupling and Reduction

The unsaturated acid analogues 3 can be synthesised in accordance with the following reaction scheme:

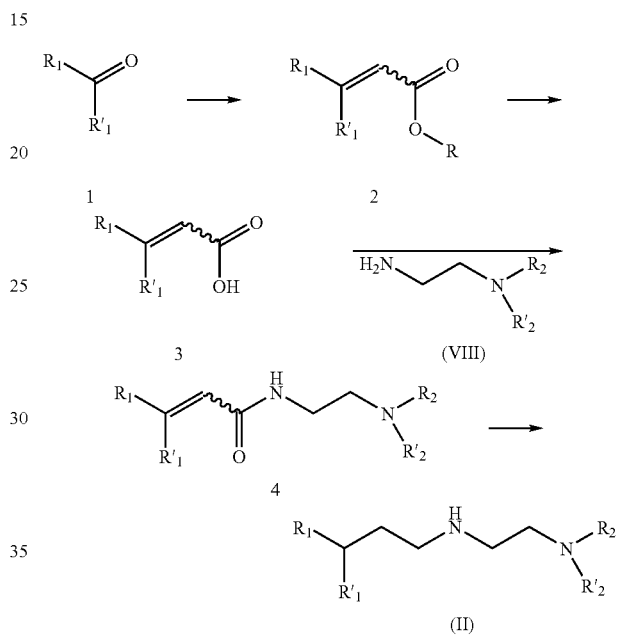

Preparation of Unsaturated Acids, 3

1 eq. of acetophenone derivative 1 is dissolved in dry THF in a flask equipped with a condenser, under argon. 1.3 eq. of triethylphosphonoacetate are introduced and 1.3 eq. of 60% NaH in oil are added batchwise to the solution. The mixture is heated under reflux for 3 hours at 70-80° C. 1 eq. of triethylphosphonoacetate and 1 eq. of 60% NaH in oil are added to the medium. The mixture is stirred for 2 hours at 70-80° C. Water is added, then the THF is concentrated. The basic aqueous phase is extracted with AcOEt and the organic phase is washed with brine, dried over $MgSO_4$, filtered and concentrated. The crude product obtained is subjected to chromatography over silica gel to give the conjugate ester 2 in the form of crystals (yield approximately 70%).

1 eq. of 2 is dissolved in EtOH, 2 eq. of 1 N sodium hydroxide are added and the mixture is stirred for 45 min. at 60° C. The reagent dissolves completely while hot. The ethanol is concentrated, the residue is taken up in the water and AcOEt is added. The aqueous phase is acidified to pH 3, then extracted with AcOEt. The organic phase is washed with brine, dried, filtered and concentrated to give the conjugate acid 3 quantitatively.

Preparation of Unsaturated Amide Derivatives, 4

1 eq. of propanoic acid analogue 3 is dissolved in a 9/1 mixture of DCM/DMF under Ar, 1.1 eq. of HOBt and 1.1 eq. of EDC, HCl are then introduced in succession. The mixture is stirred for 30 min. at room temperature and 1.1 eq. of aminoethylamine of formula (VIII) are added. The mixture is stirred for 5 hours at room temperature. 0.7 eq. of aminoethylamine of formula (VIII) and 0.7 eq. of EDC, HCl are added. The mixture is stirred for one night at room temperature. Dichloromethane is added, the organic phase is washed with a 0.1 N HCl solution, with a saturated NaHCO$_3$ solution then finally with brine. It is dried over MgSO$_4$, filtered and concentrated. The crude product obtained is subjected to chromatography over silica gel and may be recrystallised. The yields are approximately 75%.

Reduction by LiAlH$_4$/AlCl$_3$ (Synthesis of the Amine of Formula (II))

1 eq. of the unsaturated amide analogue 4 is dissolved in THF in a 250 mL flask placed in an argon atmosphere. After cooling the solution to 0° C., 0.5 eq. of AlCl$_3$ is added batchwise. Once the medium has become homogeneous, 2.5 eq. of LiAlH$_4$ in a 1 M solution in THF are added slowly. The mixture is kept at 0° C. during the addition, is then heated under reflux (60° C.) for 1 hour and cooled to 0° C. 7 mL of water are then added very slowly to the solution to avoid a violent reaction. The salts are filtered and rinsed with ethyl acetate. The filtrate is recovered, water is added and the aqueous phase is extracted with ethyl acetate. The organic phase is washed once with water then once with brine, is subsequently dried over MgSO$_4$, filtered and concentrated. The paste obtained is subjected to chromatography over silica gel in order to obtain the amine of formula (II) in a yield of approximately 80%.

Method III: Oxidation in Aldehyde and Reductive Amination

Preparation of 3,3-diphenylpropionaldehyde 4.69 mL (23.55 mmol, 1 eq.) of 3,3-diphenylpropanol are dissolved in 100 mL of CH$_2$Cl$_2$ under argon. 10.5 g (24.73 mmol, 1.05 eq.) of Dess Martin Periodinane (1,1,1-triacetoxy-1,1-dihydro-1,2-benziodoxol-3(1H)-one) are added to the mixture and the solution is stirred for 1 hour 30 min at 0° C. 100 mL of 2 M sodium hydroxide and 100 mL of CH$_2$Cl$_2$ are then added. The organic phase is washed with 2 M sodium hydroxide (twice), with water (twice), dried over MgSO$_4$, filtered and concentrated. The crude reaction product is subjected to chromatography over silica gel (eluent: 5/1 heptane/AcOEt). An oil which crystallises in the form of a white product is recovered (4.76 g, yield=96%).

Preparation of 3,3-(diphenylpropyl)(2-morpholin-4-ylethyl)amine 200 mg (0.95 mmol, 1 eq.) of 3,3-diphenylpropionaldehyde are dissolved in 2 mL of EtOH and 187 µL (1.43 mmol, 1.5 eq.) of 4-(2-aminoethyl)morpholine are added to the medium under argon. Once 20 mg (0.09 mmol, 1 eq.) of 10% Pd/C have been added, the reaction is placed under H$_2$, atmospheric pressure and the mixture is stirred for 16 hours at room temperature. The catalyst is removed by filtration over Celite®. A saturated sodium bicarbonate solution is added and the aqueous phase is extracted with AcOEt. The organic phase is subsequently washed with brine, dried over MgSO$_4$, filtered and concentrated. The crude reaction product is subjected to chromatography over alumina (eluent: 1/1 heptane/CH$_2$Cl$_2$) to give 251 mg of amine (yield=81%).

The preparation of 3,3-diphenylpropyl)(2-thiomorpholin-4-ylethyl)amine of formula (II) by method IV is described hereinafter by way of example:

Method IV: Alkylation and Amide Reduction

Preparation of N-chloromethyl-3,3-diphenylpropionamide 1 g (4.73 mmol, 1 eq.) of 3,3-diphenylpropylamine and 732 µL (5.21 mmol, 1.1 eq.) of triethylamine are diluted in 30 mL of DCM at 0° C. under argon. 300 µL (3.77 mmol, 0.8 eq.) of chloroacetyl chloride are added dropwise. White fumes form then gradually dissipate. The mixture is stirred for 45 min. at 0° C., the solution becomes red. A dilute HCl solution is added then the aqueous phase is extracted with DCM. The organic phase is washed once with water then once with brine, dried over MgSO$_4$, filtered and concentrated. The product is obtained in the form of oil (m=1.36 g, yield=100%).

Preparation of N-(3,3-diphenylpropyl)-2-thiomorpholin-4-ylacetamide 700 mg (2.43 mmol, 1 eq.) of N-chloromethyl-3,3-diphenylpropionamide, 508 µL (2.92 mmol, 1.2 eq.) of diisopropylethylamine, 245 µL (2.43 mmol, 1 eq.) of thiomorpholine and 5 mL of DMF are introduced into a sealed tube. The mixture is heated for 8 min. by microwave at 180° C. A saturated sodium bicarbonate solution is added to the mixture and the aqueous phase is extracted with ethyl acetate. The organic phase is washed with brine, dried, filtered concentrated. The solid obtained is recrystallised in diethyl ether (m=769 mg, yield=89%).

Preparation of (3,3-diphenylpropyl)(2-thiomorpholin-4-ylethyl)amine of formula (II)

Obtained from N-(3,3-diphenyl-propyl)-2-thiomorpholin-4-yl-acetamide by the above-described Method II, route b (AlCl$_3$+LiAlH$_4$).

The products of formula (IV) may be prepared by one of the following methods.

I: Route 1)—by Modification of Anilines:

a) by Esterification Starting from an Acid

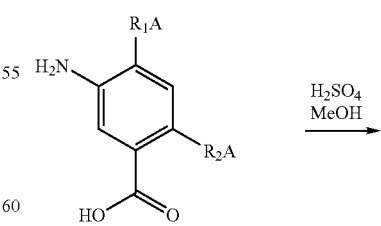

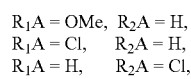

R$_1$A = OMe, R$_2$A = H,
R$_1$A = Cl, R$_2$A = H,
R$_1$A = H, R$_2$A = Cl,

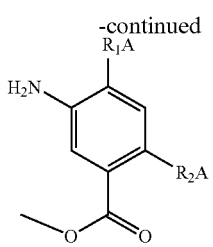

R₁A = OMe, R₂A = H, → Example 16
R₁A = Cl,   R₂A = H, → Example 17
R₁A = H,    R₂A = Cl → Example 18

Preparation of 5-amino-2-chlorobenzoic acid methyl ester, R₁A=H, R₂A=Cl:

5-amino-2-chlorobenzoic acid (87 mg, 0.5 mmol) is dissolved in 5 mL of MeOH and 0.1 mL of concentrated $H_2SO_4$ in a 10 mL flask. The solution is heated under reflux for 16 hours. The solvent is evaporated and the residue is taken up in dichloromethane. Water is added and the aqueous phase is extracted with dichloromethane. The organic phase is washed with brine, dried over $MgSO_4$, filtered and concentrated. The product is obtained in solid form (m=89 g, yield=94%).

5-amino-2-chloro-benzoic acid methyl ester
MS: 185.9⁺ (M+H)⁺
TLC: Rf: 0.26 (eluent: 4/1 dichloromethane/ethyl acetate)
3-amino-4-methoxy benzoic acid methyl ester
MS: 181.9⁺ (M+H)⁺
TLC: Rf: 0.58 (eluent: 4/1 dichloromethane/ethyl acetate)
3-amino-4-chlorobenzoic acid methyl ester
MS: 185.9⁺ (M+H)⁺
TLC: Rf: 0.31 (eluent: 4/1 dichloromethane/ethyl acetate)

b) by Oxidation of a Thiomethyl Group:

Preparation of 3-methanesulphonylphenylamine

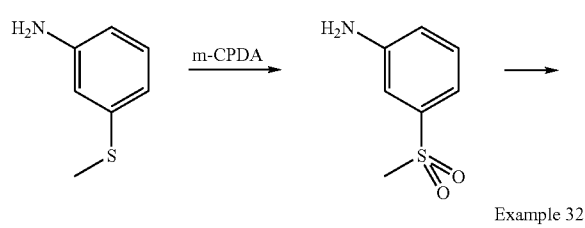

Example 32

150 mg (1.22 mmol, 1 eq.) of (3-methylmercapto)aniline are dissolved in 3 mL of chloroform. 420 mg (2.43 mmol, 2 eq.) of meta-chloroperbenzoic acid are added to this solution. The mixture is stirred for 1 hour 30 min. at 0° C. A saturated $NaHCO_3$ solution is added and the aqueous phase is extracted with DCM. The organic phase is washed with brine, dried over $MgSO_4$, filtered and concentrated. The residue is purified by chromatography over silica gel (eluent: DCM/AcOEt 8/1 to 6/1) to give 30 mg of product (yield=14%).

¹H NMR (400 MHz, CDCl₃): ppm 3.02 (s, 3H, CH3), 3.73-4.22 (m, 2H, NH2), 6.89 (d, 1H, aromatic H), 7.18-7.23 (m, 3H, aromatic H)

MS: 172.09⁺ (M+H)⁺, 213.13⁺ (M+H+CH₃CN)⁺
TLC: Rf=0.31 (eluent: DCM/AcOEt 4/1)

c) by Alkylation of a Thiol:

Preparation of 3-ethylsulphanylphenylamine, 5 and of 3-isopropylsulphanylphenylamine, 6

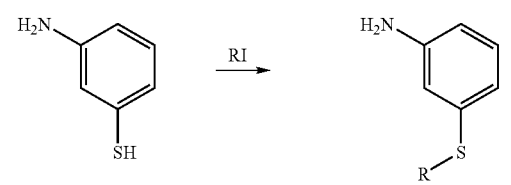

R = Et    5 → Example 33
R = iPr   6 → Example 34

300 mg (2.40 mmol, 1 eq.) of 3-aminothiophenol are dissolved in 3 mL of DMF. 96 mg (2.40 mmol, 1 eq.) of 60% NaH in oil are added then, at 0° C., 192 µL (2.40 mmol, 1 eq.) of iodoethane are added for 5 and 239 µL (2.40 mmol, 1 eq.) of 2-iodopropane are added for 6.

The solution is stirred at room temperature for 24 hours and water is added. The aqueous phase is extracted with ethyl acetate. The organic phase is washed with brine, dried over $MgSO_4$, filtered and concentrated. The residue is purified by chromatography over silica gel (eluent: heptane/AcOEt 6/1 and 4/1) (5: m=220 mg, yield=60%, 6: m=140 mg, yield=35%).

3-ethylsulphanyl-phenylamine, 5

1H NMR (400 MHz, CDCl₃): ppm 1.33 (t, 3H, CH3), 2.94 (q, 2H, CH2), 3.50-3.75 (m, 2H, NH2), 6.52 (d, 1H, aromatic H), 6.68 (s, 1H, aromatic H), 6.75 (d, 1H, aromatic H), 7.09 (t, 1H, aromatic H).

TLC: Rf=0.15 (eluent: heptane/AcOEt 4/1)

3-Isopropylsulphanyl-phenylamine, 6

¹H NMR (400 MHz, CDCl₃): ppm 1.32 (d, 6H, CH3), 3.38 (sept, 1H, CH), 3.56-3.72 (m, 2H, NH2), 6.56 (d, 1H, aromatic H), 6.76 (s, 1H, aromatic H), 6.82 (d, 1H, aromatic H), 7.10 (t, 1H, aromatic H).

TLC: Rf=0.19 (eluent: heptane/AcOEt 4/1)

II: Route 2)—Starting from Substituted Nitro-benzenes:

Preparation 1: Synthesis of 4-chloro-3-methylsulphanyl-phenylamine, 9:

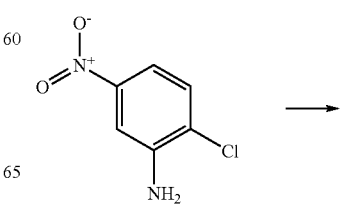

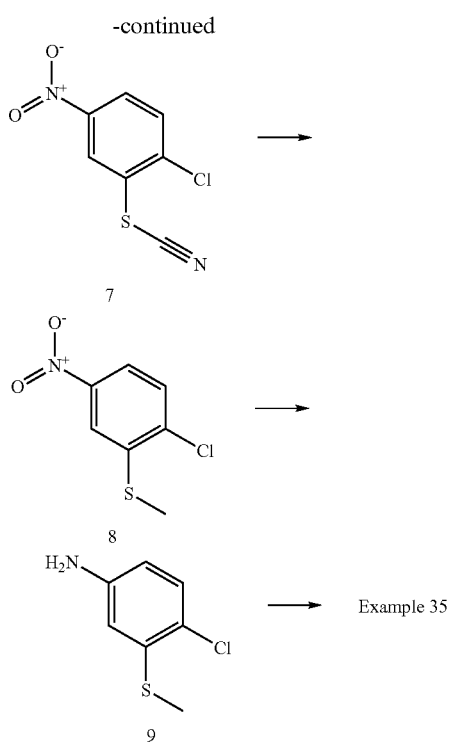

a): Preparation of 1-chloro-4-nitro-2-thiocyanatobenzene, 7

500 mg (2.90 mmol, 1 eq.) of 2-chloro-5-nitrophenylamine are dissolved in 5 mL of HCl 6 N. Once a homogeneous paste has been obtained, the mixture is cooled to 0° C., and a solution of 224 mg (3.24 mmol, 1.12 eq.) of sodium nitrite in 0.5 mL of iced water is added in 15 min. The temperature is kept between 0° C. and −3° C. during addition. After addition, the mixture is stirred for a further 30 min. Then, this mixture is added to a solution containing 0.4 g (4.12 mmol, 1.42 eq.) of KSCN and 0.35 g (2.88 mmol, 1 eq.) of CuSCN in 1 mL of water. Addition takes 20 min. at 25° C. The yellow solution becomes fuming red and a precipitate is formed. The mixture is stirred for one night at room temperature. The precipitate is filtered and washed with dichloromethane (6×3 mL). The organic phase is recovered and washed twice with water, dried over MgSO$_2$, filtered then concentrated. The crude product obtained is recrystallised in absolute EtOH (m=446 mg, yield=72%).

$^1$H NMR (400 MHz, CDCl$_3$): ppm 7.69 (d, 1H, aromatic H), 8.23 (d, 1H, aromatic H), 8.61 (s, 1H, aromatic H).

TLC: Rf: 0.26 (eluent: DCM/AcOEt 1/1)

b) Preparation of 1-chloro-2-methylsulphanyl-4-nitrobenzene, 8

324 mg (1.51 mmol, 1 eq.) of 7 are dissolved in 15 mL of MeOH, and 170 mg (3.02 mmol, 2 eq.) of potassium carbonate are added. The mixture is heated under reflux for 20 min. then cooled to room temperature. 151 μL (2.42 mmol, 1.6 eq.) of methyl iodide are added. The mixture is stirred for 1 hour at room temperature, then 47 μL (0.75 mmol, 0.5 eq.) of methyl iodide are added. The solution is stirred for one night at room temperature. Once the water has been added, the insoluble matter formed is filtered then washed with water. The crude reaction product is subjected to chromatography over silica gel (eluent: 10/1 heptane/DCM) (m=215 mg, yield=70%).

$^1$H NMR (400 MHz, CDCl$_3$): ppm 2.60 (s, 3H, SCH$_3$), 7.52 (d, 1H, aromatic H), 7.95 (d, 1H, aromatic H), 8.01 (s, 1H, aromatic H).

TLC: Rf: 0.43 (eluent: DCM/heptane 1/1)

Preparation of 4-chloro-3-methylsulphanylphenylamine, 9

204 mg (1 mmol, 1 eq.) of 8 are dissolved in 2 mL of TFA. The solution is cooled to 0° C. and 123 mg (3.41 mmol, 3.4 eq.) of zinc powder are progressively added. The ice bath is removed and stirring is continued for 30 min. The mixture is rendered basic by adding an aqueous solution at 0° C. The aqueous solution is extracted with DCM and the organic phase is washed with brine, dried over MgSO$_4$, filtered and concentrated. The crude reaction product is subjected to chromatography over silica gel (eluent: 1/1 heptane/DCM) (m=150 mg, yield=85%).

$^1$H NMR (400 MHz, CDCl$_3$): ppm 2.45 (s, 3H, SCH$_3$), 3.60-3.80 (m, 2H, NH$_2$), 6.42 (d, 1H, aromatic H), 6.49 (s, 1H, aromatic H), 7.11 (d, 1H, aromatic H).

MS: 174.10$^+$ (M+H)$^+$, 215.13$^+$ (M+H+CH$_3$CN)$^+$

TLC: Rf=0.21 (eluent: DCM/heptane 2/1)

Preparation 2: Preparation of 3-oxazol-5-ylphenylamine and 4-chloro-3-oxazol-5-yl-phenylamine for the synthesis of oxazole derivatives:

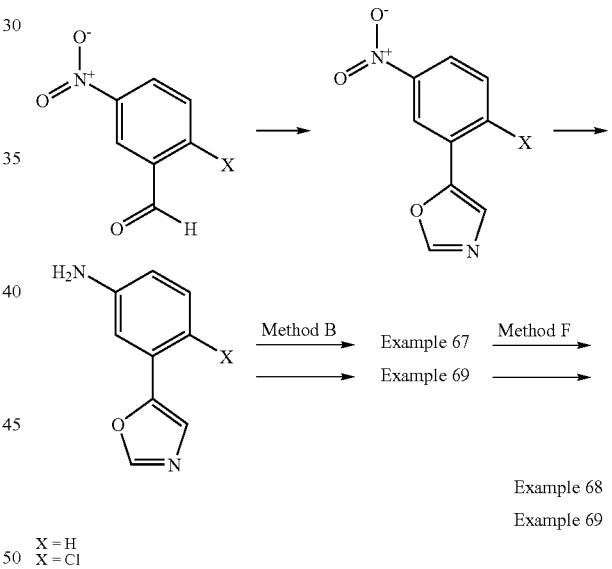

X = H
X = Cl

Preparation of 5-(3-nitrophenyl)oxazole 2.04 g (13.5 mmol, 1 eq.) of 3-nitrobenzaldehyde, 2.90 g (14.85 mmol, 1.1 eq.) of tosylmethyl isocyanide, 200 mL of MeOH and 200 mL of DME are introduced into a 1 L flask. 25 g of Amberlyst A26 OH— resin are added and the mixture is heated under reflux for 1 hour. The reaction medium is cooled to room temperature, then the resin is filtered over a frit and rinsed with methanol. After concentration to dryness, 2.56 g (yield=100%) of 5-(3-nitrophenyl)oxazole are obtained. The product is used without subsequent purification.

$^1$H NMR (400 MHz, CDCl$_3$): ppm 7.54 (s, 1H, aromatic H), 7.65 (t, 1H, aromatic H), 8.00 (d, 1H, aromatic H), 8.03 (s, 1H, H$_{oxazole}$), 8.22 (d, 1H, aromatic H), 8.53 (s, 1H, H$_{oxazole}$).

MS: 191$^+$ (M+H)$^+$

The product 5-(2-chloro-5-nitrophenyl)oxazole was prepared by the procedure described above.

$^1$H NMR (400 MHz, CDCl$_3$): ppm 7.69 (d, 1H, aromatic H), 7.95 (s, 1H, aromatic H), 8.08 (s, 1H, aromatic H), 8.15 (d, 1H, aromatic H), 8.74 (s, 1H, aromatic H).

MS: 225.19$^+$ (M+H)$^+$, 266.25$^+$ (M+H+CH$_3$CN)$^+$

TLC: Rf=0.18 (eluent: heptane/AcOEt 4/1)

Preparation of 3-oxazol-5-ylphenylamine 1 g (5.26 mmol, 1 eq.) of 5-(3-nitrophenyl)oxazole and 10 mL of TFA are introduced into a 1 L flask. 1 g of zinc is carefully added in a plurality of batches. The mixture is stirred for 2 hours at room temperature then is poured over ice. Sodium hydroxide is slowly added until the medium becomes basic, and the medium is extracted with diethyl ether. The organic phase is washed with a 1 M solution of HCl and the impurities are extracted with diethyl ether. The aqueous phase is again basified with sodium hydroxide and the product is extracted with diethyl ether. The organic phases are combined, dried over MgSO$_4$ and filtered. After concentration to dryness, 700 mg (yield=83%) of aniline 3-oxazol-5-yl-phenylamine are obtained, in the form of a beige solid. The product is used without subsequent purification.

$^1$H NMR (400 MHz, CD$_3$OD): ppm 6.74 (d, 1H, aromatic H), 7.05 (d, 1H, aromatic H), 7.09 (s, 1H, aromatic H), 7.18 (t, 1H, aromatic H), 7.41 (s, 1H, H$_{oxazole}$), 8.22 (s, 1H, H$_{oxazole}$).

MS: 161$^+$ (M+H)$^+$ 4-chloro-3-oxazol-5-ylphenylamine was prepared by the procedure described above.

$^1$H NMR (400 MHz, CD$_3$OD): ppm 6.73 (d, 1H, aromatic H), 7.17-7.26 (m, 2H, aromatic H), 7.72 (s, 1H, aromatic H), 8.29 (s, 1H, aromatic H).

MS: 195.14$^+$ (M+H)$^+$, 236.18$^+$ (M+H+CH$_3$CN)$^+$

TLC: Rf=0.32 (eluent: heptane/AcOEt 1/1)

Preparation 3: Synthesis of 4-chloro-3-(2-methyl-2H-tetrazol-5-yl)phenylamine (isomer 1) and 4-chloro-3-(1-methyl-1H-tetrazol-5-yl)phenylamine (isomer 2), for the synthesis of methyltetrazole derivatives

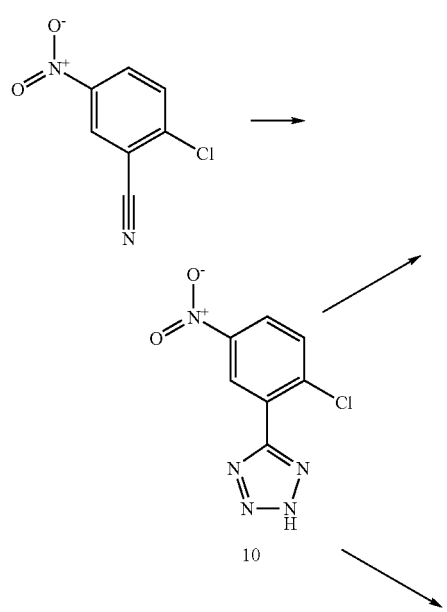

-continued

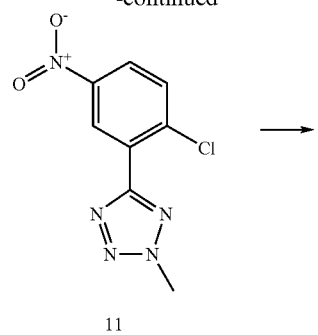

11

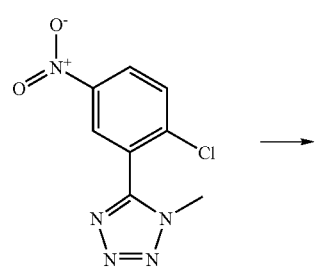

12

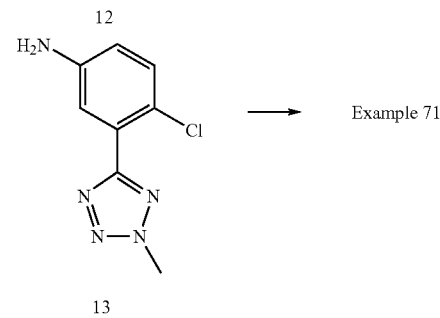

13 → Example 71

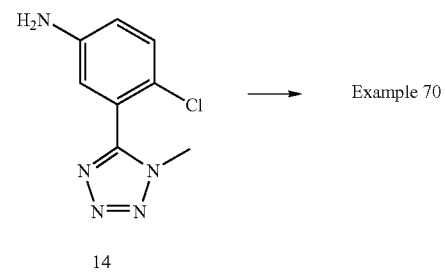

14 → Example 70

Preparation of 5-(2-chloro-5-nitrophenyl)-2H-tetrazole 10

137 mg (0.750 mmol, 1 eq.) of 2-chloro-5-nitrobenzonitrile are dissolved in 8 mL of toluene, and 411 μl (1.5 mmol, 2 eq.) of tributyl tin azide are added to the reaction mixture. Then the mixture is heated under reflux of the toluene for one night. As the reaction is incomplete, 205 μl (0.75 mmol, 1 eq.) of azide are again added and the mixture is stirred under reflux for a further 5 hours. The mixture is then concentrated and 10 mL of HCl 2 N in Et$_2$O are added, the precipitate formed is filtered and washed with pentane and diethyl ether. 216 mg of product 10 are obtained (yield=64%).

¹H NMR (400 MHz, CD₃OD): ppm 7.94 (d, 1H, aromatic H), 8.43 (d, 1H, aromatic H), 8.78 (s, 1H, aromatic H)

MS: 224.12⁻ (M–H)⁻

TLC: Rf=0.28 (eluent: DCM/MeOH 9/1)

Preparation of 5-(2-chloro-5-nitrophenyl)-2-methyltetrazole 11 and 5-(2-chloro-5-nitro-phenyl)-1-methyltetrazole 12

100 mg (0.382 mmol, 1 eq.) of 5-(2-chloro-5-nitrophenyl)-2H-tetrazole 10 are dissolved in 0.7 mL of CH₃CN and 0.2 mL of DMF. 29 µl (0.573 mmol, 1.5 eq.) of CH₃I and 63 mg (0.458 mmol, 1.2 eq.) of K₂CO₃ are added. The mixture is heated under reflux for 1 hour. The mixture is neutralised at room temperature with water and a saturated sodium bicarbonate solution. The aqueous phase is extracted with CH₂Cl₂, the organic phases collected are washed with brine, dried over MgSO₄, filtered and concentrated. The crude reaction product is subjected to chromatography over silica gel (eluent: gradient 10/1 to 1/1 heptane/AcOEt) to give 150 mg of isomer 11 and 66 mg of isomer 12 (total yield=76%).

5-(2-chloro-5-nitrophenyl)-2-methyltetrazole (isomer 1), 11

¹H NMR (400 MHz, CDCl3): ppm 4.51 (s, 3H, CH3), 7.75 (d, 1H, aromatic H), 8.28 (d, 1H, aromatic H), 8.90 (s, 1H, aromatic H).

TLC: Rf=0.55 (eluent: heptane/AcOEt 1/1)

5-(2-chloro-5-nitrophenyl)-1-methyltetrazole (isomer 2), 12

¹H NMR (400 MHz, CDCl₃): ppm 4.07 (s, 3H, CH3), 7.83 (d, 1H, aromatic H), 8.38-8.49 (m, 2H, aromatic H).

TLC: Rf=0.35 (eluent: heptane/AcOEt 1/1)

The products 13 and 14 are obtained by reduction of the products 11 and 12 with zinc, in TFA (same procedure as for the synthesis of 4-chloro-3-methylsulphanyl-phenylamine, 9 from 1-chloro-2-methylsulphanyl-4-nitrobenzene, 8).

4-chloro-3-(2-methyl-2H-tetrazol-5-yl)phenylamine (isomer 1), 13

¹H NMR (400 MHz, CDCl₃): ppm 3.20-4.00 (m, 2H, NH2), 4.44 (s, 3H, CH3), 6.72 (d, 1H, aromatic H), 7.24-7.32 (m, 2H, aromatic H).

TLC: Rf=0.29 (eluent: heptane/AcOEt 1/1)

4-chloro-3-(1-methyl-1H-tetrazol-5-yl)-phenylamine (isomer 2), 14

¹H NMR (400 MHz, CDCl₃): ppm 3.30-3.90 (m, 2H, NH2), 4.01 (s, 3H, CH3), 6.79 (s, 1H, aromatic H), 6.85 (d, 1H, aromatic H), 7.30 (d, 1H, aromatic H).

TLC: Rf=0.16 (eluent: heptane/AcOEt 1/1)

The products of Examples 70 and 71 are obtained from products 13 and 14 by employing method "B" below.

As mentioned hereinafter in the Examples, the products of formula (I) can be obtained in 5 different ways (hereinafter called Methods A), B), C), D) and E)):

Method A). By action of an isocyanate of formula (A) on an amine of formula (II).

Method B). By action of triphosgene on a product of formula (IV) and addition of an amine of formula (II).

Method C). By action of triphosgene on an amine of formula (Ii) and addition of a product of formula (IV).

Method D). By action of carbonyl diimidazole (CDI) on a product of formula (IV) and addition of an amine of formula (II).

Method E). By action of diphenylphosphoryl azide (DPPA) on a product of formula (A') and addition of an amine of formula (II).

Method A:

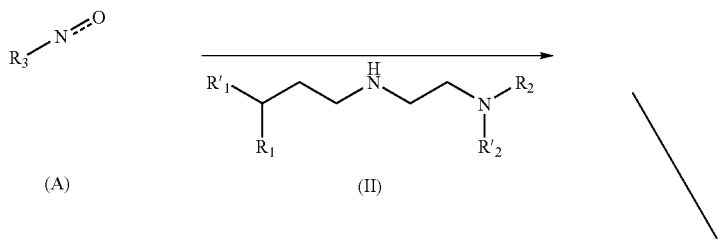

Method B:

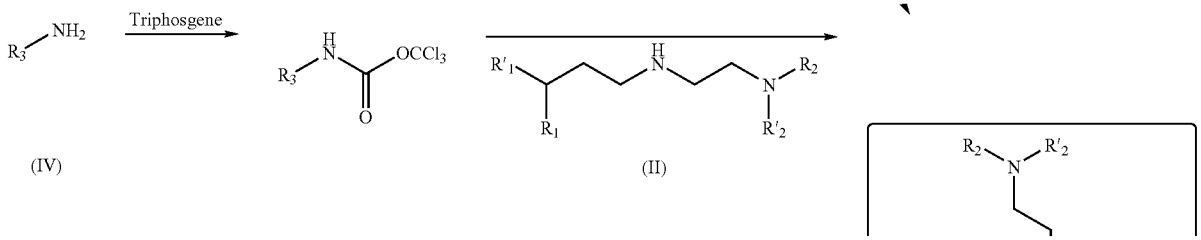

-continued

Method C:

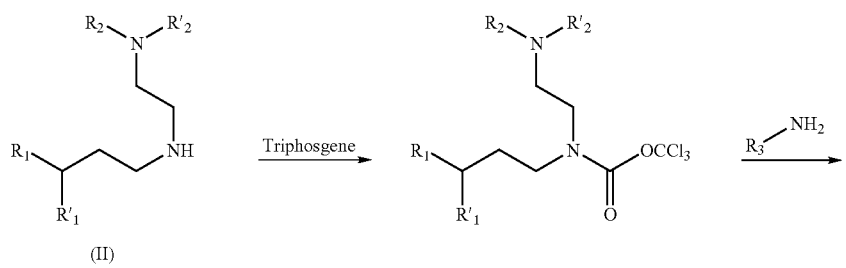

Method D:

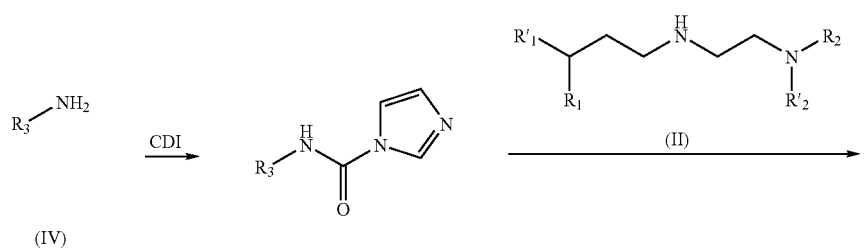

Method E followed by A:

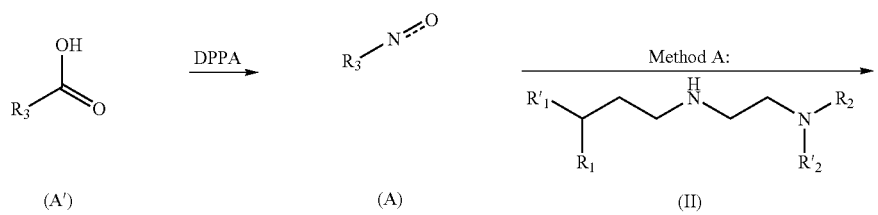

The methods are described by way of example with 3,3-(diphenylpropyl)(2-morpholin-4-yl-ethyl)amine as the amine of formula (II):

Method A). By action of an isocyanate on 3,3-diphenyl-propyl-(2-morpholin-4-yl-ethyl)amine or other secondary amine.

1 eq. of 3,3-(diphenylpropyl)(2-morpholin-4-yl-ethyl)amine of formula (II) are dissolved in dichloromethane under an argon atmosphere in a 50 mL flask. 1.2 eq. of isocyanate of formula (A) are then added. The mixture is stirred for 2 hours at room temperature, then taken up in water. The aqueous phase is extracted with dichloromethane, washed with brine, dried over $MgSO_4$, filtered and concentrated. The oil obtained is subjected to chromatography over silica gel in order to obtain the desired urea in yields of approximately 80%.

Method B). By action of triphosgene on a product of formula (IV) and addition of 3,3-diphenylpropyl-(2-morpholin-4-yl-ethyl)amine or other secondary amine of formula (II).

0.6 eq. of triphosgene, 1 mL of $CH_2Cl_2$, 1 eq. of product of formula (IV) in 2 mL of $CH_2Cl_2$ and 1.2 eq. of diisopropylethylamine are introduced in succession into a flask placed under argon. The mixture is stirred for 1 hour at room temperature. 1.5 eq. of 3,3-diphenyl-propyl(2-morpholin-4-yl-ethyl)amine dissolved in 2 mL of $CH_2Cl_2$ are then added, and stirring is maintained for one night. The reaction medium is neutralised by a saturated solution of $NaHCO_3$ and dichloromethane. The organic phases are combined, then washed with a saturated NaCl solution. After drying over $MgSO_4$, filtration and concentration to dryness, the crude reaction product is purified by chromatography over silica gel, leading to the desired urea of formula (II) in yields of from 44 to 90%.

Method C). By action of triphosgene on 3,3-diphenylpropyl(2-morpholin-4-ylethyl)-amine (or other secondary amine of formula (II) and addition of the product of formula (IV)).

The triphosgene (0.55 eq.) in solution in dichloromethane is introduced into a 10 mL flask under an argon atmosphere. 3,3-(Diphenylpropyl)(2-morpholin-4-ylethyl)amine (1 eq.) and DIEA (1.2 eq.) in solution in dichloromethane are introduced into a second 10 mL flask. The mixture of secondary amine+DIEA is added to the triphosgene solution at 0° C. Stirring is maintained for 1 hour at 0° C. then 1 hour at room temperature. The carbamoyl chloride thus formed is added to a mixture (of formula IV) $RNH_2$ (1.1 eq.)+DIEA (1.4 eq.) in dichloromethane at 0° C. Stirring is maintained for 1 hour at 0° C. then 20 hours at room temperature. Urea formation is controlled by TLC.

Once the reaction has ended, the aqueous phase is extracted with dichloromethane, and the combined organic phases are washed with brine then dried over $MgSO_4$ and finally evaporated.

The crude product thus obtained is purified by chromatography over a silica column or over a preparation plate with an eluent $CH_2Cl_2$/AcOEt or heptane/AcOEt, depending on the product obtained.

Method D). By action of CDI on a product of formula (IV) and addition of 3,3-diphenylpropyl-(2-morpholin-4-ylethyl) amine or other secondary amine of formula (II).

1.5 eq. of carbonyl diimidazole are dissolved in $CH_2Cl_2$, then 1 eq. of product of formula (IV), dissolved in $CH_2Cl_2$, is added dropwise under argon. A white precipitate appears. The suspension is stirred for 15 hours at room temperature. 1.2 eq. of 3,3-(diphenylpropyl)(2-morpholin-4-ylethyl)amine or other secondary amine of formula (II) in solution in $CH_2Cl_2$ are added to the reaction mixture. The solution, which has become clear again, is stirred for 5 hours at room temperature. A sodium bicarbonate solution is added and the aqueous phase is extracted with dichloromethane. The organic phase is washed with brine, dried over $MgSO_4$, filtered and concentrated. The crude product obtained is subjected to chromatography over silica gel.

Method E). By action of diphenylphosphoryl azide (DPPA) on a carboxylic acid of formula (A') to form an isocyanate of formula (A) and addition of 3,3-diphenylpropyl-(2-morpholin-4-ylethyl)amine or other secondary amine of formula (II).

1 eq. of carboxylic acid formula (A') are dissolved in toluene. 1.1 eq. of triethylamine are added. After checking the basicity of the medium, 1.05 eq. of diphenylphosphoryl azide (DPPA) are added to the medium. The mixture is heated to 80° C. for 2 hours then 1.2 eq. of (3,3-diphenylpropyl)(2-morpholin-4-ylethyl)amine or other secondary amine of formula (II) are added. Heating is maintained for 1 hour. The mixture is then left to return to room temperature and stirring is maintained for one night. A saturated $NaHCO_3$ solution is added and the aqueous phase is extracted with DCM. The organic phase is washed with brine, dried over $MgSO_4$, filtered and concentrated. The products are purified over an alumina column, and the yields are approximately 40%.

Non-limiting practical examples of the invention will now be described.

EXAMPLE 1

3-[3-(3,3-diphenylpropyl)-3-(2-morpholin-4-ylethyl) ureido]benzoic acid methyl ester

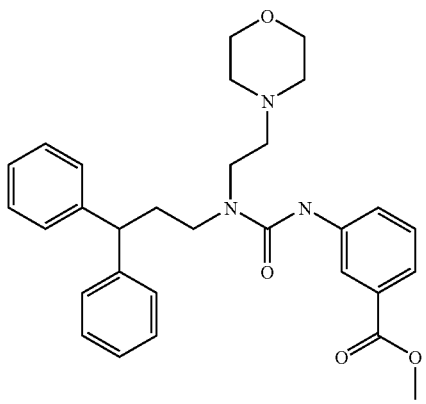

0.36 g (1.11 mmol, 1 eq.) of 3,3-(diphenylpropyl)(2-morpholin-4-ylethyl)amine are dissolved in 27 mL of dichloromethane under an argon atmosphere in a 50 mL flask. 0.232 g (1.31 mmol, 1.2 eq.) of 3-(methoxycarbonyl)phenylisocyanate are then added. The mixture is stirred for 2 hours at room temperature, then taken up in water. The aqueous phase is extracted with dichloromethane, washed with brine, dried over $MgSO_4$, filtered and concentrated. The oil obtained is subjected to chromatography over silica gel (eluent: 4/1 DCM/AcOEt) in order to obtain the expected product in the form of white crystals (0.46 g, yield=83%). This procedure is hereinafter called method "A".

$^1$H NMR (400 MHz, $CDCl_3$): ppm 2.41 (q, 2H, CH2), 2.73 (s1, 6H, 3×CH2), 3.32 (t, 2H, CH2), 3.39 (s1, 2H, CH2), 3.72 (s1, 4H, CH2), 3.93 (s, 3H, CH3), 3.98 (t, 1H, CH), 7.15-7.34 (m, 10H, aromatic H), 7.47 (t, 1H, aromatic H), 7.69 (d, 1H, aromatic H), 7.80 (d, 1H, aromatic H), 7.93 (s, 1H, aromatic H), 9.19-9.63 (s1, 1H, NH).

MS: $501.7^+$ $(M+H)^+$

TLC: Rf=0.15 (eluent: DCM/AcOEt 4/1)

EXAMPLE 2

3-(4-chlorophenyl)-1-(3,3-diphenylpropyl)-1-(2-morpholin-4-ylethyl)urea

Method "A" was used to prepare the title compound having the following formula:

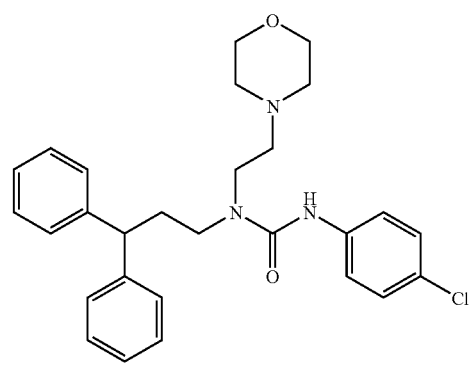

$^1$H NMR (400 MHz, $CDCl_3$): ppm 2.40 (q, 2H, $CH_2$), 2.61 (m, 6H, 3×$CH_2$), 3.29 (t, 2H, $CH_2$), 3.39 (m, 2H, $CH_2$), 3.77 (m, 4H, 2×$CH_2$), 3.96 (t, 1H, CH), 7.13-7.37 (m, 14H, aromatic H), 9.15 (bs, 1H, NH).

MS: $478^+$ $(M+H)^+$

EXAMPLE 3

3-(3-chlorophenyl)-1-(3,3-diphenylpropyl)-1-(2-morpholin-4-ylethyl)urea

Method "A" was used to prepare the title compound having the following formula:

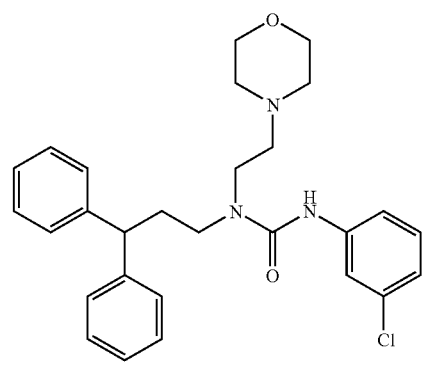

1H NMR (400 MHz, $CDCl_3$): ppm 2.40 (q, 2H, $CH_2$), 2.63 (m, 6H, 3×$CH_2$), 3.29 (t, 2H, $CH_2$), 3.40 (m, 2H, $CH_2$), 3.80

(m, 4H, 2×CH$_2$), 3.96 (t, 1H, CH), 6.98 (d, 1H, aromatic H), 7.15-7.36 (m, 12H, aromatic H), 7.47 (s, 1H, aromatic H), 9.22 (bs, 1H, NH).

MS: 478$^+$ (M+H)$^+$

EXAMPLE 4

3-(2-chlorophenyl)-1-(3,3-diphenylpropyl)-1-(2-morpholin-4-ylethyl)urea

Method "A" was used to prepare the title compound having the following formula:

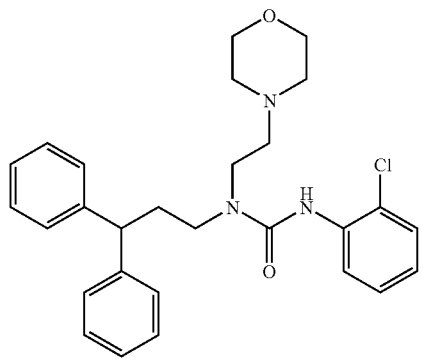

$^1$H NMR (400 MHz, CDCl$_3$): ppm 2.45 (q, 2H, CH$_2$), 2.56 (m, 6H, 3×CH$_2$), 3.34 (t, 2H, CH$_2$), 3.50 (m, 2H, CH$_2$), 3.69 (m, 4H, 2×CH$_2$), 3.99 (t, 1H, CH), 6.99 (t, 1H, aromatic H), 7.13-7.40 (m, 12H, aromatic H), 8.10 (d, 1H, aromatic H).
MS: 478$^+$ (M+H)$^+$

EXAMPLE 5

1-(3,3-diphenylpropyl)-3-(3-fluoro-5-trifluoromethylphenyl)-1-(2-morpholin-4-yl)urea Method "A" was used to prepare the title compound having the following formula:

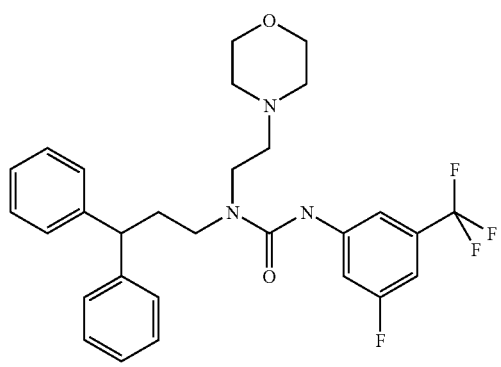

$^1$H NMR (400 MHz, CDCl$_3$): ppm 2.41 (q, 2H, CH$_2$), 2.67 (m, 6H, 3×CH$_2$), 3.32 (t, 2H, CH$_2$), 3.41 (m, 2H, CH$_2$), 3.80 (m, 4H, 2×CH$_2$), 3.98 (t, 1H, CH), 6.95 (d, 1H, aromatic H), 7.15-7.24 (m, 2H, aromatic H), 7.25-7.37 (m, 9H, aromatic H), 7.59 (d, 1H, aromatic H), 9.63 (bs, 1H, NH).

MS: 530$^+$ (M+H)$^+$

EXAMPLE 6

3-(3,4-dichlorophenyl)-1-(3,3-diphenylpropyl)-1-(2-morpholin-4-ylethyl)urea

Method "A" was used to prepare the title compound having the following formula:

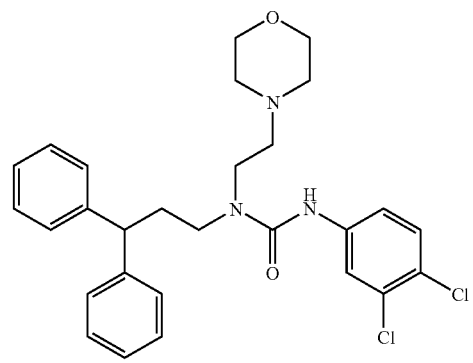

$^1$H NMR (400 MHz, CDCl$_3$): ppm 2.39 (q, 2H, CH$_2$), 2.67 (m, 6H, 3×CH$_2$), 3.31 (t, 2H, CH$_2$), 3.43 (m, 2H, CH$_2$), 3.82 (m, 4H, 2×CH$_2$), 3.98 (t, 1H, CH), 7.15-7.37 (m, 12H, aromatic H), 7.58 (s, 1H, aromatic H), 9.34 (bs, 1H, NH).

MS: 512$^+$ (M+H)$^+$

EXAMPLE 7

3-(3,4-dimethoxyphenyl)-1-(3,3-diphenylpropyl)-1-(2-morpholin-4-ylethyl)urea

Method "A" was used to prepare the title compound having the following formula:

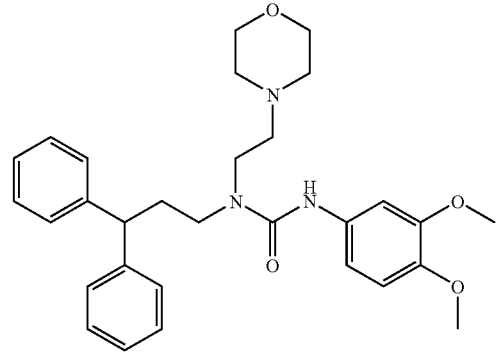

$^1$H NMR (400 MHz, CDCl$_3$): ppm 2.41 (q, 2H, CH$_2$), 2.63 (m, 6H, 3×CH$_2$), 3.30 (t, 2H, CH$_2$), 3.42 (m, 2H, CH$_2$), 3.79 (m, 4H, 2×CH$_2$), 3.86 (s, 3H, OCH$_3$), 3.90 (s, 3H, OCH$_3$), 3.97 (t, 1H, CH), 6.75 (dd, 1H, aromatic H), 6.80 (d, 1H, aromatic H), 7.13-7.23 (m, 3H, aromatic H), 7.25-7.34 (m, 8H, aromatic H), 8.95 (bs, 1H, NH).

MS: 504$^+$ (M+H)$^+$

EXAMPLE 8

1-(3,3-diphenylpropyl)-3-(3-methoxyphenyl)-1-(2-morpholin-4-ylethyl)urea

Method "A" was used to prepare the title compound having the following formula:

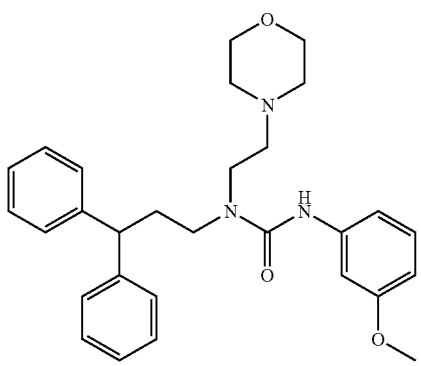

$^1$H NMR (400 MHz, CDCl$_3$): ppm 2.41 (q, 2H, CH$_2$), 2.62 (m, 6H, 3×CH$_2$), 3.30 (t, 2H, CH$_2$), 3.40 (m, 2H, CH$_2$), 3.81 (m, 7H, 2×CH$_2$, OCH$_3$), 3.98 (t, 1H, CH), 6.58 (dd, 1H, aromatic H), 6.89 (d, 1H, aromatic H), 7.11 (s, 1H, aromatic H), 7.15-7.35 (m, 11H, aromatic H), 9.05 (bs, 1H, NH).

MS: 474$^+$ (M+H)$^+$

EXAMPLE 9

4-[3-(3,3-diphenylpropyl)-3-(2-morpholin-4-ylethyl)ureido]benzoic acid ethyl ester Method "A" was used to prepare the title compound having the following formula:

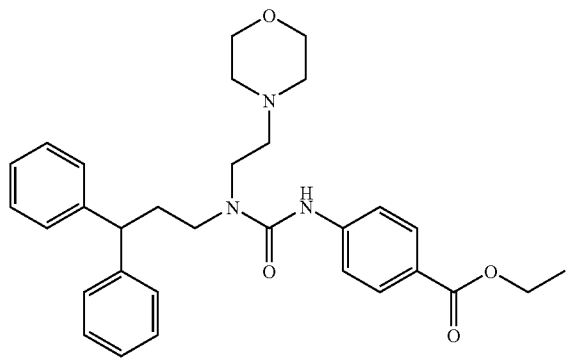

$^1$H NMR (400 MHz, CDCl$_3$): ppm 1.40 (t, 3H, CH$_3$), 2.41 (q, 2H, CH$_2$), 2.64 (m, 6H, 3×CH$_2$), 3.32 (t, 2H, CH$_2$), 3.42 (m, 2H, CH$_2$), 3.81 (m, 4H, 2×CH$_2$), 3.97 (t, 1H, CH), 4.37 (q, 2H, CH$_2$), 7.16-7.25 (m, 2H, aromatic H), 7.26-7.36 (m, 8H, aromatic H), 7.45 (d, 2H, aromatic H), 7.98 (d, 2H, aromatic H), 9.45 (bs, 1H, NH).

MS: 516$^+$ (M+H)$^+$

EXAMPLE 10

1-(3,3-diphenylpropyl)-1-(2-morpholin-4-ylethyl)-3-(4-trifluoromethoxyphenyl)urea Method "A" was used to prepare the title compound having the following formula:

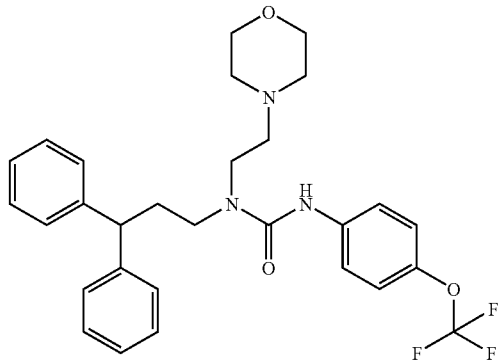

$^1$H NMR (400 MHz, CDCl$_3$): ppm 2.40 (q, 2H, CH$_2$), 2.60 (m, 6H, 3×CH$_2$), 3.30 (t, 2H, CH$_2$), 3.38 (m, 2H, CH$_2$), 3.77 (m, 4H, 2×CH$_2$), 3.96 (t, 1H, CH), 7.15 (d, 2H, aromatic H), 7.17-7.23 (m, 2H, aromatic H), 7.25-7.35 (m, 8H, aromatic H), 7.39 (d, 2H, aromatic H), 9.26 (bs, 1H, NH).

MS: 528$^+$ (M+H)$^+$

EXAMPLE 11

3-(3-Bromophenyl)-1-(3,3-diphenylpropyl)-1-(2-morpholin-4-ylethyl)urea

Method "A" was used to prepare the title compound having the following formula:

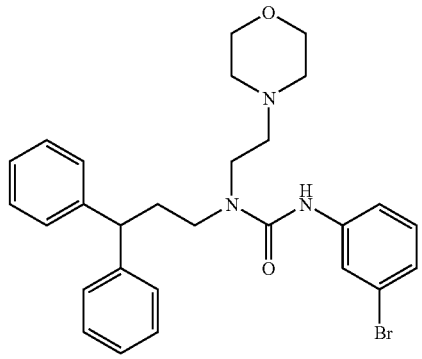

$^1$H NMR (400 MHz, CDCl$_3$): ppm 2.40 (q, 2H, CH$_2$), 2.61 (m, 6H, 3×CH$_2$), 3.30 (t, 2H, CH$_2$), 3.36 (m, 2H, CH$_2$), 3.78 (m, 4H, 2×CH$_2$), 3.97 (t, 1H, CH), 7.10-7.17 (m, 2H, aromatic H), 7.17-7.23 (m, 2H, aromatic H), 7.26-7.35 (m, 9H, aromatic H), 7.62 (s, 1H, aromatic H), 9.20 (bs, 1H, NH).

MS: 523$^+$ (M+H)$^+$

EXAMPLE 12

-(3,3-diphenylpropyl)-1-(2-morpholin-4-ylethyl)-3-(3-trifluoromethylphenyl)urea

Method "A" was used to prepare the title compound having the following formula:

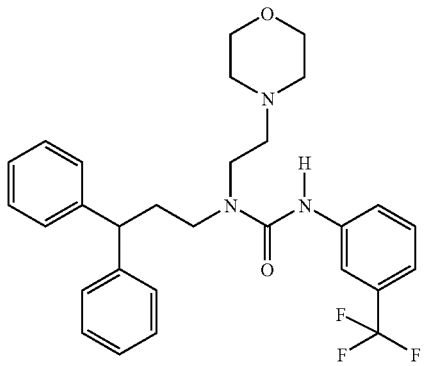

$^1$H NMR (400 MHz, CDCl$_3$): ppm 2.40 (q, 2H, CH$_2$), 2.61 (m, 6H, 3×CH$_2$), 3.30 (t, 2H, CH$_2$), 3.40 (m, 2H, CH$_2$), 3.80 (t, 4H, 2×CH$_2$), 3.99 (t, 1H, CH), 7.10-7.35 (m, 11H, aromatic H), 7.40 (t, 1H, aromatic H), 7.62 (d, 2H, aromatic H).
MS: 512$^+$ (M+H)$^+$

EXAMPLE 13

3-(3,5-bis-trifluoromethylphenyl)-1-(3,3-diphenyl-propyl)-1-(2-morpholin-4-ylethyl)urea Method "A" was used to prepare the title compound having the following formula:

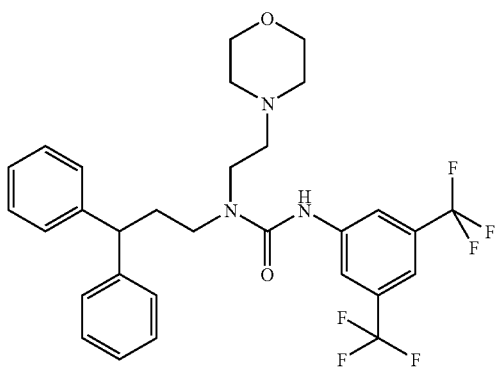

$^1$H NMR (400 MHz, CDCl$_3$) ppm 7.90 (s, 2H, aromatic H), 7.50 (s, 1H, aromatic H), 7.00-7.35 (m, 10H, aromatic H), 3.99 (t, 1H, CH), 3.80 (t, 4H, 2×CH$_2$), 3.40 (m, 2H, CH$_2$), 3.30 (t, 2H, CH$_2$), 2.61 (m, 6H, 3×CH$_2$), 2.40 (q, 2H, CH$_2$).
MS: 580$^+$ (M+H)$^+$

EXAMPLE 14

3-(4-bromo-6-trifluoromethyl-phenyl)-1-(3,3-diphenylpropyl)-1-(2-morpholin-4-ylethyl)urea Method "A" was used to prepare the title compound having the following formula:

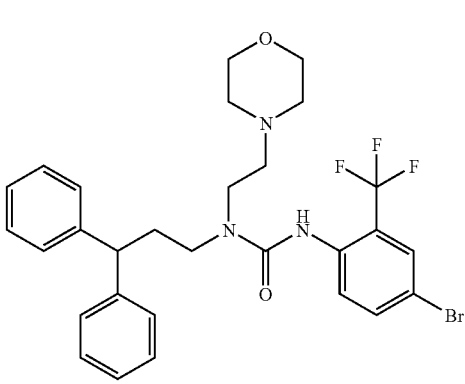

MS: 590.3$^+$ (M+H)$^+$
TLC: Rf=0.27 (eluent: DCM/AcOEt 4/1)

EXAMPLE 15

3-(4-bromophenyl)-1-(3,3-diphenylpropyl)-1-(2-morpholin-4-ylethyl)urea

Method "A" was used to prepare the title compound having the following formula:

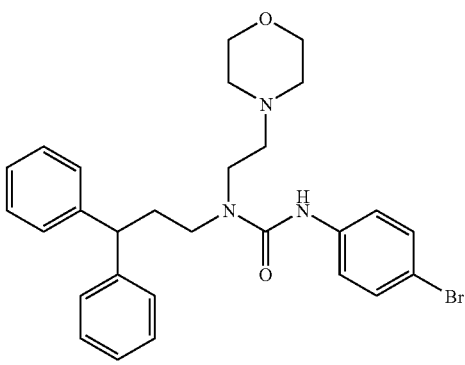

MS: 524.2$^+$ (M+H)$^+$
TLC: Rf=0.38 (eluent: 2/1 DCM/AcOEt)

EXAMPLE 16

4-methoxy-5-[3-(3,3-diphenylpropyl)-3-(2-morpholin-4-ylethyl)ureido]benzoic acid methyl ester

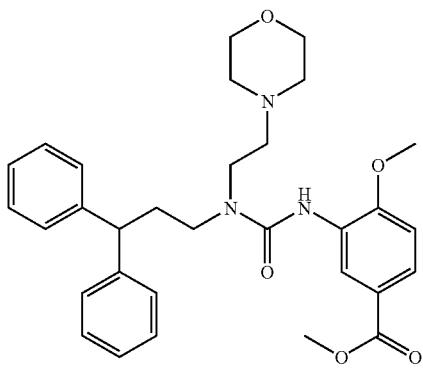

33 mg (0.11 mmol, 0.6 eq.) of triphosgene and 200 μL of CH$_2$Cl$_2$ are introduced in succession into a flask placed under argon. A solution of 34 mg (0.19 mmol, 1 eq.) of 3-amino-4-methoxybenzoic acid methyl ester and 29.5 μL (0.334 mmol, 1.8 eq.) of diisopropylethylamine, in 200 μL of CH$_2$Cl$_2$ is added to the mixture. The mixture is stirred for 1 hour at room temperature. 133 eq. (0.41 mmol, 2.2 eq.) of secondary amine dissolved in 400 μL of CH$_2$Cl$_2$ are then added, and stirring is maintained for one night. The reaction medium is neutralised by a saturated solution of NaHCO$_3$ and dichloromethane. The organic phases are combined, then washed with a saturated NaCl solution. After drying over MgSO$_4$, filtration and concentration to dryness, the crude reaction product is purified by column chromatography over silica gel (eluent: DCM/AcOEt 4/1 to 1/1) leading to the desired urea in a yield of 90%. This procedure is hereinafter called method "B".

MS: 532.1$^+$ (M+H)$^+$

TLC: Rf=0.18 (eluent: DCM/AcOEt 2/1)

EXAMPLE 17

4-chloro-5-[3-(3,3-diphenylpropyl)-3-(2-morpholin-4-ylethyl)ureido]benzoic acid methyl ester Method "B" was used to prepare the title compound having the following formula:

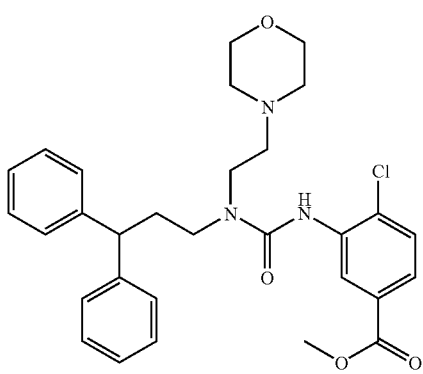

MS: 536.0$^+$ (M+H)$^+$

TLC: Rf=0.15 (eluent: DCM/AcOEt 4/1)

EXAMPLE 18

2-chloro-5-[3-(3,3-diphenylpropyl)-3-(2-morpholin-4-ylethyl)ureido]benzoic acid methyl ester

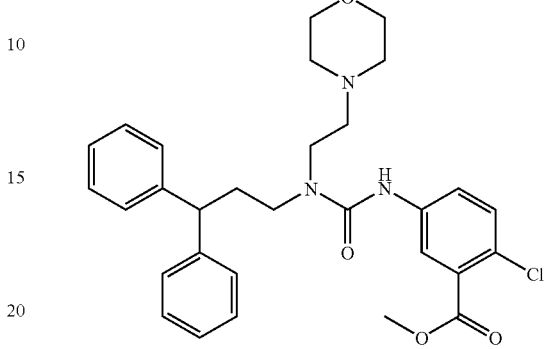

Method "B" was used to prepare the title compound having the following formula:

$^1$H NMR (400 MHz, CDCl$_3$): ppm 2.40 (q, 2H, CH2), 2.53-2.79 (m, 6H, CH2), 3.24-3.46 (m, 4H, CH2), 3.67-3.90 (m, 4H, CH2), 3.94 (s, 3H, CH3), 3.97 (t, 1H, CH), 7.16-7.40 (m, 11H, aromatic H), 7.59-7.69 (m, 1H, aromatic H), 7.84 (s, 1H, aromatic H), 9.30-9.90 (m, 1H, NH).

MS: 536.0$^+$ (M+H)$^+$

TLC: Rf=0.21 (eluent: DCM/AcOEt 4/1)

EXAMPLE 19

3-(3-cyanophenyl)-1-(3,3-diphenylpropyl)-1-(2-morpholin-4-ylethyl)urea

Method "B" was used to prepare the title compound having the following formula:

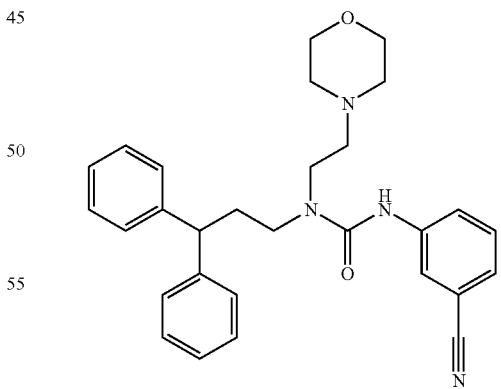

$^1$H NMR (400 MHz, CDCl$_3$) ppm 2.40 (q, 2H, CH$_2$), 2.61 (m, 6H, 3×CH$_2$), 3.30 (t, 2H, CH$_2$), 3.40 (m, 2H, CH$_2$), 3.80 (t, 4H, 2×CH$_2$), 3.99 (t, 1H, CH), 7.10-7.50 (m, 12H, aromatic H), 7.53 (d, 1H, aromatic H), 7.78 (s, 1H, aromatic H).

MS: 469.0$^+$ (M+H)$^+$

TLC: Rf=0.21 (eluent: DCM/AcOEt 4/1)

EXAMPLE 20

3-(4-cyanophenyl)-1-(3,3-diphenylpropyl)-1-(2-morpholin-4-ylethyl)urea

Method "B" was used to prepare the title compound having the following formula:

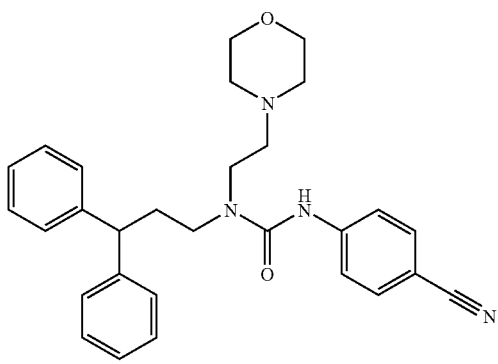

MS: 469.0+ (M+H)+
TLC: Rf=0.21 (eluent: DCM/AcOEt 4/1)

EXAMPLE 21

3-[3-(3,3-diphenylpropyl)-3-(2-morpholin-4-ylethyl)ureido]benzoic acid tertbutyl ester Method "B" was used to prepare the title compound having the following formula:

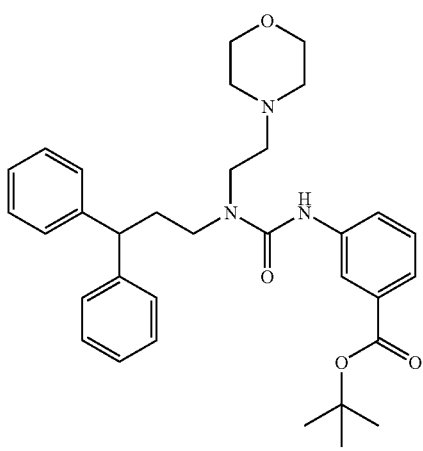

$^1$H NMR (400 MHz, CDCl$_3$): ppm 1.51 (s, 9H, CH3), 2.40 (q, 2H, CH2), 2.61 (m, 6H, CH2), 3.31 (t, 2H, CH2), 3.36 (m, 2H, CH2), 3.82 (sl, 4H, CH2), 3.98 (t, 1H, CH), 7.16-7.23 (m, 2H, aromatic H), 7.26-7.32 (m, 8H, aromatic H), 7.37 (t, 1H, aromatic H), 7.66 (d, 1H, aromatic H), 7.77 (s, 1H, aromatic H), 7.86 (d, 1H, aromatic H), 9.40-9.53 (sl, 1H, NH).

MS: 544.0+ (M+H)+
TLC: Rf=0.16 (eluent: DCM/AcOt 4/1)

EXAMPLE 22

3-(2-cyanophenyl)-1-(3,3-diphenylpropyl)-1-(2-morpholin-4-ylethyl)urea

Method "B" was used to prepare the title compound having the following formula:

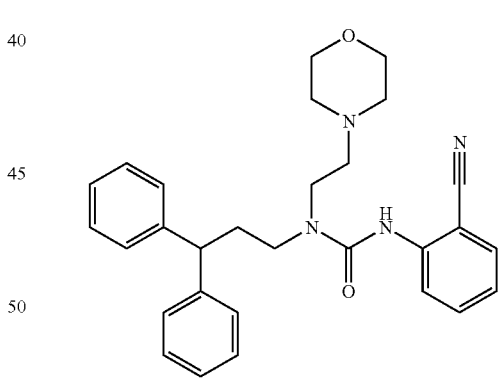

MS: 469.0+ (M+H)+
TLC: Rf=0.24 (eluent: DCM/AcOEt 2/1)

EXAMPLE 23

3-(3-acetylphenyl)-1-(3,3-diphenylpropyl)-1-(2-morpholin-4-ylethyl)urea

Method "B" was used to prepare the title compound having the following formula:

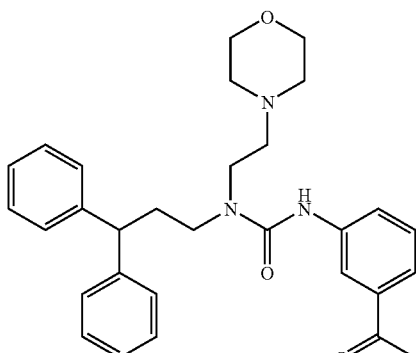

MS: 486.0+ (M+H)+
TLC: Rf=0.10 (eluent: DCM/AcOEt 2/1)

EXAMPLE 24

1-(3,3-diphenylpropyl)-3-(3-methylsulphanylphenyl)-1-(2-morpholin-4-ylethyl)urea Method "B" was used to prepare the title compound having the following formula:

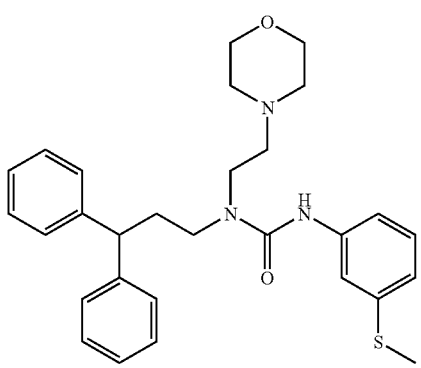

$^1$H NMR (400 MHz, CDCl$_3$): ppm 2.41 (q, 2H, CH2), 2.49 (s, 3H, CH3), 2.57 (bs, 6H, CH2), 3.29 (t, 2H, CH2), 3.35 (t, 2H, CH2), 3.77 (bs, 4H, CH2), 3.98 (t, 1H, CH), 6.93 (d, 1H, aromatic H), 7.13 (d, 1H, aromatic H), 7.16-7.24 (m, 3H, aromatic H), 7.27-7.33 (m, 8H, aromatic H), 7.40 (s, 1H, aromatic H), 8.92-9.15 (bs, 1H, NH).
MS: 490+ (M+H)+
TLC: Rf=0.39 (eluent: DCM/AcOEt 1/1)

EXAMPLE 25

1-(3,3-diphenylpropyl)-1-(2-morpholin-4-ylethyl)-3-(3-trifluoromethoxyphenyl)urea Method "B" was used to prepare the title compound having the following formula:

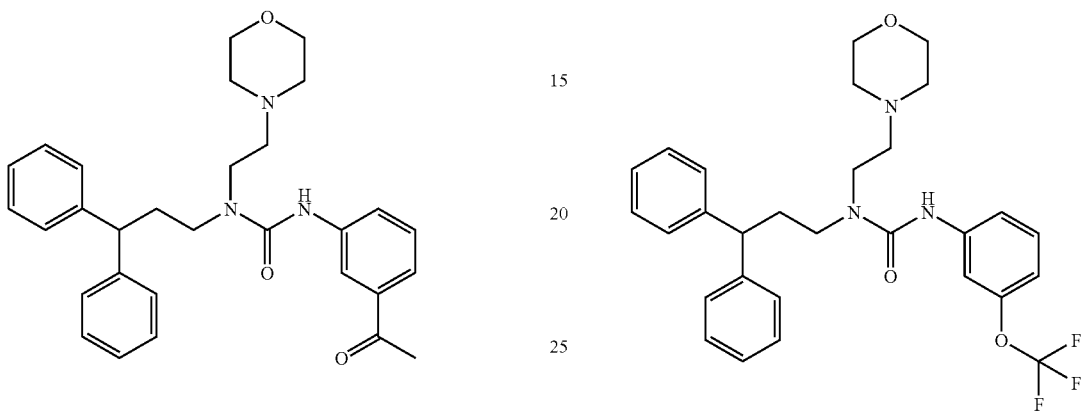

MS: 528.20+ (M+H)+
TLC: Rf=0.31 (eluent: DCM/AcOEt 4/1)

EXAMPLE 26

1-(3,3-diphenylpropyl)-1-(2-morpholin-4-ylethyl)-3-(3-ethylsulphonyl-6-methoxyphenyl)urea Method "B" was used to prepare the title compound having the following formula:

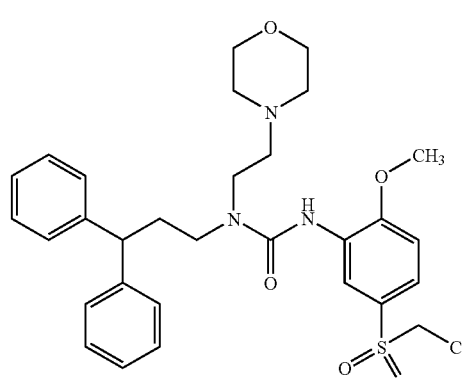

MS: 566.2+ (M+H)+
TLC: Rf=0.07 (eluent: DCM/AcOEt 4/1)

EXAMPLES 27 TO 30

Method "B" was used to prepare the compounds shown in Table 1

TABLE 1

| Formula | MS | Rf = | EXAMPLE |
|---|---|---|---|
| (structure) | 553.2+ | 0.17 (95/5 DCM/MeOH) | Example 27 |
| (structure) | 516.2+ | 0.15 (4/1 DCM/AcOEt) | Example 28 |
| (structure) | 576.1+ | 0.24 (4/1 DCM/AcOEt) | Example 29 |

TABLE 1-continued

| Formula | MS | Rf = | EXAMPLE |
|---|---|---|---|
| 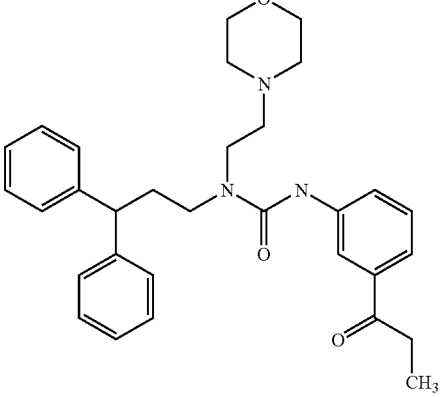 | 500.0+ | 0.16 (4/1 DCM/AcOEt) | Example 30 |

Compound of Example 30:

$^1$H NMR (400 MHz, CDCl$_3$) ppm 1.24 (t, 3H, CH3), 2.40 (q, 2H, CH2), 2.63 (m, 6H, CH2), 3.02 (q, 2H, COC$\underline{H}_2$, 3.32 (t, 2H, CH2), 3.41 (m, 2H, CH2), 3.82 (m, 4H, CH2), 3.97 (t, 1H, CH), 7.16-7.24 (m, 2H, aromatic H), 7.25-7.35 (m, 8H, aromatic H), 7.39 (t, 1H, aromatic H), 7.61 (d, 1H, aromatic H), 7.74 (d, 1H, aromatic H), 7.92 (s, 1H, aromatic H), 9.43 (bs, 1H, NH).

EXAMPLES 31 TO 35

Method "B" was used to prepare the compounds shown in Table 2

TABLE 2

| Formula | MS | Rf = | EXAMPLE |
|---|---|---|---|
| 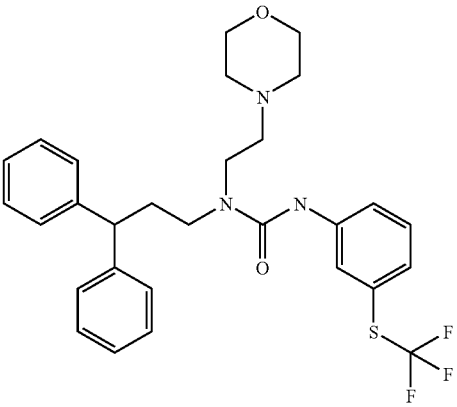 | 544.2+ | 0.41 (4/1 DCM/AcOEt) | Example 31 |

TABLE 2-continued

| Formula | MS | Rf = | EXAMPLE |
|---------|-----|------|---------|
| | 522.2+ | 0.14 (95/5 DCM/MeOH) | Example 32 |
| | 504.5+ | 0.36 (4/1 DCM/AcOEt) | Example 33 |
| | 518.5+ | 0.31 (4/1 DCM/AcOEt) | Example 34 |

TABLE 2-continued

| Formula | MS | Rf = | EXAMPLE |
|---|---|---|---|
| | 524.4+ | 0.17 (4/1 DCM/AcOEt) | Example 35 |

Compound of Example 35.
$^1$H NMR (400 MHz, CDCl$_3$): ppm 2.40 (q, 2H, CH2), 2.50 (s, 3H, SCH3), 2.54-2.68 (m, 6H, CH2), 3.30 (t, 2H, CH2), 3.34-3.42 (m, 2H, CH2), 3.73-3.82 (m, 4H, CH2), 3.98 (t, 1H, CH), 7.00 (d, 2H, aromatic H), 7.16-7.35 (m, 10H, aromatic H), 7.43 (s, 1H, aromatic H), 8.95-9.40 (m, 1H, NH).

EXAMPLE 36

3-(3,5-dichlorophenyl)-1-(3,3-diphenylpropyl)-1-(2-morpholin-4-ylethyl)urea

Method "B" was used to prepare the title compound having the following formula:

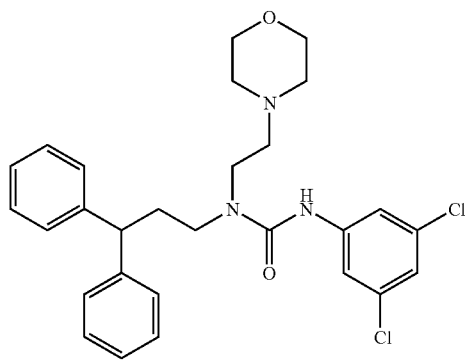

$^1$H NMR (400 MHz, CDCl$_3$): ppm 2.38 (q, 2H, CH$_2$), 2.65 (m, 6H, 3×CH$_2$), 3.30 (t, 2H, CH$_2$), 3.38 (bs, 2H, CH$_2$), 3.80 (m, 4H, 2×CH$_2$), 3.95 (t, 1H, CH), 7.00 (s, 1H, aromatic H), 7.20 (m, 2H, aromatic H), 7.30 (m, 10H, aromatic H), 9.30 (bs, 1H, NH).
MS: 512.0+ (M+H)+

EXAMPLE 37

1-(3,3-diphenylpropyl)-3-(3-iodophenyl)-1-(2-morpholin-4-ylethyl)urea

Method "B" was used to prepare the title compound having the following formula:

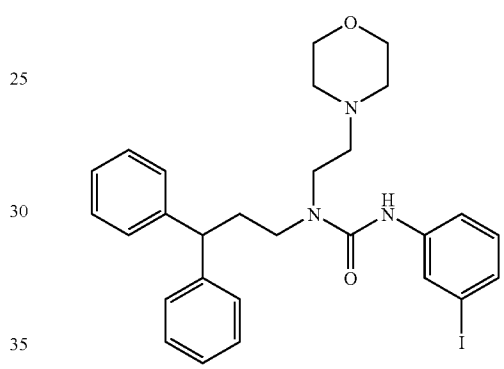

$^1$H NMR (400 MHz, CDCl$_3$): ppm 2.40 (q, 2H, CH$_2$), 2.62 (m, 6H, 3×CH$_2$), 3.37 (m, 2H, CH$_2$), 3.30 (t, 2H, CH$_2$), 3.78 (m, 4H, 2×CH$_2$), 3.96 (t, 1H, CH), 7.00 (t, 1H, aromatic H), 7.16-7.24 (m, 2H, aromatic H), 7.26-7.40 (m, 10H, aromatic H), 7.77 (s, 1H, aromatic H), 9.14 (bs, 1H, NH).
MS: 570.0+ (M+H)+

EXAMPLE 38

3-(4-chloro-3-trifluoromethylphenyl)-1-(3,3-diphenylpropyl)-1-(2-morpholin-4-ylethyl)urea Method "B" was used to prepare the title compound having the following formula:

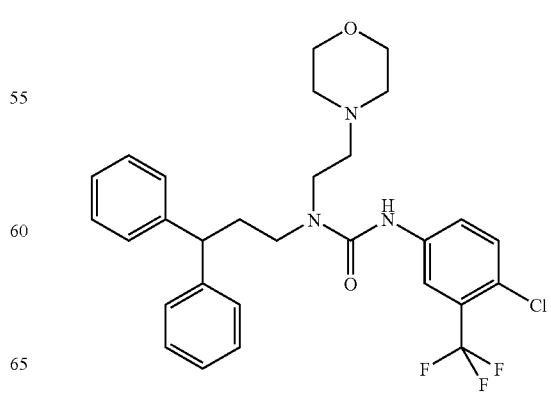

¹H NMR (400 MHz, CDCl₃): ppm 2.40 (q, 2H, CH₂), 2.64 (m, 6H, 3×CH₂), 3.32 (t, 2H, CH₂), 3.41 (m, 2H, CH₂), 3.79 (m, 4H, 2×CH₂), 3.97 (t, 1H, CH), 7.17-7.23 (m, 2H, aromatic H), 7.26-7.35 (m, 8H, aromatic H), 7.40 (d, 1H, aromatic H), 7.64 (m, 2H, aromatic H), 9.58 (bs, 1H, H11).
MS: 546.0⁺ (M+H)⁺
TLC: Rf=0.35 (eluent: DCM/AcOEt 4/1)

EXAMPLE 39

3-(3-dimethylaminophenyl)-1-(3,3-diphenylpropyl)-1-(2-morpholin-4-ylethyl)urea

Method "B" was used to prepare the title compound having the following formula:

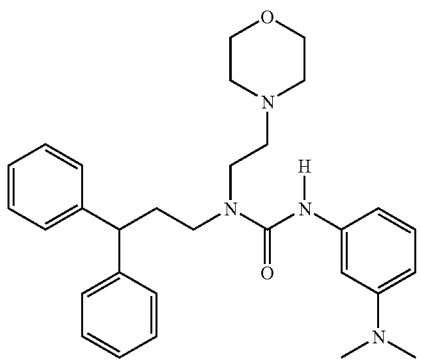

¹H NMR (400 MHz, CDCl₃): ppm 2.40 (q, 2H, CH₂), 2.60 (m, 6H, 3×CH₂), 3.00 (d, 6H, 2×NCH₃), 3.30 (t, 2H, CH₂), 3.40 (m, 2H, CH₂), 3.70 (m, 4H, 2×CH₂), 3.99 (t, 1H, CH), 7.15-7.35 (m, 14H, aromatic H).
MS: 487.0⁺ (M+H)⁺

EXAMPLE 40

3-[3-(3,3-diphenylpropyl)-3-(2-morpholin-4-ylethyl)ureido]benzoic acid tertbutyl ester hydrochloride (of the compound described in example 21)

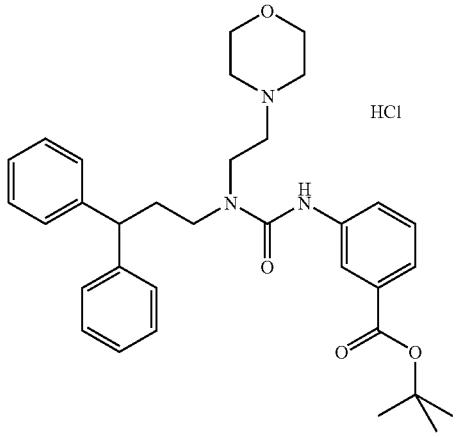

217 mg (0.41 mmol, 1 eq.) of product obtained in example 21 are dissolved in 3 mL of dichloromethane. 310 μL (0.41 mmol, 1 eq.) of 2N HCl in diethyl ether are added. The mixture is stirred for 10 sec then concentrated to dryness. The residue is taken up in the minimum of dichloromethane (2 mL) then 3 mL of diethyl ether are added to precipitate the product. The insoluble matter is filtered then washed with diethyl ether (m=224 mg, yield=96%). This procedure is hereinafter called method "F".

¹H NMR (400 MHz, CDCl₃): ppm 1.61 (s, 9H, CH3), 2.07-2.21 (m, 2H, CH2), 2.36-2.54 (m, 2H, CH2), 2.79-3.02 (m, 2H, CH2), 3.05-3.28 (m, 2H, CH2), 3.31-3.60 (m, 2H, CH2), 3.80-4.07 (m, 5H, CH2+CH), 4.12-4.28 (m, 2H, CH2), 6.78-6.96 (m, 1H, aromatic H), 7.17-7.38 (m, 10H, aromatic H), 7.55-7.63 (m, 1H, aromatic H), 7.67 (d, 1H, aromatic H), 7.80-7.90 (m, 1H, aromatic H).
MS: 544.21⁺ (M+H−HCl)⁺

EXAMPLE 41

Hydrochloride of the Compound of Example 24

Method "F", but using 3 eq. of HCl instead of 1 eq., was used to prepare the title compound having the following formula:

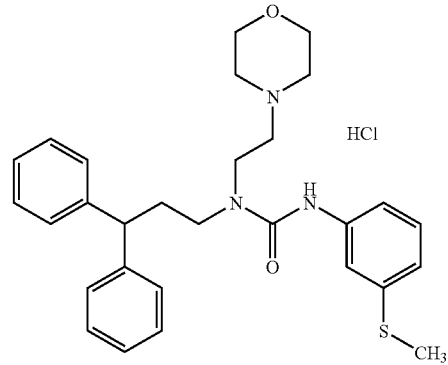

¹H NMR (400 MHz, DMSO): ppm 2.33 (q, 2H, CH2), 2.43 (s, 3H, SCH3), 2.96-3.13 (m, 2H, CH2), 3.15-3.30 (m, 4H, CH2), 3.34-3.50 (m, 2H, CH2), 3.64-3.82 (m, 4H, CH2), 3.87-3.98 (m, 2H, CH2), 4.00 (t, 1H, CH), 6.84 (d, 1H, aromatic H), 7.12-7.21 (m, 3H, aromatic H), 7.23-7.40 (m, 9H, aromatic H), 7.47 (s, 1H, aromatic H), 8.38 (bs, 1H, NH), 10.95-11.13 (m, 1H, NH⁺Cl⁻).
MS: 490⁺ (M+H−HCl)⁺

EXAMPLE 42

Hydrochloride of the Compound of Example 30

Method "F", but using 3 eq. of HCl instead of 1 eq., was used to prepare the title compound having the following formula:

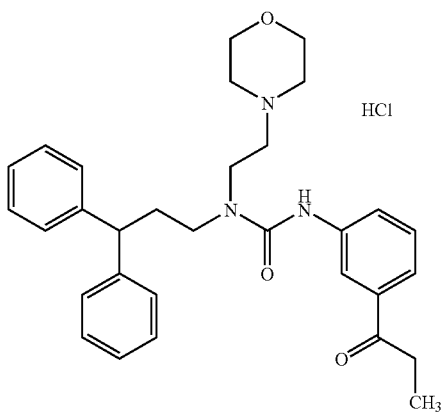

¹H NMR (400 MHz, CD₃OD): ppm 1.20 (t, 3H, CH3), 2.45-2.55 (m, 2H, CH2), 3.06 (q, 2H, COC$\underline{H}_2$), 3.10-3.20 (m, 2H, CH2), 3.25-3.35 (m, 2H, CH2), 3.38-3.48 (m, 2H, CH2), 3.55-3.65 (m, 2H, CH2), 3.66-3.82 (m, 4H, CH2), 4.00-4.12 (m, 3H, CH+CH2), 7.20 (t, 2H, aromatic H), 7.26-7.40 (m, 8H, aromatic H), 7.44 (t, 1H, aromatic H), 7.63 (d, 1H, aromatic H), 7.72 (d, 1H, aromatic H), 8.00 (s, 1H, aromatic H).

EXAMPLE 43

3-(4-chloro-3-trifluoromethylphenyl)-1-(3,3-diphenylpropyl)-1-(2-morpholin-4-ylethyl)urea hydrochloride (compound described in example 38)

Method "F", but using 3 eq. of HCl instead of 1 eq., was used to prepare the title compound having the following formula:

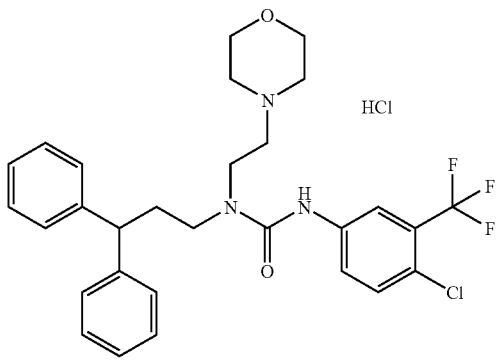

¹H NMR (400 MHz, CD₃OD): ppm 2.48 (q, 2H, CH2), 3.05-3.22 (m, 2H, CH2), 3.24-3.32 (m, 2H, CH2), 3.44 (t, 2H, CH2), 3.51-3.65 (m, 2H, CH2), 3.70 (t, 2H, CH2), 3.71-3.83 (m, 2H, CH2), 3.98-4.15 (m, 3H, CH+CH2), 7.19 (t, 2H, aromatic H), 7.24-7.38 (m, 8H, aromatic H), 7.51 (d, 1H, aromatic H), 7.64 (d, 1H, aromatic H), 7.87 (s, 1H, aromatic H).

MS: 546.03⁺ (M+H−HCl)⁺

EXAMPLE 44

1-(3,3-diphenylpropyl)-3-(3-methanesulphinylphenyl)-1-(2-morpholin-4-ylethyl)urea Starting from the product of Example 24, the corresponding sulphoxide was prepared: 1-(3,3-diphenylpropyl)-3-(3-methanesulphinylphenyl)-1-(2-morpholin-4-ylethyl)urea, using the following reaction scheme:

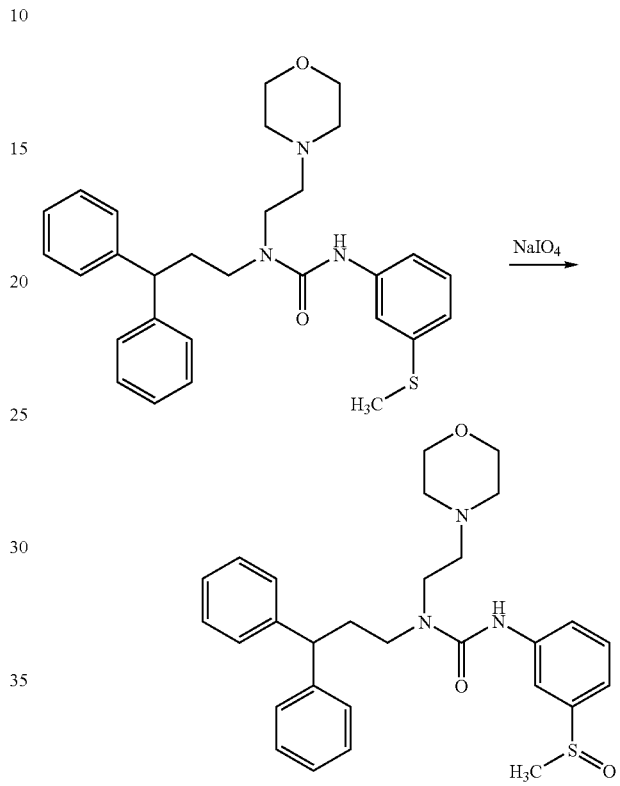

50 mg (0.102 mmol, 1 eq.) of product obtained in Example 24 are dissolved hot in 0.6 mL of methanol, then the solution is cooled to 0° C. 33 mg (0.153 mmol, 1.5 eq.) of NaIO₄ dissolved in 0.3 mL of H₂O are added. The suspension is stirred for 6 hours from 0° C. to room temperature then for 16 hours at room temperature. The suspension is taken up in water and extracted with dichloromethane. The organic phase is washed with water then brine, dried over MgSO₄, filtered and concentrated. The crude reaction product is subjected to chromatography over silica gel (eluent: 95/5 dichloromethane/methanol) (m=49 mg, yield=94%). This procedure is hereinafter called method "G".

MS: 506.3⁺ (M+H)⁺
TLC: Rf=0.38 (eluent: DCM/MeOH 9/1)

EXAMPLES 45-46

Proceeding in the manner described in the following scheme, 3-[3-(3,3-diphenylpropyl)-3-(2-morpholin-4-ylethyl)ureido]benzoic acid (Example 45) is prepared from 3-[3-(3,3-diphenylpropyl)-3-(2-morpholin-4-ylethyl)ureido] benzoic acid methyl ester (obtained in Example 1) and 2-chloro-5-[3-(3,3-diphenylpropyl)-3-(2-morpholin-4-yl-ethyl)-ureido]benzoic acid (Example 46) is obtained from 2-chloro-5-[3-(3,3-diphenylpropyl)-3-(2-morpholin-4-yl-ethyl)ureido]benzoic acid methyl ester (obtained in Example 18):

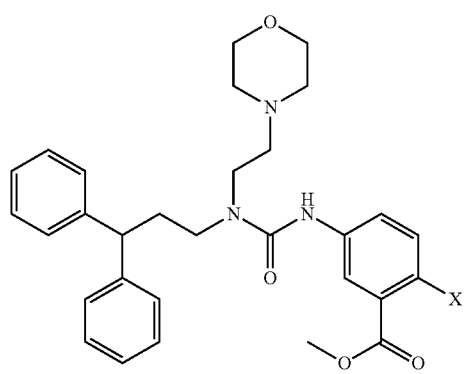

X = H, Example 1
X = Cl, Example 18

NaOH →

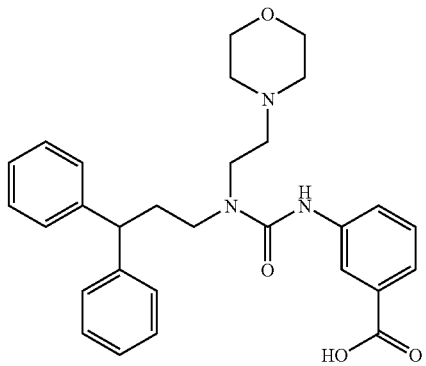

¹H NMR (400 MHz, CD₃OD): ppm 2.44 (q, 2H, CH2), 2.85 (sl, 6H, CH2), 3.38 (t, 2H, CH2), 3.54 (t, 2H, CH2), 3.68 (t, 4H, CH2), 4.03 (t, 1H, CH), 7.14-7.36 (m, 10H, aromatic H), 7.39 (t, 1H, aromatic H), 7.64 (d, 1H, aromatic H), 7.72 (d, 1H, aromatic H), 8.03 (s, 1H, aromatic H).
MS: 488.0⁺ (M+H)⁺
TLC: Rf=0.32 (eluent: DCM/MeOH/NH₄OH 90/10/0.1)

EXAMPLE 46

2-chloro-5-[3-(3,3-diphenylpropyl)-3-(2-morpholin-4-ylethyl)ureido]benzoic acid

Method "H" was used to prepare the title compound having the following formula:

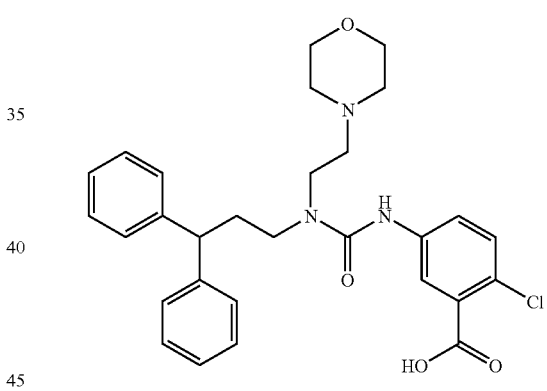

¹H NMR (400 MHz, CD₃OD): ppm 2.45 (q, 2H, CH2), 3.16-3.23 (m, 2H, CH2), 3.17-3.32 (m, 4H, CH2), 3.41 (t, 2H, CH2), 3.63-3.73 (m, 2H, CH2), 3.83-3.95 (m, 4H, CH2), 4.04 (t, 1H, CH), 7.18 (t, 2H, aromatic H), 7.26-7.41 (m, 9H, aromatic H), 7.54 (d, 1H, aromatic H), 7.85 (s, 1H, aromatic H).
MS: 521.9⁺ (M+H)⁺
TLC: Rf=0.48 (eluent: DCM/MeOH 4/1)

EXAMPLES 47-54

Proceeding as indicated in the following scheme, and starting from:
the compound obtained in Example 45, 3-[3-(3,3-diphenylpropyl)-3-(2-morpholin-4-ylethyl)ureido]benzoic acid and
the compound obtained in Example 46, 2-chloro-5-[3-(3,3-diphenylpropyl)-3-(2-morpholin-4-ylethyl)ureido]benzoic acid,
a plurality of esters are prepared by two different methods called method "I", route 1 (Examples 47-50) and method "I", route 2 (Examples 52-54):

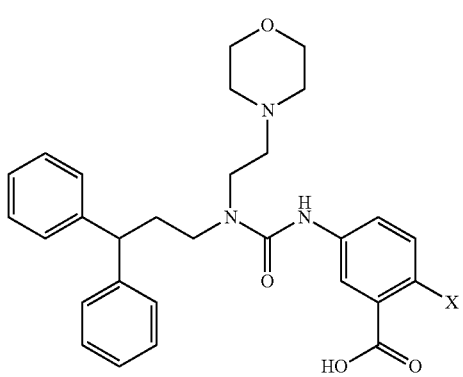

X = H, Example 45
X = Cl, Example 46

EXAMPLE 45

3-[3-(3,3-diphenylpropyl)-3-(2-morpholin-4-ylethyl)ureido]benzoic acid 60 mg (0.12 mmol, 1 eq.) of 3-[3-(3,3-diphenylpropyl)-3-(2-morpholin-4-ylethyl)-ureido]benzoic acid methyl ester (obtained in Example 1) are dissolved in 2 mL of methanol in a 10 mL flask equipped with a condenser. 240 µL of 1 N (0.24 mmol, 2 eq.) sodium hydroxide are added to the mixture and the mixture is heated under reflux for 2 hours 30 min. The methanol is evaporated and water is added. This aqueous solution is acidified with 1 N HCl to pH=6, then extracted with ethyl acetate. The organic phase is washed with brine, dried over MgSO₄, filtered and concentrated. 53 mg of a white solid are obtained (yield=92%). This procedure is hereinafter called method "H".

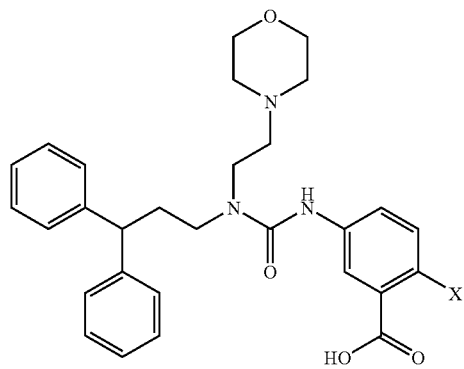

X = H, Example 45
X = Cl, Example 46

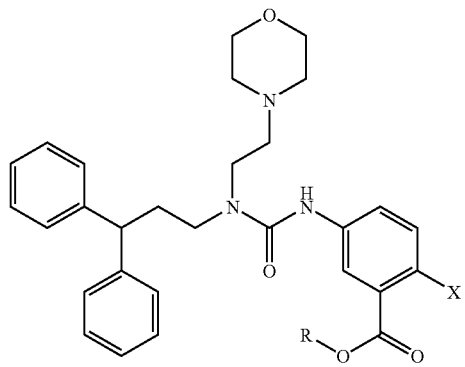

R = (CH₃)₂CH
R = (CH₂)₂OH
R = (CH₃)₂CH

X = H, R = (CH₃)₂CH, Example 47 —HCl→ Example 48
X = H, R = (CH₂)₂OH, Example 49 —HCl→
X = Cl, R = (CH₃)₂CH, Example 50 —HCl→ Example 51 route 2:
ROH

X = H, Example 45

R = CH₂Ph
R = (CH₂)₃CF₂CF₃
R = CH(CH₃)C(CH₃)₃

X = H, R = CH₂Ph, Example 52
X = H, R = (CH₂)₃CF₂CF₃, Example 53
X = H, R = CH(CH₃)C(CH₃)₃, Example 54

EXAMPLE 47

3-[3-(3,3-diphenylpropyl)-3-(2-morpholin-4-ylethyl)ureido]benzoic acid isopropyl ester 200 mg (0.41 mmol, 1 eq.) of product of Example 45 are dissolved in 2 mL of acetone and 2 mL of dry DMF under argon. 283 mg (2.05 mmol, 5 eq.) of K$_2$CO$_3$ and 328 μL (3.28 mmol, 8 eq.) of 2-iodopropane, the mixture is heated under reflux for 2 hours. The medium is then concentrated and taken up in water and the aqueous phase is extracted with ethyl acetate. The organic phase is washed with water then brine, dried over MgSO$_4$, filtered and concentrated. The oil obtained is freed from DMF by entraining the DMF to the rotary evaporator with ethyl acetate, then dried with a vane pump. The product is obtained in the form of white crystals (m=214 mg, yield=99%).

This method is hereinafter identified as: Method I route 1. This method was used to prepare the title compound having the following formula:

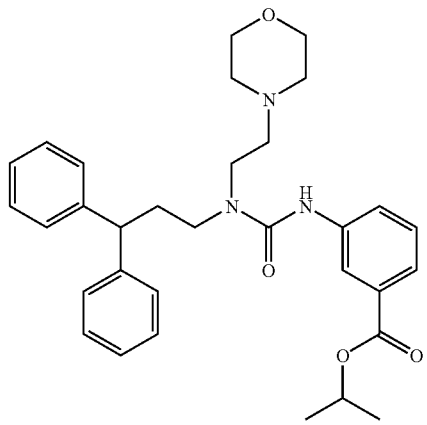

MN $^1$H (400 MHz, CDCl$_3$): ppm 1.38 (d, 6H, CH3), 2.40 (q, 2H, CH2), 2.52 (m, 6H, CH2), 3.32 (t, 2H, CH2), 3.37 (m, 2H, CH2), 3.83 (t, 4H, CH2), 3.98 (t, 1H, CH), 5.28 (sept, 1H, CH), 7.16-7.23 (m, 2H, aromatic H), 7.26-7.34 (m, 8H, aromatic H), 7.38 (t, 1H, aromatic H), 7.69 (d, 1H, aromatic H), 7.85 (s, 1H, aromatic H), 7.94 (d, 1H, aromatic H).

MS: 530.1$^+$ (M+H)$^+$

TLC: Rf=0.48 (eluent: DCM/AcOEt 1/1)

EXAMPLE 48

3-[3-(3,3-diphenylpropyl)-3-(2-morpholin-4-ylethyl)ureido]benzoic acid isopropyl ester hydrochloride Starting from the product obtained in Example 47, method "F" was used to prepare the title compound having the following formula:

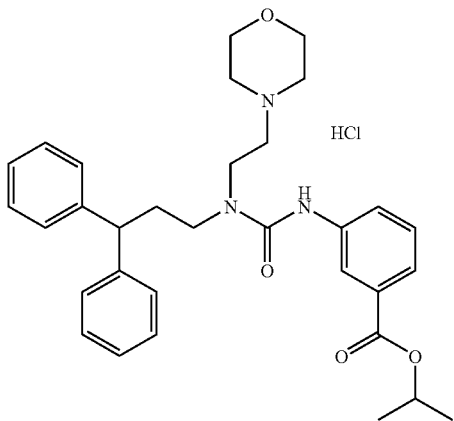

$^1$H NMR (400 MHz, CDCl$_3$): ppm 1.39 (d, 6H, CH3), 1.95-2.13 (m, 2H, CH2), 2.37-2.58 (m, 2H, CH2), 2.76-3.02 (m, 2H, CH2), 3.04-3.30 (m, 2H, CH2), 3.32-3.65 (m, 2H, CH2), 3.80-4.10 (m, 5H, CH2+CH), 4.12-4.32 (m, 2H, CH2), 5.26 (sept, 1H, CH), 6.70-6.90 (m, 1H, aromatic H), 7.14-7.45 (m, 10H, aromatic H), 7.58-7.69 (m, 1H, aromatic H), 7.71 (d, 1H, aromatic H), 7.80-7.90 (m, 1H, aromatic H).
MS: 530$^+$ (M+H−HCl)$^+$

EXAMPLE 49

3-[3-(3,3-diphenylpropyl)-3-(2-morpholin-4-ylethyl)ureido]benzoic acid 2-hydroxy ester Method "I" route 1 was used to prepare the product described hereinafter:

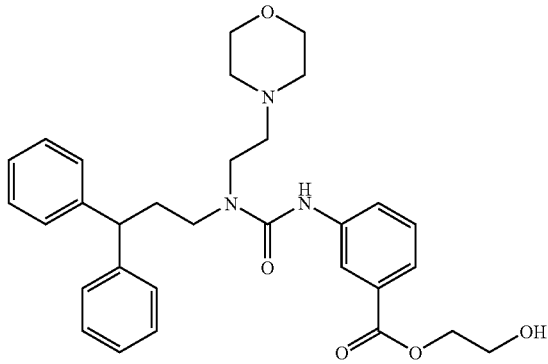

MS: 531.9$^+$ (M+H)$^+$
TLC: Rf=0.36 (eluent: DCM/MeOH 95/5)

EXAMPLE 50

2-chloro-5-[3-(3,3-diphenylpropyl)-3-(2-morpholin-4-ylethyl)ureido]benzoic acid isopropyl ester The product described hereinafter was prepared using Method "I" route 1, but starting from 2-chloro-5-[3-(3,3-diphenylpropyl)-3-(2-morpholin-4-ylethyl)ureido]benzoic acid (product of Example 46):

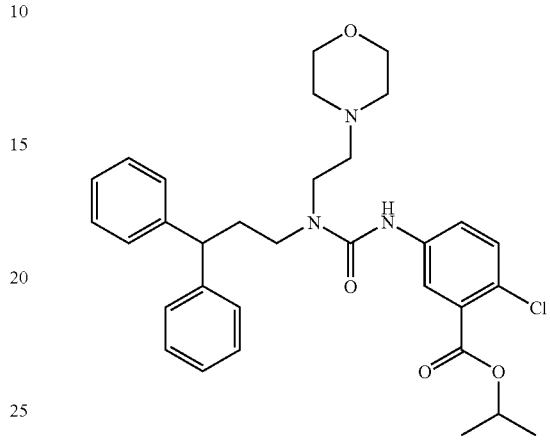

$^1$H NMR (400 MHz, CDCl$_3$): ppm 1.40 (d, 6H, CH3), 2.39 (q, 2H, CH2), 2.50-2.75 (m, 6H, CH2), 3.31 (t, 2H, CH2), 3.32-3.45 (m, 2H, CH2), 3.73-3.88 (m, 4H, CH2), 3.97 (t, 1H, CH), 5.30 (sept, 1H, CH), 7.13-7.23 (m, 2H, aromatic H), 7.25-7.40 (m, 9H, aromatic H), 7.69 (s, 1H, aromatic H), 7.71-7.78 (m, 1H, aromatic H), 9.40-9.90 (m, 1H, NH).
MS: 565.3$^+$ (M+H)$^+$
TLC: Rf=0.63 (eluent: DCM/MeOH 95/5)

EXAMPLE 51

2-chloro-5-[3-(3,3-diphenylpropyl)-3-(2-morpholin-4-ylethyl)ureido]benzoic acid isopropyl ester hydrochloride Starting from the product obtained in Example 50, method "F" was used to prepare the title compound having the following formula

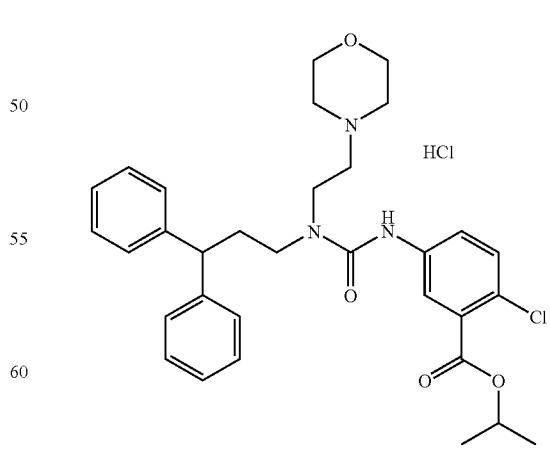

$^1$H NMR (400 MHz, CDCl$_3$): ppm 1.41 (d, 6H, CH3), 2.32-2.55 (m, 2H, CH2), 2.75-2.98 (m, 2H, CH2), 3.00-3.27 (m, 2H, CH2), 3.29-3.60 (m, 4H, CH2), 3.78-4.07 (m, 5H, CH2, CH), 4.10-4.30 (m, 2H, CH2), 5.27 (sept, 1H, CH), 7.00-7.40 (m, 11H, aromatic H), 7.46-7.59 (m, 1H, aromatic H), 7.66-7.78 (m, 1H, aromatic H).

MS: 565.26$^+$ (M+H−HCl)$^+$

TLC: Rf=0.63 (eluent: Rf=0.48 (eluent: DCM/MeOH 95/5)

EXAMPLES 52 TO 54

EXAMPLE 52

3-[3-(3,3-diphenylpropyl)-3-(2-morpholin-4-ylethyl)ureido]benzoic acid benzyl ester 20 mg (0.041 mmol, 1 eq.) of the acid of Example 45 are dissolved in 1 mL of dichloromethane under argon. 0.5 mg (0.004 mmol, 0.1 eq.) of DMAP and 9.3 mg (0.045 mmol, 1.1 eq.) of DCC are added to the medium. After stirring for 30 min. at room temperature, 4.2 µL (0.045 mmol, 1.1 eq.) of benzyl alcohol are added and the mixture is stirred for a further 24 hours. The mixture is neutralised with water and the aqueous phase is extracted with dichloromethane. The organic phase is washed with water then brine, dried over MgSO$_4$, filtered and concentrated. The crude reaction product is subjected to chromatography over silica gel (eluent: 2/1 DCM/AcOEt) (m=18.5 mg, yield=77%).

This method is hereinafter identified as: Method I route 2. This method was used to prepare the compounds having the following formulae:

TABLE 3

| Formula | MS | Rf = | EXAMPLE |
|---|---|---|---|
| | [M + H]$^+$ 578.0 | Rf = = 0.23 (2/1 dichloromethane/ | Example 52 |
| | 648.0 | Rf = 0.64 (95/5 DCM/MeOH) | Example 53 |

TABLE 3-continued

| Formula | MS | Rf = | EXAMPLE |
|---|---|---|---|
| 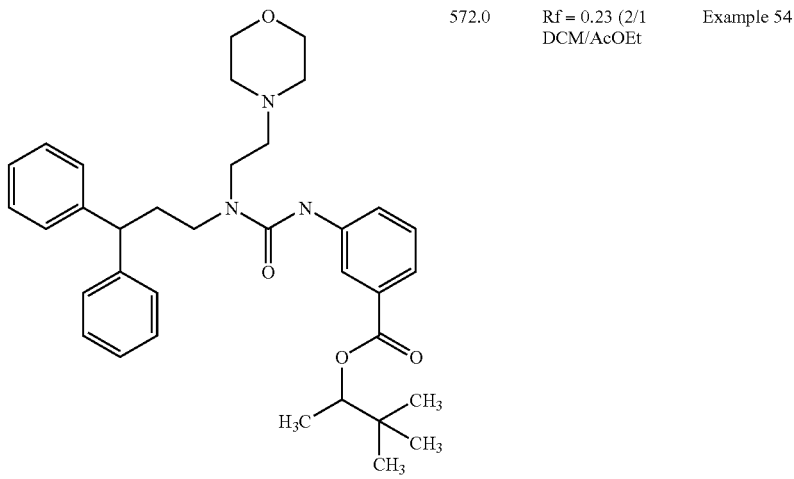 | 572.0 | Rf = 0.23 (2/1 DCM/AcOEt | Example 54 |

Starting from the benzoic acids obtained in Examples 45 or 46, amides were prepared by two different routes, hereinafter called "Method J, route 1" or "Method J, route 2". The following scheme illustrates these two routes of synthesis.

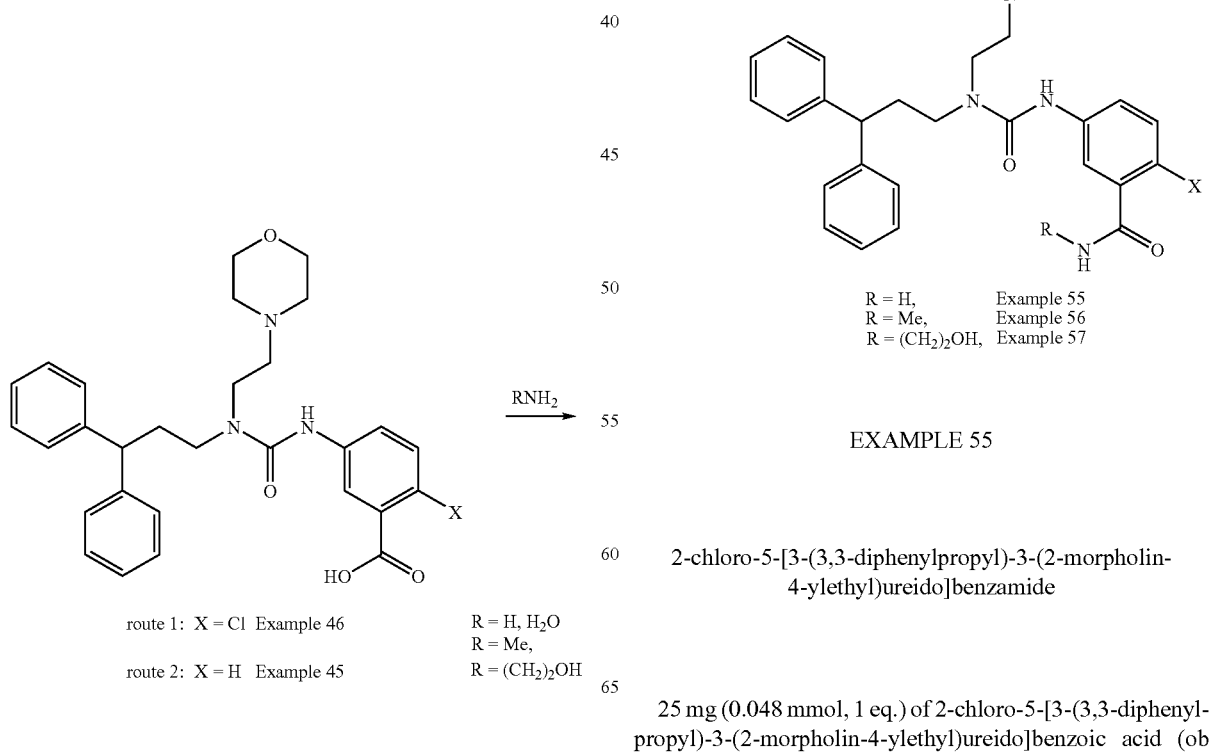

route 1: X = Cl  Example 46
route 2: X = H   Example 45

R = H, H₂O
R = Me,
R = (CH₂)₂OH

R = H,         Example 55
R = Me,        Example 56
R = (CH₂)₂OH,  Example 57

EXAMPLE 55

2-chloro-5-[3-(3,3-diphenylpropyl)-3-(2-morpholin-4-ylethyl)ureido]benzamide 25 mg (0.048 mmol, 1 eq.) of 2-chloro-5-[3-(3,3-diphenyl-propyl)-3-(2-morpholin-4-ylethyl)ureido]benzoic acid (ob tained in Example 46) are dissolved in 0.5 mL of dry THF. Once the mixture had been cooled to −15° C., 5.5 μL (0.057 mmol, 1.2 eq.) of ethyl chloroformate and 8 μL (0.057 mmol, 1.2 eq.) of triethylamine are added to the medium. The mixture is stirred for 7 min. at −15° C. and 46 μL (0.24 mmol, 5 eq.) of 20% eq. NH$_4$OH are added. The temperature is raised to 0° C. for 3 hours and then to room temperature for 15 min.

Water is added and the aqueous phase is extracted with dichloromethane. The organic phase is washed with brine, dried over MgSO$_4$, filtered and concentrated. The crude reaction product is subjected to chromatography over silica gel (eluent: AcOEt then 9/1: dichloromethane/methanol) (m=17 mg, yield=85%). This procedure is hereinafter called method "J", route 1.

TABLE 4

| Formula | MS | Rf = | EXAMPLE |
|---|---|---|---|
| 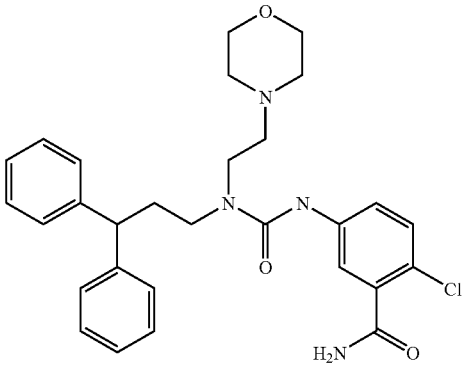 | (M + H)$^+$ = 521.0 | 0.34 (9/1 DCM/MeOH) | Example 55 |
| 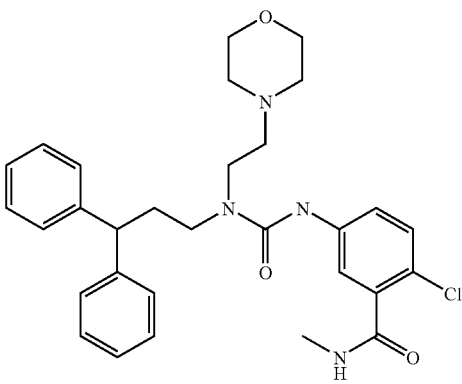 | 535.0 | 0.48 (eluent: 9/1 DCM/MeOH) | Example 56 |

EXAMPLE 57

3-[3-(3,3-diphenylpropyl)-3-(2-morpholin-4-ylethyl)ureido]-N-(2-hydroxy-ethyl)-benzamide 80 mg (0.164 mmol, 1 eq.) of 3-[3-(3,3-diphenylpropyl)-3-(2-morpholin-4-

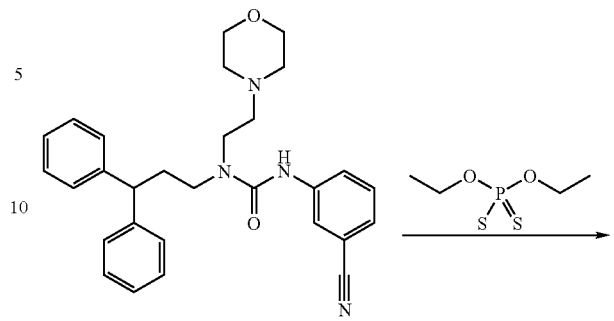

Example 19

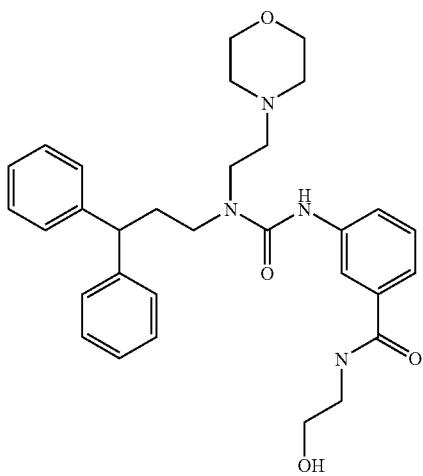

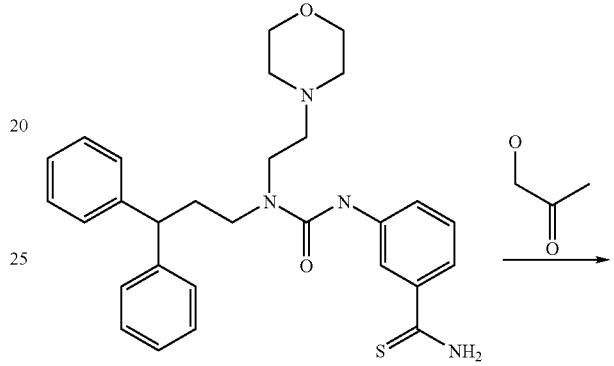

Example 58 ylethyl)ureido]benzoic acid (obtained in Example 45) dissolved in dichloromethane are introduced into a 100 mL flask under an argon atmosphere, then HOBt (27 mg, 1.2 eq.), EDC (37 mg, 1.2 eq.), and ethanolamine (12 mg, 1 eq.) are added to the medium. After reacting for 14 hours, the mixture is neutralised with water, then with a saturated $NaHCO_3$ solution and the aqueous phase is extracted with dichloromethane. The organic phases are combined and washed with brine, then, dried over $MgSO_4$ and concentrated. The crude product thus obtained is purified by silica column chromatography (eluent: $CH_2Cl_2$/MeOH 99/1 to 96/4). The desired amide, 3-[3-(3,3-diphenylpropyl)-3-(2-morpholin-4-ylethyl)ureido]-N-(2-hydroxyethyl)benzamide, is obtained in a yield of 52%. This procedure is hereinafter called method "J", route 2.

$^1$H NMR (400 MHz, $CDCl_3$): ppm 2.40 (q, 2H, $CH_2$) 2.58 (m, 6H, 3×$CH_2$), 3.28 (t, 2H, $CH_2$), 3.35 (t, 2H, $CH_2$), 3.53 (t, 2H, $CH_2$), 3.75 (m, 6H, 3×$CH_2$), 3.95 (t, 1H, CH), 7.35-7.10 (m, 10H, aromatic H), 7.50-7.35 (m, 3H, aromatic H), 7.80 (s, 1H, aromatic H).

MS: 531$^+$ (M+H)$^+$

Starting from nitriles such as those obtained in Example 19 it is possible to prepare a thioamide derivative by a procedure hereinafter called procedure "K" illustrated below:

3-[3-(3,3-diphenylpropyl)-3-(2-morpholin-4-ylethyl)ureido]thiobenzamidethioamide (Example 58) then 1-(3,3-diphenylpropyl)-3-[3-(4-methylthiazol-2-yl)phenyl]-1-(2-morpholin-4-ylethyl)urea (Example 59) are prepared from 3-(3-cyanophenyl)-1-(3,3-diphenylpropyl)-1-(2-morpholin-4-ylethyl)urea (obtained in Example 19):

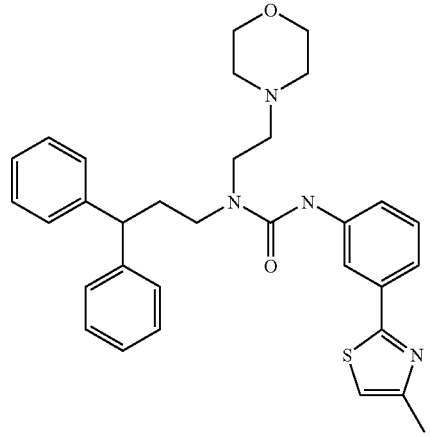

Example 59

EXAMPLE 58

3-[3-(3,3-diphenylpropyl)-3-(2-morpholin-4-ylethyl)ureido]thiobenzamide 70 mg (0.15 mmol, 1 eq.) of 3-(3-cyanophenyl)-1-(3,3-diphenylpropyl)-1-(2-morpholin-4-ylethyl)urea (obtained in Example 19) are dissolved in 0.5 mL of THF under argon. 142 µL (0.90 mmol, 6 eq.) of diethyldithiophosphate and 50 µL (0.01 mmol, 0.1 eq.) of water are added. The mixture is stirred for 27 hours at 40° C. Water is added to the medium and the aqueous phase is extracted with dichloromethane, washed twice with water then brine, dried over $MgSO_4$, filtered and concentrated. The oil obtained is subjected to chromatography over silica gel (eluent: 97/3 dichloromethane/methanol) in order to obtain the expected product in the form of a yellow powder (55 mg, yield=73%).

This procedure is hereinafter called method "K".

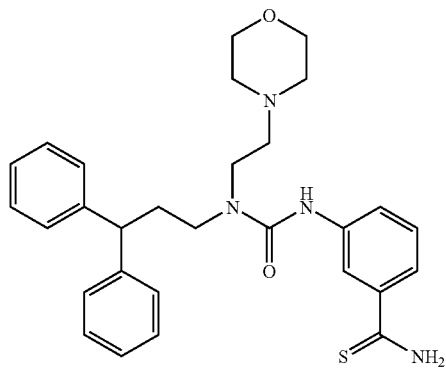

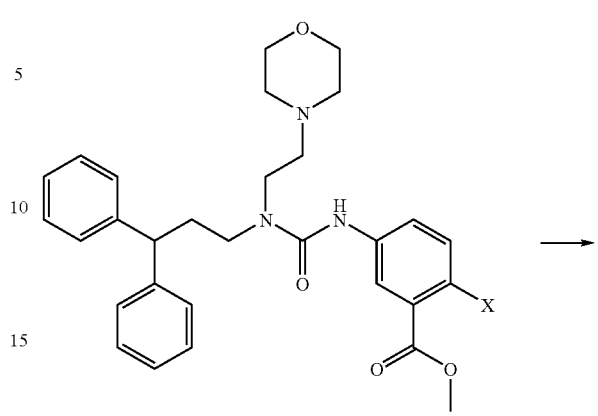

X = H, Example 1
X = Cl, Example 18

MS: 503.4⁺ (M+H)⁺

TLC: Rf=0.20 (eluent: Rf=0.48 (eluent: DCM/MeOH 9/1)

EXAMPLE 59

1-(3,3-diphenylpropyl)-3-[3-(4-methylthiazol-2-yl)-phenyl]-1-(2-morpholin-4-ylethyl)urea 30 mg (0.060 mmol, 1 eq.) of 3-[3-(3,3-diphenylpropyl)-3-(2-morpholin-4-ylethyl)ureido]thiobenzamide (obtained in Example 58) are dissolved in 0.3 mL of DMF under argon and 19 μL (0.240 mmol, 4 eq.) of chloroacetone are added. The mixture is stirred for 16 hours at room temperature. Water is added to the medium and the aqueous phase is extracted with ethyl acetate. The organic phase is washed with water then brine, dried over MgSO₄, filtered and concentrated. The crude reaction product is subjected to chromatography over a silica preparation plate (eluent: 85/15 AcOEt/heptane).

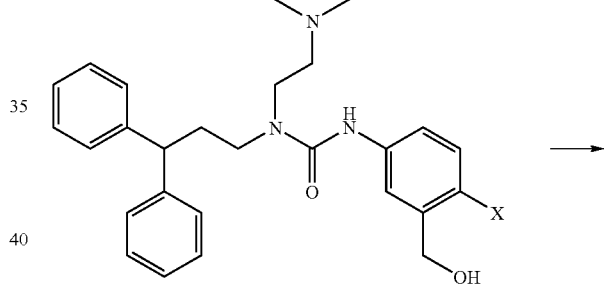

Example 60
Example 61

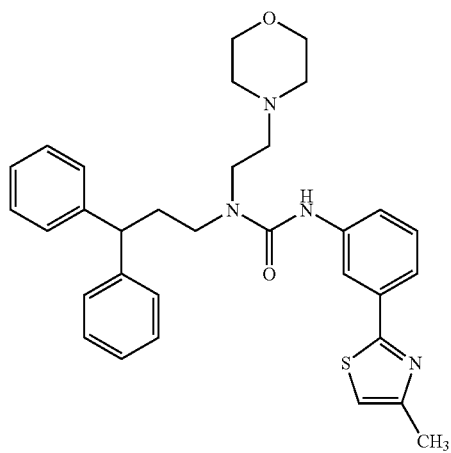

MS: 541.5⁺ (M+H)⁺

TLC: Rf=0.25 (eluent: Rf=0.48 (eluent: AcOEt/heptane 4/1)

Starting from the methyl ester of the products obtained in Examples 1 or 18, it is possible to prepare the corresponding primary alcohol, aldehyde and secondary alcohol derivatives:

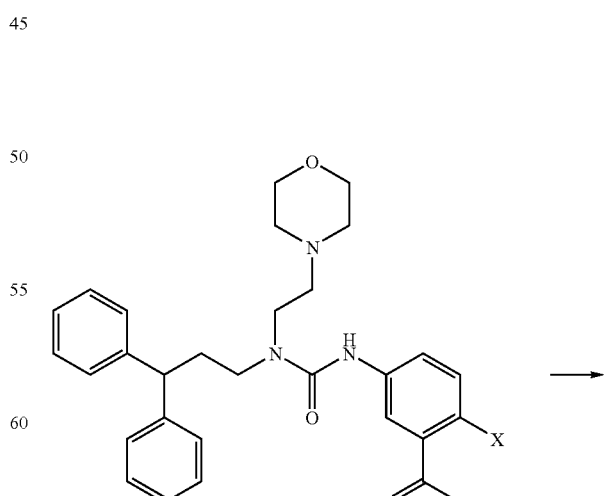

Example 62
Example 63

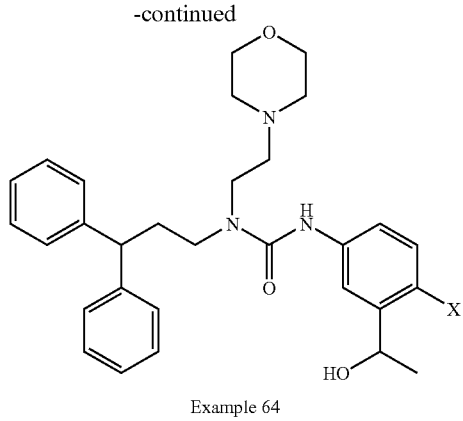

Example 64

EXAMPLE 60

1-(3,3-diphenylpropyl)-3-(3-hydroxymethylphenyl)-1-(2-morpholin-4-ylethyl)urea 135.1 mg (0.269 mmol, 1 eq.) of 3-[3-(3,3-diphenylpropyl)-3-(2-morpholin-4-ylethyl)ureido]benzoic acid methyl ester (obtained in Example 1) and 6 mL of anhydrous THF are introduced in succession into a 30 mL flask under an argon atmosphere while stirring. The mixture is cooled to −78° C., then 300 μL of a 1 M solution of DIBAL in dichloromethane (0.296 mmol, 1.1 eq.) are added slowly, the mixture is subsequently stirred for 2 hours at −78° C., then for one night in a freezer at −27° C. 300 μL of a 1 M solution of LiAlH$_4$ in THF are therefore added at −78° C. After 30 minutes at this temperature, the reaction medium is plunged into an ice bath at 0° C. for 1 hour. Complete disappearance of the ester in favour of the alcohol is observed by TLC.

6 mL of a saturated solution of sodium and potassium tartrate are added at 0° C. and, after stirring for one hour at room temperature, the mixture is extracted with dichloromethane. The organic phases are combined, washed with water then a saturated NaCl solution and dried over MgSO$_4$. After filtration and concentration to dryness, the crude reaction product is purified by flash chromatography over silica gel (eluent: CH$_2$Cl$_2$/MeOH 95/5) leads to the desired alcohol in a yield of 90%.

$^1$H NMR (400 MHz, CDCl$_3$): ppm 1.88 (bs, 1H, OH) 2.40 (q, 2H, CH$_2$), 2.61 (m, 6H, 3×CH$_2$), 3.30 (t, 2H, CH$_2$), 3.39 (m, 2H, CH$_2$), 3.79 (m, 4H, 2×CH$_2$), 3.97 (t, 1H, CH), 4.69 (s, 2H, CH$_2$), 7.01 (d, 1H, aromatic H), 7.35-7.15 (m, 12H, aromatic H), 7.45 (s, 1H, aromatic H), 9.09 (bs, 1H, NH).

MS: 474$^+$ (M+H)$^+$

EXAMPLE 61

3-(4-chloro-3-hydroxymethylphenyl)-1-(3,3-diphenylpropyl)-1-(2-morpholin-4-ylethyl)urea The title compound was obtained by proceeding as in Example 60, but starting from the product obtained in Example 18.

MS: 508$^+$ (M+H)$^+$

TLC: Rf=0.57 (eluent: DCM/MeOH 90/10)

EXAMPLE 62

1-(3,3-diphenylpropyl)-3-(3-formylphenyl)-1-(2-morpholin-4-ylethyl)urea 105.2 mg (0.222 mmol, 1 eq.) of 1-(3,3-diphenylpropyl)-3-(3-hydroxymethylphenyl)-1-(2-morpholin-4-ylethyl)urea (obtained in Example 60), 6 mL of chloroform, and 193 mg (2.22 mmol, 10 eq.) of manganese oxide are introduced in succession into a 50 mL flask under an argon atmosphere while stirring. The mixture is heated under reflux for one night, then the reaction medium is filtered over Celite®. After rinsing with dichloromethane then concentrating to dryness, the crude reaction product is purified by flash chromatography over silica gel (elution gradient: CH$_2$Cl$_2$/AcOEt 4/1 then 1/1), leading to the desired aldehyde in a yield of 84%.

$^1$H NMR (400 MHz, CDCl$_3$): ppm 2.42 (q, 2H, CH$_2$) 2.63 (m, 6H, 3×CH$_2$), 3.32 (t, 2H, CH$_2$), 3.40 (m, 2H, CH$_2$), 3.80 (m, 4H, 2×CH$_2$), 3.98 (t, 1H, CH), 7.35-7.15 (m, 10H, aromatic H), 7.46 (t, 1H, aromatic H), 7.52 (d, 1H, aromatic H), 7.71 (d, 1H, aromatic H), 7.90 (s, 1H, aromatic H), 9.43 (bs, 1H, NH), 10.00 (s, 1H, CHO).

MS: 472$^+$ (M+H)$^+$

EXAMPLE 63

3-(4-chloro-3-formylphenyl)-1-(3,3-diphenylpropyl)-1-(2-morpholin-4-ylethyl)urea The title compound was obtained by proceeding as in Example 62, but starting from the product obtained in Example 61.

MS: 506$^+$ (M+H)$^+$

TLC: Rf=0.46 (eluent: DCM/MeOH 95/5)

EXAMPLE 64

3-[4-chloro-3-(1-hydroxyethyl)phenyl]-1-(3,3-diphenylpropyl)-1-(2-morpholin-4-ylethyl)urea 16 mg (0.033 mmol, 1 eq.) of 3-(4-chloro-3-formylphenyl)-1-(3,3-diphenylpropyl)-1-(2-morpholin-4-ylethyl)urea (obtained in Example 63) are dissolved in 0.7 mL of dry THF. Once the solution has been cooled to 0° C., 17 μL (0.049 mmol, 1.5 eq.) of magnesium methyl bromide in solution (3 M in diethyl ether) are added to the medium. After stirring for 20 min. at 0° C., the reaction is neutralised with a saturated ammonium chloride solution at 0° C. The aqueous phase is extracted with dichloromethane, the organic phases are washed with brine, dried over MgSO$_4$, filtered and concentrated. The crude reaction product is subjected to chromatography over silica gel (eluent: 1/1 heptane/AcOEt). 11.4 mg of expected product are obtained (yield=67%).

$^1$H NMR (400 MHz, CDCl$_3$): ppm 1.48 (d, 3H, CH3), 2.37 (q, 2H, CH2), 2.50-2.76 (m, 6H, CH2), 3.29 (t, 2H, CH2), 3.33-3.48 (m, 2H, CH2), 3.72-3.88 (m, 4H, CH2), 3.96 (t, 1H, CH), 5.24 (q, 1H, CH), 7.13-7.38 (m, 11H, aromatic H), 7.41 (d, 1H, aromatic H), 7.50 (s, 1H, aromatic H).

MS: 522.0$^+$ (M+H)$^+$

TLC: Rf=0.69 (eluent: Rf=0.48 (eluent: DCM/MeOH 9/1)

Starting from a primary alcohol of formula (I) such as that obtained in Example 60, an diethyl ether (method L, route 1) or piperidine (method L, route 2) derivative can be prepared in accordance with the following scheme:

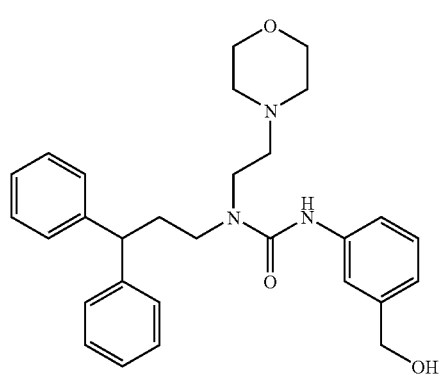

Example 60

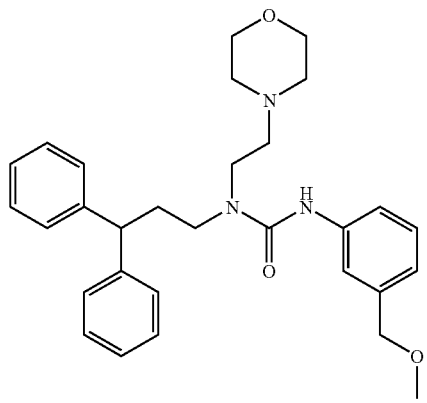

Example 65

Method L, route 1

Method L, route 2

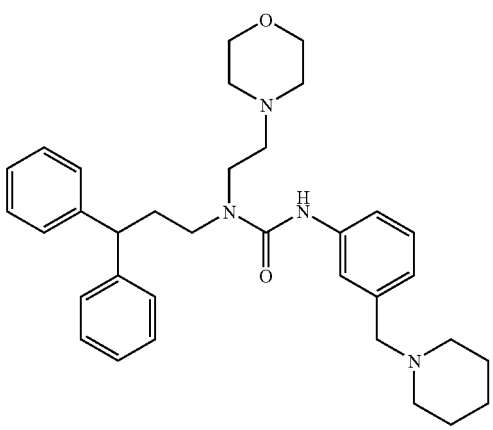

Example 66

EXAMPLE 65

1-(3,3-diphenylpropyl)-3-(3-methoxymethylphenyl)-1-(2-morpholin-4-ylethyl)urea 20 mg (0.042 mmol, 1 eq.) of 1-(3,3-diphenylpropyl)-3-(3-hydroxymethylphenyl)-1-(2-morpholin-4-ylethyl)urea (obtained in Example 60) are dissolved in 3 mL of THF under argon. 3.4 mg (0.084 mmol, 2 eq.) of 60% NaH in oil and 11 µL (0.169 mmol, 4 eq.) of methyl iodide are added. The solution is stirred for 1 hour at room temperature then 2 hours under reflux. Water is added and the aqueous phase is extracted with dichloromethane, the organic phases are washed with brine, dried over MgSO$_4$, filtered and concentrated. The crude reaction product is subjected to chromatography over a preparation plate (eluent: 1/2 DCM/AcOEt) to give 2.5 mg of desired product (yield=12%) (procedure "L", route 1)

MS: 489.2$^+$ (M+H)$^+$

TLC: Rf=0.26 (eluent: Rf=0.48 (eluent: DCM/AcOEt 1/2).

EXAMPLE 66

1-(3,3-diphenylpropyl)-1-(2-morrpholin-4-ylethyl)-3-(3-piperidin-1-ylmethyl-phenyl)urea

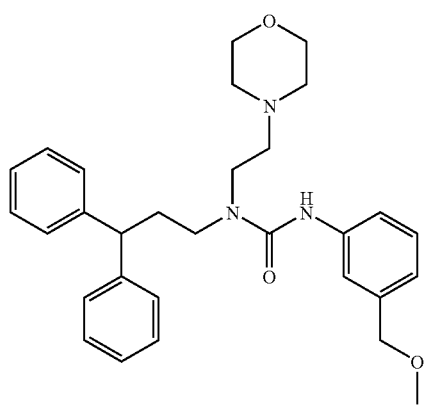

63 mg (0.133 mmol, 1 eq.) of 1-(3,3-diphenylpropyl)-3-(3-hydroxymethylphenyl)-1-(2-morpholin-4-ylethyl)urea (obtained in Example 60) are dissolved in 1.5 mL of dichloromethane under argon. 24 µL (0.173 mmol, 1.3 eq.) of triethylamine are added to the medium. Once the mixture has been cooled to 0° C., 18.4 µL (0.243 mmol, 1.8 eq.) of methane sulphonyl chloride are added. The reaction mixture is stirred for 3 hours at 0° C. and is then neutralised with water. The aqueous phase is extracted with dichloromethane, the organic phases are washed with brine, dried over MgSO$_4$, filtered and concentrated. The crude product is used as it is for the reaction sequence (m=73 mg, yield=100%)

30 mg (0.054 mmol, 1 eq.) of this mesylate derivative are dissolved in 200 μL of DMF under argon. 23 mg (0.163 mmol, 3 eq.) of K$_2$CO$_3$ and 16 μL (0.163 mmol, 3 eq.) of piperidine are added. The mixture is stirred for 3 hours at room temperature. Water is added and the aqueous phase is extracted with ethyl acetate, the organic phases are washed with

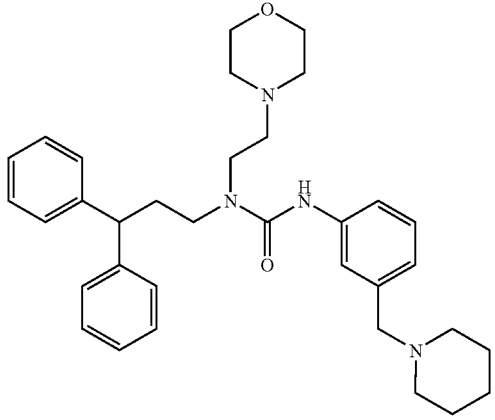

water then brine, dried over MgSO$_4$, filtered and concentrated. The crude reaction product is subjected to chromatography over silica (eluent: 95/5 dichloromethane/methanol). (m=17.2 mg, yield=59%). (Procedure "L", route 2)

MS: 541.6$^+$ (M+H)$^+$

TLC: Rf=0.13 (eluent: Rf=0.48 (eluent: DCM/MeOH 9/1)

EXAMPLE 67

1-(3,3-diphenylpropyl)-1-(2-morpholin-4-ylethyl)-3-(3-oxazol-5-ylphenyl)urea

Method "B" was used to prepare the title compound having the following formula:

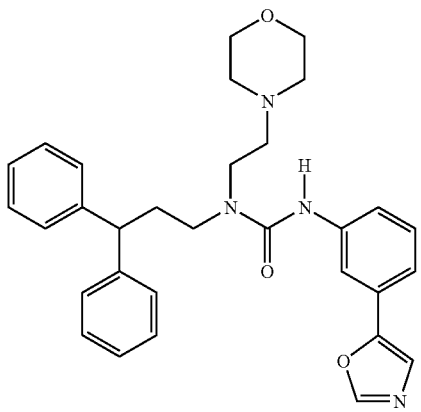

$^1$H NMR (400 MHz, CDCl$_3$): ppm 2.40 (q, 2H, CH$_2$), 2.90 (m, 6H, 3×CH$_2$), 3.38 (m, 2H, CH$_2$), 3.60 (d, 2H, CH$_2$), 3.95 (m, 5H, CH, 2×CH$_2$), 7.20 (m, 2H, aromatic H), 7.40-7.22 (m, 12H, aromatic H), 7.78 (s, 1H, H$_{oxazole}$), 7.90 (s, 1H, H$_{oxazole}$), 9.32 (bs, 1H, NH)

MS: 511.4$^+$ (M+H)$^+$.

EXAMPLE 68

1-(3,3-diphenylpropyl)-1-(2-morpholin-4-ylethyl)-3-(3-oxazol-5-ylphenyl)urea hydrochloride Method "F", but using 3 eq. of HCl instead of 1 eq., was used to prepare the title compound having the following formula:

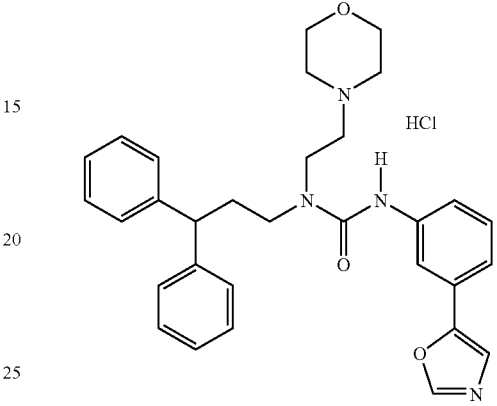

$^1$H NMR (400 MHz, CD$_3$OD): ppm 2.50 (q, 2H, CH$_2$), 3.15 (m, 4H, 2×CH$_2$), 3.45 (t, 2H, CH$_2$), 3.60 (m, 2H, CH$_2$), 3.75 (d, 4H, 2×CH$_2$), 4.05 (m, 3H, CH, CH$_2$), 7.20 (m, 2H, aromatic H), 7.48-7.25 (m, 11H, aromatic H), 7.60 (s, 1H, aromatic H), 7.80 (s, 1H, H$_{oxazole}$), 8.45 (s, 1H, H$_{oxazole}$).

MS: 511.4$^+$ (M+H−HCl)$^+$

EXAMPLE 69

1-(3,3-diphenylpropyl)-1-(2-morpholin-4-ylethyl)-3-(3-oxazol-5-yl-4-chlorophenyl)urea Method "B" was used to prepare the title compound having the following formula:

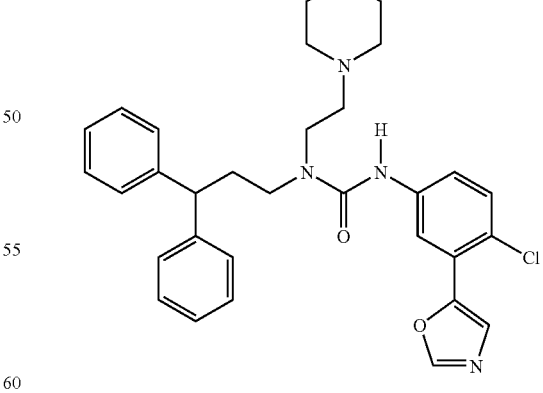

$^1$H NMR (400 MHz, CDCl$_3$): ppm 2.40 (q, 2H, CH2), 2.55-2.72 (m, 6H, CH2), 3.32 (t, 2H, CH2), 3.35-3.43 (m, 2H, CH2), 3.78-3.88 (m, 4H, CH2), 3.98 (t, 1H, CH), 7.14-7.35 (m, 10H, aromatic H), 7.38 (d, 1H, aromatic H), 7.45 (d, 1H, aromatic H), 7.82 (s, 1H, aromatic H), 7.85 (s, 1H, aromatic H), 7.96 (s, 1H, aromatic H), 9.20-9.80 (m, 1H, NH).

MS: 545.4⁺ (M+H)⁺
TLC: Rf=0.05 (eluent: DCM/AcOEt 4/1)

EXAMPLE 70

3-[4-Chloro-3-(1-methyl-1H-tetrazol-5-yl)phenyl]-1-(3,3-diphenylpropyl)-1-(2-morpholin-4-ylethyl)urea Method "B" was used to prepare the product of the following formula:

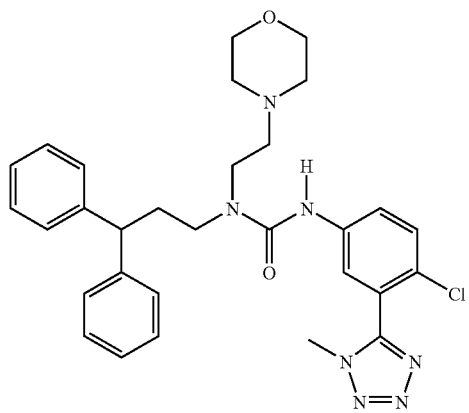

¹H NMR (400 MHz, CDCl₃): ppm 2.37 (q, 2H, CH2), 2.54-2.65 (m, 6H, CH2), 3.27 (t, 2H, CH2), 3.32-3.40 (m, 2H, CH2), 3.69-3.77 (m, 4H, CH2), 3.95 (t, 1H, CH), 4.01 (s, 3H, CH3), 7.14-7.33 (m, 10H, aromatic H), 7.39-7.52 (m, 2H, aromatic H), 7.64 (s, 1H, aromatic H), 9.30-9.80 (m, 1H, NH).
MS: 560.22⁺ (M+H)⁺
TLC: Rf=0.11 (eluent: DCM/AcOEt 4/1)

EXAMPLE 71

3-[4-Chloro-3-(2-methyl-2H-tetrazol-5-yl)phenyl]-(3,3-diphenylpropyl)-1-(2-morpholin-4-ylethyl)urea Method "B" was used to prepare the title compound having the following formula:

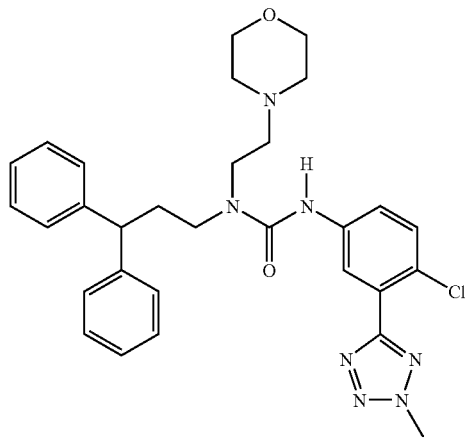

¹H NMR (400 MHz, CDCl₃): ppm 2.40 (q, 2H, CH2), 2.52-2.68 (m, 6H, CH2), 3.30 (t, 2H, CH2), 3.33-3.40 (m, 2H, CH2), 3.73-3.86 (m, 4H, CH2), 3.96 (t, 1H, CH), 4.44 (s, 3H, CH3), 7.15-7.23 (m, 2H, aromatic H), 7.26-7.35 (m, 8H, aromatic H), 7.45 (d, 1H, aromatic H), 7.67 (d, 1H, aromatic H), 7.94 (s, 1H, aromatic H), 9.26-9.80 (m, 1H, NH).
MS: 560.22⁺ (M+H)⁺
TLC: Rf: 0.21 (eluent: DCM/AcOEt 4/1)

EXAMPLE 72

3-Biphenyl-4-yl-1-(3,3-diphenylpropyl)-1-(2-morpholin-4-ylethyl)urea

Method "A" was used to prepare the title compound having the following formula:

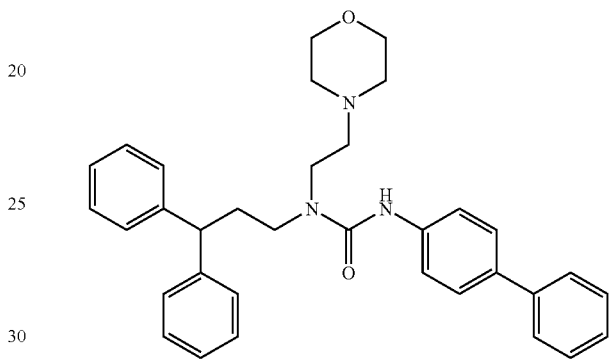

¹H NMR (400 MHz, CDCl₃): ppm 2.43 (q, 2H, CH₂), 2.61 (m, 6H, 3×CH₂), 3.32 (t, 2H, CH₂), 3.40 (m, 2H, CH₂), 3.81 (m, 4H, 2×CH₂), 3.99 (t, 1H, CH), 7.17-7.38 (m, 11H, aromatic H), 7.40-7.48 (m, 4H, aromatic H), 7.55 (d, 2H, aromatic H), 7.59 (d, 2H, aromatic H), 9.18 (bs, 1H, NH).
MS: 520⁺ (M+H)⁺

In order to obtain biaryl derivatives of formula (I) in which R₃ represents a phenyl radical substituted by an aryl group or a heterocycle, saturated or unsaturated, mono-, bi- or tricyclic, optionally containing from 1 to 5 heteroatoms and optionally being substituted by a halogen atom, an alkyl or alkoxy group containing from 1 to 6 carbon atoms, a product such as the one obtained in Example 11 can be made to react by Suzuki coupling with a boric acid derivative of formula Ar—B—(OH)₂ in accordance with the following scheme. The modes of procedure "M" or "N" below are employed.

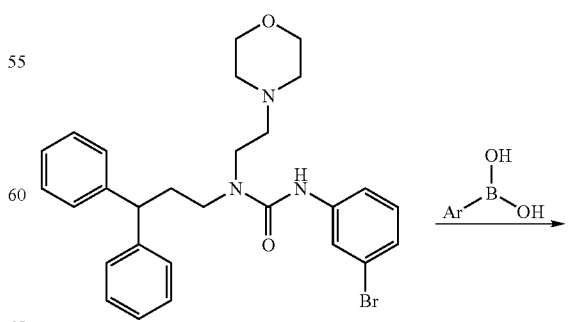

Example 11

-continued

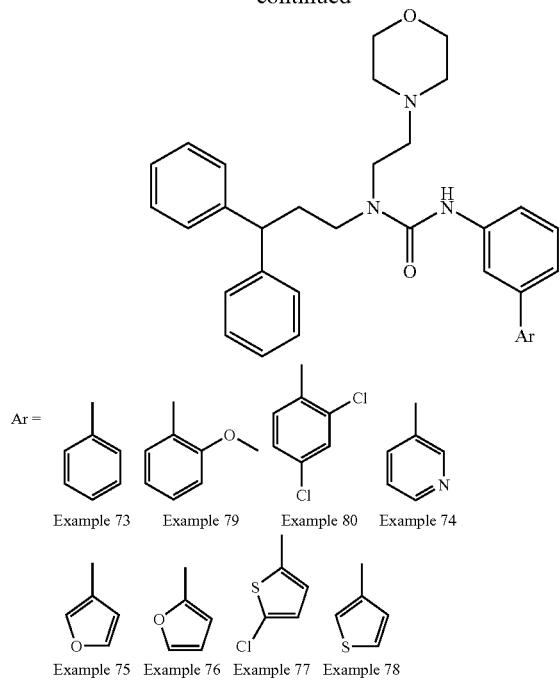

Example 73  Example 79  Example 80  Example 74

Example 75  Example 76  Example 77  Example 78

Method "M":

1 eq. of bromine derivative, obtained in Example 11, 1 eq. of boronic acid, 2 mL of THF, 2 mL of a 2 M solution of sodium carbonate in water and 0.1 eq. of palladium tetrakis are introduced into a Radley tube under nitrogen while stirring. The mixture is heated under reflux for one night. The THF is evaporated and the reaction medium is extracted with ethyl acetate. Then the organic phase is washed with water and a saturated NaCl solution. After drying over MgSO₄, filtration and concentration to dryness, the crude product is purified by column chromatography over silica gel (elution gradient: DCM/AcOEt 9/1 to 4/1) (yields ranging from 16% to 79%).

Method "N":

1 eq. of bromine derivative obtained in Example 11, 0.1 eq. of palladium tetrakis, 0.7 mL of dioxane, 0.7 mL of a 2 M solution of sodium carbonate in water and 1.5 eq. of boric acid are introduced in succession into a sealed 2-5 mL tube, adapted for microwave treatment. The mixture is stirred and heated to 100° C. for 3 to 10 minutes depending on the R group which introduces diversity. The reaction medium is subsequently extracted with ethyl acetate, then the organic phase is washed with water and a saturated NaCl solution. After drying over MgSO₄, filtration and concentration to dryness, the crude product is purified by chromatography over silica gel (yields ranging from 69% to 95%).

EXAMPLE 73

Biphenyl-3-yl-1-(3,3-diphenylpropyl)-1-(2-morpholin-4-ylethyl)urea

Method "M", starting with the product obtained in Example 11, was used to prepare the title compound having the following formula:

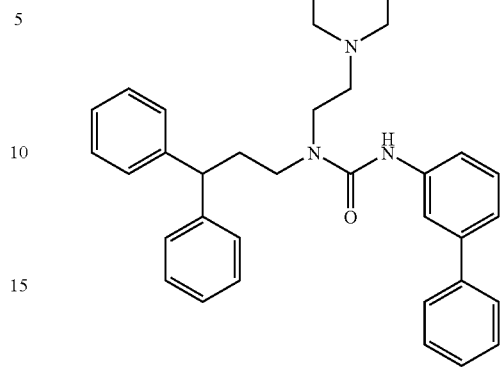

$^1$H NMR (400 MHz, CDCl$_3$): ppm 2.43 (q, 2H, CH$_2$), 2.69 (m, 6H, 3×CH$_2$), 3.33 (t, 2H, CH$_2$), 3.47 (m, 2H, CH$_2$), 3.82 (m, 4H, 2×CH$_2$), 3.98 (t, 1H, CH), 7.20 (m, 2H, aromatic H), 7.28 (m, 8H, aromatic H), 7.48 (m, 4H, aromatic H), 7.58 (m, 3H, aromatic H), 7.70 (m, 2H, aromatic H), 9.02 (bs, 1H, NH).

MS: 520.2$^+$ (M+H)$^+$

EXAMPLE 74

1-(3,3-diphenylpropyl)-1-(2-morpholin-4-ylethyl)-3-(3-pyridin-3-ylphenyl)urea

Method "M", starting with the product obtained in Example 11, was used to prepare the title compound having the following formula:

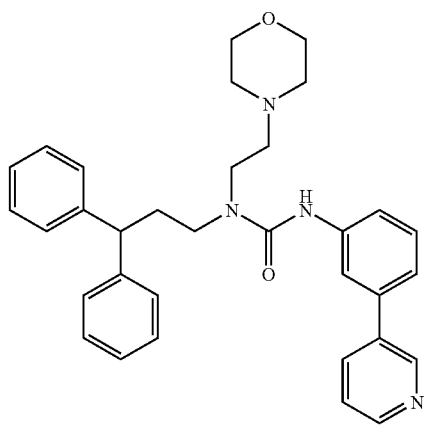

$^1$H NMR (400 MHz, CDCl$_3$): ppm 2.42 (q, 2H, CH$_2$), 2.73 (m, 6H, 3×CH$_2$), 3.35 (t, 2H, CH$_2$), 3.52 (m, 2H, CH$_2$), 3.85 (m, 4H, 2×CH$_2$), 3.98 (t, 1H, CH), 7.18-7.39 (m, 14H, aromatic H), 7.65 (s, 1H, aromatic H), 7.90 (d, 1H, aromatic H), 8.60 (d, 1H, aromatic H), 8.85 (s, 1H, aromatic H).

MS: 521.2$^+$ (M+H)$^+$

EXAMPLE 75

(1-(3,3-diphenylpropyl)-3-(3-furan-3-ylphenyl)-1-(2-morpholin-4-ylethyl)urea

Method "N", starting from the product obtained in Example 11, was used to prepare the title compound having the following formula:

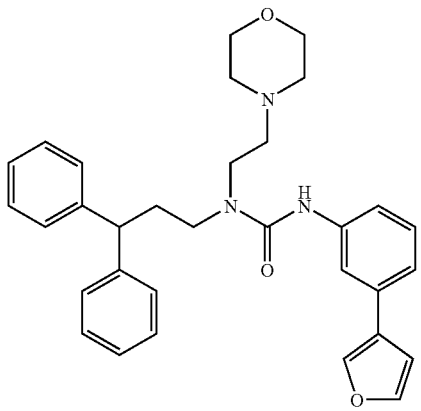

$^1$H NMR (400 MHz, CDCl$_3$): ppm 2.42 (q, 2H, CH$_2$), 2.60 (m, 6H, 3×CH$_2$), 3.32 (t, 2H, CH$_2$), 3.40 (m, 2H, CH$_2$), 3.80 (m, 4H, 2×CH$_2$), 3.98 (t, 1H, CH), 6.70 (s, 1H, H$_{furan}$), 7.12 (d, 1H, aromatic H), 7.20 (m, 2H, aromatic H), 7.29 (m, 5H, aromatic H), 7.49 (m, 3H, aromatic H), 7.55 (m, 2H, aromatic H), 7.70 (m, 3H, aromatic H), 9.09 (bs, 1H, NH).
MS: 510.2$^+$ (M+H)$^+$

EXAMPLE 76

1-(3,3-diphenylpropl)-3-(3-furan-2-ylphenyl)-1-(2-morpholin-4-ylethyl)urea

Method "N", starting from the product obtained in Example 11, was used to prepare the title compound having the following formula:

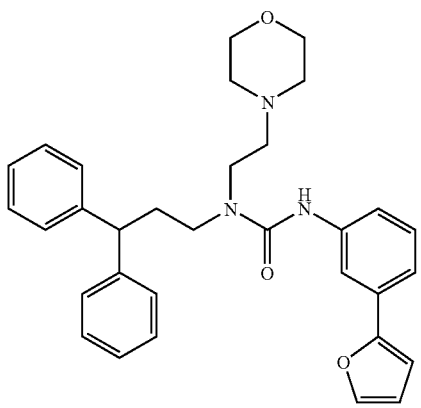

$^1$H NMR (400 MHz, CDCl$_3$): ppm 2.42 (q, 2H, CH$_2$), 2.65 (m, 6H, 3×CH$_2$), 3.33 (t, 2H, CH$_2$), 3.41 (m, 2H, CH$_2$), 3.85 (m, 4H, 2×CH$_2$), 3.99 (t, 1H, CH), 6.48 (m, 1H, H$_{oxazole}$), 6.65 (m, 1H, H$_{oxazole}$), 7.20 (m, 2H, aromatic H), 7.30 (m, 5H, aromatic H), 7.49 (m, 3H, aromatic H), 7.58 (m, 2H, aromatic H), 7.69 (m, 3H, aromatic H).
MS: 510.24$^+$ (M+H)$^+$

EXAMPLE 76A 1-(3,3-diphenylpropyl)-3-(3-furan-2-ylphenyl)-1-(2-morpholin-4-ylethyl)urea hydrochloride Method "F", starting from the product obtained in Example 76, was used to prepare the title compound having the following formula:

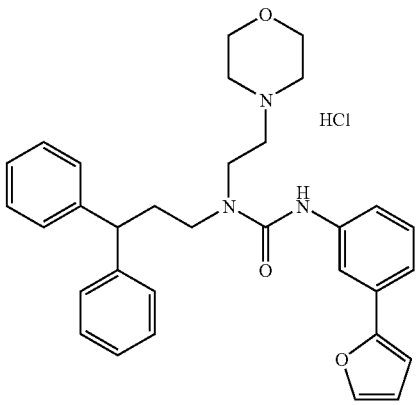

1H NMR (400 MHz, CD$_3$OD): ppm 2.50 (q, 2H, CH2), 3.12 (t, 2H, CH2), 3.30 (m, 2H, CH2), 3.43 (t, 2H, CH2), 3.60 (d, 2H, CH2), 3.75 (m, 4H, 2×CH2), 4.05 (m, 3H, CH2, CH), 6.52 (d, 1H, Hoxazole), 6.75 (d, 1H, Hoxazole), 7.20 (t, 2H, aromatic H), 7.32 (m, 6H, aromatic H), 7.40 (d, 1H, Hoxazole), 7.48 (m, 2H, aromatic H), 7.68 (m, 4H, aromatic H).
MS: 510.40$^+$ (M+H–HCl)$^+$

EXAMPLE 77

3-[3-(5-chlorothiophen-2-yl)-phenyl]-1-(3,3-diphenylpropyl)-1-(2-morpholin-4-ylethyl)urea Method "N", starting from the product obtained in Example 11, was used to prepare the title compound having the following formula:

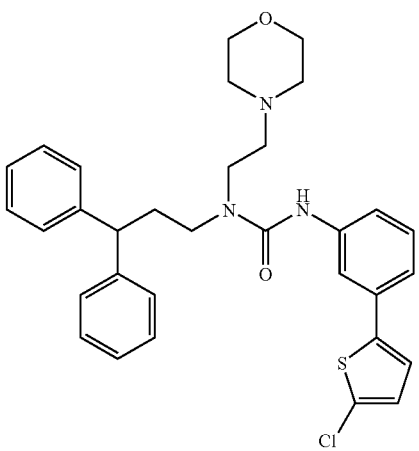

$^1$H NMR (400 MHz, CDCl$_3$): ppm 2.43 (q, 2H, CH$_2$), 2.75 (m, 6H, 3×CH$_2$), 3.35 (m, 4H, 2×CH$_2$), 3.90 (m, 4H, 2×CH$_2$), 3.97 (t, 1H, CH), 6.89 (d, 1H, aromatic H), 7.09 (d, 1H, aromatic H), 7.15-7.35 (m, 13H, aromatic H), 7.52 (s, 1H, aromatic H).
MS: 560.2$^+$ (M+H)$^+$

EXAMPLE 78

1-(3,3-diphenylpropyl)-1-(2-morpholin-4-ylethyl)-3-(3-thiophen-3-ylphenyl)urea

Method "N", starting from the product obtained in Example 11, was used to prepare the title compound having the following formula:

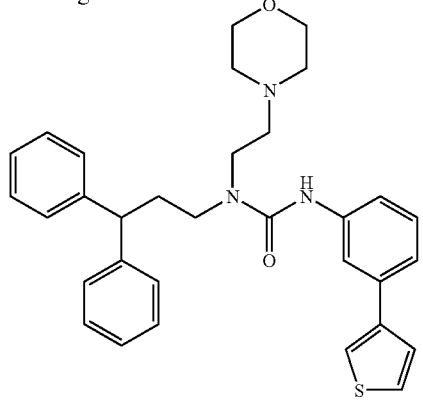

H NMR (400 MHz, CDCl$_3$): ppm 2.42 (q, 2H, CH$_2$), 2.64 (m, 6H, 3×CH$_2$), 3.32 (t, 2H, CH$_2$), 3.42 (m, 2H, CH$_2$), 3.82 (m, 4H, 2×CH$_2$), 3.98 (t, 1H, CH), 7.20 (m, 2H, aromatic H), 7.30 (m, 7H, aromatic H), 7.38 (s, 1H, aromatic H), 7.49 (m, 3H, aromatic H), 7.58 (m, 1H, aromatic H), 7.68 (m, 3H, aromatic H), 3.10 (m, 1H, NH).
MS: 526.2$^+$ (M+H)$^+$

EXAMPLE 79

1-(3,3-diphenylpropyl)-3-(2'-methoxybiphenyl-3-yl)-1-(2-morpholin-4-ylethyl)urea Method "N", starting from the product obtained in Example 11, was used to prepare the title compound having the following formula:

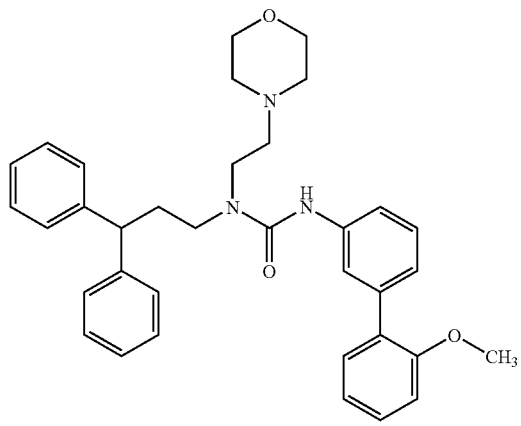

$^1$H NMR (400 MHz, CDCl$_3$): ppm 2.42 (q, 2H, CH$_2$), 2.62 (m, 6H, 3×CH$_2$), 3.32 (t, 2H, CH$_2$), 3.40 (m, 2H, CH$_2$), 3.80 (m, 4H, 2×CH$_2$), 3.82 (s, 3H, OCH$_3$), 3.97 (t, 1H, CH), 6.99 (d, 1H, aromatic H), 7.03 (t, 1H, aromatic H), 7.18 (m, 2H, aromatic H), 7.30 (m, 8H, aromatic H), 7.40 (m, 1H, aromatic H), 7.48 (m, 2H, aromatic H), 7.56 (m, 1H, aromatic H), 7.70 (m, 2H, aromatic H), 9.15 (bs, 1H, NH).
MS: 550.5$^+$ (M+H)$^+$

EXAMPLE 80

3-(2',4'-dichlorobiphenyl-3-yl)-1-(3,3-diphenylpropyl)-1-(2-morpholin-4-ylethyl)urea Method "N", starting from the product obtained in Example 11, was used to prepare the title compound having the following formula:

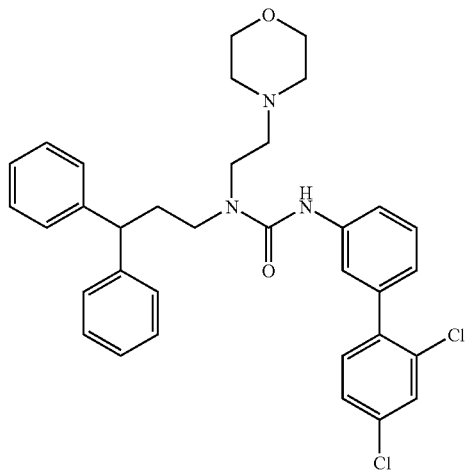

$^1$H NMR (400 MHz, CDCl$_3$): ppm 2.42 (q, 2H, CH$_2$), 2.62 (m, 6H, 3×CH$_2$), 3.30 (t, 2H, CH$_2$), 3.41 (m, 2H, CH$_2$), 3.79 (m, 4H, 2×CH$_2$), 3.97 (t, 1H, CH), 7.06 (d, 1H, aromatic H), 7.20 (m, 2H, aromatic H), 7.30 (m, 7H, aromatic H), 7.35 (m, 2H, aromatic H), 7.49 (m, 2H, aromatic H), 7.55 (m, 1H, aromatic H), 7.70 (m, 2H, aromatic H), 9.17 (bs, 1H, NH).
MS: 588.5$^+$ (M+H)$^+$ Biaryl derivatives of formula (I), in which R$^3$ represents an isoxazolylphenyl, benzimidazolylphenyl or benzothiazolylphenyl radical, can also be prepared starting from a methyl ester such as the one obtained in Example 1 by proceeding in accordance with the following scheme.

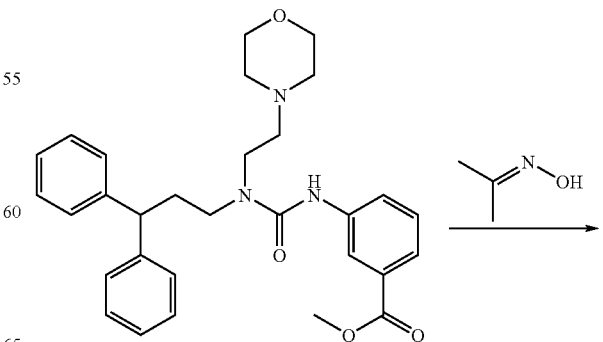

Example 1

-continued

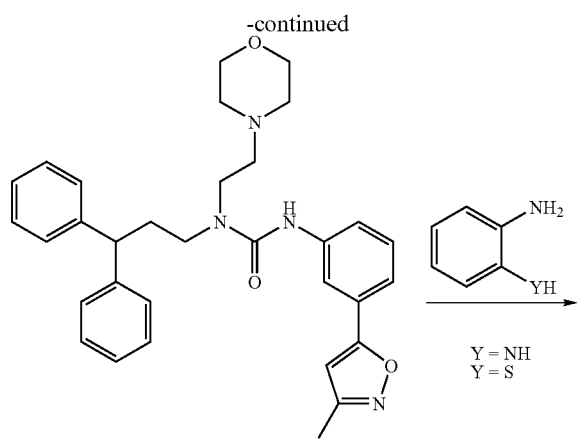

Example 81

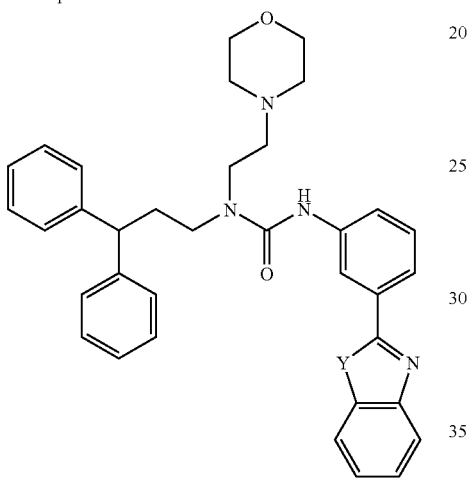

Y = NH, Example 82
Y = S,  Example 83

EXAMPLE 81

1-(3,3-diphenylpropyl)-3-[3-(3-methylisoxazol-5-yl)-phenyl]-1-(2-morpholin-4-ylethyl)urea 22 mg (0.3 mmol, 3 eq.) of oxime acetone, 0.4 mL of anhydrous THF and 376 μL of a 1.6 M solution of butyl lithium in hexane (0.6 mmol, 6 eq.) are introduced in succession into a 10 mL flask at 0° C. under argon. The mixture is stirred for 1 hour at 0° C. A solution of 50 mg (0.1 mmol, 1 eq.) of methyl ester obtained in Example 1, in 0.4 mL of anhydrous THF is then added dropwise at 0° C. Stirring is maintained for 20 hours, with the temperature passing progressively from 0° C. to room temperature. A solution of concentrated sulphuric acid (31 μL, d=1.83) in THF (0.3 mL) and water (0.1 mL) is poured into the reaction medium and the complete mixture is heated under reflux for 2 hours. After cooling, the pH of the solution is rendered basic by addition of a saturated potassium carbonate solution. The mixture is extracted with ethyl acetate and the organic phase is washed with a saturated NaCl solution. After drying over MgSO$_4$, filtration and concentration to dryness, the crude reaction product is purified by column chromatography over silica gel (elution gradient: CH$_2$Cl$_2$ then CH$_2$Cl$_2$/AcOEt 9/1 to 1/1), leading to 17.9 mg (yield=34%) of expected 3-methylisoxazole derivative.

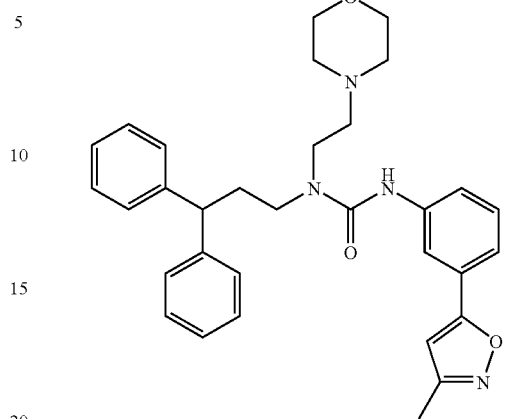

$^1$H NMR (400 MHz, CDCl$_3$): ppm 2.37 (s, 3H, CH$_3$), 2.42 (q, 2H, CH$_2$), 2.66 (m, 6H, 3×CH$_2$), 3.32 (t, 2H, CH$_2$), 3.43 (m, 2H, CH$_2$), 3.84 (m, 4H, 2×CH$_2$), 3.98 (t, 1H, CH), 6.39 (s, 1H, H$_{isoxazole}$), 7.20 (m, 2H, aromatic H), 7.28 (m, 6H, aromatic H), 7.39 (m, 2H, aromatic H), 7.49 (d, 1H, aromatic H), 7.52 (m, 1H, aromatic H), 7.75 (m, 2H, aromatic H).

MS: 525.5$^+$ (M+H)$^+$

EXAMPLE 82

3-[3-(1H-benzimidazole-2-yl)-phenyl]-1-(3,3-diphenylpropyl)-1-(2-morpholin-4-ylethyl)urea 1 mL of anhydrous toluene and 250 mL (0.5 mmol, 5 eq.) of a 2 M solution of trimethyl aluminium in toluene are introduced in succession into a 10 mL flask under argon and previously placed in an oven. The solution is cooled to 0° C., then 16.2 mg (0.15 mmol, 1.5 eq.) of 1.2-phenylenediamine are added. Stirring is continued for 30 minutes at 0° C., then for 45 minutes at room temperature. 50 mg (0.1 mmol, 1 eq.) of methyl ester obtained in Example 1 are then added and the mixture is heated under reflux for 12 hours. The reaction medium is cooled in an ice bath and 2 mL of water are added. The insoluble matter is filtered over a frit and rinsed with ethyl acetate. The organic phase is subsequently washed with saturated NaCl solution and dried over MgSO$_4$, then evaporated.

Purification of the crude reaction product by flash chromatography over silica gel (elution gradient: CH$_2$Cl$_2$ then CH$_2$Cl$_2$/MeOH 98/2 to 90/10) allows 34.5 mg of a mixture of the desired product and impurities to be obtained. The desired product is again purified by preparation LCMS, leading to 12.9 MG (yield=34%) of expected benzimidazole.

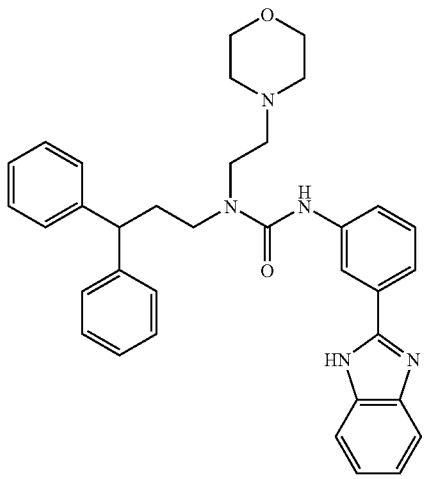

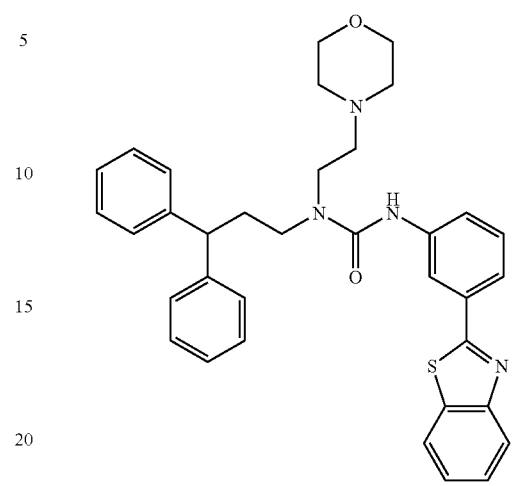

$^1$H NMR (400 MHz, CDCl$_3$): ppm 2.42 (q, 2H, CH$_2$), 2.54 (m, 6H, 3×CH$_2$), 3.32 (t, 2H, CH$_2$), 3.42 (m, 2H, CH$_2$), 3.78 (m, 4H, 2×CH$_2$), 3.97 (t, 1H, CH), 7.13-7.32 (m, 15H, aromatic H), 7.62 (m, 2H, aromatic H), 7.77 (d, 1H, aromatic H), 8.22 (s, 1H, NH), 9.32 (bs, 1H, NH).

MS: 560.5$^+$ (M+H)$^+$

EXAMPLE 83

3-(3-Benzothiazol-2-ylphenyl)-1-(3,3-diphenylpropyl)-1-(2-morpholin-4-ylethyl)urea The title compound was prepared by proceeding as indicated in Example 82 but using 2-aminothiophenol instead of 1,2-phenylenediamine.

$^1$H NMR (400 MHz, CDCl$_3$): ppm 2.43 (q, 2H, CH$_2$), 2.68 (m, 6H, 3×CH$_2$), 3.33 (t, 2H, CH$_2$), 3.48 (m, 2H, CH$_2$), 3.90 (m, 4H, 2×CH$_2$), 3.99 (t, 1H, CH), 7.20 (m, 2H, aromatic H), 7.30 (m, 8H, aromatic H), 7.41 (q, 2H, aromatic H), 7.51 (t, 1H, aromatic H), 7.72 (m, 2H, aromatic H), 7.93 (d, 1H, aromatic H), 8.08 (m, 2H, aromatic H), 9.46 (bs, 1H, NH).

MS: 577.5$^+$ (M+H)$^+$

Biaryl derivatives of general formula (I) in which R$^3$ represents a phenyl radical substituted by a tetrazolyl or N-Me tetrazolyl group can be prepared starting from the corresponding nitrile by proceeding in accordance with the following reaction scheme.

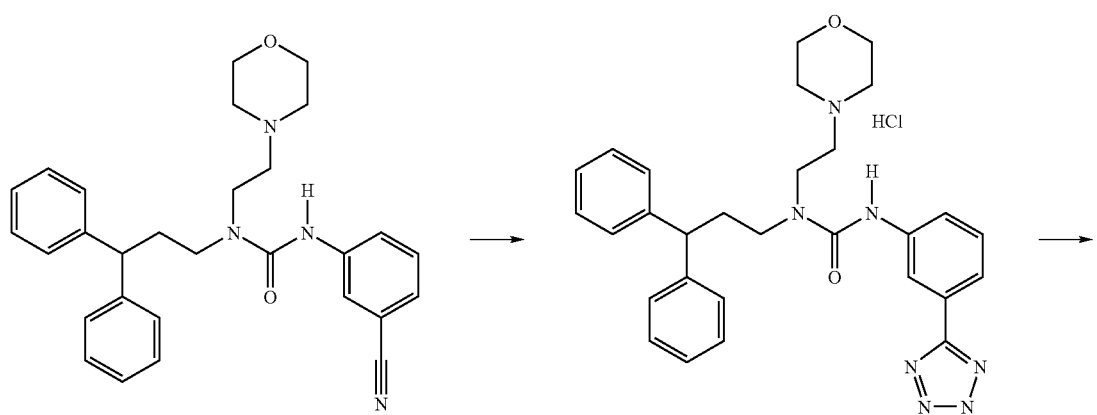

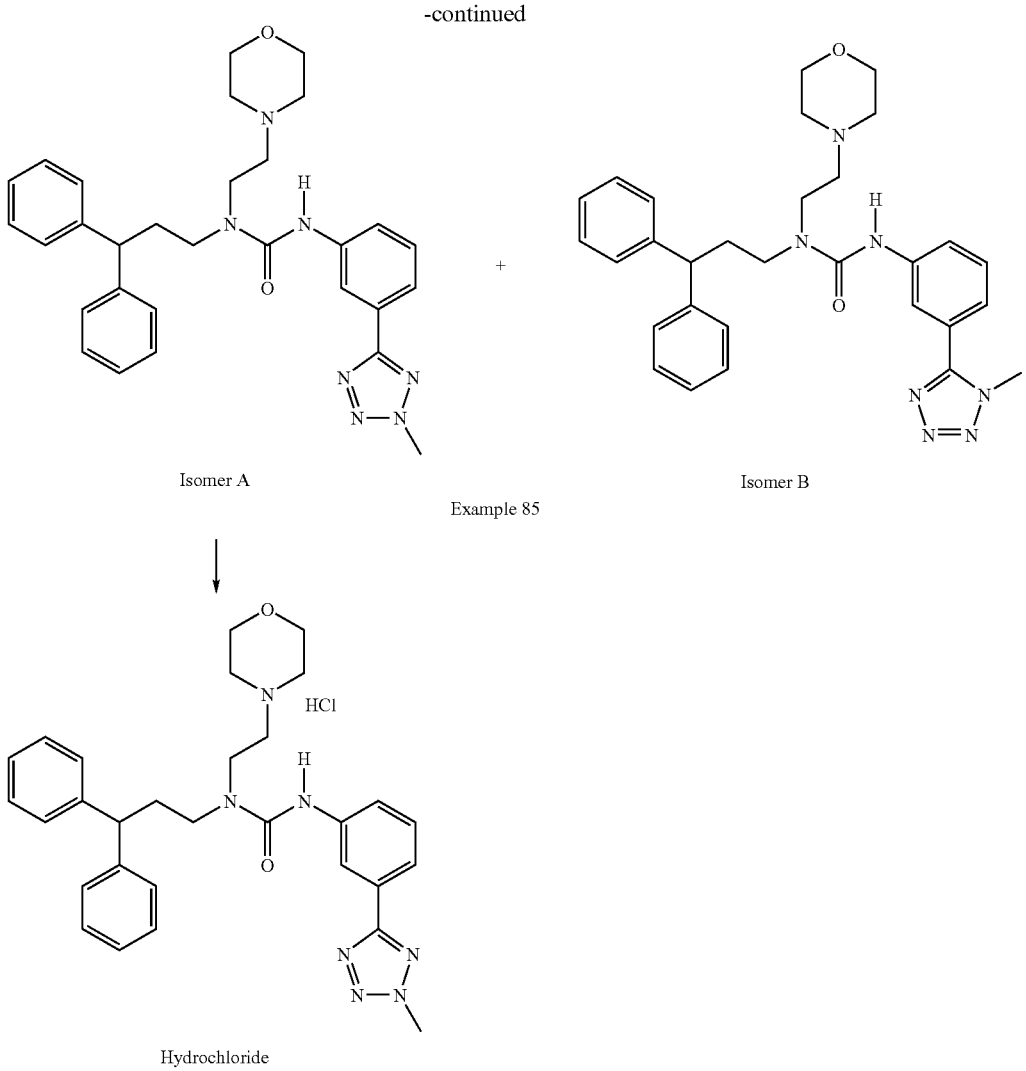

Example 85

Hydrochloride

EXAMPLE 84

1-(3,3-diphenylpropyl)-1-(2-morpholin-4-ylethyl)-3-[3-(2H-tetrazol-5-ylphenyl]urea hydrochloride 76.7 mg (0.164 mmol, 1 eq.) of nitrile derivative obtained in Example 19, 2.5 mL of toluene, and 90 µl (0.328 mmol, 2 eq.) of tributyl tin azide are introduced in succession into a 30 mL flask in an argon atmosphere while stirring. The mixture is heated under reflux for 16 hours, then the reaction medium is evaporated. 2 mL of 2 M HCl in diethyl ether are added to the mixture, the precipitate thus formed is washed with pentane, the crude reaction product is purified by flash chromatography over silica gel (elution gradient: $CH_2Cl_2$ then $CH_2Cl_2$/MeOH 95/5 then 90/10), leading to the expected derivative in hydrochloride form in a yield of 65%.

$^1$H NMR (400 MHz, $CDCl_3$): ppm 2.38 (q, 2H, CH2), 2.62-2.77 (m, 6H, CH2), 3.24-3.37 (m, 4H, CH2), 3.75-3.83 (m, 4H, CH2), 3.96 (t, 1H, CH), 7.15-7.33 (m, 12H, aromatic H), 7.63-7.69 (m, 1H, aromatic H), 8.05 (s, 1H, aromatic H).

MS: 512.4$^+$ (M+H)$^+$

TLC: Rf=0.27 (eluent: DCM/MeOH 90/10)

EXAMPLE 85

1-(3,3-diphenylpropyl)-3-[3-(2-methyl-2H-tetrazol-5-yl)phenyl]-1-(2-morpholin-4-ylethyl)urea (Isomer A) and its hydrochloride, and 1-(3,3-diphenylpropyl)-3-[3-(1-methyl-1H-tetrazol-5-yl)phenyl]-1-(2-morpholin-4-ylethyl)urea (Isomer B)

536 mg (0.978 mmol, 1 eq.) of tetrazole derivative, obtained in Example 84, 1 mL of acetonitrile, and 73.4 µL (1.173 mmol, 1.2 eq.) of methyl iodide and 162 mg of $K_2CO_3$ (1.173 mmol, 1.2 eq.) are introduced in succession into a 100 mL flask under an argon atmosphere while stirring. The mixture is heated under reflux for 30 minutes, the reaction being incomplete, 0.6 eq. (0.587 mmol) of methyl iodide are still added to the reaction mixture, stirring is maintained for 30 minutes under reflux. The reaction medium is cooled to room temperature then neutralised with water. The organic phase is extracted repeatedly with dichloromethane at pH 8 and, after washing with NaCl, drying over MgSO$_4$ and evaporation of the solvent, the crude product obtained is purified by flash chromatography over silica gel (elution gradient: heptane/AcOEt 1/1 to 1.6 then pure AcOEt) to lead to the expected product in the form of isomer A with a yield of 34% and isomer B with a yield of 10%.

Isomer A $^1$H NMR (400 MHz, CDCl$_3$): ppm 2.40 (q, 2H, CH$_2$), 2.60 (m, 6H, 3×CH$_2$), 3.30 (m, 2H, CH$_2$), 3.38 (m, 2H, CH$_2$), 3.82 (t, 4H, 2×CH$_2$), 4.00 (t, 1H, CH), 4.40 (s, 3H, NCH$_3$), 7.20 (m, 2H, aromatic H), 7.30 (m, 8H, aromatic H), 7.43 (t, 1H, aromatic H), 7.70 (d, 1H, aromatic H), 7.78 (d, 1H, aromatic H), 8.08 (s, 1H, aromatic H), 9.40 (bs, 1H, NH).

MS: 526$^+$ (M+H)$^+$

Hydrochloride of Isomer A $^1$H NMR (400 MHz, CD$_3$OD): ppm 2.50 (q, 2H, CH$_2$), 3.15 (m, 2H, CH$_2$), 3.30 (m, 2H, CH$_2$), 3.45 (t, 2H, CH$_2$), 3.60 (d, 2H, CH$_2$), 3.75 (m, 4H, 2×CH$_2$), 4.10 (m, 3H, CH, CH$_2$), 4.42 (s, 3H, NCH$_3$), 7.20 (t, 2H, aromatic H), 7.35-7.25 (m, 8H, aromatic H), 7.48 (t, 1H, aromatic H), 8.18 (s, 1H, aromatic H), 7.80 (d, 1H, aromatic H), 7.52 (bd, 1H, aromatic H).

MS: 526$^+$ (M+H−2HCl)$^+$

Isomer B $^1$H NMR (400 MHz, CDCl$_3$): ppm 2.40 (q, 2H, CH$_2$), 2.60 (m, 6H, 3×CH$_2$), 3.30 (m, 2H, CH$_2$), 3.38 (m, 2H, CH$_2$), 3.78 (t, 4H, 2×CH$_2$), 3.98 (t, 1H, CH), 4.20 (s, 3H, NCH$_3$), 7.20 (m, 2H, aromatic H), 7.30 (m, 8H, aromatic H), 7.38 (m, 1H, aromatic H), 7.48 (d, 2H, aromatic H), 8.00 (s, 1H, aromatic H), 9.50 (bs, 1H, NH).

MS: 526$^+$ (M+H)$^+$

EXAMPLE 86

1-(3,3-diphenylpropyl)-3-[3-(2-methyl-2H-tetrazol-5-yl)phenyl]-1-(2-morpholin-4-ylethyl)urea (Isomer A) and 1-(3,3-diphenylpropyl)-3-[3-(1-methyl-1H-tetrazol-5-yl)phenyl]-1-(2-morpholin-4-ylethyl)urea (Isomer B)

The title compounds (products identical to the products obtained in Example 85) were prepared by an alternative to the process of the invention, in accordance with the following scheme.

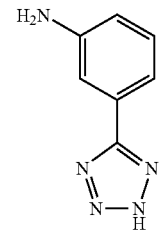

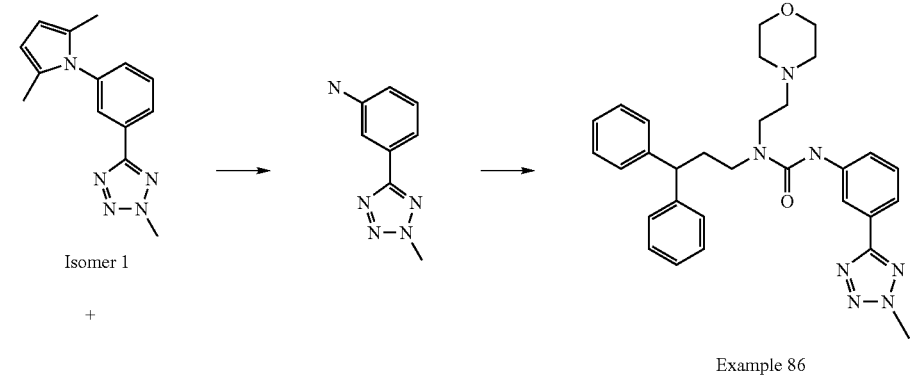

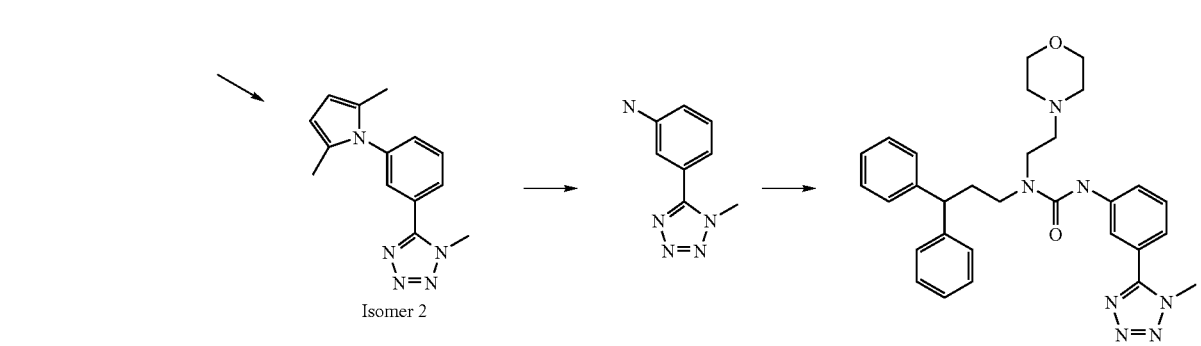

1) Synthesis of
5-[3-(2,5-dimethylpyrrol-1-yl)phenyl]-2H-tetrazole 8 g (49.64 mmol, 1 eq.) of 5-(3-aminophenyl)-tetrazole are introduced into a 500 mL flask equipped with a Dean Stark trap, with 200 mL of toluene and 0.80 mL of acetic acid.

6.89 µL (58.57 mmol, 1.18 eq.) acetonyl acetone are added. The mixture is heated under reflux for 1 hour 30 min. The initially insoluble mixture dissolves during the reaction and becomes red. The solution is left to return to room temperature and the product crystallises in the medium. The solvent is concentrated to half and the insoluble matter is filtered and rinsed 4 times with toluene (m=9.45 g, yield=80%).

2) Synthesis of isomer 1 5-[3-(2,5-Dimethylpyrrol-1-yl)phenyl]-2-methyl-2H-tetrazole and isomer 2,5-[3-(2,5-Dimethylpyrrol-1-yl)phenyl]-1-methyl-1H-tetrazole 9 g (37.61 mmol, 1 eq.) of 5-[3-(2,5-dimethylpyrrol-1-yl)phenyl]-2H-tetrazole are dissolved in 45 mL of acetonitrile in a flask equipped with a condenser. 6.24 g (45.14 mmol, 1.2 eq.) of potassium carbonate are added. The mixture is heated to 80° C., and 2.82 mL (45.14 mmol, 1.2 eq.) of methyl iodide are added. The mixture is stirred for 15 min. at 80° C. and a further 0.94 mL (15.05 mmol, 0.4 eq.) of methyl iodide are added. The mixture is stirred for 15 min. at 80° C. then left to rest for one night at room temperature. The medium is concentrated and taken up in DMF. Water is added and the basic aqueous phase is extracted with DCM. The organic phase is washed with brine, dried over MgSO$_4$, filtered and concentrated. The residue is purified by chromatography over silica gel (eluent: pure heptane to heptane/AcOEt 2/1) (6 g of Isomer 1, yield=63%; 3.54 g of Isomer 2, yield=37%).

3) Synthesis of
3-(2-methyl-2H-tetrazol-5-yl)phenylamine 5.71 g (22.54 mmol, 1 eq.) of isomer 1 obtained above are dissolved hot in 61 mL of ethanol and 23 mL of water. 7.83 g (113 mmol, 5 eq.) of hydroxylamine hydrochloride are added and the mixture is stirred for 24 h under reflux. 7.83 g (113 mmol, 5 eq.) of hydroxylamine hydrochloride are added again and the reflux is maintained for a further 24 hours. The ethanol is concentrated and a 2 N solution of hydrochloric acid is added. Diethyl ether is added and the aqueous phase is repeatedly extracted with Et$_2$O. The aqueous phase is recovered, basified with 2 N NaOH then concentrated NaOH. It is extracted with ethyl acetate. The organic phase is washed with brine, dried over MgSO$_4$, filtered and concentrated. The residue is purified by chromatography over silica gel (eluent: heptane/AcOEt 1/1) (m=3.11 g, yield=79%).

4): Synthesis of 1-(3,3-diphenylpropyl)-3-[3-(2-methyl-2H-tetrazol-5-yl)phenyl]-1-(2-morpholin-4-ylethyl)urea (Isomer 1)

Starting from the 3-(2-methyl-2H-tetrazol-5-yl)phenylamine obtained above, the expected product was prepared by method "D" (m=238 mg, yield=91%).

EXAMPLE 87

3-benzo[1,3]dioxol-5-yl-1-(3,3-diphenylpropyl)-1-(2-morpholin-4-ylethyl)urea

Method "A" was used to prepare the title compound having the following formula:

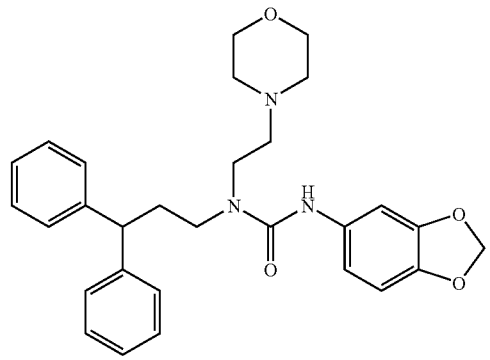

$^1$H NMR (400 MHz, CDCl$_3$): ppm 2.40 (q, 2H, CH$_2$), 2.62 (m, 6H, 3×CH$_2$), 3.29 (t, 2H, CH$_2$), 3.40 (m, 2H, CH$_2$), 3.78 (m, 4H, 2×CH$_2$), 3.97 (t, 1H, CH), 5.92 (s, 2H, CH$_2$), 6.64 (d, 1H, aromatic H), 6.72 (d, 1H, aromatic H), 7.03 (s, 1H, aromatic H), 7.15-7.23 (m, 2H, aromatic H), 7.25-7.34 (m, 8H, aromatic H), 9.00 (bs, 1H, NH).

MS: 488$^+$ (M+H)$^+$

EXAMPLE 88

3-(2,3-dihydro-benzo[1,4]dioxin-6-yl)-1-(3,3-diphenylpropyl)-1-(2-morpholin-4-ylethyl)urea Method "A" was used to prepare the title compound having the following formula:

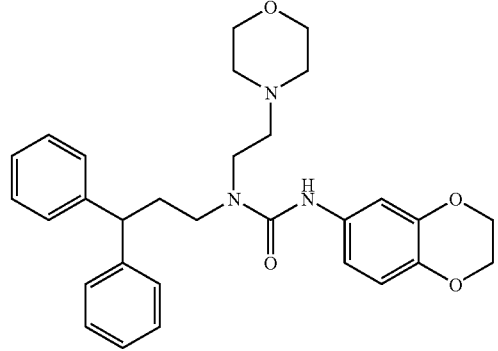

$^1$H NMR (400 MHz, CDCl$_3$): ppm 2.40 (q, 2H, CH$_2$), 2.60 (bs, 6H, 3×CH$_2$), 3.28 (t, 2H, CH$_2$), 3.35 (bs, 2H, CH$_2$), 3.78 (bs, 4H, 2×CH$_2$), 3.95 (t, 1H, CH), 4.22 (bs, 4H, 2×CH$_2$), 6.78 (s, 2H, aromatic H), 6.92 (s, 1H, aromatic H), 7.20 (m, 2H, aromatic H), 7.30 (m, 8H, aromatic H), 8.85 (bs, 1H, NH).

MS: 502$^+$ (M+H)$^+$

Method "A" was used to prepare the title compounds of the following formulae:

TABLE 5

| Formula | [M + H]+ | Rf = (DCM/AcOEt) | EXAMPLE |
|---|---|---|---|
|  | 494.1 | 0.18 (4/1) | Example 89 |
|  | 494.1 | 0.14 (4/1) | Example 90 |
|  | 574.2 | = 0.48(95/5 DCM/MeOH) | Example 91 |

EXAMPLE 92

1-(3,3-diphenylpropyl)-1-(2-morpholin-4-ylethyl)-3-(3-oxo-1,3-dihydroisobenzofuran-5-yl)urea Method "B" was used to prepare the title compounds of the following formulae:

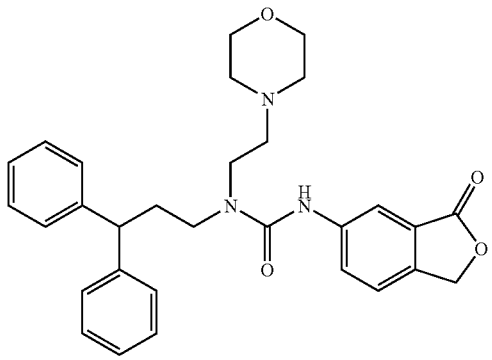

$^1$H NMR (400 MHz, CDCl$_3$): ppm 2.40 (q, 2H, CH$_2$), 2.62 (m, 6H, 3×CH$_2$), 3.32 (t, 2H, CH$_2$), 3.40 (bs, 2H, CH$_2$), 3.78 (bs, 4H, 2×CH$_2$), 3.98 (t, 1H, CH), 5.28 (s, 2H, CH$_2$), 7.20 (m, 2H, aromatic H), 7.30 (m, 8H, aromatic H), 7.40 (d, 1H, aromatic H), 7.75 (s, 1H, aromatic H), 7.85 (d, 1H, aromatic H), 9.50 (bs, 1H, NH). MS: 500.8$^+$ (M+H)$^+$

EXAMPLE 93

1-(3,3-diphenylpropyl)-1-(2-morpholin-4-ylethyl)-3-(8-oxo-5,6,7,8-tetrahydro-naphthalen-2-yl)urea Method "B" was used to prepare the title compound having the following formula:

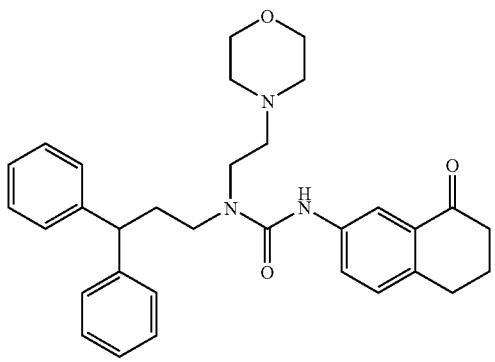

$^1$H NMR (400 MHz, CDCl$_3$): ppm 2.12 (m, 2H, CH$_2$), 2.40 (m, 2H, CH$_2$), 2.60 (m, 8H, 4×CH$_2$), 2.92 (t, 2H, CH$_2$), 3.30 (m, 2H, CH$_2$), 3.38 (m, 2H, CH$_2$), 3.80 (m, 4H, 2×CH$_2$), 3.98 (t, 1H, CH), 7.20 (m, 2H, aromatic H), 7.30 (m, 9H, aromatic H), 7.72 (s, 1H, aromatic H), 7.78 (d, 1H, aromatic H), 9.30 (bs, 1H, NH).
MS: 512$^+$ (M+H)$^+$

EXAMPLE 94

3-(1-acetyl-2,3-dihydro-1H-indol-6-yl)-1-(3,3-diphenylpropyl)-1-(2-morpholin-4-ylethyl)urea Method "B" was used to prepare the title compound having the following formula:

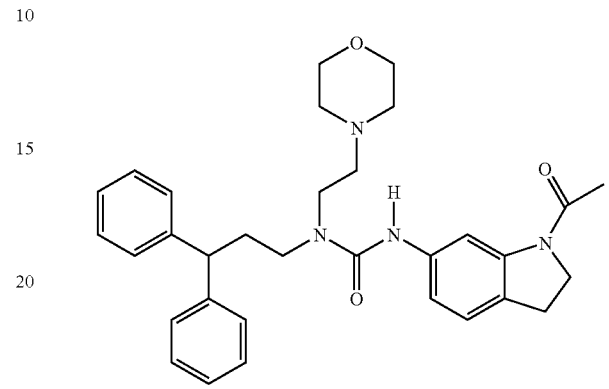

$^1$H NMR (400 MHz, CDCl$_3$): ppm 2.22 (s, 3H, CH$_3$), 2.40 (q, 2H, CH$_2$), 2.65 (m, 6H, 3×CH$_2$), 3.15 (t, 2H, CH$_2$), 3.30 (t, 2H, CH$_2$), 3.42 (m, 2H, CH$_2$), 3.87 (m, 4H, 2×CH$_2$), 3.99 (t, 1H, CH), 4.05 (t, 2H, CH$_2$), 7.10 (d, 1H, aromatic H), 7.20 (m, 2H, aromatic H), 7.30 (m, 9H, aromatic H), 7.45 (1H, aromatic H), 8.00 (s, 1H, aromatic H), 9.30 (bs, 1H, NH).
MS: 527$^+$ (M+H)$^+$

EXAMPLE 95

1-(3,3-diphenylpropyl)-3-(1H-indazol-6-yl)-1-(2-morpholin-4-ylethyl)urea

Method "B" was used to prepare the title compound having the following formula:

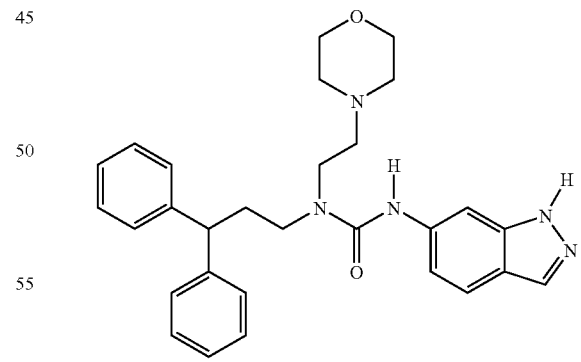

$^1$H NMR (400 MHz, CDCl$_3$): ppm 2.45 (q, 2H, CH$_2$), 2.65 (m, 6H, 3×CH$_2$), 3.35 (t, 2H, CH$_2$), 3.40 (m, 2H, CH$_2$), 3.80 (m, 4H, 2×CH$_2$), 4.00 (t, 1H, CH), 6.88 (d, 1H, aromatic H), 7.20 (m, 2H, aromatic H), 7.30 (m, 8H, aromatic H), 7.60 (d, 1H, aromatic H), 7.98 (s, 1H, aromatic H), 8.01 (s, 1H, aromatic H), 9.25 (bs, 1H, NH), 10.40 (bs, 1H, NH).
MS: 484$^+$ (M+H)$^+$

EXAMPLE 96

1-(3,3-diphenylpropyl)-3-(9-ethyl-9H-carbazol-3-yl)-1-(2-morpholin-4-ylethyl)urea Method "B" was used to prepare the title compound having the following formula:

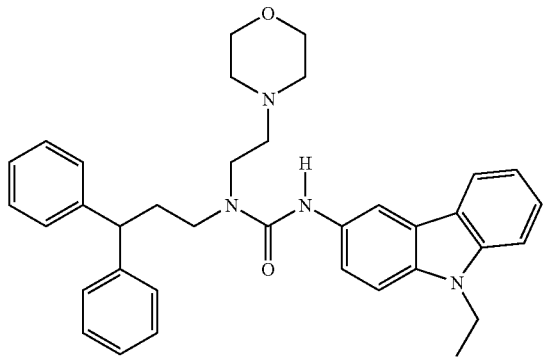

$^1$H NMR (400 MHz, CDCl$_3$): ppm 1.45 (t, 3H, CH$_3$), 2.48 (q, 2H, CH$_2$), 2.65 (m, 6H, 3×CH$_2$), 3.35 (t, 2H, CH$_2$), 3.45 (m, 2H, CH$_2$), 3.80 (m, 4H, 2×CH$_2$), 4.00 (t, 1H, CH), 4.35 (q, 2H, CH$_2$), 7.20 (m, 3H, aromatic H), 7.25-7.34 (m, 9H, aromatic H), 7.36-7.50 (m, 3H, aromatic H), 8.05 (s, 1H, aromatic H), 8.10 (s, 1H, aromatic H), 8.90 (bs, 1H, NH).

MS: 561$^+$ (M+H)$^+$

EXAMPLE 97

1-(3,3-diphenylpropyl)-3-isoquinolin-7-yl-1-(2-morpholin-4-ylethyl)urea

Method "B" was used to prepare the title compound having the following formula:

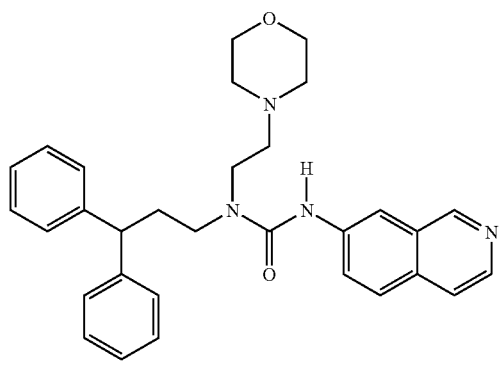

$^1$H NMR (400 MHz, CDCl$_3$): ppm 2.48 (q, 2H, CH$_2$), 2.70 (m, 6H, 3×CH$_2$), 3.40 (t, 2H, CH$_2$), 3.65 (m, 6H, 3×CH$_2$), 4.00 (t, 1H, CH), 7.20 (m, 2H, aromatic H), 7.30 (m, 9H, aromatic H), 7.62 (m, 2H, aromatic H), 7.80 (d, 1H, aromatic H), 7.88 (d, 1H, aromatic H), 8.52 (bs, 1H, aromatic H), 9.25 (bs, 1H, NH).

MS: 495$^+$ (M+H)$^+$

EXAMPLE 98

3-(2-chloro-benzyl)-1-(3,3-diphenylpropyl)-1-(2-morpholin-4-ylethyl)urea

Method "A" was used to prepare the product of the following formula:

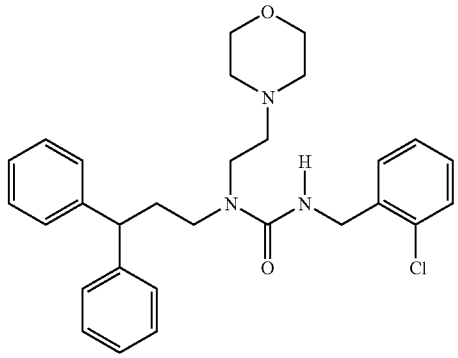

$^1$H NMR (400 MHz, CDCl$_3$): ppm 2.35 (q, 2H, CH2), 2.39-2.44 (m, 4H, CH2), 2.46 (t, 2H, CH2), 3.23 (t, 2H, CH2), 3.26 (t, 2H, CH2), 3.45 (m, 4H, CH2), 3.94 (t, 1H, CH), 4.48 (d, 2H, CH2), 7.15-7.33 (m, 12H, aromatic H), 7.37 (d, 1H, aromatic H), 7.42 (d, 1H, aromatic H).

MS: 492.2$^+$ (M+H)$^+$

TLC: Rf=0.10 (eluent: DCM/AcOEt 4/1)

EXAMPLE 99

1-(3,3-diphenylpropyl)-1-(2-morpholin-4-ylethyl)-3-thiophen-2-ylmethylurea

Method "C" was used to prepare the product of the following formula:

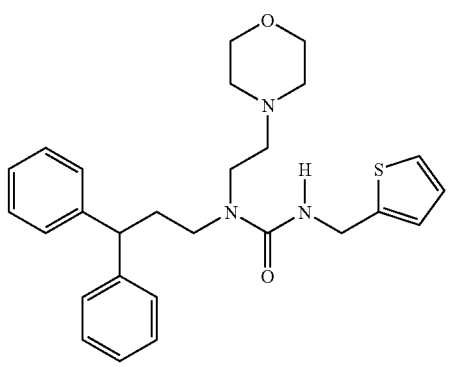

$^1$H NMR (400 MHz, CDCl$_3$): ppm 2.35 (q, 2H, CH2), 2.45 (m, 6H, CH2), 3.22 (m, 4H, CH2), 3.40 (m, 4H, CH2), 3.95 (t, 1H, CH), 4.55 (d, 2H, CH2), 6.95 (m, 2H, aromatic H), 7.12-7.32 (m, 11H, aromatic H).

MS: 463.6$^+$ (M+H)$^+$

TLC: Rf=0.27 (eluent: DCM/MeOH 95/5)

EXAMPLE 100

1-(3,3-diphenylpropyl)-1-(2-morpholin-4-ylethyl)-3-(1-naphthalen-1-ylethyl)urea

Method "A" was used to prepare the product of the following formula:

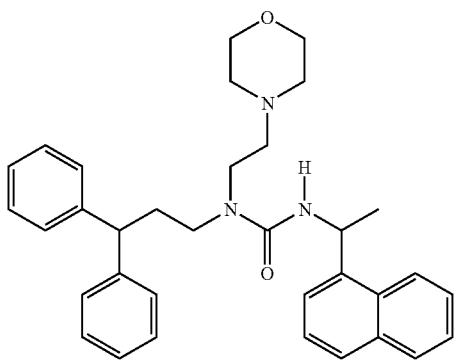

MS: 522.0⁺ (M+H)⁺
TLC: Rf=0.32 (eluent: DCM/MeOH 95/5)

EXAMPLE 101

3-[3-(3,3-diphenylpropyl)-3-(2-morpholin-4-ylethyl)ureido]thiophene-2-carboxylic acid methyl ester Method "B" was used to prepare the title compound having the following formula:

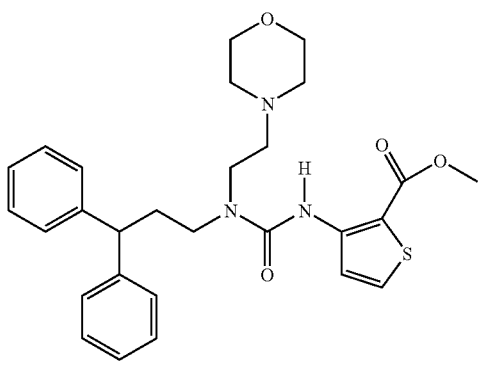

$^1$H NMR (400 MHz, CDCl3): ppm 10.02-9.95 (s e1, 1H, NH), 8.03 (d, 1H, aromatic H), 7.44 (d, 1H, aromatic H), 7.36-7.26 (m, 8H, aromatic H), 7.24-7.16 (m, 2H, aromatic H), 4.08 (t, 1H, CH), 3.90 (s, 3H, CH3), 3.70-3.55 (m, 4H, CH2), 3.50-3.35 (m, 4H, CH2), 2.60-2.30 (m, 8H, CH2).
MS: 507.3⁺ (M+H)⁺
TLC: Rf=0.19 (eluent: DCM/AcOEt 1/1)

EXAMPLE 102

1-(3,3-diphenylpropyl)-1-(2-morpholin-4-ylethyl)-3-pyridin-3-ylurea

Method "B" was used to prepare the title compound having the following formula:

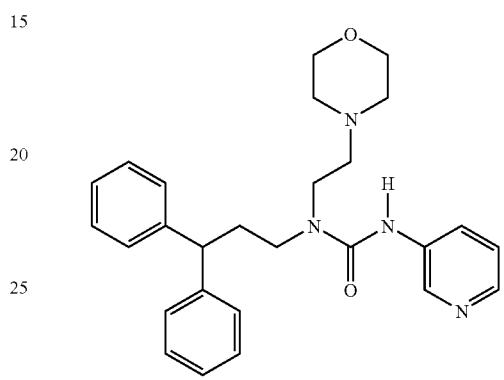

$^1$H NMR (400 MHz, CDCl$_3$): ppm 2.40 (q, 2H, CH$_2$), 2.65 (m, 6H, 3×CH$_2$), 3.32 (t, 2H, CH$_2$), 3.43 (m, 2H, CH$_2$), 3.80 (m, 4H, 2×CH$_2$), 3.98 (t, 1H, CH), 7.15-7.35 (m, 11H, aromatic H), 7.98 (d, 1H, aromatic H), 8.35 (bs, 1H, aromatic H), 8.48 ((bs, 1H, aromatic H), 9.30 (bs, 1H, NH).
MS: 445⁺ (M+H)⁺

EXAMPLE 103

1-(3,3-diphenylpropyl)-3-[3-(2-methyl-2H-tetrazol-5-yl)phenyl]-1-(2-morpholin-4-ylethyl)urea 125 mg (0.77 mmol, 1.5 eq.) of carbonyl diimidazole are dissolved in 0.4 mL of DCM then 82 mg (0.51 mmol, 1 eq.) of 3-(2-methyl-2H-tetrazol-5-yl)phenylamine, in 0.4 mL of DCM are added dropwise under argon. A white precipitate appears. The suspension is stirred for 15 hours at room temperature. 200 mg (0.615 mmol, 1.2 eq.) of [3,3-diphenylpropyl)(2-morpholin-4-ylethyl)amine] in 0.4 mL of DCM are added. The solution, which has become clear again, is stirred for 3 hours at room temperature. A sodium bicarbonate solution is added and the aqueous phase is extracted with dichloromethane. The organic phase is washed with brine, dried over MgSO$_4$, filtered and concentrated. The oil obtained is subjected to chromatography over silica gel (eluent: 1/0 to 1/1 heptane/AcOEt) (238 mg, yield=91%).

The product obtained is identical to the product obtained in Example 86. This procedure is hereinafter called method "D".

EXAMPLE 104

3-(1-benzyl-1H-benzimidazol-2-yl)-1-(3,3-diphenyl-propyl)-1-(2-morpholin-4-ylethyl)urea Method "D" was used to prepare the product of the following formula:

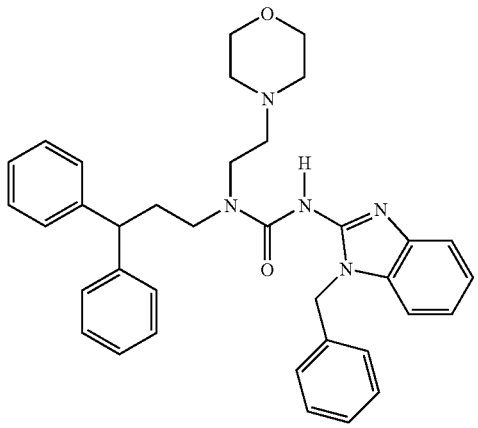

¹H NMR (400 MHz, acetone D6): ppm 12.00-11.85 (s e1, 1H, NH), 7.50-7.05 (m, 19H, aromatic H), 5.31 (s, 1H, CH), 5.20 (s, 1H, CH), 4.07-3.95 (m, 1H, CH), 3.62 (t, 1H, CH), 3.57-3.40 (m, 6H, CH2), 3.36 (t, 1H, CH), 2.52-2.32 (m, 6H, CH2), 2.30-2.20 (m, 2H, CH2).
MS: 574.54⁺ (M+H)⁺
TLC: Rf=0.13 (eluent: DCM/MeOH 97/3)

EXAMPLE 105

1-(3,3-diphenylpropyl)-3-(2-methyl-5-phenyl-2,5-dihydro-1H-pyrazol-3-yl)-1-(2-morpholin-4-ylethyl)urea Method "D" was used to prepare the product of the following formula:

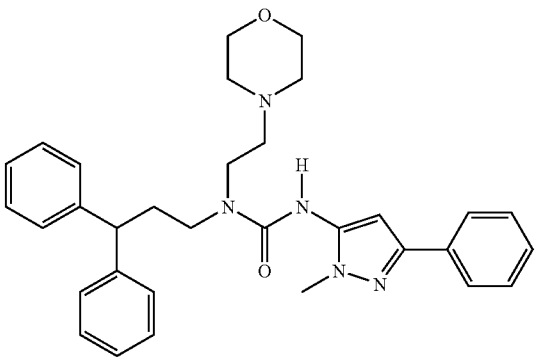

¹H NMR (400 MHz, acetone D6): ppm 9.70-9.45 (s e1, 1H, NH), 7.81 (d, 2H, aromatic H), 7.42-7.23 (m, 11H, aromatic H), 7.18 (t, 2H, aromatic H), 6.41 (s, 1H, H pyrazole), 4.04 (t, 1H, CH), 3.70 (s, 3H, CH3), 3.63-3.56 (m, 4H, CH2), 3.55-3.50 (m, 2H, CH2), 3.34 (t, 2H, CH2), 2.67-2.60 (m, 2H, CH2), 2.58-2.50 (m, 4H, CH2), 2.44 (q, 2H, CH2).
MS: 524.54⁺ (M+H)⁺
TLC: Rf=0.17 (eluent: DCM/MeOH 97/3)

EXAMPLE 106

3-(4,6-dimethylpyridin-2-yl)-1-(3,3-diphenylpropyl)-1-(morpholin-4-ylethyl)urea

Method "D" was used to prepare the product of the following formula:

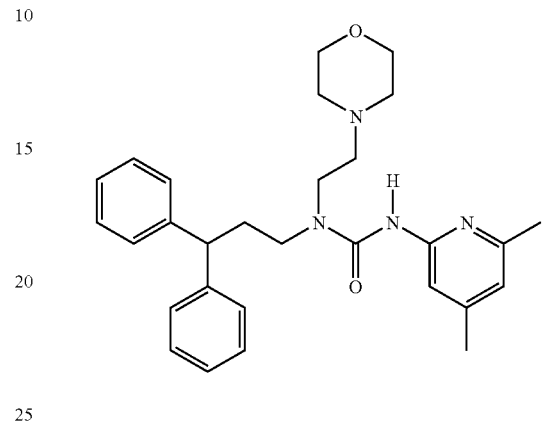

¹H NMR (400 MHz, acetone D6): ppm 10.70-10.50 (s e1, 1H, NH), 7.62 (s, 1H, aromatic H), 7.39 (d, 4H, aromatic H), 7.30 (t, 4H, aromatic H), 7.18 (t, 2H, aromatic H), 6.62 (s, 1H, aromatic H), 4.05 (t, 1H, CH), 3.98-3.87 (m, 4H, CH2), 3.47-3.40 (m, 2H, CH2), 3.30 (t, 2H, CH2), 2.65-2.52 (m, 6H, CH2), 2.43 (q, 2H, CH2), 2.33 (s, 3H, CH3), 2.26 (s, 3H, CH3).
MS: 473.51⁺ (M+H)⁺
TLC: Rf=0.36 (eluent: DCM/MeOH 97/3)

EXAMPLE 107

1-(3,3-diphenylpropyl)-3-(4-methoxy-6-methylpyrimidin-2-yl)-1-(2-morpholin-4-ylethyl)urea Method "D" was used to prepare the product of the following formula:

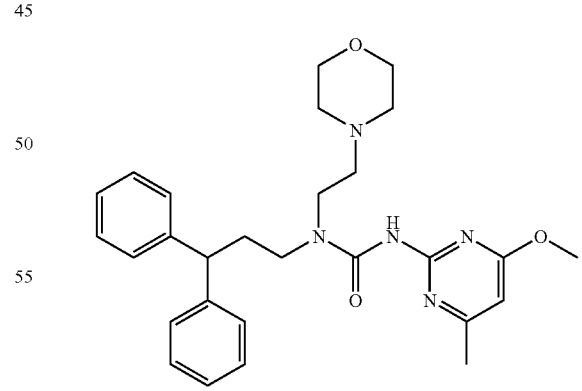

¹H NMR (400 MHz, CDCl₃): ppm 2.37 (s, 3H, CH3), 2.42 (q, 2H, CH2), 2.51 (m, 2H, CH2), 2.61 (m, 4H, 2×CH2), 3.29 (t, 2H, CH2), 3.34 (t, 2H, CH2), 3.96 (m, 8H, CH, OCH3, 2×CH2), 6.20 (s, 1H, aromatic H), 7.19 (m, 2H, aromatic H), 7.28 (m, 8H, aromatic H).
MS: 490⁺ (M+H)⁺

EXAMPLE 108

1-(3,3-diphenylpropyl)-1-(2-morpholin-4-ylethyl)-3-pyrazin-2-ylurea

Method "D" was used to prepare the product of the following formula:

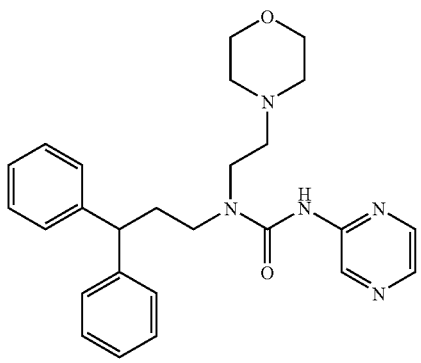

¹H NMR (400 MHz, DMSO): 2.35 (q, 2H, H5), 2.52 (m, 6H, 3×CH2), 3.32 (m, 4H, 2×CH2), 3.71 (m, 4H, 2×CH2), 4.03 (m, 1H, CH), 7.16 (m, 2H, aromatic H), 7.31 (m, 8H, aromatic H), 8.19 (s, 1H, aromatic H), 8.28 (s, 1H, aromatic H), 9.03 (s, 1H, aromatic H).

MS: 446⁺ (M+H)⁺

EXAMPLE 109

1-(3,3-diphenylpropyl)-1-(2-morpholin-4-ylethyl)-3-(4-thiazol-2-ylpyrimidin-2-yl)urea Method "D" was used to prepare the product of the following formula:

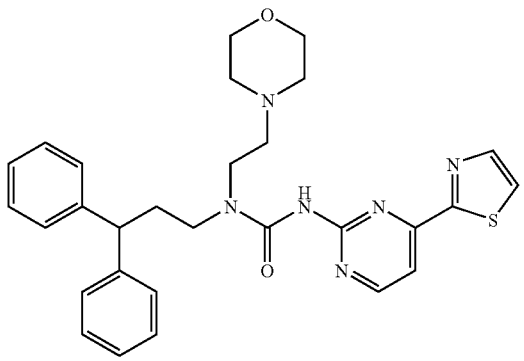

MS: 529.2⁺ (M+H)⁺
TLC: Rf=0.33 (eluent: AcOEt 100%)

EXAMPLE 110

1-(3,3-diphenylpropyl)-3-(5-methylisoxazol-3-yl)-1-(2-morpholin-4-ylethyl)urea

Method "D" was used to prepare the product of the following formula:

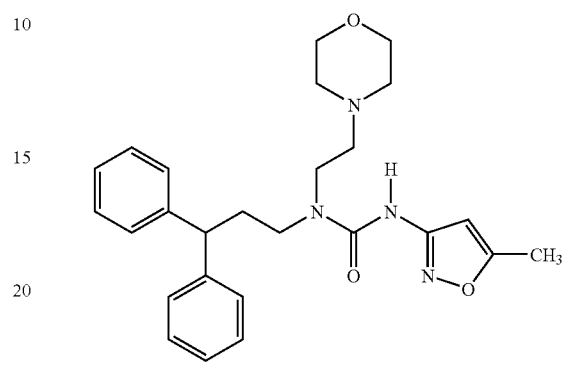

¹H NMR (400 MHz, acetone D6): ppm 11.57-11.40 (s e1, 1H, NH), 7.37 (d, 4H, aromatic H), 7.29 (t, 4H, aromatic H), 7.17 (t, 2H, aromatic H), 6.56 (s, 1H, aromatic H), 4.03 (t, 1H, CH), 3.86-3.76 (m, 4H, CH2), 3.46-3.41 (m, 2H, CH2), 3.30 (t, 2H, CH2), 2.66-2.52 (m, 6H, CH2), 2.40 (q, 2H, CH2), 2.35 (s, 3H, CH3).

MS: 449.46⁺ (M+H)⁺
TLC: Rf=0.30 (eluent: DCM/MeOH 97/3)

EXAMPLE 111

1-(3,3-diphenylpropyl)-3-(3-methyl-5-phenylisoxazol-4-yl)-1-(2-morpholin-4-ylethyl)urea Method "E" was used to prepare the product of the following formula:

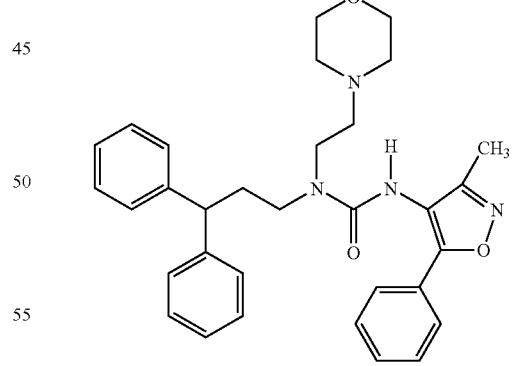

60 mg (0.30 mmol, 1 eq.) of 3-methyl-5-phenyl-4-isoxazole carboxylic acid are dissolved in 3 mL of toluene. 46 µL (0.32 mmol, 1.1 eq.) of triethylamine are added. After checking the basicity of the medium, 67 µL (0.31 mmol, 1.05 eq.) of diphenylphosphoryl azide are added to the medium. This mixture is brought to 80° C. for two hours then 115 mg (0.35 mmol, 1.2 eq.) of (3,3-diphenylpropyl)(2-morpholin-4-ylethyl)-amine are added. Heating is maintained for 1 hour. The mixture is then left to return to room temperature and stirring is maintained for one night. A saturated NaHCO₃ solution is added and the aqueous phase is extracted with DCM. The organic phase is washed with brine, dried over MgSO₄, filtered and concentrated. The product is purified over an alumina column (eluent: 1/1 heptane/AcOEt) (m=59 mg, yield=38%). This procedure is hereinafter called method "E".

¹H NMR (400 MHz, CD₃COCD₃): ppm 2.20 (s, 3H, CH3), 2.37-2.44 (m, 4H, CH₂), 2.46 (q, 2H, CH₂), 2.60 (t, 2H, CH₂), 3.26-3.35 (t, 4H, CH₂), 3.38 (t, 2H, CH₂), 3.53 (t, 2H, CH2), 4.06 (t, 1H, CH), 7.18 (t, 2H, aromatic H), 7.30 (t, 4H, aromatic H), 7.38 (d, 4H, aromatic H), 7.43-7.52 (m, 3H, aromatic H), 7.86 (d, 2H, aromatic H), 8.80-9.13 (bs, 1H, NH).

MS: 525.50⁺ (M+H)⁺

TLC: Rf=0.11 (eluent: DCM/MeOH 97/3)

EXAMPLE 112

3-[3-(2-chloro-6-fluorophenyl)-5-methylisoxazol-4-yl)-1-(3,3-diphenylpropyl)-1-(2-morpholin-4-ylethyl)urea Method "E" was used to prepare the product of the following formula:

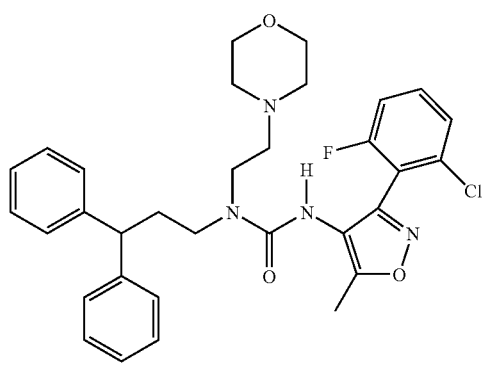

¹H NMR (400 MHz, acetone D6): ppm 8.36-8.22 (s e1, 1H, NH), 7.50-7.43 (m, 1H, aromatic H), 7.36 (d, 1H, aromatic H), 7.32-7.15 (m, 11H, aromatic H), 3.91 (t, 1H, CH), 3.49-3.42 (m, 4H, CH2), 3.30 (t, 2H, CH2), 3.18 (t, 2H, CH2), 2.45-2.39 (m, 5H, CH2+CH3), 2.37-2.30 (m, 4H, CH2), 2.23 (q, 2H, CH2).

MS: 577.48⁺ (M+H)⁺

TLC: Rf=0.11 (97/3 DCM/MeOH)

EXAMPLE 113

1-(3,3-diphenylpropyl)-3-(5-methyl-3-phenylisoxazol-4-yl)-1-(2-morpholin-4-ylethyl)urea Method "E" was used to prepare the product of the following formula:

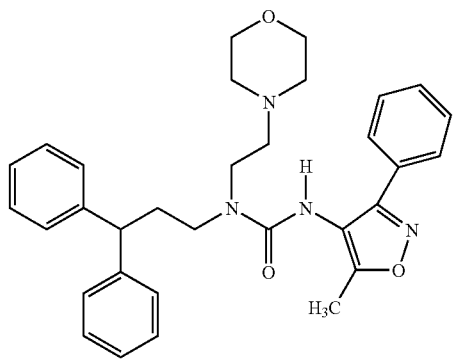

¹H NMR (400 MHz, acetone D6): ppm 8.85-8.55 (s e1, 1H, NH), 7.80-7.72 (m, 2H, aromatic H), 7.50-7.41 (m, 3H, aromatic H), 7.40-7.25 (m, 8H, aromatic H), 7.21-7.13 (m, 2H, aromatic H), 4.07-3.98 (m, 1H, CH), 3.51-3.43 (m, 2H, CH2), 3.39-3.22 (m, 6H, CH2), 2.57-2.48 (m, 2H, CH2), 2.46-2.27 (m, 9H, CH2+CH3).

MS: 525.50⁺ (M+H)⁺

TLC: Rf=0.11 (eluent: DCM/MeOH 97/3)

EXAMPLE 114

1-(3,3-diphenylpropyl)-1-(2-morpholin-4-ylethyl)-3-(5-phenyl-2H-pyrazol-3-yl)urea Method "D" was used to prepare the product of the following formula:

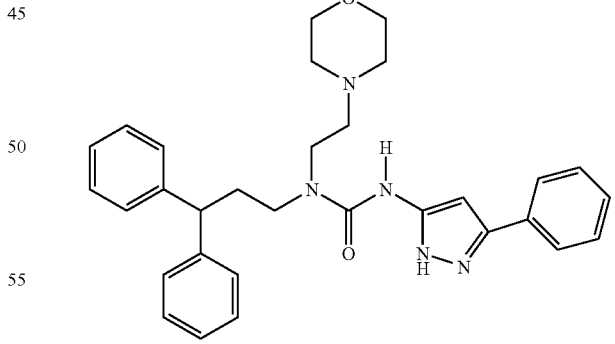

¹H NMR (400 MHz, acetone D6): 7.80 (d, 2H, aromatic H), 7.42-7.24 (m, 11H, aromatic H), 7.17 (t, 2H, aromatic H), 5.88-5.82 (s e1, 3H, aromatic H+NH), 4.08 (t, 1H, CH), 3.81-3.70 (m, 2H, CH2), 3.63-3.53 (m, 2H, CH2), 3.52-3.46 (m, 4H, CH2), 2.72-2.58 (m, 4H, CH2), 2.36-2.28 (m, 4H, CH2).

MS: 510.45⁺ (M+H)⁺

Rf=0.50 (eluent: DCM/MeOH 97/3)

EXAMPLE 115

1-(3,3-Diphenylpropyl)-1-(2-morpholin-4-ylethyl)-3-(3-phenyl-[1,2,4]thiadiazol-5-yl)urea Method "D" was used to prepare the product of the following formula:

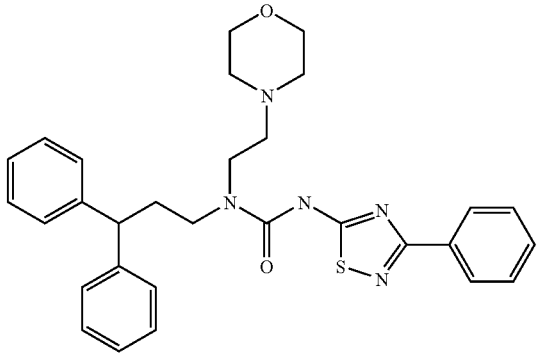

¹H NMR (400 MHz, acetone D6): 8.26 (d, 2H, aromatic H), 7.53-7.43 (m, 3H, aromatic H), 7.39 (d, 4H, aromatic H), 7.30 (t, 4H, aromatic H), 7.19 (t, 2H, aromatic H), 4.16-3.96 (m, 5H, CH+CH2), 3.63-3.57 (m, 2H, CH2), 3.43 (t, 2H, CH2), 2.88-2.65 (m, 6H, CH2), 2.44 (q, 2H, CH2).

MS: 528.40⁺ (M+H)⁺

TLC: Rf=0.66 (eluent: DCM/MeOH 97/3)

EXAMPLE 116

5-[3,3-diphenylpropyl)-3-(2-morpholin-4-ylethyl) ureido]-3-propyl-isoxazole-4-carboxylic acid ethyl ester Method "D" was used to prepare the product of the following formula:

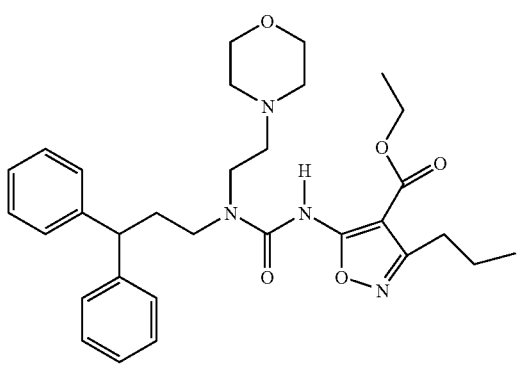

¹H NMR (400 MHz, acetone D6): 11.00-10.20 (s e1, 1H, NH), 7.40 (d, 4H, aromatic H), 7.30 (t, 4H, aromatic H), 7.18 (t, 2H, aromatic H), 4.32 (q, 2H, CH2), 4.10 (t, 1H, CH), 3.60-3.52 (m, 4H, CH2), 3.50 (t, 2H, CH2), 3.37 (t, 2H, CH2), 2.75 (t, 2H, CH2), 2.62-2.40 (m, 8H, CH2), 1.72 (sextuplet, 2H, CH2), 1.34 (t, 3H, CH3), 0.99 (t, 3H, CH3).

MS: 549.46⁺ (M+H)⁺

TLC: Rf=0.20 (eluent: DCM/MeOH 97/3)

EXAMPLE 117

3-(3,4-dimethyl-isoxazol-5-yl)-1-(3,3-diphenylpropyl)-1-(2-morpholin-4-ylethyl)urea Method "D" was used to prepare the product of the following formula:

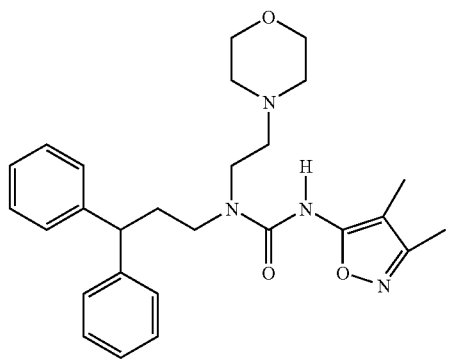

¹H NMR (400 MHz, acetone D6): 11.30-10.80 (s e1, 1H, NH), 7.38 (d, 4H, aromatic H), 7.30 (t, 4H, aromatic H), 7.18 (t, 2H, aromatic H), 4.04 (t, 1H, CH), 3.71-3.62 (m, 4H, CH2), 3.50-3.45 (m, 2H, CH2), 3.32 (t, 2H, CH2), 2.66-2.50 (m, 6H, CH2), 2.42 (q, 2H, CH2), 2.13 (s, 3H, CH3), 1.84 (s, 3H, CH3).

MS: 463.40⁺ (M+H)⁺

TLC: Rf=0.26 (eluent: DCM/MeOH 97/3)

EXAMPLE 118

3-[3-[2-(9H-fluoren-9-yl)-ethyl]-3-(2-morpholin-4-ylethyl)ureido]benzoic acid methyl ester Proceeding as indicated in the following scheme, 3-[3-[2-(9H-fluoren-9-yl)-ethyl]-3-(2-morpholin-4-ylethyl)ureido]benzoic acid methyl ester is prepared from fluorenone 1 (Method II-a).

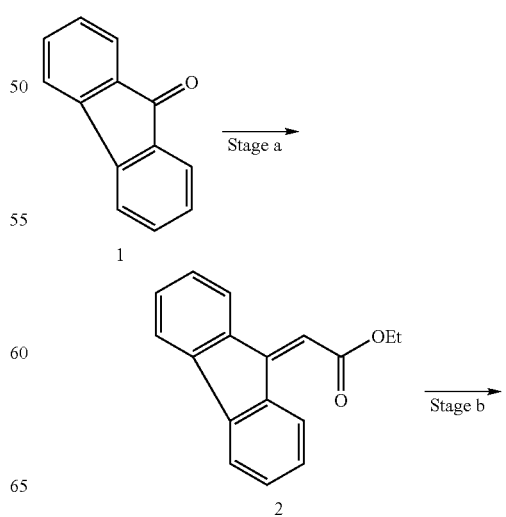

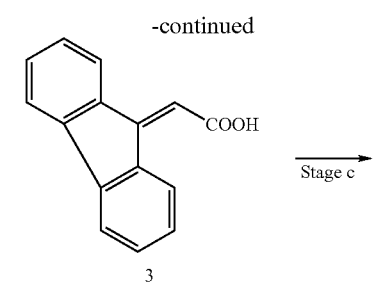

3

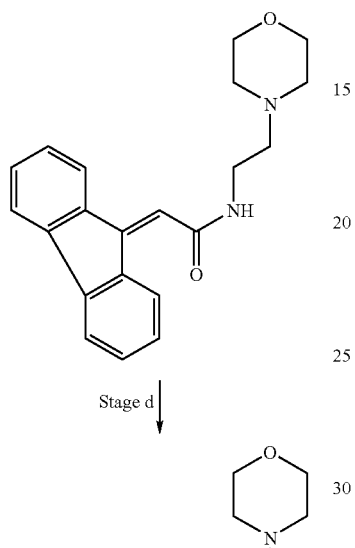

Example 118

Stage a): Synthesis of fluoren-9-ylidene-acetic acid ethyl ester 2

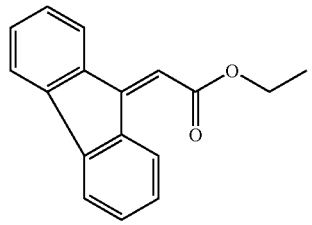

2 g (11.1 mmol, 1 eq.) of 9-fluorenone, 1 in 15 mL of dry THF are dissolved in a flask equipped with a condenser, under argon. 2.86 mL (14.43 mmol, 1.3 eq.) of triethylphosphonoacetate are introduced and 577 mg (14.43 mmol, 1.3 eq.) of 60% NaH in oil are added batchwise to the solution. The mixture is heated to 70-80° C. for 3 hours, 1.10 mL (5.55 mmol, 1 eq.) of triethylphosphonoacetate and 222 mg (5.55 mmol, 1 eq.) of 60% NaH in oil are added to the medium. The mixture is stirred for 2 hours at 70-80° C. Water is added, then the THF is concentrated. The basic aqueous phase is extracted with AcOEt and the organic phase is washed with brine, dried over MgSO$_4$, filtered and concentrated. The oil obtained is subjected to chromatography over silica gel (eluent: heptane/DCM: 1/0 to 0/1) to give the desired product in the form of yellow crystals (m=1.86 g, yield=67%).

$^1$H NMR (400 MHz, CDCl$_3$): ppm 1.42 (t, 3H, CH3), 4.37 (q, 2H, CH2), 6.77 (s, 1H, CH alkene), 7.24-7.47 (m, 7H, aromatic H), 7.60-7.72 (m, 3H, aromatic H), 8.92 (d, 1H, aromatic H).

MS: 251.05$^+$ (M+H)$^+$

TLC: Rf=0.81 (eluent: DCM 100%)

Stage b: Synthesis of fluoren-9-ylidene-acetic acid 3

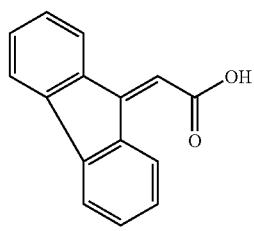

1.85 g (7.39 mmol, 1 eq.) of 2 are introduced into 40 mL of EtOH. 14.8 mL (14.78 mmol, 2 eq.) of 1 N sodium hydroxide are added and the mixture is stirred for 45 min. at 60° C. The reagent dissolves completely while hot. The ethanol is concentrated, the residue is taken up in the water and AcOEt is added. The aqueous phase is acidified to pH 3, then extracted with AcOEt. The organic phase is washed with brine, dried, filtered and concentrated (m=1.62 g, yield=99%).

$^1$H NMR (400 MHz, CD$_3$OD): ppm 6.87 (s, 1H, CH alkene), 7.26-7.33 (m, 2H, aromatic H), 7.39-7.46 (m, 2H, aromatic H), 7.71 (t, 2H, aromatic H), 7.78 (d, 1H, aromatic H), 8.76 (d, 1H, aromatic H).

MS: 221.18$^-$ (M−H)$^-$

TLC: Rf=0.31 (eluent: DCM/MeOH 9/1)

Stage c): 2-fluoren-9-ylidene-N-(2-morpholin-4-ylethyl)acetamide,

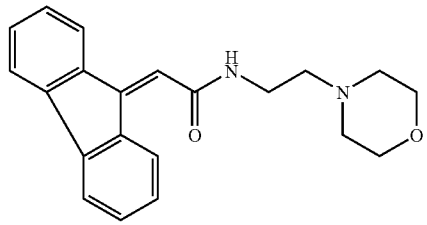

1.62 g (7.28 mmol, 1 eq.) of 3 are dissolved in 30 mL of DCM and 6 mL of DMF under argon. 1.083 g (8.01 mmol, 1.1 eq.) of HOBt and 1.536 g (8.01 mmol, 1.1 eq.) of EDC, HCl are then introduced in succession. The mixture is stirred for 30 min. at room temperature and 1.054 mL (8.01 mmol, 1.1 eq.) of 2-(4-morpholino)ethylamine are added. The mixture is stirred for 5 hours at room temperature. 670 μL (5.10 mmol, 0.7 eq.) of 2-(4-morpholino)ethylamine and 980 mg (5.10 mmol, 0.7 eq.) of EDC, HCl are added. The mixture is stirred for one night at room temperature. Dichloromethane is added, the organic phase is washed with a 0.1 N HCl solution, with a saturated NaHCO$_3$ solution then finally with brine. It is dried over MgSO$_4$, filtered and concentrated. The oil obtained is subjected to chromatography over silica gel (eluent: DCM/

MeOH 90/10). The product obtained is recrystallised in AcOEt (yellow crystals, m=1.86, yield=76%).

$^1$H NMR (400 MHz, CDCl$_3$): ppm 2.44-2.55 (m, 4H, CH2), 2.60 (t, 2H, CH2), 3.58 (q, 2H, CH2), 3.66-3.77 (m, 4H, CH2), 6.44-6.57 (m, 1H, NH), 6.78 (s, 1H, CH alkene), 7.28 (t, 2H, aromatic H), 7.40 (t, 2H, aromatic H), 7.67 (d, 3H, aromatic H), 8.60 (d, 1H, aromatic H).

MS: 335.04$^+$ (M+H)$^+$

TLC: Rf=0.46 (eluent: DCM/MeOH/NH$_4$OH: 90/10/0.5)

Stage d): [2-(9H-fluoren-9-yl)ethyl](2-morpholin-4-ylethyl)amine

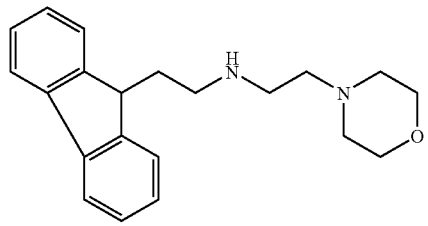

1 g (2.99 mmol, 1 eq.) of product obtained in stage c) above are dissolved in 24 ml of THF in a 250 mL flask placed in an argon atmosphere. After cooling the solution to 0° C., 200 mg (1.50 mmol, 0.5 eq.) of AlCl$_3$ are added batchwise. Once the medium has become homogeneous, 7.48 mL (7.48 mmol, 2.5 eq.) of LiAlH$_4$ in a 1 M solution in THF are added smoothly. The mixture is kept at 0° C. during addition. The mixture is subsequently heated under reflux (60° C.) for 1 hour then cooled to 0° C. 7 mL of water are then added very slowly to the solution to avoid a violent reaction. The salts are filtered and rinsed with ethyl acetate. The filtrate is recovered, water is added and the aqueous phase is extracted with ethyl acetate. The organic phase is washed once with water then once with brine, is subsequently dried over MgSO$_4$, filtered and concentrated. The paste obtained is subjected to chromatography over silica gel (eluent: DCM/MeOH gradient: 99/1 to 7/3) (colourless oil, m=801 mg, yield=83%).

$^1$H NMR (400 MHz, CDCl$_3$): ppm 2.30 (q, 2H, CH2), 2.34-2.40 (m, 4H, CH2), 2.41 (t, 2H, CH2), 2.50 (t, 2H, CH2), 2.61 (t, 2H, CH2), 3.63-3.70 (m, 4H, CH2), 4.09 (t, 1H, CH), 7.32 (t, 2H, aromatic H), 7.39 (t, 2H, aromatic H), 7.54 (d, 2H, aromatic H), 7.77 (d, 2H, aromatic H).

MS: 323.27$^+$ (M+H)$^+$

TLC: Rf=0.38 (eluent: DCM/MeOH 90/10)

EXAMPLE 118

3-[3-[2-(9H-fluoren-9-yl)ethyl]-3-(2-morpholin-4-ylethyl)ureido]benzoic acid methyl ester Method "A", but replacing (3,3-di-propyl)(2-morpholin-4-ylethyl)amine with [2-(9H-fluoren-9-yl)ethyl](2-morpholin-4-ylethyl)amine, was used to prepare the title compound having the following formula:

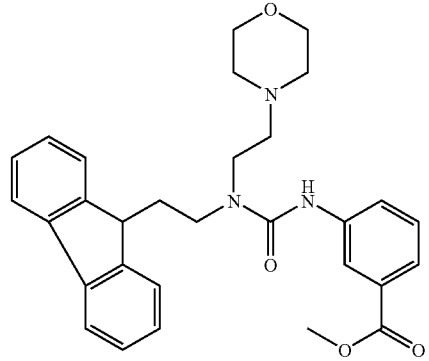

$^1$H NMR (400 MHz, CD$_3$COCD$_3$): ppm 2.40 (q, 2H, CH2), 2.48-2.56 (m, 4H, CH2), 2.58 (t, 2H, CH2), 3.28 (t, 2H, CH2), 3.44 (t, 2H, CH2), 3.66 (t, 4H, CH2), 3.89 (s, 3H, CH3), 4.10 (t, 1H, CH), 7.32-7.45 (m, 5H, aromatic H), 7.59 (d, 1H, aromatic H), 7.73 (d, 2H, aromatic H), 7.83-7.90 (m, 3H, aromatic H), 8.14 (s, 1H, aromatic H), 9.25-9.35 (m, 1H, NH).

MS: 500.27$^+$ (M+H)$^+$

TLC: Rf=0.30 (eluent: AcOEt 100%)

The secondary amine (2-morpholin-4-ylethyl)(3-phenyl-3-thiophen-2-ylpropyl)-amine (product obtained in stage d) of Example 119) is synthesised in the same way as the secondary amine [2-(9H-fluoren-9-yl)ethyl](2-morpholin-4-ylethyl)amine obtained in stage 3) of the present Example using method IIa.

EXAMPLES 119-121

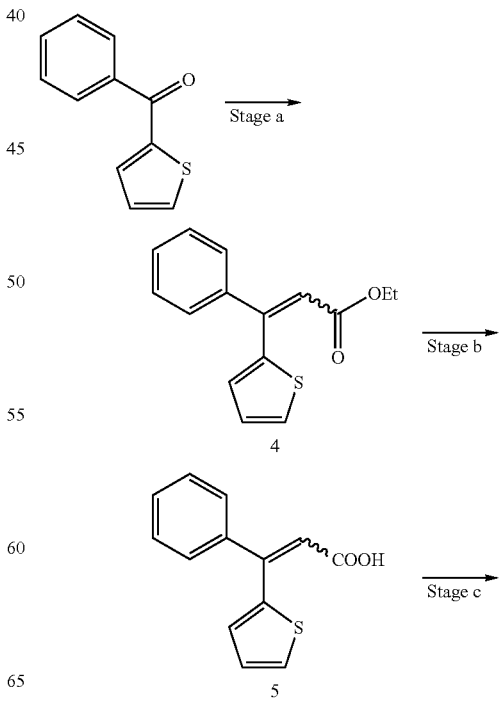

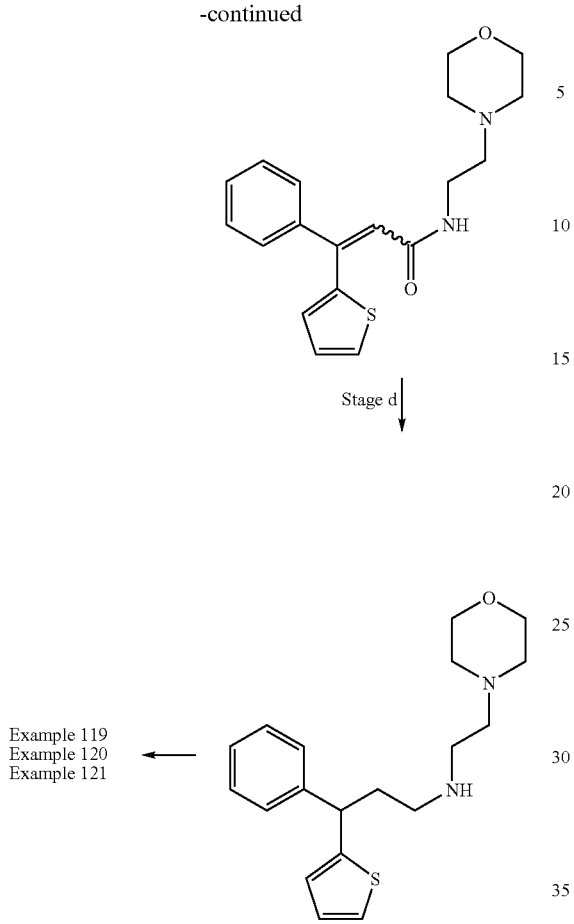

Stage a): Synthesis of 3-phenyl-3-thiophen-2-ylacrylic acid ethyl ester, 4 (mixture of 2 isomers Z and E) (proportion: 1/1)

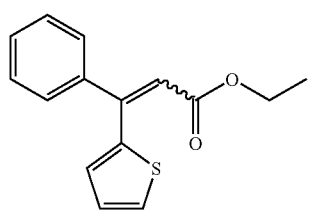

¹H NMR (400 MHz, CDCl₃): ppm 1.12 (t, 3H, CH3), 1.25 (t, 3H, CH3), 4.05 (q, 2H, CH2), 4.18 (q, 2H, CH2), 6.22 (s, 1H, CH alkene), 6.43 (s, 1H, CH alkene), 6.88 (d, 1H, aromatic H), 6.99 (t, 1H, aromatic H), 7.08 (t, 1H, aromatic H), 7.19 (d, 1H, aromatic H), 7.27-7.33 (m, 2H, aromatic H), 7.35-7.49 (m, 10H, aromatic H)

MS: 259.0⁺ (M+H)⁺

TLC: Rf:=0.64 (Alumina, eluent: heptane/DCM 2/1)

Stage b): Synthesis of 3-phenyl-3-thiophen-2-ylacrylic acid, 5 (mixture of 2 isomers Z and E) (proportion: 1/1)

¹H NMR (400 MHz, CDCl₃): ppm 6.17 (s, 1H, CH alkene), 6.41 (s, 1H, CH alkene), 6.90 (d, 1H, aromatic H), 7.00 (t, 1H, aromatic H), 7.08 (t, 1H, aromatic H), 7.25 (d, 1H, aromatic H), 7.27-7.34 (m, 2H, aromatic H), 7.35-7.45 (m, 9H, aromatic H), 7.48 (d, 1H, aromatic H).

MS: 229.17⁻ (M–H)⁻

TLC: Rf=0.46 (isomer 1) and 0.53 (isomer 2) (eluent: DCM/MeOH 9/1)

Stage c): N-(2-morpholin-4-ylethyl)-3-phenyl-3-thiophen-2-ylacrylamide (mixture of 2 isomers Z and E) (proportion: 1/1).

¹H NMR (400 MHz, CDCl₃): ppm 2.19 (t, 2H, CH2), 2.20-2.27 (m, 4H, CH2), 2.28-2.40 (m, 6H, CH2), 3.21 (q, 2H, CH2), 3.33 (q, 2H, CH2), 3.56-3.68 (m, 8H, CH2), 5.61-5.73 (m, 1H, NH), 6.01-6.13 (m, 1H, NH), 6.32 (s, 1H, CH alkene), 6.47 (s, 1H, CH alkene), 6.80 (d, 1H, aromatic H), 6.97 (t, 1H, aromatic H), 7.07 (t, 1H aromatic H), 7.16 (d, 1H, aromatic H), 7.30-7.50 (m, 12H, aromatic H).

MS: 343.10⁺ (M+H)⁺

TLC: Rf=0.44 (eluent: DCM/MeOH 95/5)

Stage d): (2-morpholin-4-ylethyl)(3-phenyl-3-thiophen-2-ylpropyl)amine

¹H NMR (400 MHz, CDCl₃): ppm 2.18-2.38 (m, 2H, CH2), 2.39-2.50 (m, 6H, CH2), 2.56-2.70 (m, 4H, CH2), 3.71 (t, 4H, CH2), 4.25 (t, 1H, CH), 6.84 (d, 1H, aromatic H), 6.92 (t, 1H, aromatic H), 7.15 (d, 1H, aromatic H), 7.19-7.35 (m, 4H, aromatic H).

MS: 331.14⁺ (M+H)⁺

TLC: Rf=0.37 (eluent: DCM/MeOH 9/1)

EXAMPLE 119

3-[3-(2-methyl-2H-tetrazol-5-yl)phenyl]-1-(2-morpholin-4-ylethyl)-1-(3-phenyl-3-thiophen-2-ylpropyl)urea Method "D" was used to prepare the title compound having the following formula:

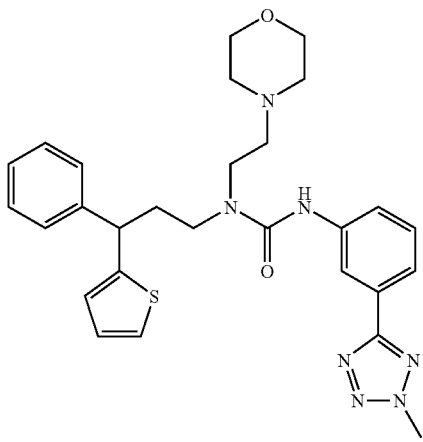

$^1$H NMR (400 MHz, CD$_3$COCD$_3$): ppm 2.40-2.58 (m, 6H, CH2), 2.62 (t, 2H, CH2), 3.30-3.54 (m, 4H, CH2), 3.69 (t, 4H, CH2), 4.32 (t, 1H, CH), 4.44 (s, 3H, CH3), 6.96 (t, 1H, aromatic H), 7.04 (s, 1H, aromatic H), 7.23 (t, 1H, aromatic H), 7.28 (d, 1H, aromatic H), 7.34 (t, 2H, aromatic H), 7.38-7.46 (m, 3H, aromatic H), 7.68-7.76 (m, 2H, aromatic H), 8.31 (s, 1H, aromatic H), 9.16-9.26 (m, 1H, NH).

MS: 532.09$^+$ (M+H)$^+$

TLC: Rf=0.59 (eluent: AcOEt)

EXAMPLE 120

1-(2-morpholin-4-ylethyl)-3-(3-oxazol-5-ylphenyl)-1-(3-phenyl-3-thiophen-2-yl-propyl)urea dihydrochloride Method "D" then "F" was used to prepare the title compound having the following formula:

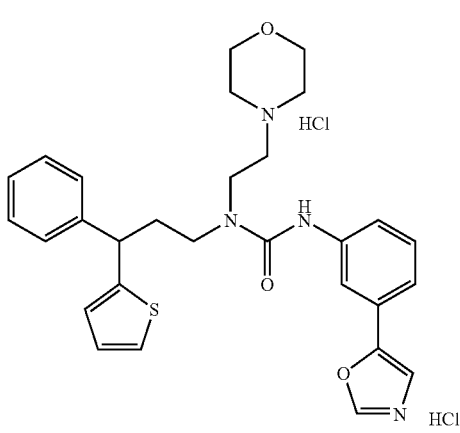

$^1$H NMR (400 MHz, DMSO): ppm 2.28-2.45 (m, 2H, CH2), 3.00-3.16 (m, 2H, CH2), 3.19-3.29 (m, 2H, CH2), 3.33-3.57 (m, 4H, CH2), 3.64-3.80 (m, 4H, CH2), 3.90-4.03 (m, 2H, CH2), 4.31 (t, 1H, CH), 6.96 (t, 1H, aromatic H), 7.04 (s, 1H, aromatic H), 7.23 (t, 1H, aromatic H), 7.28-7.42 (m, 7H, aromatic H), 7.46-7.55 (m, 1H, aromatic H), 7.60 (s, 1H, aromatic H), 7.87-7.92 (m, 1H, aromatic H), 8.45 (s, 1H, aromatic H), 8.50-8.56 (m, 1H, NH).

MS: 517.15$^+$ (M+H−2HCl)$^+$

TLC: Rf=0.30 (eluent: AcOEt 100%)

EXAMPLE 121

3-[3-(2-morpholin-4-ylethyl)-3-(3-phenyl-3-thiophen-2-ylpropyl)ureido]benzoic acid methyl ester Method "A" was used to prepare the title compound having the following formula:

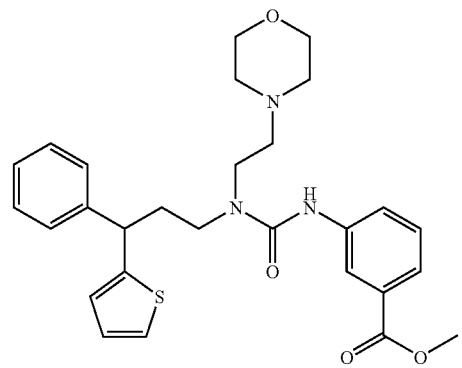

$^1$H NMR (400 MHz, CD$_3$COCD$_3$): ppm 2.39-2.51 (m, 2H, CH2), 2.52-2.57 (m, 4H, CH2), 2.61 (t, 2H, CH2), 3.29-3.38 (m, 1H, CH), 3.38-3.47 (m, 1H, CH), 3.48-3.53 (m, 2H, CH2), 3.68 (t, 4H, CH2), 3.88 (s, 3H, CH3), 4.31 (t, 1H, CH), 6.95 (t, 1H, aromatic H), 7.03 (s, 1H, aromatic H), 7.23 (t, 1H, aromatic H), 7.28 (d, 1H, aromatic H), 7.30-7.43 (m, 5H, aromatic H), 7.59 (d, 1H, aromatic H), 7.87 (d, 1H, aromatic H), 8.14 (s, 1H, aromatic H), 9.20-9.30 (m, 1H, NH).

MS: 508.23$^+$ (M+H)$^+$

TLC: Rf=0.32 (eluent: AcOEt 100%)

The secondary amine (3,3-dithiophen-2-yl-propyl)(2-morpholin-4-ylethyl)amine (product obtained in stage d) of Example 122) is synthesised in the same way as the secondary amine [2-(9H-fluoren-9-yl)ethyl](2-morpholin-4-ylethyl)amine obtained in stage d) of Example 118 using method IIa.

EXAMPLES 122-124

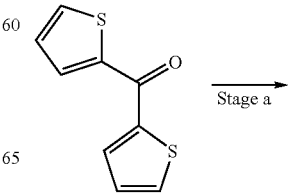

135

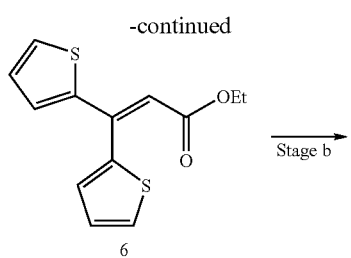

6

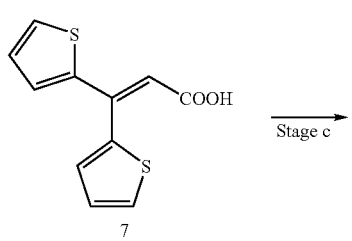

7

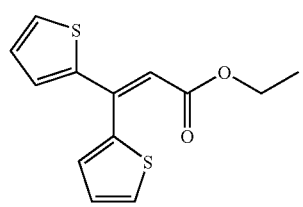

Example 122
Example 123
Example 124

Stage a): Synthesis of 3,3-dithiophen-2-ylacrylic acid diethyl ester, 6

¹H NMR (400 MHz, CDCl₃): ppm 1.20 (t, 3H, CH3), 4.12 (q, 2H, CH2), 6.42 (s, 1H, CH alkene), 7.02 (t, 1H, aromatic H), 7.07-7.13 (m, 2H, aromatic H), 7.14-7.18 (m, 1H, aromatic H), 7.38 (d, 1H, aromatic H), 7.46 (d, 1H, aromatic H).

MS: 265.0⁺ (M+H)⁺

TLC: Rf:=0.61 (Alumina, eluent: heptane/AcOEt 8/1)

136

Stage b): Synthesis of 3,3-dithiophen-2-ylacrylic acid, 7

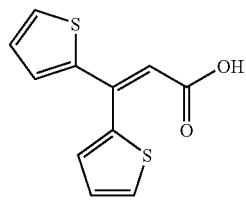

¹H NMR (400 MHz, CDCl₃): ppm 6.38 (s, 1H, CH alkene), 7.05 (t, 1H, aromatic H), 7.08-7.16 (m, 2H, aromatic H), 7.18-7.22 (m, 1H, aromatic H), 7.43 (d, 1H, aromatic H), 7.48 (d, 1H, aromatic H).

MS: 235.11⁻ (M−H)⁻

TLC: Rf=0.41 (eluent: DCM/MeOH 9/1)

Stage c): N-(2-morpholin-4-ylethyl)-3,3-dithiophen-2-ylacrylamide

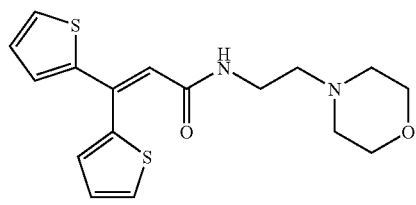

¹H NMR (400 MHz, CDCl₃): ppm 2.24-2.36 (m, 6H, CH2), 3.28 (q, 2H, CH2), 3.64 (t, 4H, CH2), 5.92-6.04 (m, 1H, NH), 6.48 (s, 1H, CH alkene), 6.98-7.03 (m, 2H, aromatic H), 7.11 (t, 1H, aromatic H), 7.21 (d, 1H, aromatic H), 7.34 (d, 1H, aromatic H), 7.46 (d, 1H, aromatic H).

MS: 349.06⁺ (M+H)⁺

TLC: Rf=0.43 (eluent: DCM/MeOH 90/10)

Stage d): (3,3-dithiophen-2-ylpropyl)(2-morpholin-4-ylethyl)amine

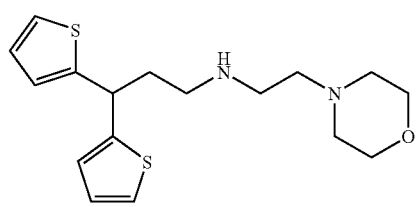

¹H NMR (400 MHz, CDCl₃): ppm 2.33 (q, 2H, CH2), 2.38-2.46 (m, 4H, CH2), 2.48 (t, 2H, CH2), 2.68 (q, 4H, CH2), 3.71 (t, 4H, CH2), 4.61 (t, 1H, CH), 6.89-6.96 (m, 4H, aromatic H), 7.17 (d, 2H, aromatic H).

MS: 337.16⁺ (M+H)⁺

TLC: Rf=0.39 (eluent: DCM/MeOH 9/1)

EXAMPLE 122

1-(3,3-di-thiophen-2-ylpropyl)-3-[3-(2-methyl-2H-tetrazol-5-yl)phenyl]-1-(2-morpholin-4-ylethyl)urea Method "D" was used to prepare the title compound having the following formula:

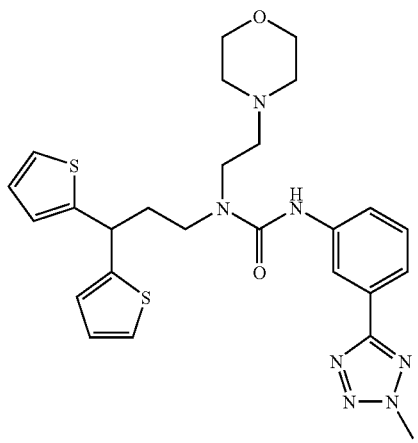

$^1$H NMR (400 MHz, CD$_3$COCD$_3$): ppm 2.49 (q, 2H, CH2), 2.54-2.59 (m, 4H, CH2), 2.61-2.66 (m, 2H, CH2), 3.44 (t, 2H, CH2), 3.54 (t, 2H, CH2), 3.67-3.74 (m, 4H, CH2), 4.45 (s, 3H, CH3), 4.66 (t, 1H, CH), 6.94-7.00 (m, 2H, aromatic H), 7.07 (s, 2H, aromatic H), 7.32 (d, 2H, aromatic H), 7.43 (t, 1H, aromatic H), 7.68-7.77 (m, 2H, aromatic H), 8.32 (s, 1H, aromatic H), 9.19-9.28 (m, 1H, NH).

MS: 538.15$^+$ (M+H)$^+$

TLC: Rf=0.26 (eluent: Rf=0.48 (eluent: AcOEt 100%)

EXAMPLE 123

3-[3-(3,3-dithiophen-2-yl-propyl)-3-(2-morpholin-4-ylethyl)ureido]benzoic acid methyl ester Method "A" was used to prepare the title compound having the following formula:

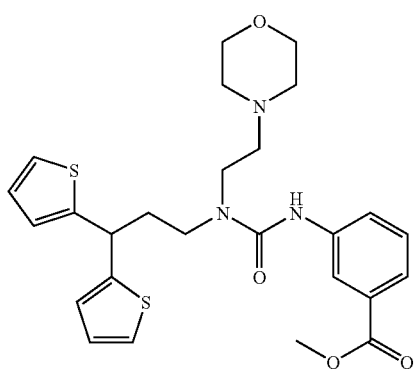

$^1$H NMR (400 MHz, CD$_3$COCD$_3$): ppm 2.47 (q, 2H, CH2), 2.52-2.59 (m, 4H, CH2), 2.63 (t, 2H, CH2), 3.42 (t, 2H, CH2), 3.52 (t, 2H, CH2), 3.66-3.73 (m, 4H, CH2), 3.88 (s, 3H, CH3), 4.65 (t, 1H, CH), 6.94-6.99 (m, 2H, aromatic H), 7.06 (s, 2H, aromatic H), 7.32 (d, 2H, aromatic H), 7.40 (t, 1H, aromatic H), 7.60 (d, 1H, aromatic H), 7.88 (d, 1H, aromatic H), 8.15 (s, 1H, aromatic H), 9.23-9.32 (m, 1H, NH).

MS: 514.21$^+$ (M+H)$^+$

TLC: Rf=0.33 (eluent: AcOEt 100%)

EXAMPLE 124

1-(3,3-dithiophen-2-ylpropyl)-1-(2-morpholin-4-ylethyl)-3-(3-oxazol-5-ylphenyl)urea dihydrochloride Method "D" then "F" was used to prepare the title compound having the following formula:

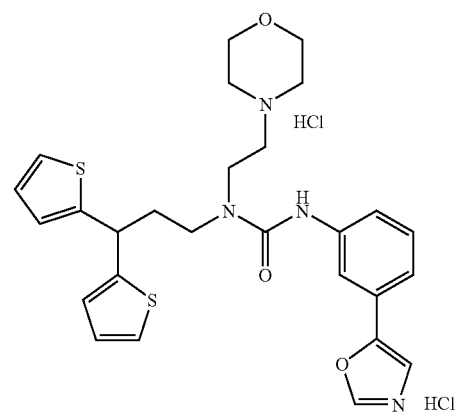

$^1$H NMR (400 MHz, DMSO): ppm 2.36 (q, 2H, CH2), 3.02-3.17 (m, 2H, CH2), 3.20-3.30 (m, 2H, CH2), 3.38 (t, 2H, CH2), 3.42-3.63 (m, 2H, CH2), 3.68-3.81 (m, 4H, CH2), 3.90-4.04 (m, 2H, CH2), 4.66 (t, 1H, CH), 6.94-6.99 (m, 2H, aromatic H), 7.06 (s, 2H, aromatic H), 7.30-7.45 (m, 4H, aromatic H), 7.49-7.56 (m, 1H, aromatic H), 7.60 (s, 1H, aromatic H), 7.86-7.94 (m, 1H, aromatic H), 8.45 (s, 1H, aromatic H), 8.56 (m, 1H, NH).

MS: 523.11$^+$ (M+H)$^+$

TLC: Rf=0.27 (eluent: AcOEt 100%)

Synthesis of a thiomorpholine derivative and a dimethylmorpholine derivative using method IV.

EXAMPLES 125-126
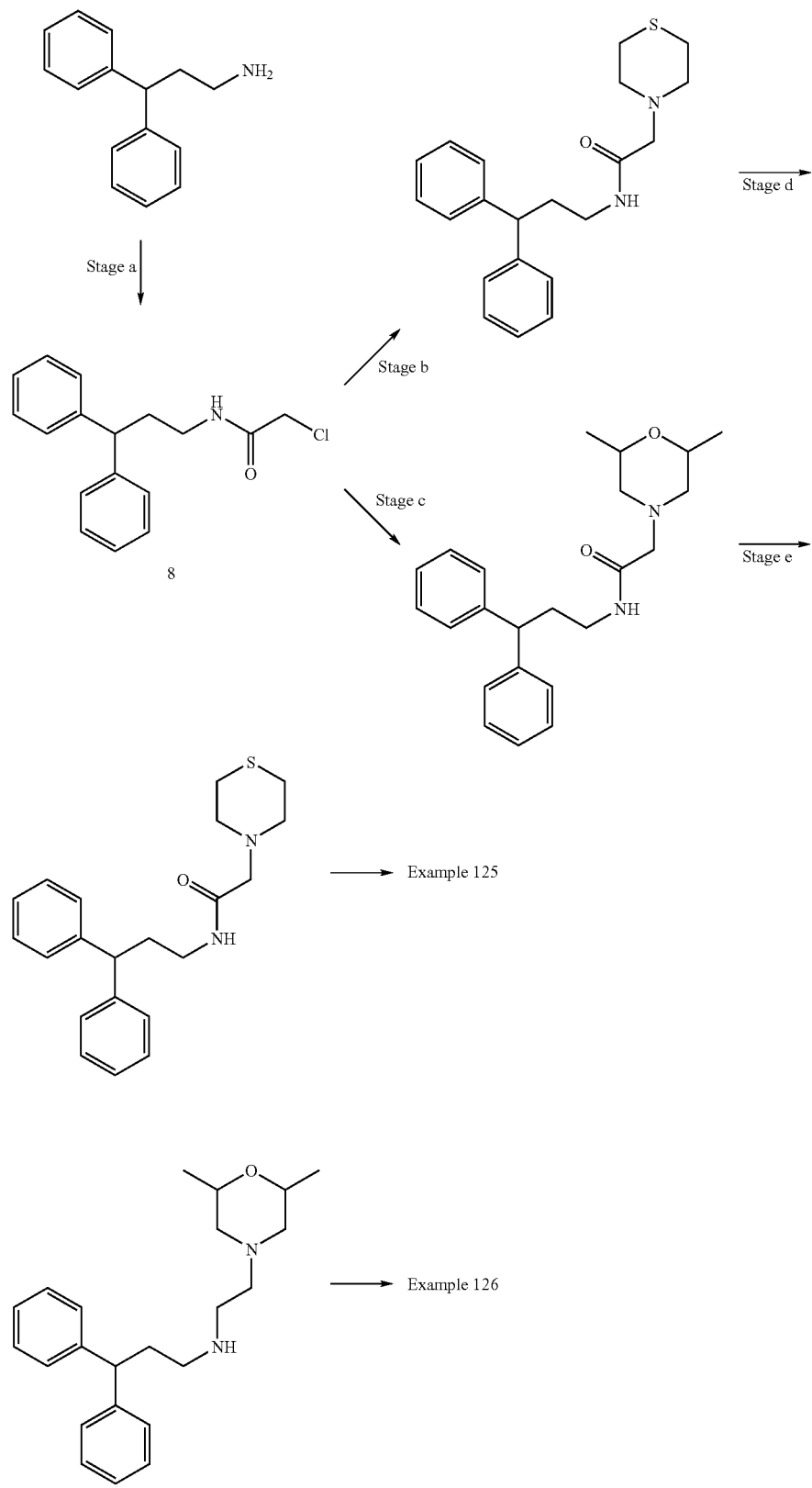

Stage a): Synthesis of N-chloromethyl-3,3-diphenylpropionamide, 8:

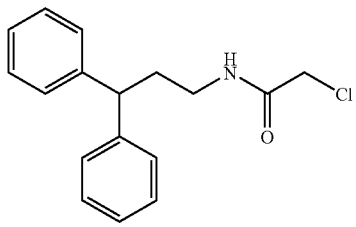

1 g (4.73 mmol, 1 eq.) of 3,3-diphenylpropylamine and 732 µL (5.21 mmol, 1.1 eq.) of triethylamine are diluted in 30 mL of DCM at 0° C. under argon. 300 µL (3.77 mmol, 0.8 eq.) of chloroacetyl chloride are added dropwise. White fumes form then gradually dissipate. The mixture is stirred for 45 min. at 0° C., the solution becomes red. A dilute HCl solution is added then the aqueous phase is extracted with DCM. The organic phase is washed once with water then once with brine, dried over MgSO$_4$, filtered and concentrated. The product is obtained in the form of an oil (m=1.36 g, yield=100%).

$^1$H NMR (400 MHz, CDCl$_3$): ppm 2.24 (q, 2H, CH2), 3.21 (q, 2H, CH2), 3.82-3.92 (m, 3H, CH+CH2), 6.37-6.50 (m, 1H, NH), 7.06-7.25 (m, 10H, aromatic H).

MS: 288.09$^+$ (M+H)$^+$, 329.11$^+$ (M+H+CH$_3$CN)$^+$

TLC: Rf=0.73 (eluent: DCM/MeOH 95/5)

Stage b: N-(3,3-diphenylpropyl)-2-thiomorpholin-4-ylacetamide

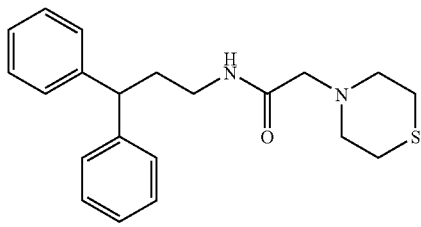

700 mg (2.43 mmol, 1 eq.) of N-chloromethyl-3,3-diphenylpropionamide, 8, 508 µL (2.92 mmol, 1.2 eq.) of diisopropylethylamine, 245 µL (2.43 mmol, 1 eq.) of thiomorpholine and 5 mL of DMF are introduced into a sealed tube. The mixture is heated for 8 min. under microwaves at 180° C. A saturated sodium bicarbonate solution is added to the mixture and the aqueous phase is extracted with ethyl acetate. The organic phase is washed with brine, dried, filtered concentrated. The solid obtained is recrystallised in diethyl ether (m=769 mg, yield=89%).

$^1$H NMR (400 MHz, CDCl$_3$): ppm 2.32 (q, 2H, CH2), 2.55-3.10 (m, 10H, CH2), 3.28 (q, 2H, CH2), 3.99 (t, 1H, CH), 7.16-7.23 (m, 2H, aromatic H), 7.24-7.36 (m, 8H, aromatic H).

MS: 355.12$^+$ (M+H)$^+$

TLC: Rf=0.20 (eluent: heptane/AcOEt 1/1)

Stage c): 2-(2,6-dimethylmorpholin-4-yl)-N-(3,3-diphenylpropyl)acetamide (mixture of 3 isomers)

Method IV, but replacing the thiomorpholine with 2,6-dimethylmorpholine (cis/trans mixture), was used to prepare the title compound having the following formula:

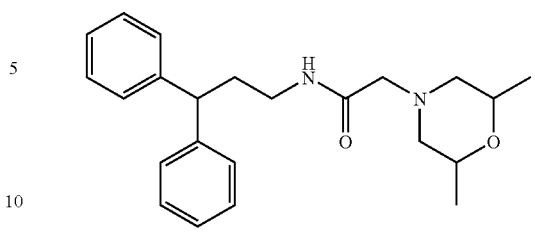

MS: 367.17$^+$ (M+H)$^+$

TLC: Rf: 0.17 (eluent: heptane/AcOEt 1/1)

Stage d): (3,3-diphenylpropyl)(2-thiomorpholin-4-ylethyl)amine

Starting from the product obtained in stage b), method II, route b was used to obtain the title compound having the following formula:

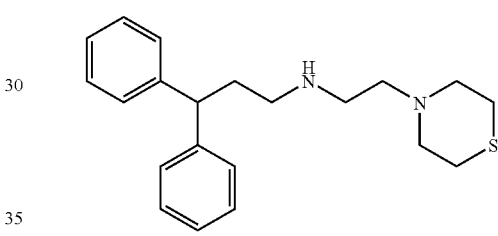

$^1$H NMR (300 MHz, CDCl$_3$): ppm 2.20 (q, 2H, CH2), 2.40 (t, 2H, CH2), 2.46-2.64 (m, 12H, CH2), 3.92 (t, 1H, CH), 7.06-7.24 (m, 10H, aromatic H).

MS: 341.25$^+$ (M+H)$^+$

TLC: Rf=0.30 (eluent: DCM/MeOH 95/5) (mixture of 3 isomers)

Stage e): [2-(2,6-dimethylmorpholin-4-yl)ethyl](3,3-diphenylpropyl)amine

Starting from the product obtained in stage c), method II, route b was used to obtain the title compound having the following formula:

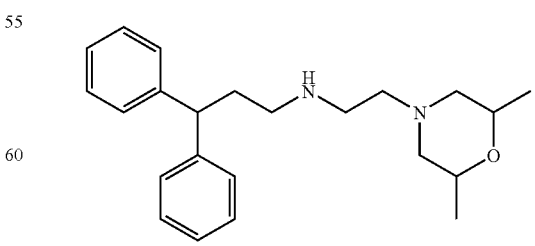

MS: 353.3$^+$ (M+H)$^+$

TLC: Rf=0.28 (eluent: DCM/MeOH 95/5)

EXAMPLE 125

1-(3,3-diphenylpropyl)-3-[3-(2-methyl-2H-tetrazol-5-yl)phenyl]-1-(2-thiomorpholin-4-ylethyl)urea Method "D" was used to prepare the title compound having the following formula:

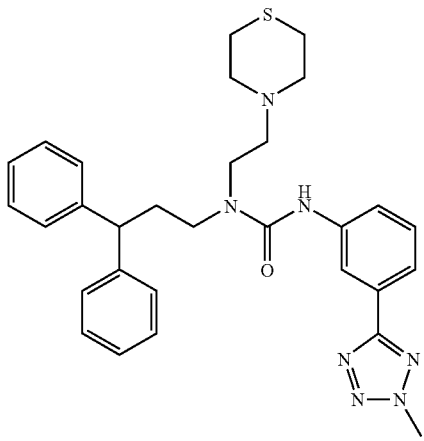

$^1$H NMR (300 MHz, CD$_3$COCD$_3$): ppm 2.46 (q, 2H, CH2), 2.62 (t, 2H, CH2), 2.66-2.72 (m, 4H, CH2), 2.76-2.86 (m, 4H, CH2), 3.36 (t, 2H, CH2), 3.50 (t, 2H, CH2), 4.06 (t, 1H, CH), 4.44 (s, 3H, CH3), 7.18 (t, 2H, aromatic H), 7.31 (t, 4H, aromatic H), 7.36-7.46 (m, 5H, aromatic H), 7.70 (d, 2H, aromatic H), 8.30 (s, 1H, aromatic H), 9.10-9.17 (m, 1H, NH).

MS: 542.15$^+$ (M+H)$^+$

TLC: Rf=0.22 (eluent: heptane/AcOEt 1/1) (mixture of 3 isomers)

EXAMPLE 126

1-[2-(2,6-dimethylmorpholin-4-yl)-ethyl]-1-(3,3-diphenylpropyl)-3-[3-(2-methyl-2H-tetrazol-5-yl)phenyl]urea Method "D" was used to prepare the title compound having the following formula:

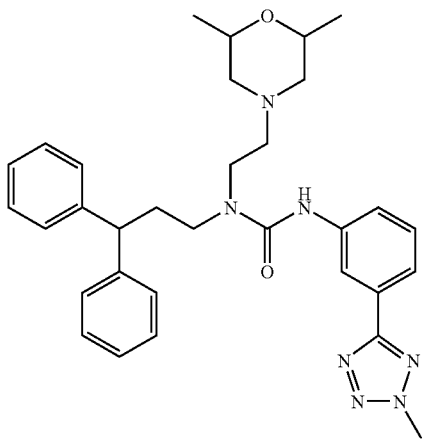

MS: 554.2$^+$ (M+H)$^+$
TLC: Rf=0.16 (eluent: heptane/AcOEt 1/1)

EXAMPLE 127

3-(5,6-Dimethyl-1H-benzoimidazol-2-yl)-1-(3,3-diphenylpropyl)-1-(2-morpholin-4-ylethyl)urea Method "D" was used to prepare the title compound having the following formula:

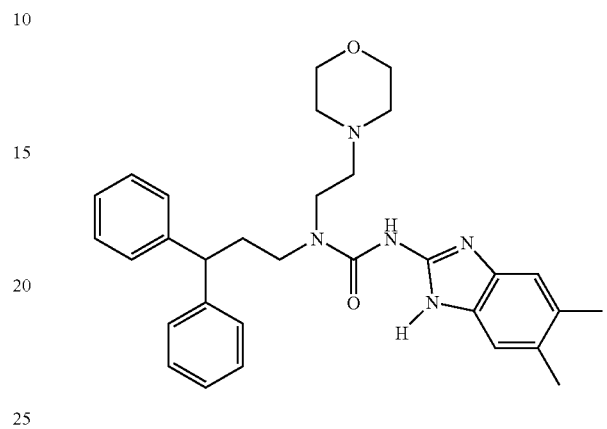

$^1$H NMR (400 MHz, DMSO) ppm 2.20 (s, 6H, 2×CH3), 2.30-2.42 (m, 8H, 4×CH$_2$), 3.25 (m, 2H, CH$_2$), 3.40 (m, 2H, CH$_2$), 3.58 (m, 4H, 2×CH$_2$), 3.98 (t, 1H, CH), 7.03 (s, 2H, aromatic H), 7.16 (m, 2H, aromatic H), 7.29 (m, 4H, aromatic H), 7.32 (m, 4H, aromatic H), 11.50 (brs, 1H, NH)

MS: ES+ 512.25$^+$ (M+H)$^+$

EXAMPLE 128

1-(3,3-Diphenylpropyl)-3-(1-methyl-1H-benzoimidazol-2-yl)-1-(2-morpholin-4-ylethyl)-urea Method "D" was used to prepare the title compound having the following formula:

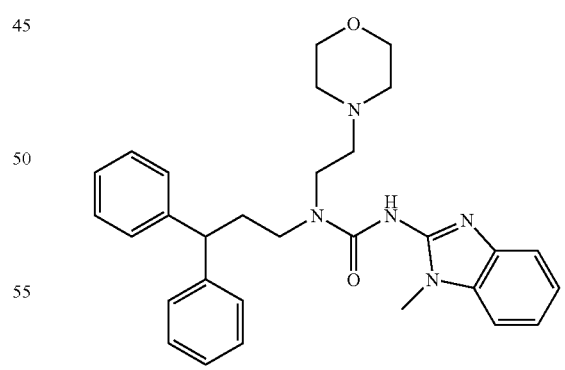

$^1$H NMR (400 MHz, DMSO) ppm 2.30-2.47 (m, 8H, 4×CH$_2$), 3.21 (m, 1H, CH), 3.28 (s, 2H, CH$_2$), 3.39 (m, 1H, CH), 3.40 (m, 2H, CH$_2$), 3.49 (m, 4H, CH$_3$, CH), 3.57 (m, 1H, CH), 3.97 (t, 1H, CH), 7.08 (m, 2H, aromatic H), 7.16 (m, 3H, aromatic H), 7.29 (m, 5H, aromatic H), 7.32 (m, 4H, aromatic H), 11.80 (s, 1H, NH).

MS: ES+ 498.3$^+$ (M+H)$^+$

EXAMPLE 129

3-(1H-Benzoimidazol-2-yl)-1-(3,3-diphenylpropyl)-1-(2-morpholin-4-ylethyl)urea

Method "D" was used to prepare the title compound having the following formula:

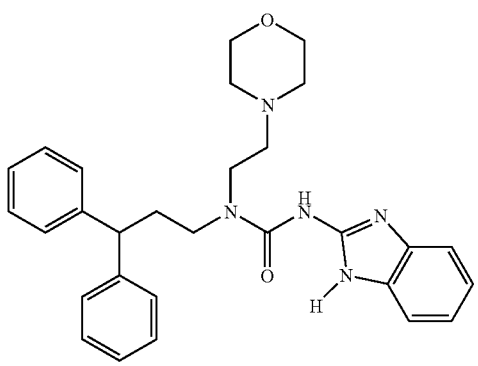

$^1$H NMR (400 MHz, DMSO) ppm 2.30-2.47 (m, 8H, 4×CH$_2$), 3.28 (m, 2H, CH$_2$), 3.42 (m, 2H, CH$_2$), 3.62 (m, 4H, 2×CH$_2$), 3.98 (t, 1H, CH), 7.08 (m, 2H, aromatic H), 7.00 (m, 2H, aromatic H), 7.16 (m, 2H, aromatic H), 7.29 (m, 6H, aromatic H), 7.32 (m, 4H, aromatic H), 11.70 (brs, 1H, NH).

MS: ES+ 484.34$^+$ (M+H)$^+$

EXAMPLE 130

1-(3,3-Diphenylpropyl)-1-(2-morpholin-4-yl-ethyl)-3-(5-phenylsulfanyl-1H-benzoimidazol-2-yl)-urea Method "D" was used to prepare the title compound having the following formula:

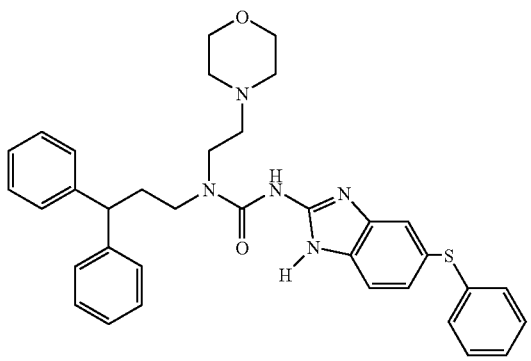

$^1$H NMR (400 MHz, DMSO) ppm 2.31 (q, 2H, CH$_2$), 2.45 (m, 6H, 3×CH$_2$), 3.28 (m, 2H, CH$_2$), 3.42 (m, 2H, CH$_2$), 3.65 (m, 4H, 2×CH$_2$), 3.98 (t, 1H, CH), 7.10 (m, 2H, aromatic H), 7.15 (m, 4H, aromatic H), 7.28 (m, 6H, aromatic H), 7.35 (m, 6H, aromatic H), 11.80 (brs, 1H, NH).

MS: ES+ 592.37$^+$ (M+H)$^+$

EXAMPLE 131

1-(3,3-Diphenylpropyl)-1-(2-morpholin-4-ylethyl)-3-(5-oxo-1-phenyl-4,5-dihydro-1H-pyrazol-3-yl)urea Method "D" was used to prepare the title compound having the following formula:

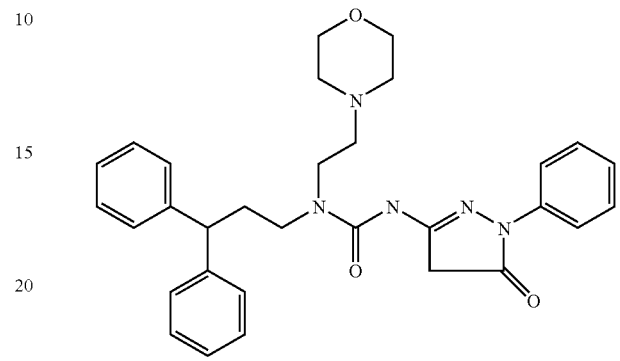

LC SM
Column Ascentis RP amide 5 cm 2.1 mn 5 microns (Supelco)
Flow: 0.4 ml/mn Gradient H$_2$O/CH$_3$CN

| T = 0 | % CH$_3$CN 20 |
|---|---|
| 5.5 mn | 100 |
| 8.00 mn | 100 |

Rt=3.70
MS: ES+ 526 (M+1) 524 (M−H)
$^1$H NMR (400 MHz, DMSO) ppm 2.3 (q, 2H) 2.5 (m, 6H) 3.17 (m, 2H) 3.35 (m, 2H s, 2H) 3.75 (m, 4H) 3.95 (t, 1H) 7.15 (m, 3H) 7.3 (m, 4H) 7.35 (m, 4H) 7.4 (m, 2H) 7.7 (d, 1H) 7.82 (d, 1H)

EXAMPLE 132

1-(3,3-Diphenylpropyl)-3-(5-methyl-2-phenyl-2H-pyrazol-3-yl)-1-(2-morpholin-4-ylethyl)urea Method "D" was used to prepare the title compound having the following formula:

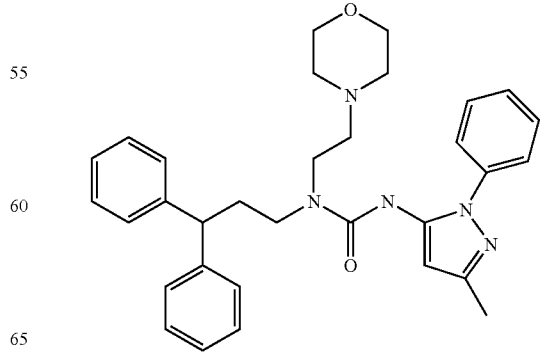

LC SM

Column synergi polar RP ref: 00B 4336-B0
50 mm 2.0 mn 4 microns (Phenomenex)
Flow: 0.4 ml/mn Gradient $H_2O/CH_3CN$

| T = 0 | % $CH_3CN$ 20 |
|---|---|
| 5.5 mn | 100 |
| 8.00 mn | 100 |

Rt=3.46 mn

MS: ES+ 524 (M+H) 522 (M−H)

$^1$H NMR (400 MHz, MeOD) ppm

En ppm 2.35 (m, 6H) 3.5 (s, 3H) 2.44 (t, 2H) 3.25 (m, 2H) 3.5 (m, 4H) 3.46 (m, 3H) 3.95 (t, 1H) 6.22 (s, 1H) 7.23 (m, 2H) 7.33 (m, 8H) 7.4 (m, 1H) 7.5 (m, 2H) 7.55 (m, 2H)

EXAMPLE 133

1-(3,3-Diphenylpropyl)-1-(2-morpholin-4-ylethyl)-3-(5-phenyl[1,3,4]thiadiazol-2-yl)-urea Method "D" was used to prepare the title compound having the following formula:

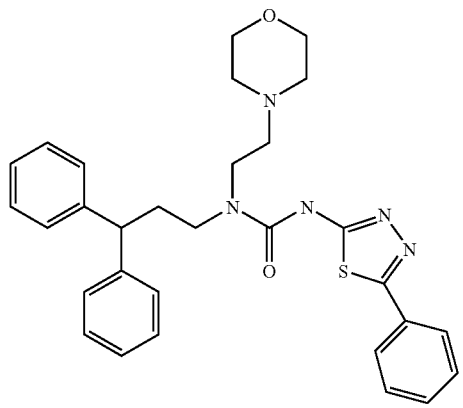

LC SM

Column synergi polar RP ref: 00B 4336-B0
50 mm 2.0 mn 4 microns (Phenomenex)
Flow: 0.4 ml/mn Gradient $H_2O/CH_3CN$

| T = 0 | % $CH_3CN$ 20 |
|---|---|
| 5.5 mn | 100 |
| 8.00 mn | 100 |

Rt=3.89 mn

MS: ES+ 528 (M+H) 325

$^1$H NMR (400 MHz, DMSO) ppm 2.33 (q, 4H) 2.5 (m, 2H) 3.3 (m, 4H) 3.45 (pic large 4H) 3.72 (large 4H) 3.98 (t, 1H) 7.17 (t, 2H) 7.3 (m, 4H) 7.35 (m, 4H) 7.5 (m, 2H) 7.88 (m, 2H)

EXAMPLE 134

3-[3-(3,3-Diphenylpropyl)-3-(2-morpholin-4-yl-ethyl)ureido]-5-phenylthiophene-2-carboxylic acid methyl ester Method "D" was used to prepare the title compound having the following formula:

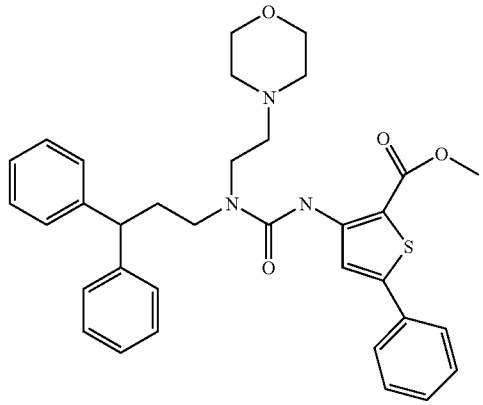

LC SM

Column synergi polar RP ref: 00B 4336-B0
50 mm 2.0 mn 4 microns (Phenomenex)
Flow: 0.4 ml/mn Gradient $H_2O/CH_3CN$

| T = 0 | % $CH_3CN$ 20 |
|---|---|
| 5.5 mn | 100 |
| 8.00 mn | 100 |

Rt=3.97 mn

MS: ES+=584 (M+H)

$^1$H NMR (400 MHz, MeOD) ppm 2.45 (m, 4H) 2.55 (m, 4H) 3.35 (m, 4H) 3.5 (m, 4H) 3.63 (m; 4H) 3.95 (s, 3H) 4.15 (m, 1H) 7.22 (m, 2H) 7.35 (m, 4H) 7.4 (m, 4H) 7.48 (m, 3H) 7.73 (m, 2H) 8.25 (s, 1H)

EXAMPLE 135

3-[2-(4-Chlorophenylsulfanyl)-6-methoxypyridin-3-yl]-1-(3,3-diphenylpropyl)-1-(2-morpholin-4-yl-ethyl)urea Method "D" was used to prepare the title compound having the following formula:

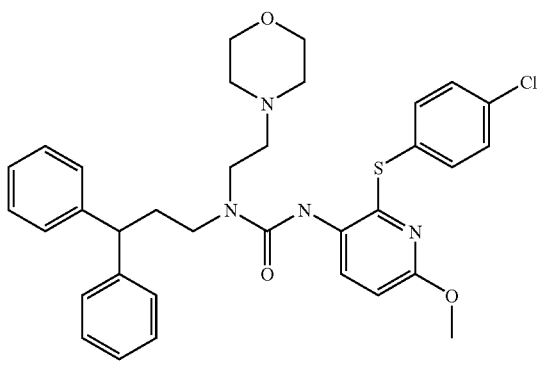

LC SM

Column synergi polar RP ref: 00B 4336-B0
50 mm 2.0 mn 4 microns (Phenomenex)
Flow: 0.4 ml/mn Gradient $H_2O/CH_3CN$

| T = 0 | % $CH_3CN$ 20 |
|---|---|
| 5.5 mn | 100 |
| 8.00 mn | 100 |

Rt=3.96 mn
MS: ES+ 618-619 (M+H)
$^1$H NMR (400 MHz, DMSO) ppm 2.32 (m, 4H) 2.42 (t, 2H) 3.2 (m, 2H) 3.35 (m, 4H) 3.45 (m, 4H) 3.5 (s, 3H) 4.0 (t, 1H) 6.6 (d, 1H) 7.15 (m, 2H) 7.28 (m, 4H) 7.35 (m, 4H) 7.45 (s, 4H) 7.54 (d, 1H)

EXAMPLE 136

2-[3-(3,3-Diphenylpropyl)-3-(2-morpholin-4-ylethyl)ureido]-4,5,6,7-tetrahydrobenzo[b]thiophene-3-carboxylic acid ethyl ester Method "D" was used to prepare the title compound having the following formula:

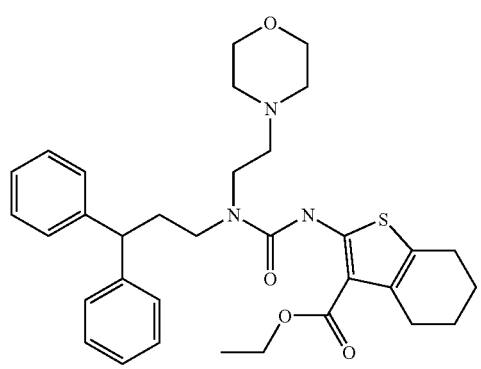

LC SM

Column synergi polar RP ref: 00B 4336-B0
50 mm 2.0 mn 4 microns (Phenomenex)
Flow: 0.4 ml/mn Gradient $H_2O/CH_3CN$

| T = 0 | % $CH_3CN$ 20 |
|---|---|
| 5.5 mn | 100 |
| 8.00 mn | 100 |

Rt=2.44 mn
MS: ES+ 576 (M+H)
$^1$H NMR (400 MHz, MeOD) ppm 1.42 (t, 3H) 1.85 (large 4H) 2.44 (m, 4H) 2.53 (m, 4H) 2.65 (m, 2H) 2.82 (m, 2H) 3.45 (m, 4H) 3.61 (t, 4H) 4.12 (m, 1H) 4.37 (q, 2H) 7.22 (m, 2H) 7.35 (m, 4H) 7.4 (m, 4H)

EXAMPLE 137

6-[3-(3,3-Diphenylpropyl)-3-(2-morpholin-4-ylethyl)ureido]nicotinic acid methyl ester Method "D" was used to prepare the title compound having the following formula:

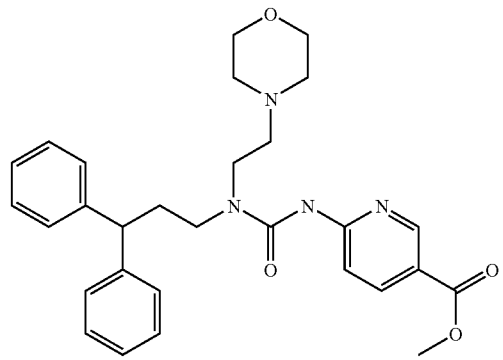

LC SM

Column Ascentis RP amide 5 cm 2.1 mn 5 microns (Supelco)
Flow: 0.4 ml/mn Gradient $H_2O/CH_3CN$

| T = 0 | % $CH_3CN$ 20 |
|---|---|
| 5.5 mn | 100 |
| 8.00 mn | 100 |

Rt=3.67 MS: ES+503$^+$ (M+H)
$^1$H NMR (400 MHz, DMSO) ppm 2.32 (q, 2H) 2.47 (m, 6H) 3.32 (m, 2H) 3.39 (m, 2H) 3.7 (m, 4H) 3.97t(1H) 7.15 (m, 2H) 7.27 (m, 4H) 7.35 (m, 4H) 7.9 (d, 1H) 8.15 (dd, 1H) 8.75 (d, 1H)

EXAMPLE 138

3-(3-Chloro-5-trifluoromethylpyridin-2-yl)-1-(3,3-diphenylpropyl)-1-(2-morpholin-4-ylethyl)-urea Method "D" was used to prepare the title compound having the following formula

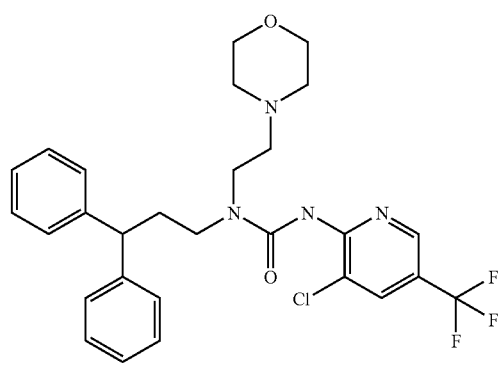

LC MS

Column synergi polar RP ref: 00B 4336-B0
50 mm 2.0 mn 4 microns (Phenomenex)
Flow: 0.4 ml/mn Gradient H₂O/CH₃CN

| T = 0 | % CH₃CN 20 |
|---|---|
| 5.5 mn | 100 |
| 8.00 mn | 100 |

Rt=3.68 mn

MS: ES+ 547 (M+H) 545 (M−H)

¹H NMR (400 MHz, MeOD) ppm 2.49 (m, 2H) 2.65 (m, 6H) 3.38 (m, 2H) 3.58 (m, 2H) 3.8 (m, 4H) 4.08 (t, 1H) 7.22 (m, 2H) 7.35 (m, 8H) 8.21 (s, 1H) 8.63 (s, 1H)

EXAMPLE 139

3-(6-Chloro-2-methylsulfanylpyrimidin-4-yl)-1-(3,3-diphenylpropyl)-1-(2-morpholin-4-ylethyl)-urea Method "D" was used to prepare the title compound having the following formula

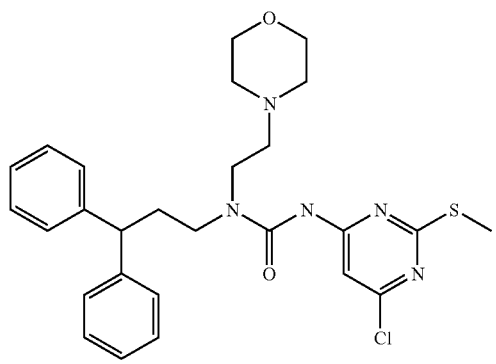

LC SM

Column Ascentis RP amide 5 cm 2.1 mn 5 microns (Supelco)
Flow: 0.4 ml/mn Gradient H₂O/CH₃CN

| T = 0 | % CH₃CN 20 |
|---|---|
| 5.5 mn | 100 |
| 8.00 mn | 100 |

Rt=4.08

MS: ES+ 527 (M+H)

¹H NMR (400 MHz, DMSO) ppm 2.3 (q, 2H) 2.5 (s, 3H+m, 6H) 3.2 (m, 2H) 3.38 (m, 2H) 3.71 (m, 4H) 3.95 (t, 1H) 7.15 (m, 2H) 7.28 (m, 4H) 7.35 (m, 2H) 7.51 (s, 1H)

EXAMPLE 140

2-(4-Chlorobenzyl)-5-[3-(3,3-diphenylpropyl)-3-(2-morpholin-4-ylethyl)-ureido]oxazole-4-carboxylic acid ethyl ester Method "D" was used to prepare the title compound having the following formula

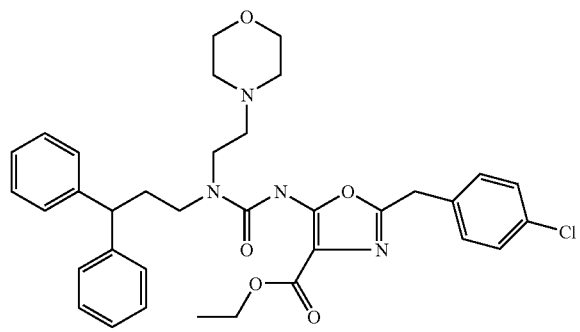

LC SM

Column synergi polar RP ref: 00B 4336-B0
50 mm 2.0 mn 4 microns (Phenomenex)
Flow: 0.4 ml/mn Gradient H₂O/CH₃CN

| T = 0 | % CH₃CN 20 |
|---|---|
| 5.5 mn | 100 |
| 8.00 mn | 100 |

Rt=3.82

MS: ES+ 632 (M+H)

¹H NMR (400 MHz, MeOD) ppm 1.35 (t, 3H, CH3 ester), 2.45 (q, 2H), 2.5 (m, 4H), 2.6 (m, 2H) 3.47 (t 2, H) 3.57 (m, 3H) 3.35 (4H) 4.1 (t, 1H) 4.15 (s, 2H) 4.35 (q, 2H, ester) 7.2 (m, 2H,) 7.35 (m, 12H,)

EXAMPLE 141

1-(3,3-Diphenylpropyl)-3-(4-methoxybenzo[d]isoxazol-3-yl)-1-(2-morpholin-4-ylethyl)urea Method "D" was used to prepare the title compound having the following formula

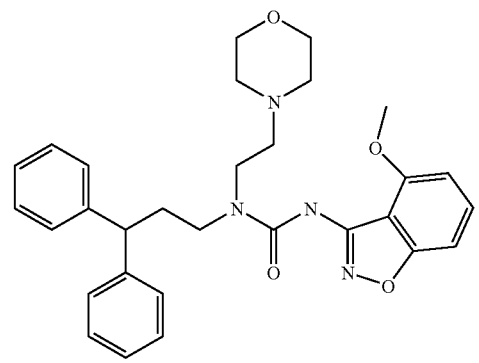

LC SM

Column Ascentis RP amide 5 cm 2.1 mn 5 microns (Supelco)

Flow: 0.4 ml/mn Gradient H₂O/CH₃CN

| T = 0 | % CH₃CN 20 |
|---|---|
| 5.5 mn | 100 |
| 8.00 mn | 100 |

Rt=3.47

MS: ES+ 515 (M+H) 513 (M−H)

¹H NMR (400 MHz, DMSO) ppm 2.37 (m, 6H) 2.47 (m, 2H) 3.22 (m, 2H) 3.5 (m, 2H) 3.41 (m, 2H) 3.5 (m, 4H) 3.78 (s, 3H) 4.0 (t, 1H) 6.68 (d, 1H) 7.16 (m, 3H) 7.3 (m, 4H) 7.46 (m, 4H) 7.52 (t, 1H)

EXAMPLE 142

1-(3,3-Diphenylpropyl)-3-(2-methyl-5-thiophen-2-yl-2H-pyrazol-3-yl)-1-(2-morpholin-4-ylethyl)urea Method "D" was used to prepare the title compound having the following formula

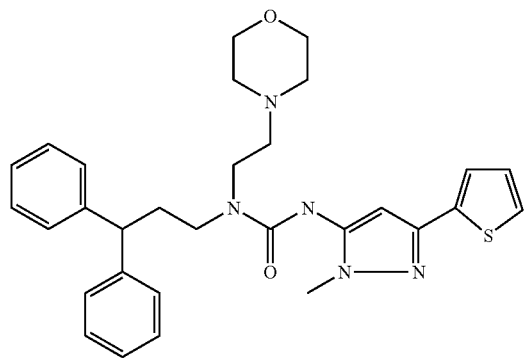

LC SM

Column Ascentis RP amide 5 cm 2.1 mn 5 microns (Supelco)

Flow: 0.4 ml/mn Gradient H₂O/CH₃CN

| T = 0 | % CH₃CN 20 |
|---|---|
| 5.5 mn | 100 |
| 8.00 mn | 100 |

Rt=3.50

MS: ES+ 530 (M+H) 528 (M−H)

¹H NMR (400 MHz, DMSO) ppm 2.32 (m, 6H) 2.4 (t, 2H) 3.22 (m, 2H) 3.35 (t, 2H) 3.45 (m, 4H) 3.95 (t, 1H) 6.36 (s, 1H) 7.05 (m, 1H) 7.17 (m, 2H) 7.3 (m, 4H) 7.33 (d, 1H) 7.36 (m, 4H) 7.4 (d, 1H)

EXAMPLE 143

6-[3-(3,3-Diphenylpropyl)-3-(2-morpholin-4-ylethyl)ureido]nicotinamide

Method "D" was used to prepare the title compound having the following formula:

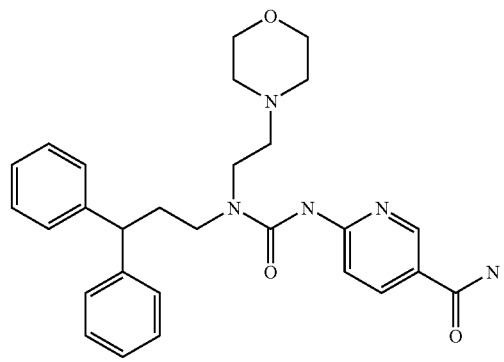

LC SM

Column Ascentis RP amide 5 cm 2.1 mn 5 microns (Supelco)

Flow: 0.4 ml/mn Gradient H₂O/CH₃CN

| T = 0 | % CH₃CN 20 |
|---|---|
| 5.5 mn | 100 |
| 8.00 mn | 100 |

Rt=3.4 MS:

ES+ 488 (M+H)

¹H NMR (400 MHz, DMSO) ppm 2.3 (m, 4H) 2.48 (m, 4H) 3.2 (, 2H) 3.38 (m; 2H) 3.72 (, 4H) 3.98 (t, 1H) 7.15 (m, 2H) 7.3 (m, 4H) 7.35 (m, 4H) 7.83 (d, 1H) 7.95 (H mobile) 8.1 (dd, 1H) 8.72 (d, 1H)

EXAMPLE 144

1-(3,3-Diphenylpropyl)-1-(2-morpholin-4-ylethyl)-3-(1,4,6-trimethyl-1H-pyrazolo[3,4-b]pyridin-3-yl)urea hydrochloride Method "D" was used to prepare the title compound having the following formula:

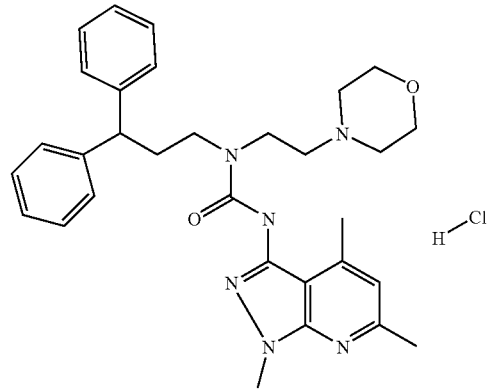

LC SM
Column synergi polar RP ref: 00B 4336-B0
50 mm 2.0 mn 4 microns (Phenomenex)
Flow: 0.4 ml/mn Gradient $H_2O/CH_3CN$

| T = 0            | % $CH_3CN$ 20 |
|------------------|---------------|
| 5.5 mn           | 100           |
| 8.00 mn          | 100           |

Rt=3.95 mass: 527 M(+H)

EXAMPLE 145

Pharmaceutical Composition

Tablets were prepared, which contained

| Product of Example 68   | 30 mg |
|-------------------------|-------|
| Excipient, sufficient for | 1 g |

Details of the excipient: starch, talc, magnesium stearate.
Injectable solutions were also prepared from the salified products.

EXAMPLE 146

Pharmaceutical Composition

Tablets were prepared, which contained

| Product of Example 76A   | 30 mg |
|--------------------------|-------|
| Excipient, sufficient for | 1 g  |

Details of the excipient: starch, talc, magnesium stearate

EXAMPLE 147

Pharmaceutical Composition

Tablets were prepared, which contained

| Product of Example 85    | 50 mg |
|--------------------------|-------|
| Excipient, sufficient for | 1 g  |

Details of the excipient: starch, talc, magnesium stearate.

Biological Activity

In Vivo Evaluation of the Compounds of the Present Invention

I—PTH Measurement on Intact Rats

After fasting for 16 hours, some male rats (Sprague-Dawley, 250-300 g, Charles River France or CERJ) received an oral administration of the compounds to be tested or their vehicle. 30 min. after this bolus, the animals were slaughtered by decapitation using a guillotine. The arterial and venous blood was collected at 4° C. and centrifuged cold, then the sera were frozen at –20° C. After thawing, the serum level of PTH (1-34+1-84) was measured by a radioimmunology test (IRMA kit, rat, Immutopics).

In this test, oral administration of the compound of Example 68 in a dose of 30 mg/kg enabled the PTH level to be reduced by 94% relative to the control group.

II—Rats with Chronic Renal Failure

Chronic renal failure (CRF) was induced in male rats (220-250 g, Sprague-Dawley, CERJ) by ablation of ⅚ of the total renal mass. After anaesthesia (Imalgene 1000), the rats were subjected to exeresis of the right kidney and ablation of both ends of the left kidney, representing approximately ⅔ of the organ).

The incision was cauterised by application of dry ice. To compensate for the loss of blood volume, the animals received an intravenous injection of physiological serum. Two days after the procedure and for the remainder of the trial, the rats were fed with a standard diet (UAR or Safe) and drank phosphate-enriched (1.2%) Volvic® water at will. The procedure was carried out either at the supplier's or at the laboratory. Ten days after nephrectomy, the animals which had been fasting for 16 hours entered the trial. The compounds to be tested or their vehicle were administered orally 30 min. prior to sacrifice. The arterial and venous blood was at 4° C. after decapitation using a guillotine and was centrifuged cold. The sera were frozen a –20° C. After thawing, the serum level of PTH (1-34+1-84) was measured by a radioimmunology test (IRMA kit, rat, Immutopics).

TABLE 6

| Example | Dose (mg/kg) | % PTH reduction at 30 min. relative to the untreated group (intact rat) | Dose (mg/kg) | % PTH reduction at 30 min. relative to the untreated group (CRF rat) |
|---------|--------------|--------------------------------------------------------------------------|--------------|-----------------------------------------------------------------------|
| Example 1   | 30 | 56 |    |    |
| Example 85  | 30 | 88 | 10 | 70 |
| Example 76A | 30 | 14 |    |    |
| Example 40  | 30 | 21 |    |    |
| Example 42  | 30 | 69 |    |    |
| Example 43  | 30 | 43 |    |    |
| Example 48  | 30 | 32 |    |    |
| Example 51  | 30 | 13 |    |    |
| Example 68  | 30 | 94 | 10 | 67 |

In Vitro Evaluation of the Compounds of the Present Invention

The activities of the compounds of the present invention on calcium receptors were measured in accordance with the method described hereinbelow.

Human $Ca^{2+}$ receptor cDNA was subcloned into the mammalian expression vector PECE as described in Ellis, L et al. (1986) Cell vol. 45, 721-732. The luciferase reporter was subcloned into the mammalian expression vector pGL3basic (Promega). Resistance to neomycin (pSV2-neo) and resistance to puromycin (pSG5-puro) were used as selection markers. All these plasmids were simultaneously transfected into CHO cells by calcium phosphate precipitation. Transfected cells were grown in F12 medium containing 7.5% foetal bovine serum, 100 U/ml penicillin and 100 µg/ml streptomycin (as 1% Pen-Strep, Bio Withaker), neomycin (750 µg/ml) and puromycin (5 µg/ml). Neomycin and puromycin resistant colonies were subcloned and assayed for activation against a range of calcium concentration. Clone 8-5-5 was used to assess the effects of compounds on $[Ca^{2+}]_i$. This stably transfected cell line was termed ET8-5-5.

For measurements of $[Ca^{2+}]_i$, the cells were recovered from tissue culture flasks by brief treatment with Trypsin-EDTA (Invitrogen; containing 0.53 mM EDTA.4Na in HBSS) and then seeded in culture-treated 96-well plates (Greiner) at 50 k cells per well in the growth media (same as above, except neomycin 400 µg/ml). Cells were grown in 37° C. TC incubator for 24 h. The culture medium was then removed and replaced with F12 medium, 1% Pen-Strep for an overnight foetal bovine serum starvation in 37° C. TC incubator. Then the starvation medium was removed and replaced with a test buffer (20 mM HEPES pH 7.4, 125 mM NaCl, 5 mM KCl, 1 mM $MgCl_2$, 5.5 mM Glucose, 2 g/l lysosyme and 0.3 mM $CaCl_2$) supplemented with a range of test compound concentrations crossed against a super-added range of $CaCl_2$ concentrations. The cells were incubated with the test compounds for 5 h in 37° C. TC incubator. Then the test buffer was discarded, and cells were added with the substrate for Luciferase from SteadyLite Kit (Perkin-Elmer). The luminescence was recorded.

The compounds of Examples 1 to 144 were tested according to this procedure described above and all were found to have an $EC_{50}$ of 10 µM or less.

Ref 1: Replacement of Insulin Receptor tyrosine Residues 11621 and 1163 compromises Insulin-Stimulated Kinase activity and Uptake of 2-deoxyglucose (1986) L. Ellis, E. Clauser, D. O. Morgan, M. Edery, R. A. Roth and W. J. Rutter Cell vol. 45, 721-732

What is claimed is:
1. A compound of formula (I):

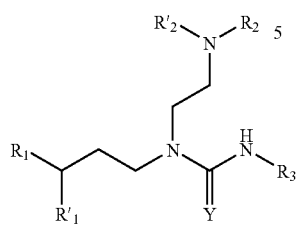

(I)

wherein:
Y is oxygen;
$R_1$ and $R'_1$ are the same or different, and each represents an aryl group or a heteroaryl group,
$R_2$ and $R'_2$, which may be the same or different, each represents: a linear or branched alkyl group containing from 1 to 6 carbon atoms and optionally substituted by at least one halogen atom, hydroxy or alkoxy group containing from 1 to 6 carbon atoms; an alkylaminoalkyl or dialkylaminoalkyl group wherein each alkyl group contains from 1 to 6 carbon atoms,
or $R_2$ and $R'_2$, together with the nitrogen atom to which they are linked, form a saturated or unsaturated heterocycle containing 0, 1 or 2 additional heteroatoms and having 5, 6, or 7 ring atoms, said heterocycle being optionally substituted by at least one substituent selected from the group c,
wherein the group c consists of: halogen atoms, hydroxyl, carboxyl, linear and branched alkyl, hydroxyalkyl, haloalkyl, thioalkyl, alkenyl, and alkynyl groups; linear and branched alkoxyl groups; linear and branched alkylthio groups; hydroxycarbonylalkyl; alkylcarbonyl; alkoxycarbonylalkyl; alkoxycarbonyl; trifluoromethyl; trifluoromethoxyl; —CN; —$NO_2$; alkylsulfonyl groups optionally in the sulfoxide or sulfone forms; wherein any alkyl component has from 1 to 6 carbon atoms, and any alkenyl or alkynyl components have from 2 to 6 carbon atoms,
and wherein, when there is more than one substituent, said substituent is the same or different,
$R_3$ represents a group of formula —$(CH_2)_p$—Ar—$R_n$,
in which p is 0 or 1 and, when p is 1, $(CH_2)_p$ may be substituted by methyl, chlorine, fluorine, hydroxy, or trimethyl, Ar represents an aryl or heteroaryl group, n is equal to the number of positions that can be substituted on Ar, and wherein each R, which may be the same or different, represents a hydrogen atom or a substituent selected from the group consisting of:
group a, in which group a consists of: halogen atoms; hydroxyl; trifluoromethyl; linear and branched alkyl, alkenyl, alkynyl, and alkoxyl groups, all optionally further substituted by one or more of hydroxy groups, halogen atoms, alkoxy groups, amino groups, and alkylthio groups; linear and branched alkoxyl groups; linear and branched thioalkyl groups; aryl groups; aralkyl groups; aralkoxy groups; aryloxy groups; perfluoroalkyl; perfluoroalkoxy; —CN;
the groups —$NR_4R_5$, —C(=X)$NR_4R_5$, —O—C(=X)$NR_4R_5$, —$SO_2NR_4R_5$, or -Alk-$NR_4R_5$, in which X is oxygen or sulfur,
Alk is an alkyl group, and
$R_4$ and $R_5$ are the same or different and are H, alkyl, aralkyl, aryl, heteroaryl or heteroaralkyl and are optionally further substituted by one or more substituents selected from trifluoromethyl, halogen atoms and hydroxyl groups;
the groups —NZC(=X)(NH)$_q R_6$, -Alk-NZC(=X)(NH)$_q R_6$, —C(=X)$R_6$, or -Alk-C(=X)(NH)$_q R_6$,
in which Z is H or C(=X)$R_6$ wherein each X and each $R_6$ is the same or different, q is 0 or 1 and, when q is 1, (NH)$_q$ is optionally substituted with a methyl, ethyl, or trifluoromethyl group,
X is oxygen or sulfur,
Alk is an alkyl group, and
$R_6$ is H, OH, alkyl, aralkyl, aryl, heteroaryl or heteroaralkyl and is optionally further substituted by one or more substituents selected from trifluoromethyl, halogen atoms and hydroxyl groups or,
when C(=X) is CO, then C(=X)$R_6$ may form an ester or thioester grouping;
the groups —$NHSO_2R_7$, —$SO_2R_7$, —$SOR_7$, or —$SR_7$,
in which $R_7$ is OH or amino, or $R_7$ is alkyl, aralkyl, alkylamino, aralkylamino, aryl, heteroaryl or heteroaralkyl, optionally further substituted by one or more substituents selected from trifluoromethyl, halogen atoms and hydroxyl groups;
and saturated or unsaturated heterocyclyl groups, said heterocyclyl groups being mono- or bi-cyclic and being optionally substituted by one or more substituents, which may be the same or different, selected from the group b,
wherein the group b consists of: halogen atoms; hydroxyl; carboxyl; aldehyde groups; linear and branched alkyl, alkenyl, alkynyl, hydroxyalkyl, hydroxyalkenyl, hydroxyalkynyl, haloalkyl, haloalkenyl, and haloalkynyl groups; linear and branched alkoxyl groups; linear and branched thioalkyl groups; alkoxycarbonyl; hydroxycarbonylalkyl; alkoxycarbonylalkyl; perfluoroalkyl; perfluoroalkoxy; —CN; acyl; amino, alkylamino, dialkylamino, acylamino, and diacylamino groups; alkyl groups substituted with an amino, alkylamino, dialkylamino, acylamino, or diacylamino group; CONH$_2$; alkylamido groups; alkylthio and the oxidised sulfoxide and sulfone forms thereof; alkylsulfonyl groups; and sulfonamide, alkylsulfonamide, and di(alkylsulfonyl)amino groups, wherein, in groups a and b, any alkyl components contain from 1 to 6 carbon atoms, and any alkenyl or alkynyl components contain from 2 to 6 carbon atoms, and are optionally substituted by at least one halogen atom or hydroxy group, and wherein any aryl component is optionally a heteroaryl group, and when n is at least two, then two adjacent groups R may form a 5, 6, or 7 membered fused carbocyclic or heterocyclic ring with Ar, said fused ring being optionally further substituted with an oxo group or a substituent selected from group b as defined above, provided that, when p is 0, then Ar is not thiazolyl or oxazolyl, either unfused or fused with a monocyclic aryl or a monocyclic heteroaryl, and salts and esters thereof.

2. The compound, salt, or ester, of claim 1, wherein R$_1$ and R'$_1$ each represents a phenyl, pyridinyl, or thienyl radical, wherein each of R$_1$ and R'$_1$ is optionally substituted as defined.

3. The compound, salt, or ester, of claim 2, wherein each of R$_1$ and R'$_1$, is optionally substituted by at least one substituent selected from the group consisting of: fluorine and chlorine atoms, hydroxy groups, linear or branched alkoxy groups containing from 1 to 5 carbon atoms, linear or branched alkyl groups containing from 1 to 5 carbon atoms, trifluoromethyl and trifluoromethoxy groups, and —CN groups, and wherein, when there is more than one substituent, then each said substituent is the same or different.

4. The compound, salt, or ester, of claim 1, wherein R$_2$ and R'$_2$, together with the nitrogen atom to which they are linked, form a saturated heterocycle containing 5, 6, or 7 ring atoms, said heterocycle being optionally substituted by at least one substituent selected from the group c.

5. The compound, salt, or ester, of claim 1, wherein R$_2$ and R'$_2$, which may be the same or different, each represents a methyl or ethyl group, or, together with the nitrogen atom to which they are linked, form a morpholinyl, thiomorpholinyl, piperazinyl, homopiperazinyl, or piperidinyl group, optionally substituted at least one substituent selected from the group consisting of: chlorine atoms, hydroxyl groups, trifluoromethyl groups, alkoxy groups, hydroxyalkyl groups, and alkyl groups.

6. The compound, salt, or ester, of claim 5, wherein R$_2$ and R'$_2$, together with the nitrogen atom to which they are linked, form a morpholinyl group optionally substituted by at least one substituent selected from the group consisting of: trifluoromethyl groups and alkyl groups.

7. The compound, salt, or ester, of claim 5, wherein R$_2$ and R'$_2$, together with the nitrogen atom to which they are linked, form a morpholinyl group.

8. The compound, salt, or ester, of claim 5, wherein R$_2$ and R'$_2$, together with the nitrogen atom to which they are linked, form a thiomorpholinyl group.

9. The compound, salt, or ester, of claim 1, wherein Ar is an aryl or heteroaryl group selected from the group consisting of: phenyl, naphthyl, monocyclic heteroaryls, and bicyclic heteroaryls.

10. The compound, salt, or ester, of claim 1, wherein Ar is selected from the group consisting of: phenyl, naphthyl, thienyl, thiazolyl, isothiazolyl, furanyl, oxazolyl, isoxazolyl, imidazolyl, triazolyl, indolyl, pyrrolyl, pyridinyl, pyrazinyl, pyrimidinyl, and pyridazinyl groups.

11. The compound, salt, or ester, of claim 10, wherein Ar is phenyl.

12. The compound, salt, or ester, of claim 1, wherein R$_1$ and R'$_1$ are the same or different, and each represents an optionally substituted phenyl, pyridinyl, or thienyl group, Y is oxygen, R$_2$ and R'$_2$, together with the nitrogen atom to which they are linked, form a morpholinyl group, and Ar is phenyl.

13. The compound, salt, or ester, of claim 1, wherein p is 0.

14. The compound, salt, or ester, of claim 1, wherein p is 1 and (CH$_2$)$_p$ is unsubstituted.

15. The compound, salt, or ester, of claim 1, wherein p is 1 and (CH$_2$)$_p$ is substituted by methyl.

16. The compound, salt, or ester, of claim 1, wherein at least one R represents a group —C(=X)NR$_4$R$_5$, —O—C(=X)NR$_4$R$_5$—NZC(=X)(NH)$_q$R$_6$, -Alk-NZC(=X)(NH)$_q$R$_6$, —C(=X)R$_6$, or -Alk-C(=X)(NH)$_q$R$_6$, wherein X is oxygen.

17. The compound, salt, or ester, of claim 16, wherein every C(=X) therein is CO.

18. The compound, salt, or ester, of claim 1, wherein at least one R represents a group -Alk-NR$_4$R$_5$, -Alk-NZC(=X)(NH)$_q$R$_6$, or -Alk-C(=X)(NH)$_q$R$_6$, wherein Alk is methylene or ethylene.

19. The compound, salt, or ester, of claim 1, wherein at least one R represents a group —NR$_4$R$_5$, —C(=X)NR$_4$R$_5$, —O—C(=X)NR$_4$R$_5$, —SO$_2$NR$_4$R$_5$, or -Alk-NR$_4$R$_5$, wherein each of R4 and R5 is selected from the group consisting of: hydrogen, methyl, ethyl, hydroxymethyl and hydroxyethyl.

20. The compound, salt, or ester, of claim 19, wherein each R$_4$ and R$_5$ is hydrogen or methyl.

21. The compound, salt, or ester, of claim 1, wherein at least one R represents a group —NR$_4$R$_5$, —C(=X)NR$_4$R$_5$, —O—C(=X)NR$_4$R$_5$, —SO$_2$NR$_4$R$_5$, or -Alk-NR$_4$R$_5$, wherein each of R$_4$ and R$_5$ is selected from the group consisting of hydrogen, methyl, ethyl, hydroxymethyl and hydroxyethyl.

22. The compound, salt, or ester, of claim 1, wherein at least one R represents the group —NZC(=X)(NH)$_q$R$_6$ or -Alk-NZC(=X)(NH)$_q$R$_6$ wherein Z is hydrogen.

23. The compound, salt, or ester, of claim 22, wherein every Z therein is hydrogen.

24. The compound, salt, or ester, of claim 12, wherein at least one R represents the group —NZC(=X)(NH)$_q$R$_6$ or -Alk-NZC(=X)(NH)$_q$R$_6$ wherein Z is hydrogen.

25. The compound, salt, or ester, of claim 24, wherein every Z therein is hydrogen.

26. The compound, salt, or ester, of claim 1, wherein at least one R represents a group —NZC(=X)(NH)$_q$R$_6$, -Alk-NZC(=X)(NH)$_q$R$_6$, —C(=X)(NH)$_q$R$_6$, or -Alk-C(=X)(NH)$_q$R$_6$, wherein q is 1.

27. The compound, salt, or ester, of claim 12, wherein at least one R represents a group —NZC(=X)(NH)$_q$R$_6$, -Alk-NZC(=X)(NH)$_q$R$_6$, —C(=X)(NH)$_q$R$_6$, or -Alk-C(=X)(NH)$_q$R$_6$, wherein q is 1.

28. The compound, salt, or ester, of claim 26, wherein (NH)$_q$R$_6$ is a dimethylamino group.

29. The compound, salt, or ester, of claim 1, wherein at least one R represents a group —NZC(=X)(NH)$_q$R$_6$, -Alk-NZC(=X)(NH)$_q$R$_6$, —C(=X)(NH)$_q$R$_6$, or -Alk-C(=X)(NH)$_q$R$_6$, wherein q is 0.

30. The compound, salt, or ester, of claim 12, wherein at least one R represents a group —NZC(=X)(NH)$_q$R$_6$, -Alk-NZC(=X)(NH)$_q$R$_6$, —C(=X)(NH)$_q$R$_6$, or -Alk-C(=X)(NH)$_q$R$_6$, wherein q is 0 and any Z is H.

31. The compound, salt, or ester, of claim 1, wherein at least one R represents a group —NZC(=X)(NH)$_q$R$_6$, -Alk-NZC(=X)(NH)$_q$R$_6$, —C(=X)(NH)$_q$R$_6$, or -Alk-C(=X)(NH)$_q$R$_6$, wherein —C(=X)(NH)$_q$R$_6$ represents a carboxylic ester moiety.

32. The compound, salt, or ester, of claim 12, wherein at least one R represents a group —NZC(=X)(NH)$_q$R$_6$, -Alk-NZC(=X)(NH)$_q$R$_6$, —C(=X)(NH)$_q$R$_6$, or -Alk-C(=X)(NH)$_q$R$_6$, wherein —C(=X)(NH)$_q$R$_6$ represents a carboxylic ester moiety and any Z is H.

33. The compound, salt, or ester, of claim 31, wherein R$_6$ is an alkoxy group optionally substituted by one or more substituents selected from the group consisting of chlorine, fluorine, hydroxy, and phenyl.

34. The compound, salt, or ester, of claim 1, wherein at least one R represents a group —NHSO$_2$R$_7$, —SO$_2$R$_7$, —SOR$_7$, or —SR$_7$, wherein R$_7$ is OH, amino, alkyl, hydroxyalkyl, or trifluoromethyl.

35. The compound, salt, or ester, of claim 1, wherein at least one R represents an aryl, aralkyl, heteroaryl, or heteroaralkyl group.

36. The compound, salt, or ester, of claim 1, wherein at least one R represents a group selected from the group consisting of oxazolyl, methyltetrazolyl, isoxazolyl, furanyl, isoxazolyl, benzimidazolyl, and thiophene.

37. The compound, salt, or ester, of claim 12, wherein at least one R represents a group selected from the group consisting of oxazolyl, methyltetrazolyl, isoxazolyl, furanyl, isoxazolyl, benzimidazolyl, and thiophene.

38. The compound, salt, or ester, of claim 1, wherein no more than two substituents R are selected from said substituents a.

39. The compound, salt, or ester, of claim 1, wherein each R is selected from hydrogen and substituents a': fluorine atoms; chlorine atoms; hydroxyl groups; carboxyl groups; aldehyde groups; linear and branched alkyl, hydroxyalkyl, and fluoroalkyl groups; linear and branched alkoxyl groups; linear and branched thioalkyl groups; alkoxycarbonyl groups; benzylcarbonyl groups; hydroxycarbonylalkyl groups; alkoxycarbonylalkyl groups; trifluoromethyl groups; trifluoromethoxy groups; —CN groups; amino, alkylamino, dialkylamino, acylamino, and diacylamino groups; alkoxycarbonylamino, alkylcarbonylamino groups; alkylaminocarbonyloxy groups; alkyl groups substituted with an amino, alkylamino, dialkylamino, acylamino, or diacylamino group; CONH$_2$; alkylamido groups; alkylthio; alkylsulfoxide; alkylsulfonyl groups; sulfonamide, alkylsulfonamide, and di(alkylsulfonyl)amino groups; trifluoromethylsulfoxide; trifluoromethylsulfonyl groups; trifluoromethylsulfonamide, and di(trifluoromethylsulfonyl)amino groups; alkylcarbonylalkyl; and saturated monocyclic heterocyclyl groups, said heterocyclyl groups being optionally substituted by one or more substituents, which may be the same or different, selected from the group b.

40. The compound, salt, or ester, of claim 1, wherein each R is selected from hydrogen and substituents a": chlorine atoms; hydroxyl groups; carboxyl groups; linear and branched alkyl, hydroxyalkyl; linear and branched alkoxyl groups; alkoxycarbonyl groups; hydroxycarbonylalkyl groups; alkoxycarbonylalkyl groups; trifluoromethyl groups; trifluoromethoxy groups; —CN groups; amino, alkylamino, and dialkylamino groups; alkoxycarbonylamino, alkylcarbonylamino groups; alkylaminocarbonyloxy groups; alkyl groups substituted with an amino, alkylamino, or dialkylamino group; CONH$_2$; alkylcarbonylalkyl; alkylthio; alkylsulfonyl groups; sulfonamide, alkylsulfonamide, and di(alkylsulfonyl)amino groups; trifluoromethylsulfoxide; trifluoromethylsulfonyl groups; trifluoromethylsulfonamide, and di(trifluoromethylsulfonyl)amino groups; pyrrolidinyl, piperidinyl piperazinyl, morpholinyl, and thiomorpholinyl groups optionally substituted by one or more substituents, which may be the same or different, selected from the group b.

41. The compound, salt, or ester, of claim 1, wherein substituents b are selected from substituents b' consisting of: chlorine atoms; hydroxyl groups; linear and branched alkyl, hydroxyalkyl, and alkoxyl groups; trifluoromethyl groups; trifluoromethoxy groups; —CN groups; amino, alkylamino, and dialkylamino groups; alkylsulfonyl groups; and sulfonamide, alkylsulfonamide, and di(alkylsulfonyl)amino groups.

42. The compound, salt, or ester, of claim 1, wherein each R is selected from hydrogen and the group consisting of substituents a''': chlorine atoms; hydroxyl groups; carboxyl groups; linear and branched alkyl, hydroxyalkyl; linear and branched alkoxyl groups; alkoxycarbonyl groups; hydroxycarbonylalkyl groups; alkoxycarbonylalkyl groups; trifluoromethyl groups; trifluoromethoxy groups; —CN groups; amino, alkylamino, and dialkylamino groups; alkoxycarbonylamino, alkylcarbonylamino groups; alkylaminocarbonyloxy groups; alkyl groups substituted with an amino, alkylamino, or dialkylamino group; CONH$_2$; alkylcarbonylalkyl; alkylthio; alkylsulfonyl groups; sulfonamide, alkylsulfonamide, and di(alkylsulfonyl)amino groups; trifluoromethylsulfoxide; trifluoromethylsulfonyl groups; trifluoromethylsulfonamide, and di(trifluoromethylsulfonyl)amino groups; pyrrolidinyl, piperidinyl piperazinyl, morpholinyl, and thiomorpholinyl groups optionally substituted by one or more substituents, which may be the same or different, selected from the group b, and wherein any pyrrolidinyl, piperidinyl piperazinyl, morpholinyl, and thiomorpholinyl groups are not further substituted.

43. The compound, salt, or ester, of claim 1, wherein any alkyl, alkenyl or alkynyl component has no more than 4 carbon atoms.

44. The compound, salt, or ester, of claim 1, wherein any alkylsulfonyl substituent is a methylsulfonyl substituent.

45. The compound, salt, or ester, of claim 1, selected from:
3-[3-(3,3-diphenylpropyl)-3-(2-morpholin-4-ylethyl)ureido]benzoic acid methyl ester;
3-(4-chlorophenyl)-1-(3,3-diphenylpropyl)-1-(2-morpholin-4-ylethyl)urea;
3-(3-chlorophenyl)-1-(3,3-diphenylpropyl)-1-(2-morpholin-4-ylethyl)urea;
3-(2-chlorophenyl)-1-(3,3-diphenylpropyl)-1-(2-morpholin-4-ylethyl)urea;
1-(3,3-diphenylpropyl)-3-(3-fluoro-5-trifluoromethylphenyl)-1-(2-morpholin-4-yl)urea;
3-(3,4-dichlorophenyl)-1-(3,3-diphenylpropyl)-1-(2-morpholin-4-ylethyl)urea;
3-(3,4-dimethoxyphenyl)-1-(3,3-diphenylpropyl)-1-(2-morpholin-4-ylethyl)urea;
1-(3,3-diphenylpropyl)-3-(3-methoxyphenyl)-1-(2-morpholin-4-ylethyl)urea;
4-[3-(3,3-diphenylpropyl)-3-(2-morpholin-4-ylethyl)ureido]benzoic acid ethyl ester;
1-(3,3-diphenylpropyl)-1-(2-morpholin-4-ylethyl)-3-(4-trifluoromethoxyphenyl)urea;
3-(3-bromophenyl)-1-(3,3-diphenylpropyl)-1-(2-morpholin-4-ylethyl)urea;
1-(3,3-diphenylpropyl)-1-(2-morpholin-4-ylethyl)-3-(3-trifluoromethylphenyl)urea;
3-(3,5-bis-trifluoromethylphenyl)-1-(3,3-diphenylpropyl)-1-(2-morpholin-4-ylethyl)urea;

3-(4-bromo-6-trifluoromethyl-phenyl)-1-(3,3-diphenyl-propyl)-1-(2-morpholin-4-ylethyl)urea;
3-(4-bromophenyl)-1-(3,3-diphenylpropyl)-1-(2-morpholin-4-ylethyl)urea;
4-methoxy-5-[3-(3,3-diphenylpropyl)-3-(2-morpholin-4-ylethyl)ureido]benzoic acid methyl ester;
4-chloro-5-[3-(3,3-diphenylpropyl)-3-(2-morpholin-4-ylethyl)ureido]benzoic acid methyl ester;
2-chloro-5-[3-(3,3-diphenylpropyl)-3-(2-morpholin-4-ylethyl)ureido]benzoic acid methyl ester;
3-(3-cyanophenyl)-1-(3,3-diphenylpropyl)-1-(2-morpholin-4-ylethyl)urea;
3-(4-cyanophenyl)-1-(3,3-diphenylpropyl)-1-(2-morpholin-4-ylethyl)urea;
3-[3-(3,3-diphenylpropyl)-3-(2-morpholin-4-ylethyl)ureido]benzoic acid tertbutyl ester;
3-(2-cyanophenyl)-1-(3,3-diphenylpropyl)-1-(2-morpholin-4-ylethyl)urea;
3-(3-acetylphenyl)-1-(3,3-diphenylpropyl)-1-(2-morpholin-4-ylethyl)urea;
1-(3,3-diphenylpropyl)-3-(3-methylsulphanylphenyl)-1-(2-morpholin-4-ylethyl)urea;
1-(3,3-diphenylpropyl)-1-(2-morpholin-4-ylethyl)-3-(3-trifluoromethoxyphenyl)urea;
1-(3,3-diphenylpropyl)-1-(2-morpholin-4-ylethyl)-3-(3-ethylsulphonyl-6-methoxyphenyl)urea;
1-(3,3-diphenylpropyl)-3-[3-(2-hydroxyethanesulfonyl)phenyl]-1-(2-morpholin-4-yl-ethyl)urea;
3-[3-(3,3-diphenylpropyl)-3-(2-morpholin-4-ylethyl)ureido]-2-methylbenzoic acid methyl ester;
1-(3,3-diphenylpropyl)-1-(2-morpholin-4-ylethyl)-3-(3-trifluoromethanesulfonyl-phenyl)urea;
1-(3,3-diphenylpropyl)-1-(2-morpholin-4-ylethyl)-3-(3-propionylphenyl)urea;
1-(3,3-diphenylpropyl)-1-(2-morpholin-4-ylethyl)-3-(3-trifluoromethylsulfanyl-phenyl)urea;
1-(3,3-diphenylpropyl)-3-(3-methanesulfonylphenyl)-1-(2-morpholin-4-ylethyl)urea;
1-(3,3-diphenylpropyl)-3-(3-ethylsulfanylphenyl)-1-(2-morpholin-4-ylethyl)urea;
1-(3,3-diphenylpropyl)-3-(3-isopropylsulfanylphenyl)-1-(2-morpholin-4-ylethyl)urea;
3-(4-chloro-3-methylsulfanylphenyl)-1-(3,3-diphenylpropyl)-1-(2-morpholin-4-yl-ethyl)urea;
3-(3,5-dichlorophenyl)-1-(3,3-diphenylpropyl)-1-(2-morpholin-4-ylethyl)urea;
1-(3,3-diphenylpropyl)-3-(3-iodophenyl)-1-(2-morpholin-4-ylethyl)urea;
3-(4-chloro-3-trifluoromethylphenyl)-1-(3,3-diphenyl-propyl)-1-(2-morpholin-4-ylethyl)urea;
3-(3-dimethylaminophenyl)-1-(3,3-diphenylpropyl)-1-(2-morpholin-4-ylethyl)urea;
3-[3-(3,3-diphenylpropyl)-3-(2-morpholin-4-ylethyl)ureido]benzoic acid tertbutyl ester hydrochloride;
3-(4-chloro-3-trifluoromethylphenyl)-1-(3,3-diphenyl-propyl)-1-(2-morpholin-4-ylethyl)urea hydrochloride;
1-(3,3-diphenylpropyl)-3-(3-methanesulphinylphenyl)-1-(2-morpholin-4-ylethyl)urea;
3-[3-(3,3-diphenylpropyl)-3-(2-morpholin-4-ylethyl)ureido]benzoic acid;
2-chloro-5-[3-(3,3-diphenylpropyl)-3-(2-morpholin-4-ylethyl)ureido]benzoic acid;
3-[3-(3,3-diphenylpropyl)-3-(2-morpholin-4-ylethyl)ureido]benzoic acid isopropyl ester;
3-[3-(3,3-diphenylpropyl)-3-(2-morpholin-4-ylethyl)ureido]benzoic acid isopropyl ester hydrochloride;
3-[3-(3,3-diphenylpropyl)-3-(2-morpholin-4-ylethyl)ureido]benzoic acid 2-hydroxy ester;
2-chloro-5-[3-(3,3-diphenylpropyl)-3-(2-morpholin-4-ylethyl)ureido]benzoic acid isopropyl ester;
2-chloro-5-[3-(3,3-diphenylpropyl)-3-(2-morpholin-4-ylethyl)ureido]benzoic acid isopropyl ester hydrochloride;
3-[(3,3-diphenylpropyl)-3-(2-morpholin-4-ylethyl)ureido]benzoic acid benzyl ester;
2-chloro-5-[3-(3,3-diphenylpropyl)-3-(2-morpholin-4-ylethyl)ureido]benzamide;
3-[3-(3,3-diphenylpropyl)-3-(2-morpholin-4-ylethyl)ureido]-n-(2-hydroxy-ethyl)-benzamide;
3-[3-(3,3-diphenylpropyl)-3-(2-morpholin-4-ylethyl)ureido]thiobenzamide;
1-(3,3-diphenylpropyl)-3-[3-(4-methylthiazol-2-yl)-phenyl]-1-(2-morpholin-4-ylethyl)urea;
1-(3,3-diphenylpropyl)-3-(3-hydroxymethylphenyl)-1-(2-morpholin-4-ylethyl)urea;
3-(4-chloro-3-hydroxymethylphenyl)-1-(3,3-diphenyl-propyl)-1-(2-morpholin-4-ylethyl)urea;
1-(3,3-diphenylpropyl)-3-(3-formylphenyl)-1-(2-morpholin-4-ylethyl)urea;
3-(4-chloro-3-formylphenyl)-1-(3,3-diphenylpropyl)-1-(2-morpholin-4-ylethyl)urea;
3-[4-chloro-3-(1-hydroxyethyl)phenyl]-1-(3,3-diphenyl-propyl)-1-(2-morpholin-4-ylethyl)urea;
1-(3,3-diphenylpropyl)-3-(3-methoxymethylphenyl)-1-(2-morpholin-4-ylethyl)urea;
1-(3,3-diphenylpropyl)-1-(2-morpholin-4-ylethyl)-3-(3-piperidin-1-ylmethyl-phenyl)urea;
1-(3,3-diphenylpropyl)-1-(2-morpholin-4-ylethyl)-3-(3-oxazol-5-ylphenyl)urea;
1-(3,3-diphenylpropyl)-1-(2-morpholin-4-ylethyl)-3-(3-oxazol-5-ylphenyl)urea hydrochloride;
1-(3,3-diphenylpropyl)-1-(2-morpholin-4-ylethyl)-3-(3-oxazol-5-yl-4-chlorophenyl)urea;
3-[4-chloro-3-(1-methyl-1h-tetrazol-5-yl)phenyl]-1-(3,3-diphenylpropyl)-1-(2-morpholin-4-ylethyl)urea;
3-[4-chloro-3-(2-methyl-2h-tetrazol-5-yl)phenyl]-1-(3,3-diphenylpropyl)-1-(2-morpholin-4-ylethyl)urea;
3-biphenyl-4-yl-1-(3,3-diphenylpropyl)-1-(2-morpholin-4-ylethyl)urea;
biphenyl-3-yl-1-(3,3-diphenylpropyl)-1-(2-morpholin-4-ylethyl)urea;
1-(3,3-diphenylpropyl)-1-(2-morpholin-4-ylethyl)-3-(3-pyridin-3-ylphenyl)urea;
(1-(3,3-diphenylpropyl)-3-(3-furan-3-ylphenyl)-1-(2-morpholin-4-ylethyl)urea;
1-(3,3-diphenylpropyl)-3-(3-furan-2-ylphenyl)-1-(2-morpholin-4-ylethyl)urea;
1-(3,3-diphenylpropyl)-3-(3-furan-2-ylphenyl)-1-(2-morpholin-4-ylethyl)urea hydrochloride;
3-[3-(5-chlorothiophen-2-yl)-phenyl]-1-(3,3-diphenyl-propyl)-1-(2-morpholin-4-ylethyl)urea;
1-(3,3-diphenylpropyl)-1-(2-morpholin-4-ylethyl)-3-(3-thiophen-3-ylphenyl)urea;
1-(3,3-diphenylpropyl)-3-(2'-methoxybiphenyl-3-yl)-1-(2-morpholin-4-ylethyl)urea;
3-(2',4'-dichlorobiphenyl-3-yl)-1-(3,3-diphenylpropyl)-1-(2-morpholin-4-ylethyl)urea;
1-(3,3-diphenylpropyl)-3-[3-(3-methylisoxazol-5-yl)-phenyl]-1-(2-morpholin-4-ylethyl)urea;
3-[3-(1 h-benzimidazole-2-yl)-phenyl]-1-(3,3-diphenyl-propyl)-1-(2-morpholin-4-ylethyl)urea;
3-(3-benzothiazol-2-ylphenyl)-1-(3,3-diphenylpropyl)-1-(2-morpholin-4-ylethyl)urea;

1-(3,3-diphenylpropyl)-1-(2-morpholin-4-ylethyl)-3-[3-(2h-tetrazol-5-yl)phenyl]urea hydrochloride;
1-(3,3-diphenylpropyl)-3-[3-(2-methyl-2h-tetrazol-5-yl)phenyl]-1-(2-morpholin-4-ylethyl)urea;
1-(3,3-diphenylpropyl)-3-[3-(1-methyl-1 h-tetrazol-5-yl)phenyl]-1-(2-morpholin-4-ylethyl)urea;
1-(3,3-diphenylpropyl)-3-[3-(2-methyl-2h-tetrazol-5-yl)phenyl]-1-(2-morpholin-4-ylethyl)urea;
1-(3,3-diphenylpropyl)-3-[3-(1-methyl-1 h-tetrazol-5-yl)phenyl]-1-(2-morpholin-4-ylethyl)urea;
3-benzo[1,3]dioxol-5-yl-1-(3,3-diphenylpropyl)-1-(2-morpholin-4-ylethyl)urea;
3-(2,3-dihydro-benzo[1,4]dioxin-6-yl)-1-(3,3-diphenylpropyl)-1-(2-morpholin-4-ylethyl)urea;
1-(3,3-diphenylpropyl)-1-(2-morpholin-4-ylethyl)-3-(3-oxo-1,3-dihydroisobenzofuran-5-yl)urea;
1-(3,3-diphenylpropyl)-1-(2-morpholin-4-ylethyl)-3-(8-oxo-5,6,7,8-tetrahydro-naphthalen-2-yl)urea;
3-(1-acetyl-2,3-dihydro-1 h-indol-6-yl)-1-(3,3-diphenylpropyl)-1-(2-morpholin-4-ylethyl)urea;
1-(3,3-diphenylpropyl)-3-(1 h-indazol-6-yl)-1-(2-morpholin-4-ylethyl)urea;
1-(3,3-diphenylpropyl)-3-(9-ethyl-9h-carbazol-3-yl)-1-(2-morpholin-4-ylethyl)urea;
1-(3,3-diphenylpropyl)-3-isoquinolin-7-yl-1-(2-morpholin-4-ylethyl)urea;
3-(2-chloro-benzyl)-1-(3,3-diphenylpropyl)-1-(2-morpholin-4-ylethyl)urea;
1-(3,3-diphenylpropyl)-1-(2-morpholin-4-ylethyl)-3-thiophen-2-ylmethyl)urea;
1-(3,3-diphenylpropyl)-1-(2-morpholin-4-ylethyl)-3-(1-naphthalen-1-ylethyl)urea;
3-[3-(3,3-diphenylpropyl)-3-(2-morpholin-4-ylethyl)ureido]thiophene-2-carboxylic acid methyl ester;
1-(3,3-diphenylpropyl)-1-(2-morpholin-4-ylethyl)-3-pyridin-3-ylurea;
1-(3,3-diphenylpropyl)-3-[3-(2-methyl-2h-tetrazol-5-yl)phenyl]-1-(2-morpholin-4-ylethyl)urea;
3-(1-benzyl-1 h-benzimidazol-2-yl)-1-(3,3-diphenylpropyl)-1-(2-morpholin-4-ylethyl)urea;
1-(3,3-diphenylpropyl)-3-(2-methyl-5-phenyl-2,5-dihydro-1h-pyrazol-3-yl)-1-(2-morpholin-4-ylethyl)urea;
3-(4,6-dimethylpyridin-2-yl)-1-(3,3-diphenylpropyl)-1-(morpholin-4-ylethyl)urea;
1-(3,3-diphenylpropyl)-3-(4-methoxy-6-methylpyrimidin-2-yl)-1-(2-morpholin-4-ylethyl)urea;
1-(3,3-diphenylpropyl)-1-(2-morpholin-4-ylethyl)-3-pyrazin-2-ylurea;
1-(3,3-diphenylpropyl)-1-(2-morpholin-4-ylethyl)-3-(4-thiazol-2-ylpyrimidin-2-yl)urea;
1-(3,3-diphenylpropyl)-3-(5-methylisoxazol-3-yl)-1-(2-morpholin-4-ylethyl)urea;
1-(3,3-diphenylpropyl)-3-(3-methyl-5-phenylisoxazol-4-yl)-1-(2-morpholin-4-ylethyl)urea;
3-[3 (2-chloro-6-fluorophenyl)-5-methylisoxazol-4-yl)-1-(3,3-diphenylpropyl)-1-(2-morpholin-4-ylethyl)urea;
1-(3,3-diphenylpropyl)-3-(5-methyl-3-phenylisoxazol-4-yl)-1-(2-morpholin-4-ylethyl)urea;
1-(3,3-diphenylpropyl)-1-(2-morpholin-4-ylethyl)-3-(5-phenyl-2h-pyrazol-3-yl)urea;
1-(3,3-diphenylpropyl)-1-(2-morpholin-4-ylethyl)-3-(3-phenyl-[1,2,4]thiadiazol-5-yl)urea;
5-[3,3-diphenylpropyl)-3-(2-morpholin-4-ylethyl)ureido]-3-propyl-isoxazole-4-carboxylic acid ethyl ester;
3-(3,4-dimethyl-isoxazol-5-yl)-1-(3,3-diphenylpropyl)-1-(2-morpholin-4-ylethyl)urea;
3-[3-[2-(9h-fluoren-9-yl)-ethyl]-3-(2-morpholin-4-ylethyl)ureido]benzoic acid methyl ester;
3-[3-[2-(9h-fluoren-9-yl)ethyl]-3-(2-morpholin-4-ylethyl)ureido]benzoic acid methyl ester;
3-[3-(2-methyl-2h-tetrazol-5-yl)phenyl]-1-(2-morpholin-4-ylethyl)-1-(3-phenyl-3-thiophen-2-ylpropyl)urea;
1-(2-morpholin-4-ylethyl)-3-(3-oxazol-5-ylphenyl)-1-(3-phenyl-3-thiophen-2-yl-propyl)urea dihydrochloride;
3-[3-(2-morpholin-4-ylethyl)-3-(3-phenyl-3-thiophen-2-ylpropyl)ureido]benzoic acid methyl ester;
1-(3,3-di-thiophen-2-ylpropyl)-3-[3-(2-methyl-2h-tetrazol-5-yl)phenyl]-1-(2-morpholin-4-ylethyl)urea;
3-[3-(3,3-dithiophen-2-yl-propyl)-3-(2-morpholin-4-ylethyl)ureido]benzoic acid methyl ester;
1-(3,3-dithiophen-2-ylpropyl)-1-(2-morpholin-4-ylethyl)-3-(3-oxazol-5-ylphenyl)urea dihydrochloride;
1-(3,3-diphenylpropyl)-3-[3-(2-methyl-2h-tetrazol-5-yl)phenyl]-1-(2-thiomorpholin-4-ylethyl)urea;
1-[2-(2,6-dimethylmorpholin-4-yl)-ethyl]-1-(3,3-diphenylpropyl)-3-[3-(2-methyl-2h-tetrazol-5-yl)phenyl]urea;
3-(5,6-dimethyl-1h-benzoimidazol-2-yl)-1-(3,3-diphenylpropyl)-1-(2-morpholin-4-ylethyl)urea;
1-(3,3-diphenylpropyl)-3-(1-methyl-1 h-benzoimidazol-2-yl)-1-(2-morpholin-4-ylethyl)-urea;
3-(1h-benzoimidazol-2-yl)-1-(3,3-diphenylpropyl)-1-(2-morpholin-4-ylethyl)urea;
1-(3,3-diphenylpropyl)-1-(2-morpholin-4-yl-ethyl)-3-(5-phenylsulfanyl-1 h-benzoimidazol-2-yl)-urea;
1-(3,3-diphenylpropyl)-1-(2-morpholin-4-ylethyl)-3-(5-oxo-1-phenyl-4,5-dihydro-1h-pyrazol-3-yl)urea;
1-(3,3-diphenylpropyl)-3-(5-methyl-2-phenyl-2h-pyrazol-3-yl)-1-(2-morpholin-4-ylethyl)urea;
1-(3,3-diphenylpropyl)-1-(2-morpholin-4-ylethyl)-3-(5-phenyl[1,3,4]thiadiazol-2-yl)-urea;
3-[3-(3,3-diphenylpropyl)-3-(2-morpholin-4-yl-ethyl)ureido]-5-phenylthiophene-2-carboxylic acid methyl ester;
3-[2-(4-chlorophenylsulfanyl)-6-methoxypyridin-3-yl]-1-(3,3-diphenylpropyl)-1-(2-morpholin-4-yl-ethyl)urea;
2-[3-(3,3-diphenylpropyl)-3-(2-morpholin-4-ylethyl)ureido]-4,5,6,7-tetrahydrobenzo[b]thiophene-3-carboxylic acid ethyl ester;
6-[3-(3,3-diphenylpropyl)-3-(2-morpholin-4-ylethyl)ureido]nicotinic acid methyl ester;
3-(3-chloro-5-trifluoromethylpyridin-2-yl)-1-(3,3-diphenylpropyl)-1-(2-morpholin-4-ylethyl)urea;
3-(6-chloro-2-methylsulfanylpyrimidin-4-yl)-1-(3,3-diphenylpropyl)-1-(2-morpholin-4-ylethyl)urea;
2-(4-chlorobenzyl)-5-[3-(3,3-diphenylpropyl)-3-(2-morpholin-4-ylethyl)-ureido]oxazole-4-carboxylic acid ethyl ester;
1-(3,3-diphenylpropyl)-3-(4-methoxybenzo[d]isoxazol-3-yl)-1-(2-morpholin-4-ylethyl)urea;
1-(3,3-diphenylpropyl)-3-(2-methyl-5-thiophen-2-yl-2h-pyrazol-3-yl)-1-(2-morpholin-4-ylethyl)urea;
6-[3-(3,3-diphenylpropyl)-3-(2-morpholin-4-ylethyl)ureido]nicotinamide; and
1-(3,3-diphenylpropyl)-1-(2-morpholin-4-ylethyl)-3-(1,4,6-trimethyl-1 h-pyrazolo[3,4-b]pyridin-3-yl)urea hydrochloride.

46. The compound, salt, or ester, of claim 1, selected from:
3-[3-(3,3-diphenylpropyl)-3-(2-morpholin-4-ylethyl)ureido]benzoic acid methyl ester and the hydrochloride thereof, 3-[3-(3,3-diphenylpropyl)-3-(2-morpholin-4-ylethyl)ureido]benzoic acid isopropyl ester and the hydrochloride thereof, 2-chloro-5-[3-(3,3-diphenylpropyl)-3-(2-morpholin-4-ylethyl)ureido]benzoic acid isopropyl ester and the hydrochloride thereof, 3-[3-(3,3-diphenylpropyl)-3-(2-morpholin-4-ylethyl)ureido]benzoic acid tertbutyl ester and the hydrochloride thereof, 1-(3,3-diphenylpropyl)-3-(3-ethylcarbonylphenyl)-1-(2-morpholin-4-ylethyl)urea and the hydrochloride thereof, 1-(3,3-diphenylpropyl)-3-[3-(2-methyl-2H-tetrazol-5-yl)phenyl]-1-(2-morpholin-4-ylethyl)urea and the hydrochloride thereof, 3-(4-chloro-3-trifluoromethylphenyl)-1-(3,3-diphenylpropyl)-1-(2-morpholin-4-ylethyl)urea and the hydrochloride thereof, 1-(3,3-diphenylpropyl)-1-(2-morpholin-4-ylethyl)-3-(3-oxazol-5-ylphenyl)urea and the hydrochloride thereof, 1-(3,3-diphenylpropyl)-3-(3-furan-2-ylphenyl)-1-(2-morpholin-4-ylethyl)urea and the hydrochloride thereof, 1-(3,3-diphenylpropyl)-3-(3-methylsulfanylphenyl)-1-(2-morpholin-4-ylethyl)urea and the hydrochloride thereof, 3-[3-(2-methyl-2H-tetrazol-5-yl)phenyl]-1-(2-morpholin-4-ylethyl)-1-(3-phenyl-3-thiophen-2-ylpropyl)urea, 3-[3-(2-morpholin-4-ylethyl)-3-(3-phenyl-3-thiophen-2-ylpropyl)ureido]benzoic acid methyl ester, 1-(3,3-diphenylpropyl)-3-(4-methoxy-6-methylpyrimidin-2-yl)-1-(2-morpholin-4-ylethyl)urea, 3-(4,6-dimethylpyridin-2-yl)-1-(3,3-diphenylpropyl)-1-(morpholin-4-ylethyl)urea, and 1-(3,3-diphenylpropyl)-3-(5-methylisoxazol-3-yl)-1-(2-morpholin-4-ylethyl)urea.

47. A pharmaceutically acceptable composition comprising the compound of claim 1 and a pharmaceutically acceptable carrier or diluent.

48. A method for the treatment of cancers of the parathyroid and the digestive tract, comprising the administration of an effective amount of a compound of claim 1 to a patient in need thereof, wherein treatment is other than for prophylaxis.

49. A method for the treatment of Alzheimer's disease, Parkinson's disease or Huntington's chorea, comprising the administration of an effective amount of a compound of claim 1 to a patient in need thereof, wherein treatment is other than for prophylaxis.

50. A method for the treatment of osteoporosis, osteopaenia and Paget's disease, rheumatoid arthritis and osteoarthritis, comprising the administration of an effective amount of a compound of claim 1 to a patient in need thereof, wherein treatment is other than for prophylaxis.

51. A method for the treatment of abnormal calcium homeostasis, comprising the administration of an effective amount of a compound of claim 1 to a patient in need thereof, wherein treatment is other than for prophylaxis.

52. A method for the treatment of parathyroid hyperplasia and parathyroid adenoma, comprising the administration of an effective amount of a compound of claim 1 to a patient in need thereof, wherein treatment is other than for prophylaxis.

53. A method for the treatment of intestinal malabsorption, comprising the administration of an effective amount of a compound of claim 1 to a patient in need thereof, wherein treatment is other than for prophylaxis.

54. A method for the treatment of biliary lithiasis and renal lithiasis, comprising the administration of an effective amount of a compound of claim 1 to a patient in need thereof, wherein treatment is other than for prophylaxis.

55. A method for the treatment of hyperparathyroidism, comprising the administration of an effective amount of a compound of claim 1 to a patient in need thereof, wherein treatment is other than for prophylaxis.

56. The method of claim 55, wherein secondary hyperparathyroidism is observed in the event of renal insufficiency.

57. A method for the reduction of ionised serum calcium level during the treatment of hypercalcaemia, comprising the administration of an effective amount of a compound of claim 1 to a patient in need thereof, wherein treatment is other than for prophylaxis.

58. A method for the treatment of hypertension, comprising the administration of an effective amount of a compound of claim 1 to a patient in need thereof, wherein treatment is other than for prophylaxis.

59. A method for the treatment of vascular calcification, comprising the administration of an effective amount of a compound of claim 1 to a patient in need thereof, wherein treatment is other than for prophylaxis.

60. A method for the treatment of diarrhea, comprising the administration of an effective amount of a compound of claim 1 to a patient in need thereof, wherein treatment is other than for prophylaxis.

* * * * *